US010130694B2

(12) United States Patent
Boutriau et al.

(10) Patent No.: US 10,130,694 B2
(45) Date of Patent: Nov. 20, 2018

(54) IMMUNOGENIC COMPOSITION

(71) Applicant: GLAXOSMITHKLINE BIOLOGICALS S.A., Rixensart (BE)

(72) Inventors: Dominique Boutriau, Rixensart (BE); Sophie Marie Jeanne Valentine Germain, Rixensart (BE); Hugues Wallemacq, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 15/606,439

(22) Filed: May 26, 2017

(65) Prior Publication Data

US 2017/0340719 A1   Nov. 30, 2017

Related U.S. Application Data

(62) Division of application No. 14/649,940, filed as application No. PCT/EP2013/075405 on Dec. 3, 2013, now Pat. No. 9,694,064.

(30) Foreign Application Priority Data

Dec. 5, 2012  (GB) .................................. 1221875.6

(51) Int. Cl.
| | | |
|---|---|---|
| *A61K 39/00* | (2006.01) | |
| *A61K 39/02* | (2006.01) | |
| *A61K 39/08* | (2006.01) | |
| *A61K 39/39* | (2006.01) | |
| *C07K 14/33* | (2006.01) | |

(52) U.S. Cl.
CPC .............. *A61K 39/08* (2013.01); *A61K 39/39* (2013.01); *C07K 14/33* (2013.01); *A61K 2039/55505* (2013.01); *A61K 2039/55511* (2013.01); *A61K 2039/55555* (2013.01); *A61K 2039/55566* (2013.01); *A61K 2039/55572* (2013.01); *A61K 2039/55577* (2013.01); *C07K 2319/40* (2013.01)

(58) Field of Classification Search
CPC ..................................................... A61K 39/08
See application file for complete search history.

(56) References Cited

U.S. PATENT DOCUMENTS

| | | | | |
|---|---|---|---|---|
| 9,694,064 B2* | 7/2017 | Boutriau | ................ | A61K 39/08 |
| 2003/0129198 A1* | 7/2003 | Wilkins | ................ | A61K 39/08 |
| | | | | 424/190.1 |
| 2009/0028903 A1* | 1/2009 | Hanon | ................ | A61K 39/145 |
| | | | | 424/206.1 |

FOREIGN PATENT DOCUMENTS

| | | |
|---|---|---|
| WO | WO 2007/068907 | 6/2007 |
| WO | WO 2008/043774 | 4/2008 |
| WO | WO 2008/155316 | 12/2008 |
| WO | WO 2009/127676 | 10/2009 |
| WO | WO 2010/017383 | 2/2010 |
| WO | WO 2012/028741 | 3/2012 |
| WO | WO 2012/163817 | 12/2012 |

OTHER PUBLICATIONS

Foglia, et al, Clostridium difficile: Development of a novel candidate vaccine, Vaccine 30(29):4307-4309(2012).
Garcon and Mechelen, Recent clinical experience with vaccines using MPL- and QS-21-containing adjuvant systems, Expert Rev. Vaccines 10(4): 471-486 (2011).
Garcon, et al., Development and evaluation of AS03, an Adjuvant System containing [alpha]-tocopherol and squalene in an oil-in-water emulsion, Expert Rev. Vaccines 11(3):349-366 (2012).
Morel, et al., Adjuvant System AS03 containing [alpha]-tocopherol modulates innate immune response and leads to improved adaptive immunity, Vaccine 29(13):2461-2473 (2011).
Tian, et al, A novel fusion protein containing the receptor binding domains of C. difficile toxin A and toxin B elicits protective immunity against lethal toxin and spore challenge in preclinical efficacy models, Vaccine 30(28):4249-4258 (2012).
Wang, et al, A Chimeric Toxin Vaccine Protects against Primary and Recurrent Clostridium difficile Infection, Infection & Immunity 80(8):2678-2688 (2012).

* cited by examiner

*Primary Examiner* — Albert M Navarro
(74) *Attorney, Agent, or Firm* — Birch, Stewart, Kolasch & Birch, LLP

(57) ABSTRACT

The present invention relates to immunogenic compositions comprising a *Clostridium difficile* (*C. difficile*) polypeptide and an aluminum-free adjuvant.

19 Claims, 25 Drawing Sheets

Specification includes a Sequence Listing.

Figure 1
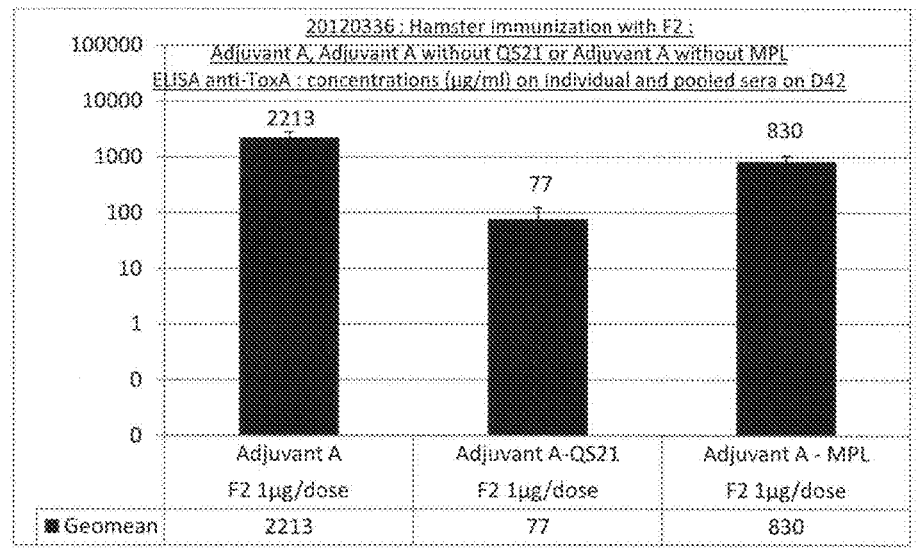
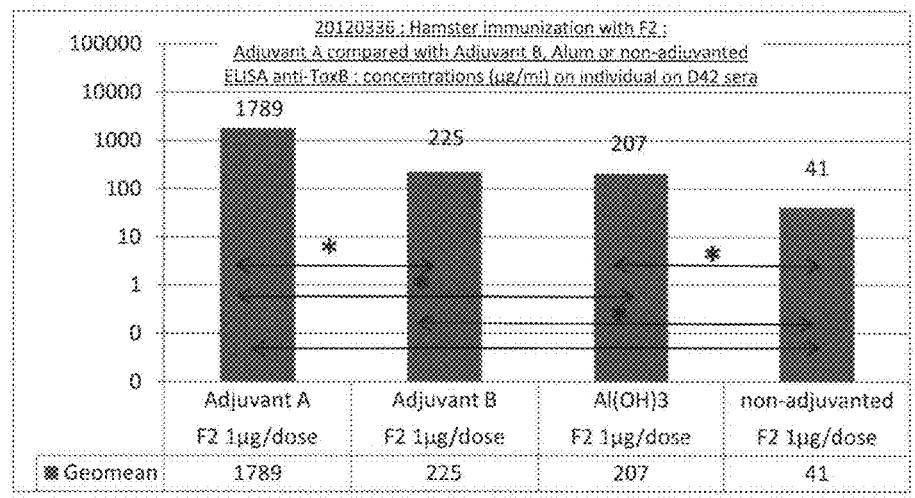

Figure 2
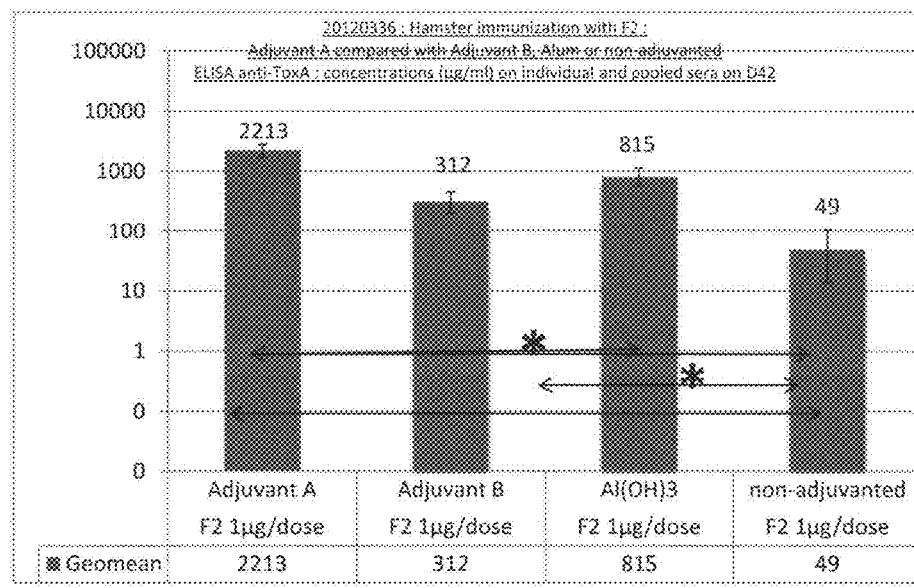
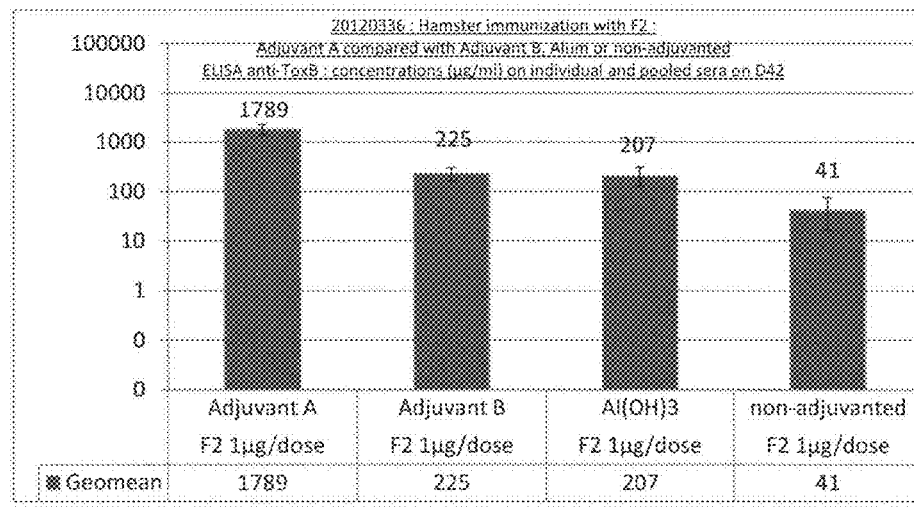

Figure 4
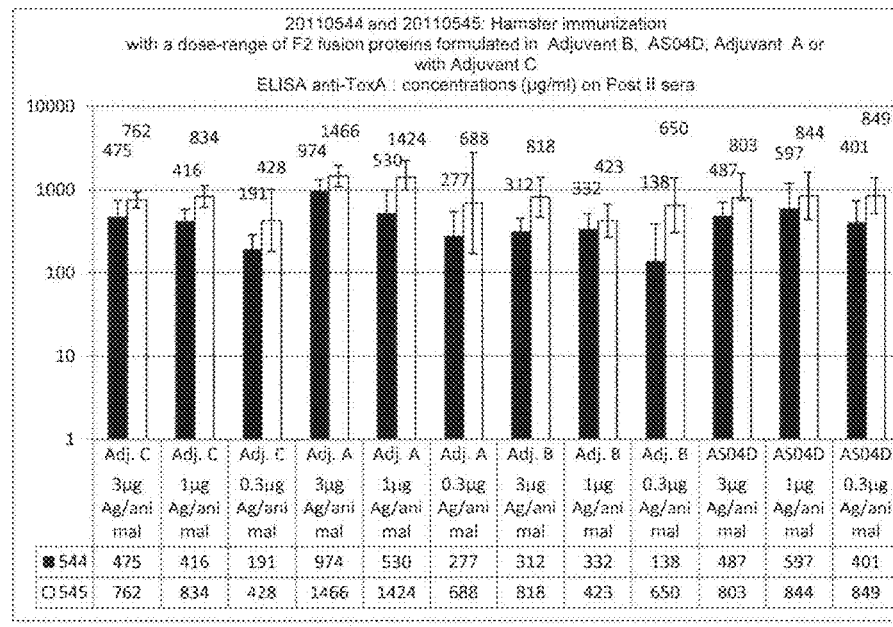
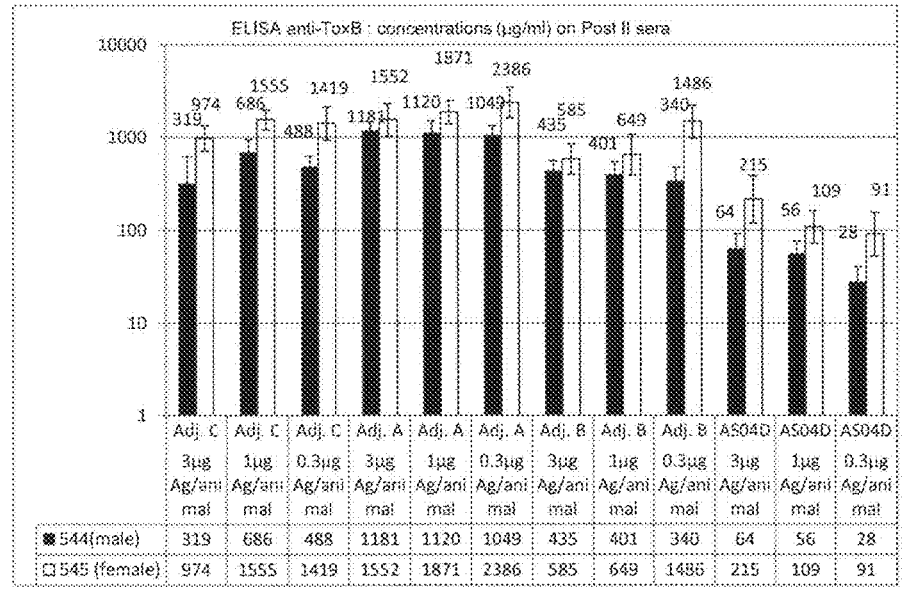

Figure 5
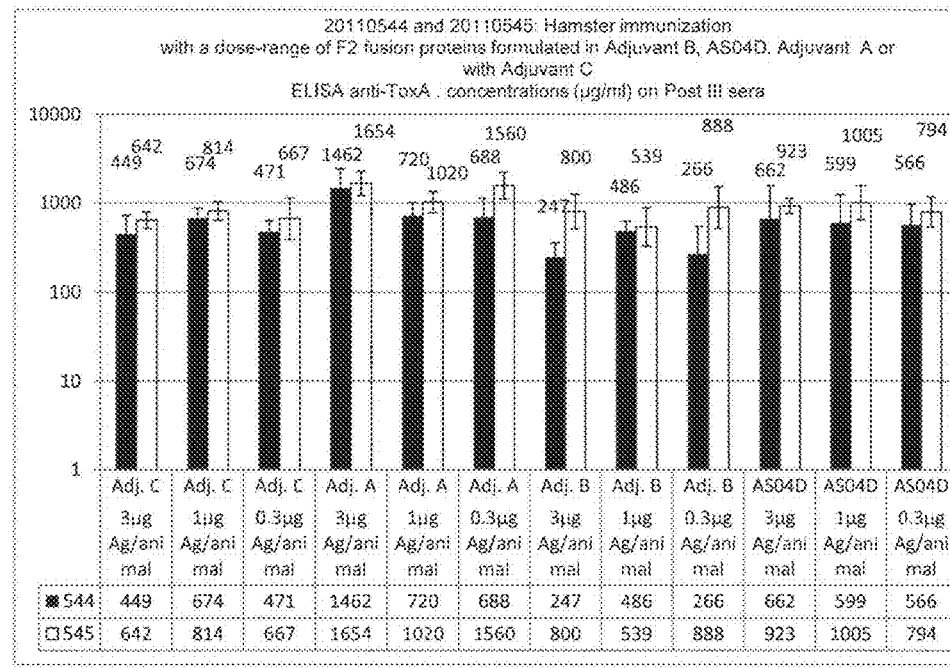
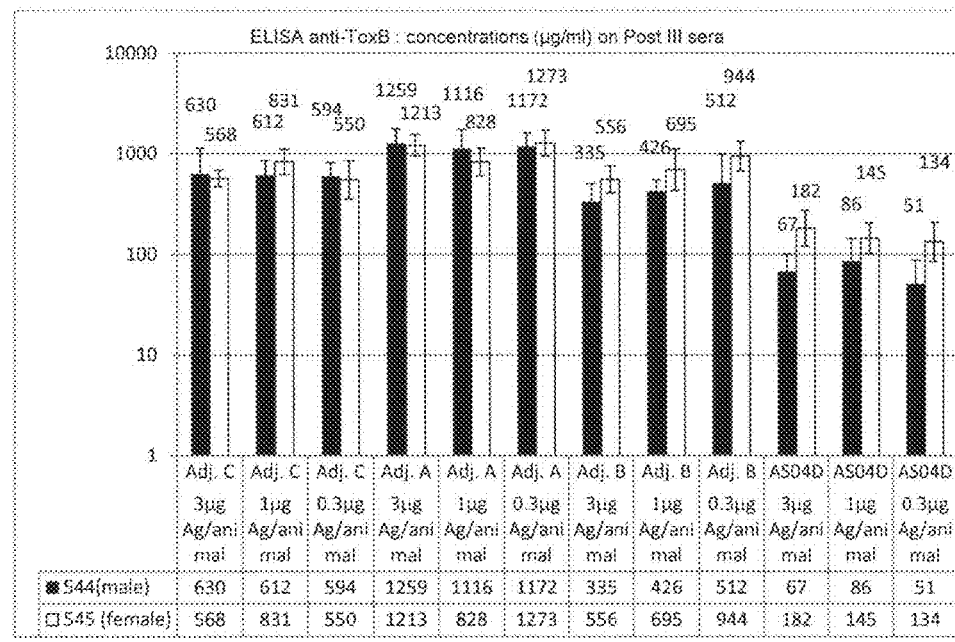

Figure 7
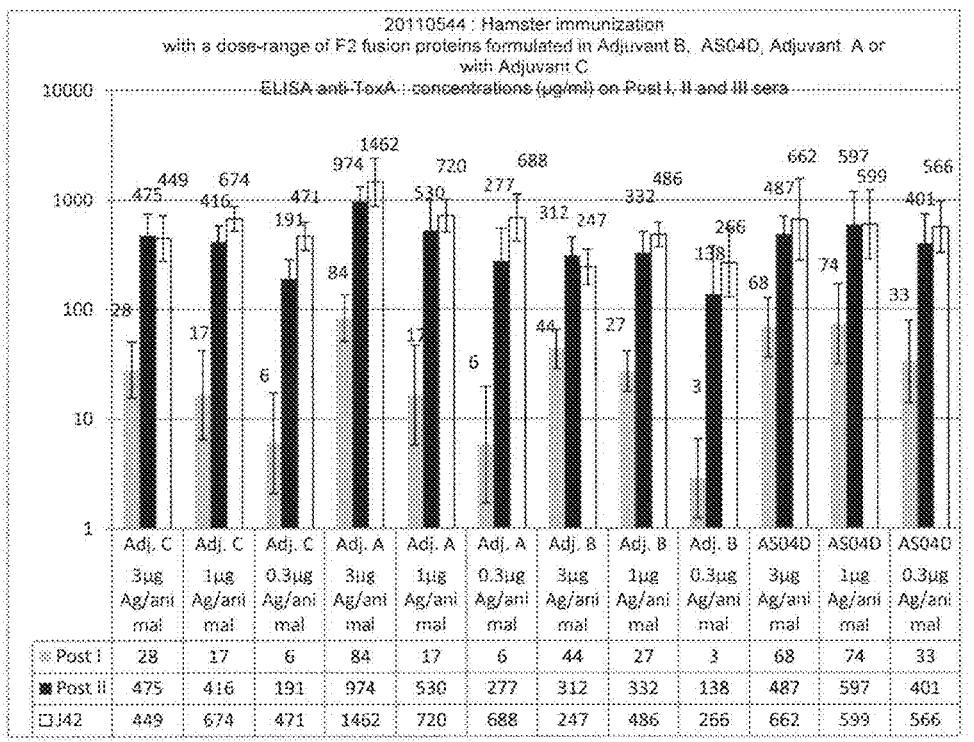
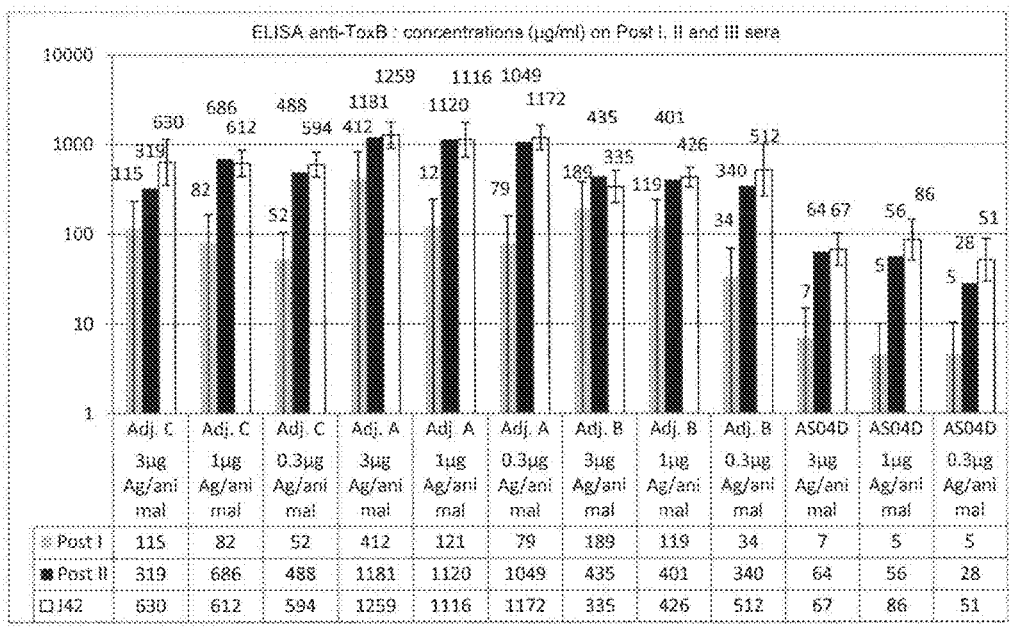

Figure 8
20120008 and 20120011 : Female and Male hamster immunization. Comparison of the immunogenicity of a Mix (ToxA+ToxB) with the F2 fusion protein formulated in Alum or Adjuvant A
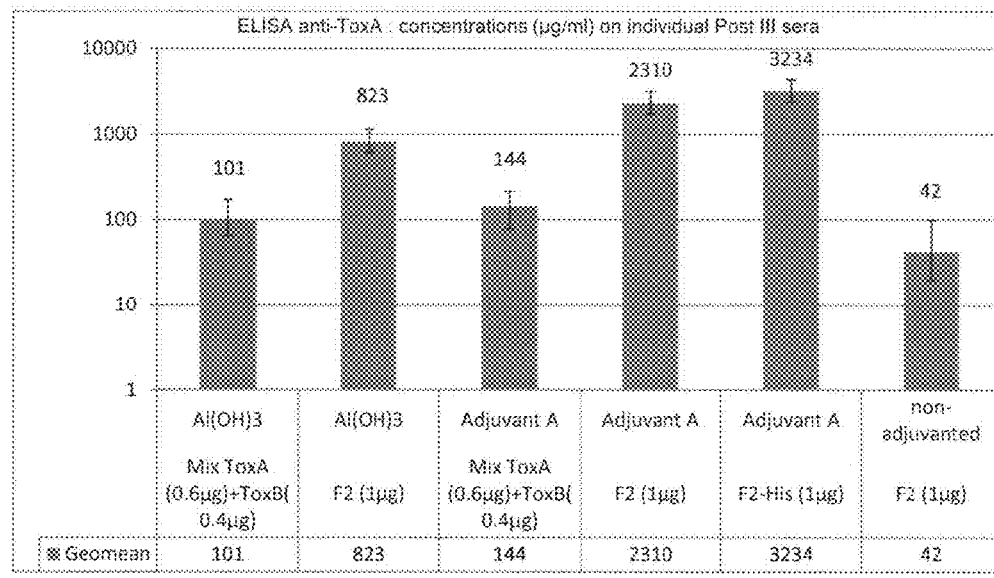
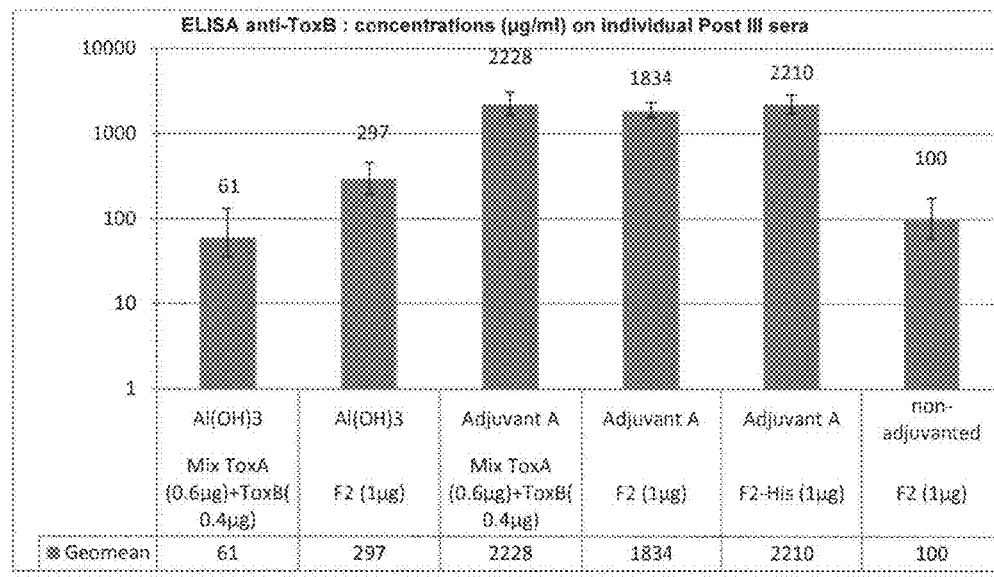

Figure 11

20100673 : Mice immunization with C. difficile ToxA-Cter, ToxB-Cter and fusion proteins 2nd generation formulated in Adjuvant B
ELISA anti-ToxB : concentrations (µg/ml) on Post III sera

Figure 12

20100973 : Mice immunization with *C. difficile* ToxA-Cter, ToxB-Cter and fusion proteins 2nd generation formulated in Adjuvant B
Cytotoxicity inhibition ToxB Assay, mid-point titers on Post III sera

| | 10μg Ag/dose | 10μg Ag/dose | 10μg Ag/dose | 10μg Ag/dose | 10μg Ag/dose | 10μg Ag/dose | 10μg Ag/dose | 3μg Ag/dose | 3μg Ag/dose | 3μg Ag/dose | 3μg Ag/dose | 3μg Ag/dose | 3μg Ag/dose | 3μg Ag/dose | adjuvant only |
|---|---|---|---|---|---|---|---|---|---|---|---|---|---|---|---|
| | ToxA (aa 2387-2706) | ToxB (aa 1750-2360) | F1 | F2 | F3 | F4 | F5 | ToxA (aa 2387-2706) | ToxB (aa 1750-2360) | F1 | F2 | F3 | F4 | F5 | |
| Titer | 20 | 320 | 40 | 160 | 160 | 320 | 80 | 20 | 640 | 80 | 320 | 160 | 320 | 80 | 20 |

Near-UV CD of ToxA-ToxB fusions

IMMUNOGENIC COMPOSITION

CROSS-REFERENCE

This application is a Divisional of copending application Ser. No. 14/649,940, filed on Jun. 5, 2015, which is the National Phase under 35 U.S.C. § 371 of International Application No. PCT/EP2013/075405, filed on Dec. 3, 2013, which claims the benefit under 35 U.S.C. § 119(a) to Patent Application No. GB 1221875.6, filed on Dec. 5, 2012, all of which are hereby expressly incorporated by reference into the present application.

TECHNICAL FIELD

The present invention relates to immunogenic compositions comprising a *Clostridium difficile* (*C. difficile*) polypeptide and an aluminum-free adjuvant. The invention also relates to vaccine compositions and the use of the vaccines and immunogenic compositions of the invention in prophylaxis or therapy or in the manufacture of a medicament.

BACKGROUND

*C. difficile* is the most important cause of nosocomial intestinal infections and is the major cause of pseudomembranous colitis in humans (Bartlett et al Am. J. Clin. Nutr. 11 suppl: 2521-6 (1980)). The overall associated mortality rate for individuals infected with *C. difficile* was calculated to be 5.99% within 3 months of diagnosis, with higher mortality associated with advanced age, being 13.5% in patients over 80 years (Karas et al *Journal of Infection* 561:1-9 (2010)). The current treatment for *C. difficile* infection is the administration of antibiotics (metronidazole and vancomycin), however there has been evidence of strains which are resistant to these antibiotics (Shah et al., Expert Rev. Anti Infect. Ther. 8(5), 555-564 (2010)). Accordingly there is a need for immunogenic compositions capable of inducing antibodies to, and/or a protective immune response to, *C. difficile*.

The enterotoxicity of *C. difficile* is primarily due to the action of two toxins, toxin A ('ToxA') and toxin B ('ToxB'). The C-terminal domains of toxin A and toxin B comprise repeating units, for example the C-terminal domain of toxin A is made up of contiguous repeating units (Dove et al Infect. Immun. 58:480-499 (1990)). For this reason the C-terminal domain may be referred to as the 'repeating domain'. These repeat portions can be separated further into short repeats (SRs) and long repeats (LRs) as described in Ho et al (PNAS 102:18373-18378 (2005)).

Immunogenic compositions comprising antigens from *C. difficile* have been described. WO96/12802 and WO00/61762 and Lyerly et al (Current Microbiology 21:29-32 (1990)) relate to fragments of toxin A, in particular fragments of the C-terminal domain, for inducing a protective immune response in hamsters. WO9920304 relates to a mixture of co-purified toxin A and toxin B inactivated by incubation in formaldehyde. WO00/61762 relates to immunogenic compositions comprising either the full length C-terminal domain or fragments of the C-terminal domain of toxin A and toxin B of *C. difficile*. Similarly WO2012/163817, WO2012/163811 and WO2012/163810 provide disclosures of possible fragments of toxin A and toxin B as well as fusion proteins thereof.

New compositions or vaccines with improved immunogenicity are needed. As one strategy, adjuvants have been used to try and improve the immune response raised to any given antigen. For example, WO2009035707 describes a composition comprising a toxoid of *C. difficile* toxins A and B and an adjuvant such as aluminum hydroxide compound.

Adjuvants containing combinations of lipopolysaccharide and Quillaja saponins have been disclosed previously, for example in EP0671948. Oil in water emulsions per se are well known in the art, and have been suggested to be useful as adjuvant compositions (EP 399843; WO 95/17210).

There is still a need for vaccine and immunogenic compositions that provide a suitable immune response against *C. difficile*.

SUMMARY

In one aspect, the invention relates to an immunogenic composition comprising a polypeptide comprising a *Clostridium difficile* (*C. difficile*) toxin A fragment and/or a *C. difficile* toxin B fragment and an adjuvant comprising an immunologically active saponin fraction presented in the form of a liposome. The immunologically active saponin fraction may be QS21 and the lipopolysaccharide may be 3D-MPL. Suitably, the immunogenic composition may comprise about 50 μg 3D-MPL, and about 50 μg QS21.

In one aspect, the invention relates to an immunogenic composition comprising a polypeptide comprising a *C. difficile* toxin A fragment and/or a *C. difficile* toxin B fragment and an adjuvant comprising an oil in water emulsion, wherein said oil in water emulsion comprises a metabolisable oil, a tocol and an emulsifier. The metabolisable oil may be present at an amount of about 5.35 mg. The tocol may be present at an amount of about 5.94 mg. Suitably, the emulsifying agent may be present at an amount of about 2.425 mg. Suitably, the metabolisable oil is squalene, the tocol is alpha-tocopherol and the emulsifying agent is polyoxyethylene sorbitan monooleate.

Suitably, the immunogenic composition according to any aspect of the invention comprises a *C. difficile* toxin A repeating domain fragment and a *C. difficile* toxin B repeating domain fragment and elicits antibodies that neutralize toxin A and toxin B. In a further embodiment of the invention, the immunogenic composition comprises a *C. difficile* toxin A fragment and a *C. difficile* toxin B fragment wherein one of the fragments is a N-terminal fragment and the other is a repeating domain fragment.

Suitably, the immunogenic composition according to any aspect of the invention comprises a polypeptide variant of SEQ ID NO:3, SEQ ID NO:4, SEQ ID NO:6, SEQ ID NO:7 SEQ ID NO:21, SEQ ID NO:23, SEQ ID NO:25 or SEQ ID NO:27.

Suitably, the immunogenic composition according to any aspect of the invention comprises a polypeptide comprising SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:28, SEQ ID NO:29, SEQ ID NO:30, SEQ ID NO:31, SEQ ID NO: 32, SEQ ID NO:33 or SEQ ID NO:34 or SEQ ID NO:35 or a variant or fragment of any of these sequences.

The immunogenic compositions according to the invention may comprise additional antigens such as antigens derived from a bacterium selected from the group consisting of *Streptococcus pneumoniae* (*S. pneumonia*), *Haemophilus influenzae* (*H. influenzae*), *Neisseria meningitidis* (*N. meningitidis*), *Escherichia coli* (*E. coli*), *Moraxella catarrhalis* (*M. cattarhalis*), *Clostridium tetani* (*C. tetani*), *Corynebacterium diptherieriae* (*C. diptherieriae*), *Bordetella pertussis* (*B. pertussis*), *Staphylococcus epidermidis* (*S. epidermidis*), enterococci, and *Staphylococcus aureus* (*S. aureus*).

In one aspect, the invention relates to a vaccine comprising the immunogenic composition according to the invention and a pharmaceutically acceptable excipient.

In one aspect, the invention relates to a use of the immunogenic composition or the vaccine according to the invention in the treatment or prevention of *C. difficile* disease.

In one aspect, the invention relates to the immunogenic composition or the vaccine according to the invention for use in the treatment or prevention of *C. difficile* disease.

In one aspect, the invention relates to use of the immunogenic composition or the vaccine of according to the invention in the preparation of a medicament for the prevention or treatment of *C. difficile* disease.

In one aspect, the invention relates to a method of preventing or treating *C. difficile* disease comprising administering the immunogenic composition or the vaccine according to the invention to a subject.

BRIEF DESCRIPTION OF THE DRAWINGS

FIG. 2—Graphs showing anti-ToxA and anti-ToxB ELISA results for hamsters immunised with non-adjuvanted F2 or F2 formulated with Adjuvant A, Adjuvant B and Alum.

FIG. 4—Graphs showing anti-ToxA and anti-ToxB ELISA results for Post II sera of male and female hamsters immunised with a dose-range of F2 fusion proteins formulated in Adjuvant B, AS04D, Adjuvant A or Adjuvant C.

FIG. 5—Graphs showing anti-ToxA and anti-ToxB ELISA results for Post III sera of male and female hamsters immunised with a dose-range of F2 fusion proteins formulated in Adjuvant B, AS04D, Adjuvant A or Adjuvant C.

FIG. 7—Graphs showing anti-ToxA and anti-ToxB ELISA results for male hamsters immunised with a dose-range of F2 fusion proteins formulated in Adjuvant B, AS04D, Adjuvant A or Adjuvant C on Post I, II and III sera.

FIG. 8—Graphs showing anti-ToxA and anti-ToxB ELISA results for male and female hamsters immunised with a Mix (ToxA+ToxB) or with the F2 fusion protein formulated in Alum or Adjuvant A.

FIG. 11—Graph showing anti-ToxB immunogenicity in mice immunised with a fragment of the C-terminus of toxin A (aa 2387-2706), a fragment of the C-terminus of toxin B (aa 1750-2360), or fusions 1, 2, 3, 4 or 5 formulated in Adjuvant B.

FIG. 12—Cyotoxicity inhibition titres from mice immunised with a fragment of the C-terminus of toxin A (aa 2387-2706), a fragment of the C-terminus of toxin B (aa 1750-2360), or fusions 1, 2, 3, 4 or 5 formulated in Adjuvant B.

FIG. 15—Graph showing hemagglutination inhibition in mice immunised with the F2, F52New, F54Gly, F54New or F5ToxB fusions formulated in Adjuvant B.

FIG. 22—Graph describing the Far-UV spectrum of Fusions, 2, 3, 4, and 5 measured using circular dichroism. The spectrum for fusion 2 is represented by a line with the points depicted as small squares, the spectrum for fusion 3 is represented by a line with the points depicted as small diamond shapes, fusion 4 is represented by a line with the points depicted as circles, and fusion 5 is represented by a line with the points depicted as cross shapes.

FIG. 23—Graph describing the near-UV spectrum of Fusions 2, 3, 4, and 5 measured using circular dichroism. The spectrum for fusion 2 is represented by a line with the points depicted as cross shapes, the spectrum for fusion 3 is represented by a line with the points depicted as circles, the spectrum for fusion 4 is represented by a line with the points depicted as triangles, and the spectrum for fusion 5 is represented by a line with the points depicted as small diamond shapes.

DETAILED DESCRIPTION

Figure 3:
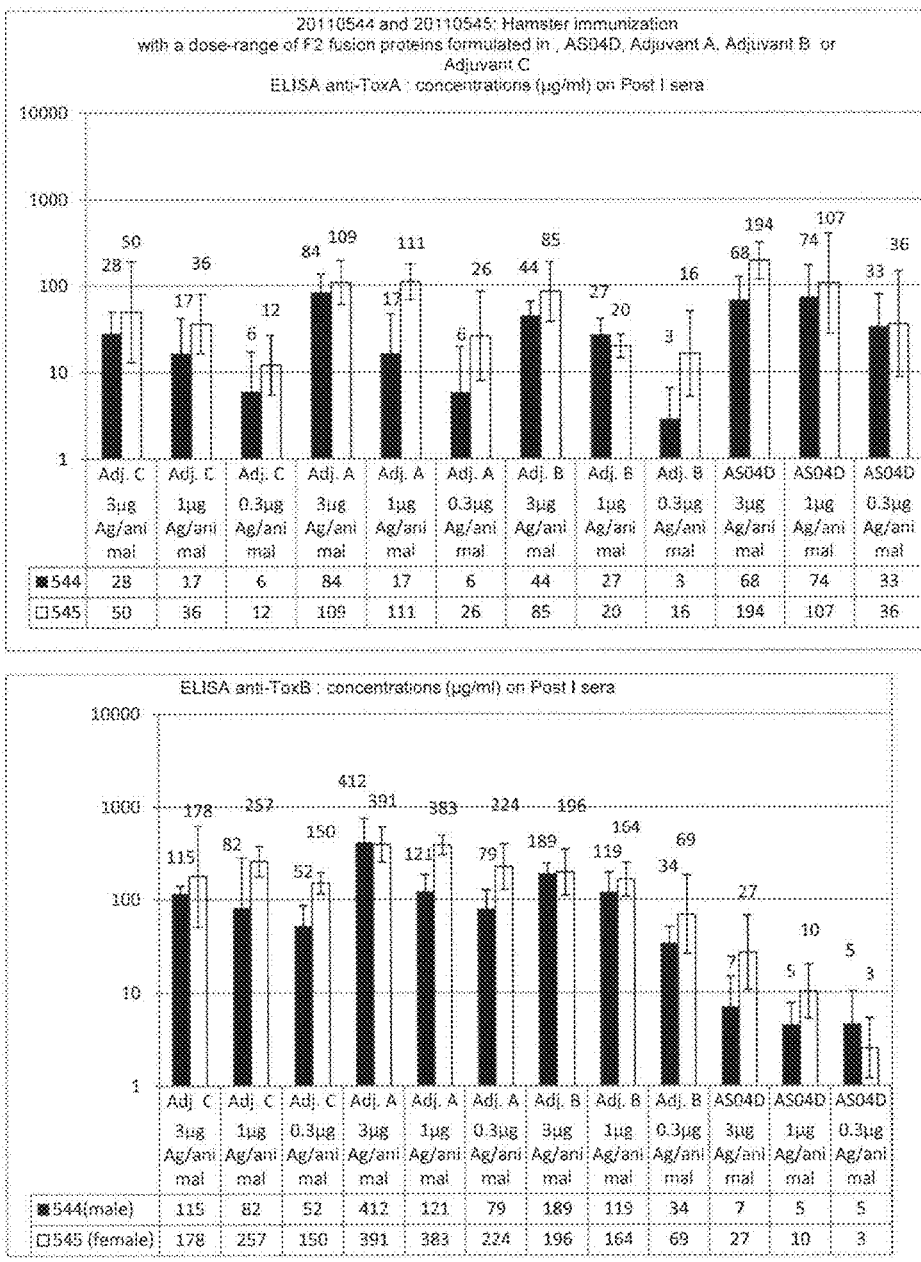
FIG. 3—Graphs showing anti-ToxA and anti-ToxB ELISA results for Post I sera of male and female hamsters immunised with a dose-range of F2 fusion proteins formulated in Adjuvant B, AS04D, Adjuvant A or Adjuvant C.
Figure 6:
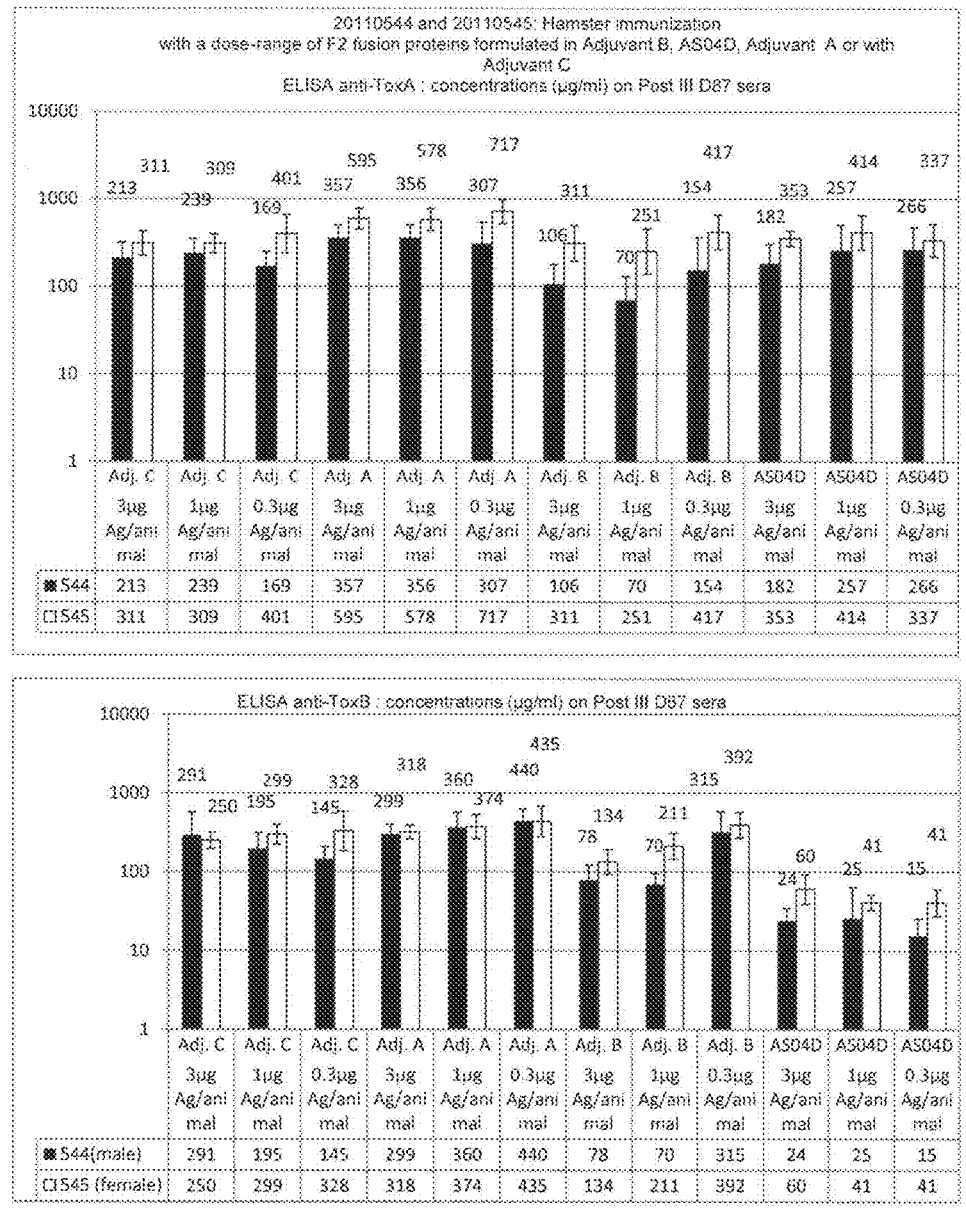
FIG. 6—Graphs showing anti-ToxA and anti-ToxB ELISA results for Post III day 87 sera of male and female hamsters immunised with a dose-range of F2 fusion proteins formulated in Adjuvant B, AS04D, Adjuvant A or Adjuvant C.
Figure 9:
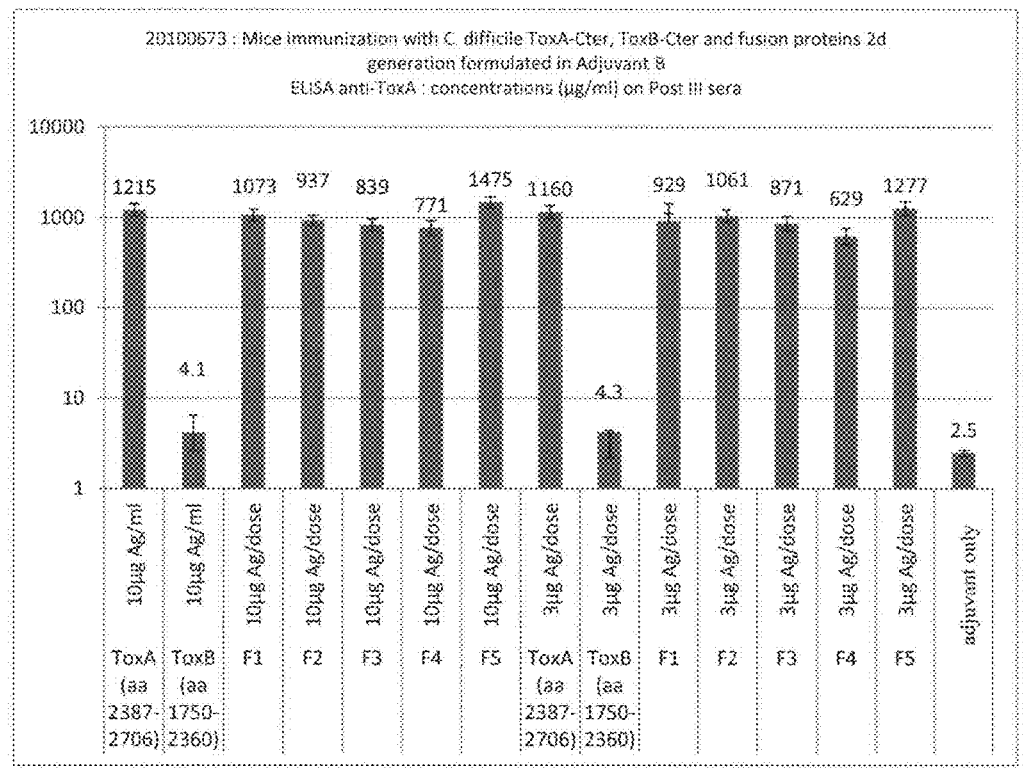
FIG. 9—Graph showing anti-ToxA immunogenicity in mice immunised with a fragment of the C-terminus of toxin A (aa 2387-2706), a fragment of the C-terminus of toxin B (aa 1750-2360), or fusions 1, 2, 3, 4 or 5 formulated in Adjuvant B.
Figure 10:
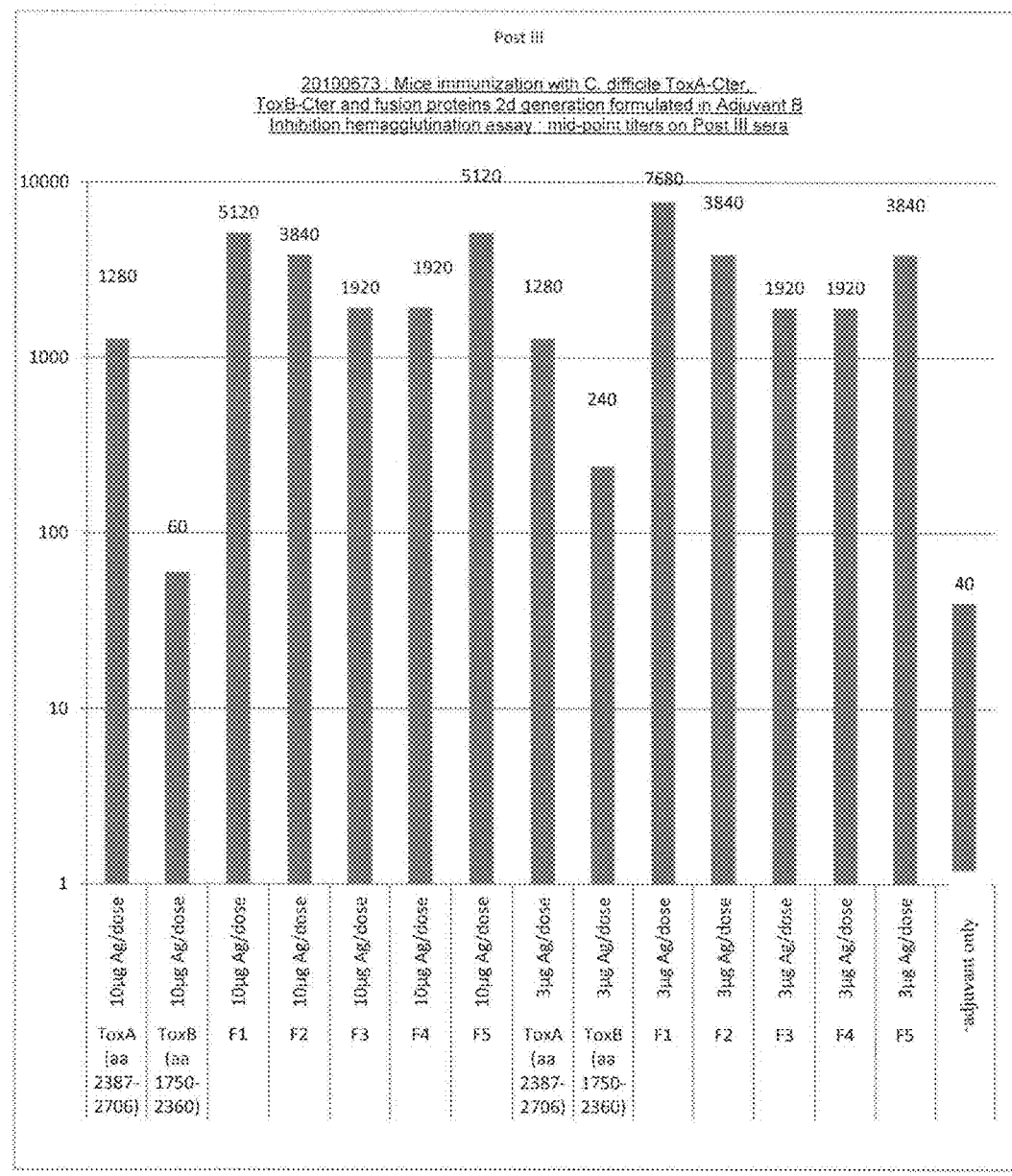
FIG. 10—Graph showing hemagglutination inhibition in mice immunised with a fragment of the C-terminus of toxin A (aa 2387-2706), a fragment of the C-terminus of toxin B (aa 1750-2360), or fusions 1, 2, 3, 4 or 5 formulated in Adjuvant B.

The inventors have shown immunogenic compositions comprising a polypeptide comprising a *C. difficile* toxin A fragment and/or a *C. difficile* toxin B fragment formulated with alum free adjuvants, particularly adjuvants such as Adjuvant A and Adjuvant B described herein, provide an improved immune response against *C. difficile* as compared to non-adjuvanted *C. difficile* polypeptide containing compositions. Immunogenic compositions according to the invention may also provide an improved immune response against *C. difficile* as compared to *C. difficile* polypeptides formulated with alum.

Polypeptides

The polypeptide comprising a *C. difficile* toxin A fragment and/or a *C. difficile* toxin B fragment may be a mixture of co-purified toxin A and toxin B which have been inactivated, suitably by incubation in formaldehyde, such as those described in WO9920304.

The polypeptide may comprise a *C. difficile* toxin A N-terminal fragment and a *C. difficile* toxin B repeating domain fragment. The polypeptide may contain a *C. difficile* toxin A repeating domain fragment and a *C. difficile* toxin B N-terminal fragment. The polypeptide may comprise a *C. difficile* toxin A repeating domain fragment and a *C. difficile* toxin B repeating domain fragment.

The polypeptide may comprise either the full length N-terminal and/or C-terminal domain of toxin A and toxin B of *C. difficile* or fragments thereof.

In one embodiment, the polypeptide in the immunogenic compositions according to the invention does not contain the full length N-terminal domain of toxin A and/or toxin B of *C. difficile*. In one embodiment, the polypeptide in the immunogenic compositions according to the invention does not contain an N-terminal domain fragment of toxin A and/or toxin B of *C. difficile*.

The polypeptide may be a fusion protein. For example, the fusion protein may comprise a fusion sequence such as Seq ID NOS: 36 and 37 or other sequences described in WO2012/028741.

The polypeptide may comprise a first fragment and a second fragment, wherein (i) the first fragment is a toxin A repeating domain fragment;

(ii) the second fragment is a toxin B repeating domain fragment;

(iii) the first fragment comprises a first proximal end within a first repeat portion;

(iv) the second fragment comprises a second proximal end within a second repeat portion; and wherein the first fragment and the second fragment are adjacent to one another and wherein the first repeat portion and the second repeat portion have structural similarity.

The term polypeptide refers to a contiguous sequence of amino acids.

The term 'toxin A repeating domain' refers to the C-terminal domain of the toxin A protein from *C. difficile* comprising repeated sequences. For example, the C-terminal domain of the toxin A protein may be amino acids 1832-2710 of toxin A from strain VP110463 (ATCC43255) and/or their equivalent in a different strain. Amino acids 1832-2710 from strain VP110463 (ATCC43255) corresponds to amino acids 1832-2710 of SEQ ID NO:1.

The term 'toxin B repeating domain' refers to the C-terminal domain of the toxin B protein from *C. difficile*. For example, the C-terminal domain of the toxin B protein may be amino acids 1834-2366 from strain VP110463 (ATCC43255) and/or their equivalent in a different strain. Amino acids 1834-2366 from strain VP110463 (ATCC43255) corresponds to amino acids 1834-2366 of SEQ ID NO:2.

The full length N-terminal domain of toxin A may be amino acids 1-542 of toxin A from strain VPI10463 (ATCC43255) and/or their equivalent in a different strain. Thus the term "a *C. difficile* toxin A N-terminal fragment" or "an N-terminal domain fragment of toxin A" refers to a fragment of amino acids 1-542 of toxin A from strain VP110463 (ATCC43255) and/or their equivalent in a different strain. Amino acids 1-542 from strain VP110463 (ATCC43255) corresponds to amino acids 1-542 of SEQ ID NO: 1.

The full length N-terminal domain of toxin B may be amino acids 1-543 from strain VP110463 (ATCC43255) and/or their equivalent in a different strain. Thus the term "a *C. difficile* toxin B N-terminal fragment" or "an N-terminal domain fragment of toxin B" refers to a fragment of amino acids 1-543 of toxin B from strain VP110463 (ATCC43255) and/or their equivalent in a different strain. Amino acids 1-543 from strain VP110463 (ATCC43255) corresponds to amino acids 1-543 of SEQ ID NO: 2.

*C. difficile* toxins A and B are conserved proteins. However the sequence differs a small amount between strains. Moreover the amino acid sequence for toxins A and B in different strains may differ in number of amino acids.

In one embodiment, the toxin A repeating domain and/or toxin B repeating domain may be a sequence which is a variant with at least 90%, 95%, 98%, 99% or 100% sequence identity to amino acids 1832-2710 of SEQ ID NO:1 or a variant with at least 90%, 95%, 98%, 99% or 100% sequence identity to amino acids 1834-2366 of SEQ ID NO:2.

In one embodiment, the toxin A N-terminal domain may be a sequence which is a variant with at least 90%, 95%, 98%, 99% or 100% sequence identity to amino acids 1-542. In one embodiment, the toxin B N-terminal domain may be a sequence which is a variant with at least 90%, 95%, 98%, 99% or 100% sequence identity to amino acids 1-543 of SEQ ID NO: 2.

A 'variant' is a polypeptide that varies from the referent polypeptides by conservative amino acid substitutions, whereby a residue is substituted by another with the same physico-chemical properties. Typically such substitutions are among Ala, Val, Leu and Ile; among Ser and Thr; among the acidic residues Asp and Glu; among Asn and Gln, and among the basic residues Lys and Arg; or aromatic residues Phe and Tyr.

Furthermore the amino acid numbering may differ between the C-terminal domains or N-terminal domains of toxin A (or toxin B) from one strain and toxin A (or toxin B) from another strain. For this reason the term 'equivalent in a different strain' refers to amino acids which correspond those of a reference strain (e.g., *C. difficile* VP110463), but which are found in a toxin from a different strain and which may thus be numbered differently. A region of 'equivalent' amino acids may be determined by aligning the sequences of the toxins from the different strains. The amino acids numbers provided throughout refer to those of strain VPI10463.

The term 'fragment' of a polypeptide or protein refers to a contiguous portion, such as at least 100, 150, 180, 200, 230, 250, 300, 350, 380, 400, 450, 480, 500, 530, 550, 580 or 600 amino acids, from that polypeptide or protein.

"N-terminal domain fragment of toxin A" of *C. difficile* refers to a contiguous portion, such as at least 100, 150, 180, 200, 230, 250, 300, 350, 380, 400, 450, 480, 500 or 530 amino acids, from the full length N-terminal domain of toxin A. "N-terminal domain fragment of toxin B" of *C. difficile* refers to a contiguous portion, such as at least 100, 150, 180, 200, 230, 250, 300, 350, 380, 400, 450, 480, 500 or 530 amino acids, from the full length N-terminal domain of toxin B.

Toxin A repeating domain fragment may be a contiguous portion of at least 100, 200, 230, 250, 300, 350, 380, 400, 450, 480, 500, 530, 550, 580 or 600 amino acids from the toxin A repeating domain. Toxin A repeating domain fragment may be a contiguous portion of less than 750, less than 700, less than 650, less than 600 or less than 580 amino acids. Toxin B repeating domain fragment may be a contiguous portion of at least 100, 200, 230, 250, 300, 350, 380, 400, 450, 480, 500, 530, 550, 580 or 600 amino acids from the toxin B repeating domain. Toxin B repeating domain fragment may be a contiguous portion of less than 530, less than 500, less than 480, or less than 450 amino acids.

The term 'first fragment' refers to a contiguous portion of at least 100, such as 150, 180, 250, 300, 350, 380, 400, 450, 480, 500, 530, 550, 580 or 600, amino acids of the toxin A repeating domain. The term 'second fragment' refers to a contiguous portion of at least 100, such as 200, 230, 250, 280, 300, 350, 400, 450 or 500, amino acids of the toxin B repeating domain.

The term 'first proximal end' refers to the end of the first fragment (Tox A fragment) which is covalently linked to the second fragment (Tox B fragment) or covalently linked to a linker sequence between the first and second fragment. The term 'second proximal end' refers to the end of the second fragment which is closest to the first fragment in primary structure (amino acid sequence).

The C-terminal domain of toxin A is made up of 8 repeat portions (designated repeat portion I, repeat portion II, repeat portion III, repeat portion IV, repeat portion V, repeat portion VI, repeat portion VII and repeat portion VIII). Each of these repeat portions can be further divided into short repeats (SRs) and long repeats (LRs) (except for Tox A repeat portion VIII which does not have a long repeat). Each of the long repeats has some structural and sequence similarity to the other long repeats. Similarly the short repeats have some sequence and structural similarity to one another. Similarly the C-terminal domain of toxin B is made up of 5 repeat portions subdivided into SRs and LRs. Each repeat portion contains one LR and between 2 and 5 SRs (except for Tox B repeat portion V which does not have a long repeat). For the purposes of the disclosure 'a'repeat portion' refers to one of the eight repeat portions of ToxA (designated I, II, III, IV, V, VI, VII or VIII) or one of the five repeat portions of ToxB (designated I, II, III, IV or V) or a partial repeat portion from the toxin A or toxin B repeating domain. As used herein the term 'first repeat portion' refers to a repeat portion (or partial repeat portion) from the toxin A repeating domain. The term 'second repeat portion' refers to a repeat portion (or partial repeat portion) from the toxin B repeating domain.

For example, repeat portion I of ToxA contains three SRs and one LR, which can be referred to as the first SRI of ToxA, the second SRI of ToxA, the third SRI of ToxA and the LRI of ToxA, respectively.

The first proximal end is considered to be within a 'repeat portion' if the first fragment ends in an amino acid that is within that repeat portion (i.e., the first proximal end contains only part of the repeat portion sequence). Similarly the second proximal end is considered to be within a 'repeat portion' if the second fragment ends in an amino acid that is within that repeat portion. For example the first proximal end is within 'repeat portion I of ToxA if the first fragment ends with any one of amino acids 1833-1923 (inclusive) of VPI10463 or their equivalent in another strain. The first proximal end is within a 'long repeat' or a 'short repeat' if the first fragment ends in an amino acid that is within a 'long repeat' or a 'short repeat', similarly the second proximal end is within a 'long repeat' or a 'short repeat' if the second fragment ends in an amino acid that is within a 'long repeat' or a 'short repeat'.

The amino acid positions of each domain has been defined for toxin A and toxin B from strain VPI10463 (ATCC43255). These are as follows (Table 1)

| Name | | Start position | End position |
|---|---|---|---|
| ToxA_I | SR1 | 1832 | 1852 |
| | SR2 | 1853 | 1873 |
| | SR3 | 1874 | 1893 |
| | LR | 1894 | 1924 |
| ToxA_II | SR1 | 1925 | 1944 |
| | SR2 | 1945 | 1965 |
| | SR3 | 1966 | 1986 |
| | SR4 | 1987 | 2007 |
| | SR5 | 2008 | 2027 |
| | LR | 2028 | 2058 |
| ToxA_III | SR1 | 2059 | 2078 |
| | SR2 | 2079 | 2099 |
| | SR3 | 2100 | 2120 |
| | SR4 | 2121 | 2141 |
| | SR5 | 2142 | 2161 |
| | LR | 2162 | 2192 |
| ToxA_IV | SR1 | 2193 | 2212 |
| | SR2 | 2213 | 2233 |
| | SR3 | 2234 | 2253 |
| | SR4 | 2254 | 2275 |
| | LR | 2276 | 2306 |
| ToxA_V | SR1 | 2307 | 2326 |
| | SR2 | 2327 | 2347 |
| | SR3 | 2348 | 2368 |
| | SR4 | 2369 | 2389 |
| | SR5 | 2390 | 2409 |
| | LR | 2410 | 2440 |
| ToxA_VI | SR1 | 2441 | 2460 |
| | SR2 | 2461 | 2481 |
| | SR3 | 2482 | 2502 |
| | SR4 | 2503 | 2522 |
| | LR | 2523 | 2553 |
| ToxA_VII | SR1 | 2554 | 2573 |
| | SR2 | 2574 | 2594 |
| | SR3 | 2595 | 2613 |
| | LR | 2614 | 2644 |
| ToxA_VIII | SR1 | 2645 | 2664 |
| | SR2 | 2665 | 2686 |
| | SR3 | 2687 | 2710 |
| ToxB_I | SR1 | 1834 | 1854 |
| | SR2 | 1855 | 1876 |
| | SR3 | 1877 | 1896 |
| | LR | 1897 | 1926 |
| ToxB_II | SR1 | 1927 | 1946 |
| | SR2 | 1947 | 1967 |
| | SR3 | 1968 | 1987 |
| | SR4 | 1988 | 2007 |
| | SR5 | 2008 | 2027 |
| | LR | 2028 | 2057 |
| ToxB_III | SR1 | 2058 | 2078 |
| | SR2 | 2079 | 2099 |
| | SR3 | 2100 | 2119 |
| | SR4 | 2120 | 2139 |
| | SR5 | 2140 | 2159 |
| | LR | 2160 | 2189 |
| ToxB_IV | SR1 | 2190 | 2212 |
| | SR2 | 2213 | 2233 |
| | SR3 | 2234 | 2253 |

| Name | | Start position | End position |
|---|---|---|---|
| | SR4 | 2254 | 2273 |
| | SR5 | 2274 | 2293 |
| | LR | 2294 | 2323 |
| ToxB_V | SR1 | 2324 | 2343 |
| | SR2 | 2344 | 2366 |

In one embodiment, the repeat portion of toxin A refers to amino acids 1832-1924, 1925-2058, 2059-2192, 2193-2306, 2307-2440, 2441-2553, 2554-2644 or 2645-2710 of toxin A (SEQ ID NO:1) or an equivalent in a different strain of *C. difficile*. In another embodiment, the repeat portion of toxin B refers to amino acids 1834-1926, 1927-2057, 2058-2189, 2190-2323 or 2324-2366 of toxin B (SEQ ID NO:2) or an equivalent in a different strain of *C. difficile*.

The term 'short repeat' may refer to amino acids 1832-1852, 1853-1873, 1874-1893, 1925-1944 1945-1965, 1966-1986, 1987-2007, 2008-2027, 2059-2078, 2079-2099, 2100-2120, 2121-2141, 2142-2161, 2193-2212, 2213-2233, 2234-2253, 2254-2275, 2307-2326, 2327-2347, 2348-2368, 2369-2389, 2390-2409, 2441-2460, 2461-2481, 2482-2502, 2503-2522, 2554-2573, 2574-2594, 2595-2613, 2645-2664, 2665-2686 or 2687-2710 of toxin A (SEQ ID NO:1) or amino acids 1834-1854, 1855-1876, 1877-1896, 1927-1946, 1947-1967, 1968-1987, 1988-2007, 2008-2027, 2058-2078, 2079-2099, 2100-2119, 2120-2139, 2140-2159, 2190-2212, 2213-2233, 2234-2253, 2254-2273, 2274-2293, 2324-2343 or 2344-2366 of toxin B (SEQ ID NO:2) or their equivalents in a different strain of *C. difficile*.

Similarly the term 'long repeat' may refer to amino acids 1894-1924, 2028-2058, 2162-2192, 2276-2306, 2410-2440, 2523-2553 or 2614-2644 of toxin A (SEQ ID NO:1) or amino acids 1897-1926, 2028-2057, 2160-2189 or 2294-2323 of toxin B (SEQ ID NO:2) or their equivalents in a different strain of *C. difficile*.

The polypeptides of the invention may be part of a larger protein such as a precursor or a fusion protein. It is often advantageous to include an additional amino acid sequence which contains sequences which aid in purification, such as multiple histidine residues, or an additional sequence for stability during recombinant production. Furthermore, addition of exogenous polypeptide or lipid tail or polynucleotide sequences to increase the immunogenic potential of the final molecule is also considered.

The word 'adjacent' means separated by less than or exactly 20, 15, 10, 8, 5, 2, 1 or 0 amino acids in the primary structure.

The fragments may be positioned such that the N-terminus of the first fragment is adjacent to the C-terminus of the second fragment, alternatively the C-terminus of the first fragment may be adjacent to the N-terminus of the second fragment, or the C-terminus of the first fragment may be adjacent to the C-terminus of the second fragment, or the N-terminus of the first fragment may be adjacent to the N-terminus of the second fragment.

Two sequences will have 'sequence similarity to one another' if they have greater than 30%, 50%, 70%, 75%, 80%, 85%, 90%, 95%, 98%, 99% or 100% sequence identity.

The term 'identity' is known in the art. Identity is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the Needle program, BLASTP, BLASTN (Altschul, S. F. et al., J. Molec. Biol. 215: 403-410 (1990)), and FASTA Pearson and Lipman Proc. Natl. Acad. Sci. USA 85; 2444-2448 (1988)). The BLAST family of programs is publicly available from NCBI and other sources (BLAST Manual, Altschul, S., et al., NCBI NLM NIH Bethesda, Md. 20894; Altschul, S., et al., J. Mol. Biol. 215: 403-410 (1990)). The well known Smith Waterman algorithm may also be used to determine identity.

In one example, parameters for polypeptide sequence comparison include the following:

Algorithm: Needleman and Wunsch, J. Mol Biol. 48: 443-453 (1970)

Comparison matrix: BLOSSUM62 from Henikoff and Henikoff,

Proc. Natl. Acad. Sci. USA. 89:10915-10919 (1992)

Gap Penalty: 10

Gap extension penalty: 0.5

A program useful with these parameters is publicly available as the 'Needle' program from EMBOSS package (Rice P. et al, Trends in Genetics 2000 col. 16(6):276-277). The aforementioned parameters are the default parameters for peptide comparisons (along with no penalty for end gaps).

In one embodiment the first repeat portion and the second repeat portion have high structural similarity to one another. Two sequences can be considered to have high structural similarity when their percentage identity is higher than 40%, 45%, 50% or 60% (M. Marty-Renom et al. Annu. Rev. Biophys. Biomol Struct. 2000 vol. 29:291-325). The presence of high structural similarity can be determined by comparing the two sequences using the SwissModel and SwissPDB Viewer softwares.

In one embodiment the polypeptide of the invention elicits antibodies that neutralise toxin A or toxin B. In a further embodiment the polypeptide elicits antibodies that neutralise toxin A. In a further embodiment the polypeptide elicits antibodies that neutralise toxin B. In a further embodiment the polypeptide elicits antibodies that neutralise toxin A and toxin B. The phrase 'elicits neutralising antibodies' means that the when the compositions are used to immunise a mammal, for example a mouse, a guinea pig or a human, the mammal generates neutralising antibodies.

Whether a polypeptide elicits neutralizing antibodies against a toxin can be measured by immunising mice with an immunogenic composition comprising the polypeptide, collecting sera and analysing the anti-toxin titres of the sera using by enzyme-linked immunosorbent assay (ELISA). The sera could be compared to a reference sample obtained from mice which have not been immunised. An example of this technique can be found in example 6. The polypeptide of the invention elicits antibodies that neutralise toxin A if the sera against the polypeptide gives an ELISA readout more than 10%, 20%, 30%, 50%, 70%, 80%, 90% or 100% higher than the reference sample.

In a further embodiment the polypeptide of the invention elicits a protective immune response in a mammalian host against strains of C. difficile. The phrase 'elicit a protective immune response' means that when the immunogenic composition of the invention is used to immunise a mammal such as a mouse, guinea pig or human, the mammal generates antibodies capable of protecting the mammal from death caused by C. difficile. In one embodiment the mammalian host is selected from the group consisting of mouse, rabbit, guinea pig, monkey, non-human primate or human. In one embodiment the mammalian host is a mouse. In a further embodiment the mammalian host is a human.

Whether a polypeptide elicits a protective immune response in a mammalian host against strains of C. difficile can be determined using a challenge assay. In such an assay the mammalian host is vaccinated with the polypeptide and challenged by exposure to C. difficile. The time which the mammal survives after challenge is compared with the time which a reference mammal that has not been immunised with the polypeptide survives. A polypeptide elicits a protective immune response if a mammal immunised with the polypeptide survives at least 10%, 20%, 30%, 50%, 70%, 80%, 90%, or 100% longer after challenge with C. difficile than a reference mammal which has not been immunised with the polypeptide. In one embodiment the polypeptide of the invention elicits a protective immune response against C. difficile in a mammal selected from the group consisting of mouse, guinea pig, monkey or human. In one embodiment the mammal is a mouse, in a further embodiment the mammal is a human.

The native structure of the C-terminal (repeat) domains from toxins A and B consist of an extended β solenoid-like structure. This structure consists of primarily β sheet structures, with a minority of α helical structures as seen in Ho et al (PNAS 102:18373-18378 (2005)). The secondary structures present can be determined using circular dichroism (CD). For example, the secondary structure may be determined by measuring the shape and the magnitude of the CD spectra in the far-UV region (190-250 nm) and comparing the results with those of known structures. This can be carried out using an optical path of 0.01 cm from 178 to 250 nm, with a 1 nm resolution and bandwidth on a Jasco J-720 spectropolarimeter, for example as seen in example 5 below.

In one embodiment the first fragment comprises less than 28%, 25%, 23%, 20%, 18%, 15%, 10%, or 7% alpha helical secondary structure. In one embodiment the second fragment comprises less than 28%, 25%, 23%, 20%, 18%, 15%, 10%, or 7% alpha helical secondary structure. In a further embodiment both the first fragment and the second fragment comprise less than 28%, 25%, 23%, 20%, 18%, 15%, 10%, or 7% alpha helical secondary structure.

In one embodiment the first fragment comprises more than 20%, 25%, 28%, 30%, 33%, 35%, 38%, 40%, or 42% beta sheet structure. In one embodiment the second fragment comprises more than 20%, 25%, 28%, 30%, 33%, 35%, 38%, 40%, or 42% beta sheet structure. In a further embodiment both the first fragment and the second fragment comprises more than 20%, 25%, 28%, 30%, 33%, 35%, 38%, 40%, or 42% beta sheet structure.

In one embodiment the first proximal end is within repeat portion V (amino acids 2307-2440 of SEQ ID NO:1 or their equivalent in a different strain), repeat portion VI (amino acids 2441-2553 of SEQ ID NO:1 or their equivalent in a different strain), repeat portion VII (amino acids 2554-2644 of SEQ ID NO:1 or their equivalent in a different strain) or repeat portion VIII (amino acids 2645-2710 of SEQ ID NO:1 or their equivalent in a different strain) of toxin A. In a further embodiment the first proximal end is within repeat portion VII (amino acids 2554-2644 of SEQ ID NO:1 or their equivalent in a different strain) of toxin A. In a further embodiment the first proximal end repeat portion VIII (amino acids 2645-2710 of SEQ ID NO:1 or their equivalent in a different strain) of toxin A.

In one embodiment the second proximal end is within repeat portion I (amino acids 1834-1926 of SEQ ID NO:2 or their equivalent in a different strain), repeat portion II (amino acids 1927-2057 of SEQ ID NO:2 or their equivalent in a different strain), or repeat portion III (amino acids 2058-2189 of SEQ ID NO:2 or their equivalent in a different strain) of toxin B. In a further embodiment the second proximal end is within repeat portion II (amino acids 1927-2057 of SEQ ID NO:2 or their equivalent in a different strain) of toxin B. In a further embodiment the second proximal end is within repeat portion I (amino acids 1834-1926 of SEQ ID NO:2 or their equivalent in a different strain) of toxin B.

In one embodiment the first proximal end is within a long repeat. The first proximal end may be within long repeat V of toxin A (amino acids 2410-2440 of SEQ ID NO:1 or their equivalent in a different strain), or within long repeat VI of toxin A (amino acids 2523-2553 of SEQ ID NO:1 or their equivalent in a different strain), or within long repeat VII of toxin A (amino acids 2614-2644 of SEQ ID NO:1 or their equivalent in a different strain).

In one embodiment the second proximal end is within a long repeat. The second proximal end may be within long repeat I of toxin B (amino acids 1897-1926 of SEQ ID NO:2 or their equivalent in a different strain), or within long repeat II of toxin B (amino acids 2028-2057 of SEQ ID NO:2 or their equivalent in a different strain), or within long repeat III of toxin B (amino acids 2160-2189 of SEQ ID NO:2 or their equivalent in a different strain).

In a further embodiment the first proximal end and the second proximal end are both within long repeats. In one embodiment the first proximal end is within long repeat V of toxin A (amino acids 2410-2440 of SEQ ID NO:1 or their equivalent in a different strain), or within long repeat VI of toxin A (amino acids 2523-2553 of SEQ ID NO:1 or their equivalent in a different strain), or within long repeat VII of toxin A (amino acids 2614-2644 of SEQ ID NO:1 or their equivalent in a different strain) and the second proximal end is within long repeat III of toxin B (amino acids 1897-1926 of SEQ ID NO:2 or their equivalent in a different strain), or within long repeat II of toxin B (amino acids 2028-2057 of SEQ ID NO:2 or their equivalent in a different strain), or within long repeat III of toxin B (amino acids 2160-2189 of SEQ ID NO:2 or their equivalent in a different strain). In one embodiment the first proximal end is within long repeat VII of toxin A (amino acids 2614-2644 of SEQ ID NO:1 or their equivalent in a different strain) and the second proximal end is within long repeat II of toxin B (amino acids 2028-2057 of SEQ ID NO:2 or their equivalent in a different strain).

In one embodiment the first proximal end is within amino acids 2620-2660 of toxin A. In one embodiment the second proximal end is within amino acids 2030-2050 of toxin B. In a further embodiment the first proximal end is within amino acids 2620-2660 of toxin A and the second proximal end is within amino acids 2030-2050 of toxin B.

In one embodiment the first fragment comprises at least 100, 150, 180, 200, 240, 250, 280, 300, 330, 350, 380, 400, 430, 450, 480, 500 or 530 amino acids. In one embodiment the second fragment comprises at least 100, 130, 150, 180, 200, 230, 250, 270, 300, 330, 350, 390, or 400 amino acids.

In one embodiment the polypeptide further comprises a linker. This linker may be between the first proximal end and the second proximal end, alternatively the linker may link the distal ends of the first fragment and/or the second fragment to a further sequence of amino acids.

A peptide linker sequence may be employed to separate the first fragment and second fragment. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first fragment and/or the second fragments; and (3) the lack of hydrophobic or charged residues that might react with the ToxA and/or ToxB functional epitopes. Peptide linker sequences may contain Glycine (Gly), Asparagine (Asn) and Serine (Ser) residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. No. 4,935,233 and U.S. Pat. No. 4,751,180. The linker sequence may generally be from 1 to about 50 amino acids in length.

In one embodiment the linker comprises 1-20, 1-15, 1-10, 1-5, 1-2, 5-20, 5-15, 5-15, 10-20, or 10-15 amino acids. In one embodiment the linker is a glycine linker, the linker may comprise multiple contiguous glycine residues (1, 2, 3, 4, 5, 6, 7, 8, 9, 10, 11, 12, 13, 14, 15, 17, or 20), or alternatively the linker may comprise some glycine residues and some residues of other amino acids such as alanine. In a further embodiment the linker comprises a single glycine residue.

In an embodiment the polypeptide of the invention is part of a larger fusion protein. The fusion proteins may further comprise amino acids encoding an immunogenic portion of a further protein antigen. For example the fusion protein may further comprise an immunogenic portion of a protein antigen obtained or derived from a bacterium selected from the group consisting of *S. pneumoniae*, *H. influenzae*, *N. meningitidis*, *E. coli*, *M. cattarhalis*, *C. tetanii*, *C. diphtheriae*, *B. pertussis*, *S. epidermidis*, enterococci, *S. aureus*, and *Pseudomonas aeruginosa*. In this case the linker may be between the first fragment or the second fragment and a further immunogenic portion of a protein antigen.

The term "immunogenic portion thereof" or 'immunogenic fragment' refers to a fragment of a polypeptide wherein the fragment comprises an epitope that is recognized by cytotoxic T lymphocytes, helper T lymphocytes or B cells. Suitably, the immunogenic portion will comprise at least 30%, suitably at least 50%, especially at least 75% and in particular at least 90% (e.g. 95% or 98%) of the amino acids in the reference sequence. In one embodiment, the immunogenic portion will comprise all of the epitope regions of the reference sequence.

Immunogenic compositions according to the invention comprising the specific fusion proteins of *C. difficile* toxin A repeating domain fragment and a *C. difficile* toxin B repeating domain fragment described herein are also expected to provide an improved immune response against *C. difficile* as compared to compositions comprising known *C. difficile* polypeptides or fragments.

Adjuvants

The immunogenic compositions disclosed herein include at least one *C. difficile* polypeptide in combination with an aluminum-free adjuvant. The polypeptides are formulated with an adjuvant that is free of aluminum or aluminum salts, that is, an aluminum-free adjuvant or adjuvant system.

In certain embodiments, the *C. difficile* polypeptide is formulated with an adjuvant comprising an immunologically active saponin fraction presented in the form of a liposome. The adjuvant may further comprise a lipopolysaccharide. The adjuvant may include QS21. For example, in one embodiment, the adjuvant contains QS21 in a liposomal formulation. In one embodiment, the adjuvant system includes 3D-MPL and QS21. For example, in one embodiment, the adjuvant contains 3D-MPL and QS21 in a liposomal formulation. Optionally, the adjuvant system also contains cholesterol. In one specific embodiment, the adjuvant includes QS21 and cholesterol. Optionally, the adjuvant system contains 1,2-Dioleoyl-sn-Glycero-3-phosphocholine (DOPC). For example, in one specific adjuvant system contains cholesterol, DOPC, 3D-MPL and QS21.

In one specific example, the immunogenic composition includes an adjuvant formulated in a dose that includes: from about 0.1 to about 0.5 mg cholesterol; from about 0.25 to about 2 mg DOPC; from about 10 μg to about 100 μg 3D-MPL; and from about 10 μg to about 100 μg QS21. In a further specific example the immunogenic composition includes and adjuvant formulated in a dose that includes: from about 0.1 to about 0.5 mg cholesterol, from about 0.25 to about 2 mg DOPC, from about 10 μg to about 100 μg 3D-MPL, and from about 10 μg to about 100 μg QS21. In one specific formulation, the adjuvant is formulated in a single dose that contains: about 0.25 mg cholesterol; about 1.0 mg DOPC; about 50 μg 3D-MPL; and about 50 μg QS21. In other embodiments, the immunogenic composition is formulated with a fractional dose (that is a dose, which is a fraction of the preceding single dose formulations, such as one half of the preceding quantity of components (cholesterol, DOPC, 3D-MPL and QS21), ¼ of the preceding quantity of components, or another fractional dose (e.g., ⅓, ⅙, etc.) of the preceding quantity of components.

In one embodiment, the immunogenic compositions according to the invention include an adjuvant containing combinations of lipopolysaccharide and Quillaja saponins that have been disclosed previously, for example in EP0671948. This patent demonstrated a strong synergy when a lipopolysaccharide (3D-MPL) was combined with a Quillaja saponin (QS21).

The adjuvant may further comprise immunostimulatory oligonucleotides (for example, CpG) or a carrier.

A particularly suitable saponin for use in the present invention is Quil A and its derivatives. Quil A is a saponin preparation isolated from the South American tree *Quillaja Saponaria Molina* and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of *Quillaja saponaria Molina*, which induces CD8+ cytotoxic T cells (CTLs), Th1 cells and a predominant IgG2a antibody response and is a preferred saponin in the context of the present invention.

In a specific embodiment, QS21 is provided in its less reactogenic composition where it is quenched with an exogenous sterol, such as cholesterol for example. Several particular forms of less reactogenic compositions wherein QS21 is quenched with an exogenous cholesterol exist. In a specific embodiment, the saponin/sterol is in the form of a liposome structure (WO 96/33739, Example 1). In this embodiment the liposomes suitably contain a neutral lipid, for example phosphatidylcholine, which is suitably non-crystalline at room temperature, for example eggyolk phosphatidylcholine, dioleoyl phosphatidylcholine (DOPC) or dilauryl phosphatidylcholine. The liposomes may also contain a charged lipid which increases the stability of the lipsome-QS21 structure for liposomes composed of saturated lipids. In these cases the amount of charged lipid is suitably 1-20% w/w, preferably 5-10%. The ratio of sterol to phospholipid is 1-50% (mol/mol), suitably 20-25%.

Suitable sterols include β-sitosterol, stigmasterol, ergosterol, ergocalciferol and cholesterol. In one particular embodiment, the adjuvant composition comprises cholesterol as sterol. These sterols are well known in the art, for example cholesterol is disclosed in the Merck Index, 11th Edn., page 341, as a naturally occurring sterol found in animal fat.

Where the active saponin fraction is QS21, the ratio of QS21:sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol.

In one embodiment, the invention provides a dose of an immunogenic composition comprising immunologically active saponin, preferably QS21, at a level of 60 µg or less, for example between 1 and 60 µg. In one embodiment, the dose of the immunogenic composition comprises QS21 at a level of approximately around 50 µg, for example between 45 and 55 µg, suitably between 46-54 µg or between 47 and 53 µg or between 48 and 52 µg or between 49 and 51 µg, or 50 µg per dose.

In another embodiment the dose of the immunogenic composition comprises QS21 at a level of around 25 µg, for example between 20-30 µg, suitably between 21-29 µg or between 22 and 28 µg or between 23 and 27 µg or between 24 and 26 µg, or 25 µg.

In another embodiment, the dose of the immunogenic composition comprises QS21 at a level of around 10 µg per, for example between 5 and 15 µg, suitably between 6 and 14 µg, for example between 7 and 13 µg or between 8 and 12 µg or between 9 and 11 µg, or 10 µg.

Specifically, a 0.5 ml vaccine dose volume contains 25 µg or 50 µg of QS21 per dose. Specifically, a 0.5 ml vaccine dose volume contains 50 µg of QS21 per dose.

The lipopolysaccharide may be a non-toxic derivative of lipid A, particularly monophosphoryl lipid A or more particularly 3-Deacylated monophoshoryl lipid A (3D-MPL).

3D-MPL is sold under the name MPL by GlaxoSmith-Kline Biologicals N.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-(Th1) phenotype. 3D-MPL can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3D-MPL is used. Small particle 3D-MPL has a particle size such that it may be sterile-filtered through a 0.22 µm filter. Such preparations are described in WO 94/21292.

The invention therefore provides a dose of an immunogenic composition comprising lipopolysaccharide, preferably 3D-MPL, at a level of 75 µg or less, for example between 1 and 60 µg. In one embodiment the lipopolysaccharide is present at an amount of about 50 µg per dose.

In one embodiment, the dose of the immunogenic composition comprises 3D-MPL at a level of around 50 µg, for example between 45-55 µg, suitably between 46-54 µg or between 47 and 53 µg or between 48 and 52 µg or between 49 and 51 µg, or 50 µg.

In one embodiment, the dose of the immunogenic composition comprises 3D-MPL at a level of around 25 µg, for example between 20-30 µg, suitably between 21-29 µg or between 22 and 28 µg or between 23 and 27 µg or between 24 and 26 µg, or 25 µg.

In another embodiment, the dose of the immunogenic composition comprises 3D-MPL at a level of around 10 µg, for example between 5 and 15 µg, suitably between 6 and 14 µg, for example between 7 and 13 µg or between 8 and 12 µg or between 9 and 11 µg, or 10 µg.

In one embodiment, the volume of the dose is 0.5 ml. In a further embodiment, the immunogenic composition is in a volume suitable for a dose which volume is higher than 0.5 ml, for example 0.6, 0.7, 0.8, 0.9 or 1 ml. In a further embodiment, the human dose is between 1 ml and 1.5 ml.

Specifically, a 0.5 ml vaccine dose volume contains 25 µg or 50 µg of 3D-MPL per dose. Specifically, a 0.5 ml vaccine dose volume contains 50 µg of 3D-MPL per dose.

The dose of the immunogenic composition according to any aspect of the invention suitably refers to human dose. By the term "human dose" is meant a dose which is in a volume suitable for human use. Generally this is between 0.3 and 1.5 ml. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml.

Suitable compositions of the invention are those wherein liposomes are initially prepared without MPL (as described in WO 96/33739), and MPL is then added, suitably as small particles of below 100 nm particles or particles that are susceptible to sterile filtration through a 0.22 µm membrane. The MPL is therefore not contained within the vesicle membrane (known as MPL out). Compositions where the MPL is contained within the vesicle membrane (known as MPL in) also form an aspect of the invention. The polypeptide comprising a *C. difficile* toxin A fragment and/or a *C. difficile* toxin B fragment can be contained within the vesicle membrane or contained outside the vesicle membrane.

In a specific embodiment, QS21 and 3D-MPL are present in the same final concentration per dose of the immunogenic composition. In one aspect of this embodiment, a dose of immunogenic composition comprises a final level of 25 µg of 3D-MPL and 25 µg of QS21 or 50 µg of 3D-MPL and 50 µg of QS21.

In one embodiment, the adjuvant includes an oil-in-water emulsion. For example, the oil-in-water emulsion can include an oil phase that incorporates a metabolisable oil, and an additional oil phase component, such as a tocol. The oil-in-water emulsion may also contain an aqueous component, such as a buffered saline solution (e.g., phosphate buffered saline). In addition, the oil-in-water emulsion typically contains an emulsifier. In one embodiment, the metabolizable oil is squalene. In one embodiment, the tocol is alpha-tocopherol. In one embodiment, the emulsifier is a nonionic surfactant emulsifier (such as polyoxyethethylene sorbitan monooleate, TWEEN80™). In exemplary embodiments, the oil-in-water emulsion contains squalene and alpha tocopherol in a ratio which is equal or less than 1 (w/w).

The metabolisable oil in the oil-in-water emulsion may be present in an amount of 0.5-10 mg. The tocol in the oil-in-water emulsion may be present in an amount of 0.5-11 mg. The emulsifying agent may be present in an amount of 0.4-4 mg, In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® (caprylic/capric triglycerides made using glycerol from vegetable oil sources and medium-chain fatty acids (MCTs) from coconut or palm kernel oils) and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10th Edition, entry no. 8619).

Suitably the metabolisable oil is present in the adjuvant composition in an amount of 0.5-10 mg, preferably 1-10, 2-10, 3-9, 4-8, 5-7, or 5-6 mg (e.g. 2-3, 5-6, or 9-10 mg), specifically about 5.35 mg.

Tocols are well known in the art and are described in EP0382271. Suitably the tocol is alpha-tocopherol or a derivative thereof such as alpha-tocopherol succinate (also known as vitamin E succinate). Said tocol is suitably present in an amount of 0.5-11 mg, preferably 1-11, 2-10, 3-9, 4-8, 5-7, 5-6 mg (e.g. 10-11, 5-6, 2.5-3.5 or 1-3 mg). In a specific embodiment the tocol is present in an amount of about 5.94 mg.

The oil in water emulsion further comprises an emulsifying agent. The emulsifying agent may suitably be polyoxyethylene sorbitan monooleate. In a particular embodiment the emulsifying agent may be Polysorbate® 80 (Polyoxyethylene (20) sorbitan monooleate) or Tween® 80.

Said emulsifying agent is suitably present in the adjuvant composition in an amount of 0.1-5, 0.2-5, 0.3-4, 0.4-3 or 2-3 mg (e.g. 0.4-1.2, 2-3 or 4-5 mg) emulsifying agent. In a specific embodiment the emulsifying agent is present in an amount of about 0.97 mg or about 2.425 mg.

In one embodiment, the amounts of specific components present in the composition are the amounts present in a 0.5 ml human dose. In a further embodiment, the immunogenic composition is in a volume suitable for a human dose which volume is higher than 0.5 ml, for example 0.6, 0.7, 0.8, 0.9 or 1 ml. In a further embodiment, the human dose is between 1 ml and 1.5 ml.

Where the adjuvant is in a liquid form and is to be combined with a liquid form of a polypeptide composition, the adjuvant composition in a human dose will be a fraction of the intended final volume of the human dose, for example approximately half of the intended final volume of the human dose, for example a 350 µl volume for an intended human dose of 0.7 ml, or a 250 µl volume for an intended human dose of 0.5 ml. The adjuvant composition is diluted when combined with the polypeptide antigen composition to provide the final human dose of vaccine. The final volume of such dose will of course vary dependent on the initial volume of the adjuvant composition and the volume of polypeptide antigen composition added to the adjuvant composition. In an alternative embodiment, a liquid adjuvant is used to reconstitute a lyophilised polypeptide composition. In this embodiment, the human dose of the adjuvant composition is approximately equal to the final volume of the human dose. The liquid adjuvant composition is added to the vial containing the lyophilised polypeptide composition. The final human dose can vary between 0.5 and 1.5 ml.

The method of producing oil-in-water emulsions is well known to the person skilled in the art. Commonly, the method comprises mixing the tocol-containing oil phase with a surfactant such as a PBS/polyoxyethylene sorbitan monooleate solution, followed by homogenisation using a homogenizer. It would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil in water emulsion, the oil and emulsifier should be in an aqueous carrier. The aqueous carrier may be, for example, phosphate buffered saline.

Preferably the oil-in-water emulsion systems of the present invention have a small oil droplet size in the sub-micron range. Suitably the droplet sizes will be in the range 120 to 750 nm, more preferably sizes from 120 to 600 nm in diameter. Most preferably the oil-in water emulsion contains oil droplets of which at least 70% by intensity are less than 500 nm in diameter, more preferably at least 80% by intensity are less than 300 nm in diameter, more preferably at least 90% by intensity are in the range of 120 to 200 nm in diameter.

In one embodiment, the immunogenic composition is not 3 µg or 10 µg of any of SEQ ID Nos. 1 to 7 combined with an adjuvant comprising an oil in water emulsion having 0.125 mL SB62 emulsion (Total volume), 5.35 mg squalene, 5.94 mg DL-α-tocopherol and 2.425 mg polysorbate 80 per 0.5 ml dose. In one embodiment, the immunogenic composition is not 3 µg or 10 µg of any of SEQ ID Nos. 1 to 7 combined with an adjuvant comprising an oil in water emulsion 5.35 mg squalene, 5.94 mg DL-α-tocopherol and 2.425 mg polysorbate 80 per 0.5 ml dose. In one embodiment, the immunogenic composition does not contain an adjuvant comprising a oil in water emulsion having squalene, DL-α-tocopherol and polysorbate 80.

Immunogenic Compositions and Vaccines

In one embodiment the immunogenic composition further comprises additional antigens. In one embodiment the additional antigens are antigens derived from a bacterium selected from the group consisting of *Streptococcus pneumoniae* (*S. pneumoniae*), *Haemophilus influenzae* (*H. influenzae*), *Neisseria meningitidis* (*N. meningitidis*), *Escherichia coli* (*E. coli*), *Moraxella catarrhalis* (*M. cattarhalis*), *Clostridium tetani* (*C. tetani*), *Corynebacterium diptherieriae* (*C. diptherieriae*), *Bordetella pertussis* (*B. pertussis*), Staphylococcus epidermidis (S. epidermidis), enterococci, and Staphylococcus aureus (S. aureus). In a further embodiment the immunogenic composition of the invention may comprise further antigens from C. difficile for example the S-layer proteins (WO01/73030). Optionally the immunogenic composition further comprises a saccharide from C. difficile.

There is further provided a vaccine comprising the immunogenic composition. This vaccine may further comprise a pharmaceutically acceptable excipient. In a further aspect of the invention there is provided a vaccine comprising the immunogenic composition of the invention and an adjuvant.

The vaccine preparations containing immunogenic compositions of the present invention may be used to protect a mammal susceptible to C. difficile infection or treat a mammal with a C. difficile infection, by means of administering said vaccine via a systemic or mucosal route. These administrations may include injection via the intramuscular, intraperitoneal, intradermal or subcutaneous routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for coordination of the immune responses with respect to each other). In addition to a single route of administration, 2 different routes of administration may be used. For example, saccharides or saccharide conjugates may be administered intramuscularly (IM) or intradermally (ID) and bacterial proteins may be administered intranasally (IN) or intradermally (ID). In addition, the vaccines of the invention may be administered IM for priming doses and IN for booster doses.

The content of toxins in the vaccine will typically be in the range 1-250 μg, preferably 5-50 μg, most typically in the range 5-25 μg. Following an initial vaccination, subjects may receive one or several booster immunizations adequately spaced. Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

A further aspect of the invention is a method of preventing or treating C. difficile infection comprising administering to the subject an immunoprotective dose of the immunogenic composition or vaccine of the invention. In one embodiment there is provided a method of preventing or treating primary and/or recurrence episodes of C. difficile infection comprising administering to the subject an immunoprotective dose of the immunogenic composition or vaccine of the invention. In one embodiment the subject is selected from the group consisting of mouse, rabbit, guinea pig, monkey, non-human primate or human. In one embodiment the subject is a mouse. In a further embodiment the subject is a human A further aspect of the invention is an immunogenic composition or vaccine or kit of the invention for use in the treatment or prevention of infection or disease caused by C. difficile. In one embodiment there is provided an immunogenic composition or vaccine or kit of the invention for use in the treatment or prevention of primary and/or recurrence episodes of C. difficile disease.

A further aspect of the invention is use of the immunogenic composition or vaccine or kit of the invention in the manufacture of a medicament for the treatment or prevention of C. difficile disease. In one embodiment there is provided an immunogenic composition or vaccine or kit of the invention for use in the manufacture of a medicament for the treatment or prevention of primary and/or recurrence episodes of C. difficile disease.

"C. difficile disease" refers to any infection or disease caused by toxins released by C. difficile. Examples of C. difficile disease are antibiotic-associated diarrhea (AAD), pseudomembranous colitis and toxic megacolon, which can be life-threatening.

"Around" or "approximately" are defined as within 10% more or less of the given figure for the purposes of the invention.

The terms "comprising", "comprise" and "comprises" herein are intended by the inventors to be optionally substitutable with the terms "consisting of", "consist of" and "consists of", respectively, in every instance. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

Embodiments herein relating to "vaccine" of the invention are also applicable to embodiments relating to "immunogenic compositions" of the invention, and vice versa.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are estimates, and are provided for description. Additionally, numerical limitations given with respect to concentrations or levels of a substance, such as a polypeptide antigen, may be approximate.

All references or patent applications cited within this patent specification are incorporated by reference herein in their entirety.

These examples set forth below are for purposes of illustration only, and are not to be construed as limiting the scope of the invention in any manner.

It will be understood that particular aspects and embodiments described herein are shown by way of illustration and not as limitations of the invention. The principal features of this invention can be employed in various embodiments without departing from the scope of the invention. Those skilled in the art will recognize, or be able to ascertain using routine study, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. All documents referred to herein are incorporated by reference to the fullest extent permissible.

The use of the word "a" or "an" when used in conjunction with the term "comprising" in the claims and/or the specification may mean "one," but it is also consistent with the meaning of "one or more," "at least one," and "one or more than one."

The invention will be further described by reference to the following, non-limiting, figures and examples.

EXAMPLES

Adjuvants Used in the Experiments:
Adjuvant A
Adjuvant having 50 µg QS21 presented in the form of a liposome, 50 µg 3D-MPL, 0.25 mg cholesterol and 1.0 mg DOPC per 0.5 ml dose. A dose of 50 µl suitable for immunizing mice contains 5 µg QS21, 5 µg 3D-MPL, 0.025 mg cholesterol and 0.1 mg DOPC.
Adjuvant B
Adjuvant consisting of an oil in water emulsion having 0.125 mL SB62 emulsion (Total volume), 5.35 mg squalene, 5.94 mg DL-α-tocopherol and 2.425 mg polysorbate 80 per 0.5 ml dose.
Adjuvant C
Adjuvant having 25 µg QS21 presented in the form of a liposome, 25 µg 3D-MPL, 0.25 mg cholesterol and 1.0 mg DOPC.
GSK Adjuvant AS04D
Alum
Protocols
Anti-ToxA and Anti-ToxB ELISA Response: Protocol for Examples 2 to 4, 7 and 8

ToxA or ToxB fragments (for the examples 2 and 4-ToxA (2121-2686) and ToxB (1968-2366) for the examples 3, 5, 6, 7 and 8-ToxA (2387-2706) and ToxB (1750-2360)) were coated at 2 µg/ml (for ToxA) or 1 µg/ml (for ToxB) in phosphate buffered saline (PBS) on high-binding microtitre plates (Nunc MAXISORP™), overnight at 4° C. The plates were blocked with PBS+1% Bovine serum albumin (BSA) for 30 min at RT with agitation. Hamster or mice sera are prediluted 1/100 (for post dose I or II samples) or 1/500 (for post dose III samples) in PBS-BSA0.2%-TWEEN™ 0.05% and then, further twofold dilutions were made in microplates and incubated at room temperature (RT) for 30 min. After washing, bound hamster or mouse antibody was detected using Jackson ImmunoLaboratories Inc. peroxidase-conjugated Anti-Mouse (ref: 110-035-003) or Anti-Hamster (ref: 107-035-142) diluted 1:5000 in PBS-BSA0.2%-tween 0.05% ('detection antibody'). The detection antibodies were incubated for 30 min at room temperature (RT) with agitation. The color was developed using 4 mg O-phenylenediamine (OPD)+5 µl $H_2O_2$ per 10 ml pH 4.5 0.1M citrate buffer for 15 minutes in the dark at room temperature. The reaction was stopped with 50 µl HCl, and the optical density (OD) was read at 490 nm relative to 620 nm.

The level of anti-ToxA or anti-ToxB antibodies present in each individual sera is determined by comparison to a reference serum (calibrated against Jackson Global IgG) added on each plate and expressed in µg/ml. A geometric mean titer GMT was calculated using Excel software for the samples in each treatment group for the hamster or mice immunizations.

Example 1

Design of Five *C. difficile* ToxA-ToxB Fusion Proteins

Fusion proteins (also called 'fusions') containing fragments of the C-terminal repeating domains of ToxA and ToxB were designed. These fusion proteins contained a fragment of the C-terminal repeating domain of ToxA and a fragment of the C-terminal repeating domain of ToxB, and a junction between the C-terminal end of the ToxA fragment and the N terminal end of the ToxB fragment. Two strategies were devised, in the first strategy; the fusion was designed such that the long solenoid structure was maintained at the junction between the two fragments. In the second strategy, the two fragments of the fusions are separated by a linker to allow their independent correct folding.

The C-terminal part of ToxA and ToxB is composed of repeated sequences: short repeats (SR) and long repeats (LR) (PNAS 2005 vol 102: 18373-18378).

The partial known 3D structure for the C-terminal domain of ToxA has been described (PNAS 2005 Greco et al., vol 102: 18373-18378; Nature Structural & Molecular biology 2006 vol 13(5): 460-461; PDB codes: 2F6E, 2G7C and 2QJ6).

The inventors predicted that there are two kinds of important interactions between residues of the C-terminal part of ToxA and ToxB. The first interaction occurs between residues contained in a LR and its preceding SR and is important to maintain the solenoid-like structure. The second type of interaction occurs between residues contained in a LR and the following SR and this interaction is mediating the carbohydrate-binding function of the toxin.

A new "structural-functional" repeat SR-LR-SR was defined. The structure of this repeat was maintained intact in the designed fusions.

The positions of the short (SR) and long repeats (LR) of ToxA and ToxB repeats are presented in Table 1.

A list of the "SR-LR-SR" boxes contained in the C-terminal domain of ToxA and ToxB is presented in Table 2 below.

| Name | Start position | End position |
| --- | --- | --- |
| ToxA_1 | 1874 | 1944 |
| ToxA_2 | 2008 | 2078 |
| ToxA_3 | 2142 | 2212 |
| ToxA_4 | 2254 | 2326 |
| ToxA_5 | 2390 | 2460 |
| ToxA_6 | 2503 | 2573 |
| ToxA_7 | 2595 | 2664 |
| ToxB_1 | 1877 | 1946 |
| ToxB_2 | 2008 | 2078 |
| ToxB_3 | 2140 | 2212 |
| ToxB_4 | 2274 | 2343 |

Finally, the number of SRs between two LRs were maintained in the designed fusions to keep the long solenoid-like structure.

Before the design of junctions for the fusions, two working hypotheses were defined: first hypothesis, the shorter the fusions, the better the probability for the fusions to be stably over expressed; second hypothesis, according to the concept of "SR-LR-SR" boxes, the start position has to be chosen in order to ensure a correct folding of the first SR of this previously defined SR-LR-SR box. Thus the fusions start at the beginning of the SR that precedes the SR-LR-SR box. Using these two hypotheses, three start positions were analysed: residue 2370, 2234 and 2121 of ToxA.

The start position 2370 was excluded. The start position 2234 was also excluded because one of the residues involved in interactions important for the protein structural stability is not conserved. So, it was decided that all the designed fusion will begin at residue 2121 of ToxA.

All fusions will end at the last residue of ToxB.

Four fusions (F1-4) were designed in order to maintain the entire fusion in a long solenoid-like structure between the two fusion fragments.

Fusions 1 (F1) and 2 (F2) were designed using the same hypothesis. All SR protein sequences of ToxA and ToxB had been compared using a multiple alignment software (ClustalW—Thompson J D et al. (1994) *Nucleic Acids Res.*, 22, 4673-4680). The more similar sequences were the third SR VIII of ToxA and the third SR II of ToxB and third SR III of ToxB. In order to make a choice between these two SR of ToxB, a structural homology modelling (using the Swiss-Model interface—Arnold K et al. (2006) *Bioinformatics*, 22, 195-201) was performed on the C-terminal part of ToxB using the known 3D structure of partial ToxA C-terminal domain (PDB code: 2QJ6). Using the third SR VIII of ToxA, the best local structural superposition (performed using SwissPDBViewer—Guex N et al. (1997), *Electrophoresis* 18, 2714-2723) was obtained with the third SR II of ToxB. So, two junctions were designed: the first one is between the third SR VIII of ToxA and the fourth SR II of ToxB (F1) and the second one is between the second SR VIII of ToxA and the third SR II of ToxB (F2).

To design fusion 3 (F3), a global structural superposition was performed between both the known structure of the partial C-terminal domain of ToxA and the predicted structure of C-terminal domain of ToxB (using SwissModel and SwissPDBViewer softwares). The best superposition was found between LR VII of ToxA and LR II of ToxB. So, it was decided to make a junction in this similar LR. The junction was performed firstly in a region where the sequence is conserved between ToxA and ToxB, after that in order to keep in the ToxA part of the fusion, the residues in interaction with the preceding SR and lastly, in order to keep in the ToxB part, the residues in interaction with the following SR.

For the design of fusion 4 (F4), the C-terminal domain of ToxB was divided in 4 fragments and a more precise homology modelling (SwissModel) was performed on them. The split was realised in order to keep intact the "SR-LR-SR" boxes (each domain finishes at the end of the SR that follows a LR). A structural superposition between the predicted structures of these fragments and the known 3D structure of ToxA was made and the best structural superposition was obtained for the third SR of ToxB (SR I) and the last SR of ToxA (third SR VIII). So, the junction was done between the second SR VIII of ToxA and the third SRI of ToxB.

The last fusion (F5) was designed in order to allow an independent correct folding of the two fragments of the fusion. A linker was added between the last residue of the ToxA protein sequence and the beginning of the fourth SR II of ToxB (always taking into account the importance of an intact "SR-LR-SR" box). Only one exogenous residue (Glycine) was added as a linker and located between two existing Glycines. Thus, the linker can also be described as composed of 3 Glycines surrounding by known (for ToxA) and predicted (for ToxB) beta-strand.

Example 2

Immunisation of Hamsters with F2 Fusion Protein: Adjuvant A, Adjuvant A without QS21 or Adjuvant A without MPL and Comparison with Adjuvant B, Alum or Non Adjuvanted Formulations.

Groups of 16 hamsters (mix of male and female) were immunized IM at days 0, 14 and 28 with 1 µg of the F2 fusion protein adjuvanted with 50 µl of Adjuvant A, Adjuvant A without MPL, Adjuvant A without QS21, Adjuvant B, Alum or non adjuvanted.

Anti-ToxA and anti-ToxB ELISA titers were determined in individual sera collected at day 41/42 (Post III). The results are described in tables 3 and 4 and FIGS. 1 and 2.

TABLE 3

ELISA anti-ToxA: concentrations (µg/ml) on individual day 42 sera

| | 1<br>F2<br>1 µg/dose | 2<br>F2<br>1 µg/dose | 3<br>F2<br>1 µg/dose | 4<br>F2<br>1 µg/dose | 5<br>F2<br>1 µg/dose | 6<br>F2<br>1 µg/dose |
|---|---|---|---|---|---|---|
| | | | ADJUVANT | | | |
| Groups | A | A − QS21 | A − MPL | B | Al(OH)3 | non-adjuvanted |
| 1 | 1472 | 29 | 935 | 457 | 577 | 3 |
| 2 | 1828 | 39 | 414 | 197 | 329 | 23 |
| 3 | 4928 | 35 | 747 | 375 | 401 | 64 |
| 4 | 2966 | 28 | 550 | 60 | 769 | 25 |
| 5 | 2025 | 19 | 388 | 408 | 652 | 3 |
| 6 | 1116 | 155 | 1498 | 173 | 449 | 37 |
| 7 | 2579 | 43 | 879 | 732 | 360 | 179 |
| 8 | 2463 | 33 | 780 | 196 | 1342 | 31 |
| 9 | 1425 | 52 | 1183 | 681 | 817 | 7 |
| 10 | 1984 | 307 | 696 | 190 | 534 | 199 |
| 11 | 1093 | 198 | 572 | 344 | 2665 | 106 |
| 12 | 2080 | 126 | 972 | 508 | 1944 | 22 |
| 13 | 3541 | 403 | 1823 | 193 | 1603 | 221 |
| 14 | 1635 | 152 | 813 | 1142 | 2209 | 680 |

TABLE 3-continued

ELISA anti-ToxA: concentrations (µg/ml) on individual day 42 sera

| | 1<br>F2<br>1 µg/dose | 2<br>F2<br>1 µg/dose | 3<br>F2<br>1 µg/dose | 4<br>F2<br>1 µg/dose | 5<br>F2<br>1 µg/dose | 6<br>F2<br>1 µg/dose |
|---|---|---|---|---|---|---|
| | | | ADJUVANT | | | |
| Groups | A | A − QS21 | A − MPL | B | Al(OH)3 | non-adjuvanted |
| 15 | 4688 | 630 | 1046 | 494 | 855 | 359 |
| 16 | 3360 | 21 | 1119 | 163 | 664 | 100 |
| Geomean | 2213 | 77 | 830 | 312 | 815 | 49 |
| CI− | 1717 | 40 | 655 | 202 | 563 | 14 |
| CI+ | 2802 | 124 | 1032 | 454 | 1129 | 104 |
| St dev min | 496 | 37 | 174 | 111 | 251 | 36 |
| St dev max | 589 | 47 | 202 | 141 | 314 | 55 |

CI = confidence interval
St Dev = standard deviation

TABLE 4

ELISA anti-ToxB: concentrations (µg/ml) on individual day 42 sera

| | 1<br>F2<br>1 µg/dose | 2<br>F2<br>1 µg/dose | 3<br>F2<br>1 µg/dose | 4<br>F2<br>1 µg/dose | 5<br>F2<br>1 µg/dose | 6<br>F2<br>1 µg/dose |
|---|---|---|---|---|---|---|
| | | | ADJUVANT | | | |
| Groups | A | A − QS21 | A − MPL | B | Al(OH)3 | non-adjuvanted |
| 1 | 811 | 33 | 817 | 65 | 63 | 5 |
| 2 | 1186 | 88 | 1144 | 107 | 177 | 5 |
| 3 | 4388 | 90 | 943 | 207 | 216 | 92 |
| 4 | 1158 | 66 | 1224 | 464 | 239 | 26 |
| 5 | 1992 | 53 | 1088 | 212 | 91 | 5 |
| 6 | 1518 | 305 | 1070 | 193 | 138 | 44 |
| 7 | 5437 | 54 | 1021 | 244 | 44 | 57 |
| 8 | 1493 | 74 | 899 | 266 | 313 | 28 |
| 9 | 1488 | 281 | 1506 | 189 | 135 | 30 |
| 10 | 2637 | 346 | 1588 | 214 | 318 | 256 |
| 11 | 1568 | 215 | 1125 | 251 | 863 | 95 |
| 12 | 1879 | 50 | 1890 | 549 | 534 | 93 |
| 13 | 1920 | 237 | 1724 | 147 | 355 | 57 |
| 14 | 1709 | 266 | 2450 | 606 | 543 | 57 |
| 15 | 1553 | 492 | 2033 | 301 | 251 | 178 |
| 16 | 1556 | 95 | 744 | 167 | 115 | 88 |
| Geomean | 1789 | 125 | 1254 | 225 | 207 | 41 |
| CI− | 1387 | 76 | 1039 | 162 | 128 | 16 |
| CI+ | 2264 | 186 | 1498 | 301 | 308 | 76 |
| St dev min | 402 | 49 | 215 | 63 | 79 | 25 |
| St dev max | 475 | 61 | 244 | 75 | 101 | 34 |

Figure 1S:
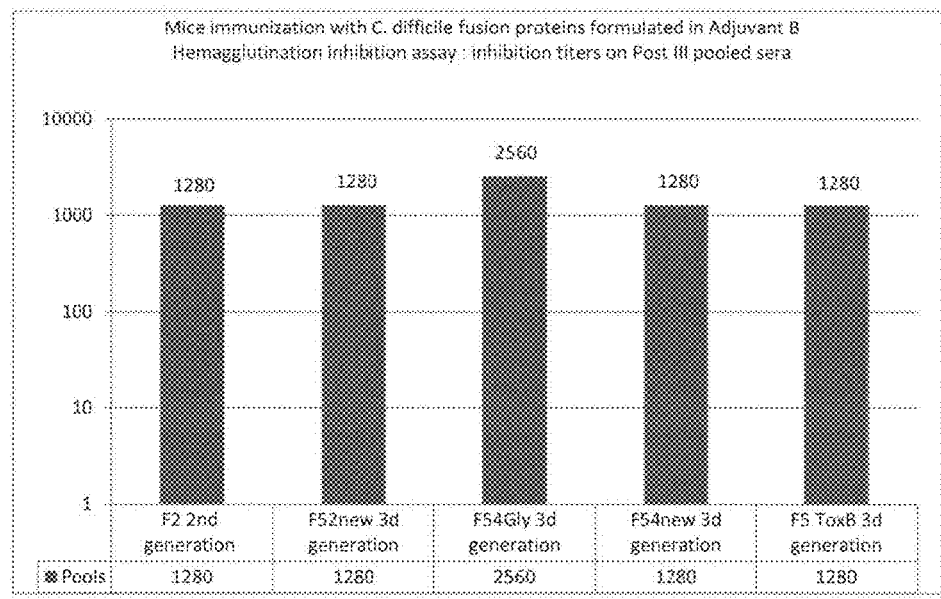
FIG. 1—Graphs showing anti-ToxA and anti-ToxB ELISA results for hamsters immunised with F2 formulated with Adjuvant A; Adjuvant A without QS21 and Adjuvant A without MPL.

FIGS. 1 and 2

Results for FIG. 1:

The F2 was injected with the full Adjuvant A, a similar formulation without QS21, or without MPL.

For the anti-ToxA response, both MPL and QS21 have an added value even if the QS21 seems the most effective.

For the anti-ToxB response, the effect of the MPL is less clear while the QS21 removal has a drastic effect on the IgG titers.

Results for FIG. 2:

Regarding the adjuvant comparison, the adjuvant A induced significant higher anti-ToxA and anti-ToxB antibodies compared to Alum, Adjuvant B or non adjuvanted formulations. Adjuvant B induced higher anti-ToxA and anti-ToxB antibodies compared to the non adjuvanted formulations.

Example 3

Pims 20110544—Immunisation of Male Hamsters with a Dose-Range of F2 Fusion Protein Formulated in Adjuvant B, AS04D, Adjuvant A or Adjuvant C.

Groups of 10 male hamsters were immunized IM at days 0, 14 and 28 with 0.3 µg, 1 µg or 3 µg of the F2 fusion protein adjuvanted with 50 µl doses of Adjuvant B, AS04D, Adjuvant A or Adjuvant C.

Anti-ToxA and anti-ToxB ELISA titers were measured from individual sera collected at day 13 (post I), day 27 (Post II), day 42 (Post III 14) and day 84 (Post III 56)

Pims 20110545—Immunisation of Female Hamsters with a Dose-Range of F2 Fusion Protein Formulated in Adjuvant B, AS04D, Adjuvant A or Adjuvant C.

Groups of 10 female hamsters were immunized IM at days 0, 14 and 28 with 0.3 µg, 1 µg or 3 µg of the F2 fusion protein adjuvanted with Adjuvant B, AS04D, Adjuvant A or Adjuvant C. Anti-ToxA and anti-ToxB ELISA titers were measured from individual sera collected at day 13 (post I), day 27 (Post II), day 42 (Post III 14) and day 84 (Post III 56) FIGS. 3 to 7

Pims 20110544 and 20110545

TABLE 5

Post I Anti-ToxA ELISA titers (Geometric mean titre or GMT)

| Group | 1 | 2 | 3 | 4 | 5 | 6 | 7 | 8 | 9 | 10 | 11 | 12 |
|---|---|---|---|---|---|---|---|---|---|---|---|---|
| Ag/animal | 3 µg | 1 µg | 0.3 µg | 3 µg | 1 µg | 0.3 µg | 3 µg | 1 µg | 0.3 µg | 3 µg | 1 µg | 0.3 µg |
| Adj. | C | C | C | A | A | A | B | B | B | AS04D | AS04D | AS04D |
| 544 | 28 | 17 | 6 | 84 | 17 | 6 | 44 | 27 | 3 | 68 | 74 | 33 |
| 545 | 50 | 36 | 12 | 109 | 111 | 26 | 85 | 20 | 16 | 194 | 107 | 36 |

TABLE 6

Post I Anti-ToxB ELISA titers (GMT)

| | Group | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ag/animal | 3 µg | 1 µg | 0.3 µg | 3 µg | 1 µg | 0.3 µg | 3 µg | 1 µg | 0.3 µg | 3 µg | 1 µg | 0.3 µg |
| Adj | C | C | C | A | A | A | B | B | B | AS04D | AS04D | AS04D |
| 544 | 115 | 82 | 52 | 412 | 121 | 79 | 189 | 119 | 34 | 7 | 5 | 5 |
| 545 (female) | 178 | 257 | 150 | 391 | 383 | 224 | 196 | 164 | 69 | 27 | 10 | 3 |

TABLE 7

Post II Anti-ToxA ELISA titers (GMT)

| | Groups | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ag/animal | 3 µg | 1 µg | 0.3 µg | 3 µg | 1 µg | 0.3 µg | 3 µg | 1 µg | 0.3 µg | 3 µg | 1 µg | 0.3 µg |
| Adjuvant | C | C | C | A | A | A | B | B | B | AS04D | AS04D | AS04D |
| 544 | 475 | 416 | 191 | 974 | 530 | 277 | 312 | 332 | 138 | 487 | 597 | 401 |
| 545 | 762 | 834 | 428 | 1466 | 1424 | 688 | 818 | 423 | 650 | 803 | 844 | 849 |

TABLE 8

Post II Anti-ToxB ELISA titers (GMT)

| | Groups | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ag/animal | 3 µg | 1 µg | 0.3 µg | 3 µg | 1 µg | 0.3 µg | 3 µg | 1 µg | 0.3 µg | 3 µg | 1 µg | 0.3 µg |
| Adjuvant | C | C | C | A | A | A | B | B | B | AS04D | AS04D | AS04D |
| 544 (male) | 319 | 686 | 488 | 1181 | 1120 | 1049 | 435 | 401 | 340 | 64 | 56 | 28 |
| 545 (female) | 974 | 1555 | 1419 | 1552 | 1871 | 2386 | 585 | 649 | 1486 | 215 | 109 | 91 |

TABLE 9

Post III day 42 Anti-ToxA ELISA titers (GMT)

| | Groups | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ag/animal | 3 µg | 1 µg | 0.3 µg | 3 µg | 1 µg | 0.3 µg | 3 µg | 1 µg | 0.3 µg | 3 µg | 1 µg | 0.3 µg |
| Adjuvant | C | C | C | A | A | A | B | B | B | AS04D | AS04D | AS04D |
| 544 | 449 | 674 | 471 | 1462 | 720 | 688 | 247 | 486 | 266 | 662 | 599 | 566 |
| 545 | 642 | 814 | 667 | 1654 | 1020 | 1560 | 800 | 539 | 888 | 923 | 1005 | 794 |

TABLE 10

Post III day 42 Anti-ToxB ELISA titers (GMT)

| | Groups | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ag/animal | 3 µg | 1 µg | 0.3 µg | 3 µg | 1 µg | 0.3 µg | 3 µg | 1 µg | 0.3 µg | 3 µg | 1 µg | 0.3 µg |
| Adjuvant | C | C | C | A | A | A | B | B | B | AS04D | AS04D | AS04D |
| 544 | 630 | 612 | 594 | 1259 | 1116 | 1172 | 335 | 426 | 512 | 67 | 86 | 51 |
| 545 | 568 | 831 | 550 | 1213 | 828 | 1273 | 556 | 695 | 944 | 182 | 145 | 134 |

TABLE 11

Post III day 84 Anti-ToxA ELISA titers (GMT)

| | Groups | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ag/animal | 3 µg | 1 µg | 0.3 µg | 3 µg | 1 µg | 0.3 µg | 3 µg | 1 µg | 0.3 µg | 3 µg | 1 µg | 0.3 µg |
| Adjuvant | C | C | C | A | A | A | B | B | B | AS04D | AS04D | AS04D |
| 544 | 213 | 239 | 169 | 357 | 356 | 307 | 106 | 70 | 154 | 182 | 257 | 266 |
| 545 | 311 | 309 | 401 | 595 | 578 | 717 | 311 | 251 | 417 | 353 | 414 | 337 |

TABLE 12

Post III day 84 Anti-ToxB ELISA titers (GMT)

| | Groups | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ag/animal | 3 µg | 1 µg | 0.3 µg | 3 µg | 1 µg | 0.3 µg | 3 µg 1 | 1 µg | 0.3 µg | 3 µg | 1 µg | 0.3 µg |
| Adjuvant | C | C | C | A | A | A | B | B | B | AS04D | AS04D | AS04D |
| 544 (male) | 291 | 195 | 145 | 299 | 360 | 440 | 78 | 70 | 315 | 24 | 25 | 15 |
| 545 (female) | 250 | 299 | 328 | 318 | 374 | 435 | 134 | 211 | 392 | 60 | 41 | 41 |

Example 4

Pims 20120011 and 20120008—Immunisation of Hamsters with F2 Fusion Protein Formulated in Alum, Adjuvant A or Non Adjuvanted.

Groups of 8 female and 8 male hamsters were immunized IM at days 0, 14 and 28 with 1 µg of the F2 fusion protein, His tagged F2 fusion, or a mix of C-terToxA (2387-2706) (0.6 µg)+C-terToxB (1750-2360) (0.4 µg) formulated in Alum, Adjuvant A or non adjuvanted.

Anti-ToxA and anti-ToxB ELISA titers were determined in individual sera collected at day 13, day 27 and day 42 (Post III). FIG. 8

TABLE 13

20120008 and 20120011: Female and Male hamster immunization.
Comparison of the immunogenicity of a Mix (ToxA + ToxB) with the F2 fusion protein formulated in Alum or Adjuvant A ELISA anti-ToxA: concentrations (µg/ml) on individual Post III sera

| Groups | 1 | 2 | 3 | 4 | 5 | 6 |
|---|---|---|---|---|---|---|
| | Mix ToxA (0.6 µg) + ToxB (0.4 µg) | F2 (1 µg) | Mix ToxA (0.6 µg) + ToxB (0.4 µg) | F2 (1 µg) | F2-His tagged (1 µg) | F2 (1 µg) |
| | Al(OH)3 | Al(OH)3 | Adj. A | Adj. A | Adj. A | non-adjuvanted |
| 1 | 62 | 1156 | 41 | 3075 | 4006 | 195 |
| 2 | 77 | 871 | 105 | 1385 | 2463 | 127 |
| 3 | 104 | 833 | 239 | 3119 | 1202 | 31 |
| 4 | 66 | 506 | 143 | 3806 | 3903 | 574 |
| 5 | 179 | 736 | 340 | 3180 | 6852 | 116 |
| 6 | 641 | 1239 | 48 | Dead | 5571 | 32 |
| 7 | 128 | 328 | 345 | 5327 | 3174 | 10 |
| 8 | 48 | 3998 | 63 | 3542 | 4990 | 47 |
| 9 | 59 | 681 | 296 | 888 | 6769 | 13 |
| 10 | 352 | 491 | 164 | 978 | 1192 | 2 |
| 11 | Dead | 604 | 363 | 2913 | 1791 | 3 |

TABLE 13-continued 20120008 and 20120011: Female and Male hamster immunization.
Comparison of the immunogenicity of a Mix (ToxA + ToxB) with the F2 fusion protein formulated in Alum or Adjuvant A
ELISA anti-ToxA: concentrations (µg/ml) on individual Post III sera

| Groups | 1 | 2 | 3 | 4 | 5 | 6 |
|---|---|---|---|---|---|---|
| 12 | 47 | 1524 | 87 | 1231 | 4362 | 68 |
| 13 | 88 | 486 | 77 | 3473 | 1647 | 123 |
| 14 | 23 | 1185 | 62 | 1341 | 4929 | 35 |
| 15 | 254 | 602 | 644 | 2794 | 3085 | 136 |
| 16 | 206 | 1094 | 24 | 2975 | 3354 | 90 |
| Geomean | 101 | 823 | 144 | 2310 | 3234 | 42 |
| CI− | 65 | 612 | 78 | 1727 | 2398 | 20 |
| CI+ | 172 | 1148 | 213 | 3196 | 4381 | 99 |

TABLE 14

20120008 and 20120011: Female and Male hamster immunization.
Comparison of the immunogenicity of a Mix (ToxA + ToxB) with the F2 fusion protein formulated in Alum or Adjuvant A ELISA anti-ToxB: concentrations (µg/ml) on individual Post III sera
Groups

| | 1 | 2 | 3 | 4 | 5 | 6 |
|---|---|---|---|---|---|---|
| | Mix ToxA (0.6 µg) + ToxB(0.4 µg) | F2 (1 µg) | Mix ToxA (0.6 µg) + ToxB(0.4 µg) | F2 (1 µg) | F2-His tagged (1 µg) | F2 (1 µg) |
| | Al(OH)3 | Al(OH)3 | ADJUVANT A | ADJUVANT A | ADJUVANT A | non-adjuvanted |
| 1 | 58 | 591 | 2510 | 2364 | 2647 | 304 |
| 2 | 172 | 302 | 4981 | 952 | 1021 | 302 |
| 3 | 14 | 167 | 1409 | 2630 | 804 | 125 |
| 4 | 53 | 186 | 4158 | 2261 | 1090 | 299 |
| 5 | 107 | 408 | 3046 | 2553 | 2682 | 296 |
| 6 | 925 | 373 | 1190 | Dead | 3808 | 193 |
| 7 | 40 | 65 | 1673 | 2938 | 2820 | 170 |
| 8 | 112 | 1112 | 1809 | 1404 | 3186 | 51 |
| 9 | 160 | 652 | 2701 | 1385 | 2837 | 128 |
| 10 | 24 | 75 | 1210 | 2252 | 1676 | 38 |
| 11 | Dead | 242 | 546 | 1749 | 2174 | 12 |
| 12 | 61 | 1081 | 5746 | 1623 | 2557 | 74 |
| 13 | 15 | 193 | 1975 | 1507 | 2020 | 130 |
| 14 | 56 | 344 | 3499 | 1018 | 4735 | 14 |
| 15 | 15 | 237 | 2897 | 2554 | 2673 | 80 |
| | 332 | 309 | 2489 | 2894 | 2148 | 127 |
| Geomean | 61 | 297 | 2228 | 1834 | 2210 | 100 |
| CI− | 35 | 194 | 1626 | 1542 | 1708 | 59 |
| CI+ | 132 | 457 | 3094 | 2319 | 2850 | 176 |

Geomean = Geometric Mean Titre

Results:

Anti-ToxA and anti-ToxB antibodies were induced after immunization with the F2 fusion protein but also with the mix of ToxA and ToxB. Adjuvant A induces significantly higher ELISA titers compared to other formulations.

Example 5

Immunisation of Mice with Tox A or Tox B Fragments and ToxA-ToxB Fusions
FIGS. 9 to 12

Balb/C mice were immunized with the constructs described in example 1.

Groups of 15 female Balb/c mice were immunized IM at days 0, 14 and 28 with 3 µg or 10 µg of the separate fragments of ToxA and ToxB (ToxA C-term (2387-2706) (0.6 µg)+C-terToxB (1750-2360) as well as with ToxA-ToxB fusions proteins adjuvanted with Adjuvant B. A control group of 10 mice was vaccinated with Adjuvant B alone.

Anti-ToxA and anti-ToxB ELISA titers were determined in individual sera collected at day 42 (post III).

Hemagglutination inhibition titers were determined in pooled Post III sera.

Anti-ToxA and Anti-ToxB ELISA Response: Protocol

Samples of the ToxA or ToxB fragments were coated at 1 µg/ml in phosphate buffered saline (PBS) on high-binding microtitre plates (Nunc MAXISORP™), overnight at 4° C. The plates were blocked with PBS-BSA 1% for 30 min at RT with agitation. The mice anti-sera are prediluted 1/500 in PBS-BSA0.2%-TWEEN™ 0.05%. and then, further two-fold dilutions were made in microplates and incubated at RT for 30 min with agitation. After washing, bound murine antibody was detected using Jackson ImmunoLaboratories Inc. peroxidase-conjugated affiniPure Goat Anti-Mouse IgG (H+L) (ref: 115-035-003) diluted 1:5000 in PBS-BSA0.2%-tween 0.05%. The detection antibodies were incubated for 30 min. at room temperature (RT) with agitation. The color was developed using 4 mg O-phenylenediamine (OPD)+5 µl $H_2O_2$ per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-ToxA or anti-ToxB antibodies present in the sera was expressed in mid-point titers. A GMT was calculated for the 15 samples in each treatment group (10 for the control group).

Hemagglutination Inhibition Assay: Protocol

Serial twofold dilutions of mice pooled antisera (25 μl) were performed in phosphate buffered saline (PBS) in 96-well U-bottom microplates.

25 μl of native Toxin A (0.2 μg/well) were then added and the plates were incubated at room temperature for 30 minutes.

After incubation, 50 μl of purified rabbit erythrocytes diluted at 2% were added to each well. The plates were incubated at 37° C. for 2 hours.

Plates were analysed visually, with hemagglutination presenting as diffuse red cells in the well and the inhibition of hemagglutination observed as a red point settled in the well.

The inhibition titers were defined as the reciprocal of the highest dilution of the serum inhibiting hemagglutination.

Cytotoxicity Assay

IMR90 fibroblast cells were cultured at 37° C. with 5% $CO_2$, in Eagle's Minimal Essential Medium EMEM+10% fetal bovine serum+1% glutamine+1% antibiotics (penicillin-streptomycin-amphotericin) and were seeded in 96-well tissue culture plates at a density of $5.10^4$ cells/well.

After 24 h, the cell media was removed from the wells.

Serial twofold dilutions of mice pooled antisera (50 μl) were performed in cell media.

50 μl of native Toxin B (0.5 ng/ml) is then added and the plates incubated at 37° C. with 5% CO2 for 24 hours.

Cells were observed after 24 hours, and the proportion of rounded cells was determined.

The inhibition titers were defined as the reciprocal of the highest dilution of the serum inhibiting 50% cell rounding.

Results:

Anti-Tox A antibodies were induced after immunization with the ToxA fragment alone but also with each of the 5 fusions.

The functional properties of these antibodies were tested in the hemagglutination assay. This assay is only adapted for Tox A evaluation as no hemagglutination is observed with ToxB.

Haemaglutination inhibition was observed with the anti-Tox A fragment sera or sera directed against each of the ToxA-ToxB fusions.

An ELISA using ToxB antibodies was also performed. Anti-Tox B antibodies were induced after immunization with the ToxB fragment alone but also with the F2, F3 and F4 fusions.

Inhibition titers obtained using sera from mice immunised with the ToxB fragment or the ToxA-ToxB fusions were greater than that obtained using control sera.

Example 6

Immunisation of Mice with Tox A-Tox B Fusions

Balb/c mice were immunised with the four fusion protein constructs F54 Gly (SEQ ID NO:11), F54 New (SEQ ID NO:13), F5 ToxB (SEQ ID NO:15) and F52 New (SEQ ID NO:17) as described in example 5.

An ELISA was carried out using the anti-ToxA and anti-ToxB ELISA response:protocol described in example 5 except here the samples of the toxA or toxB fragments were coated at 2 μg/ml in phosphate buffered saline on high-binding microtitre plates. A hemagglutination inhibition assay was performed as described in example 5. A toxB cytotoxicity assay was performed as described in example 5. A further toxA cytotoxicity assay was performed as described below.

Groups of 25 female mice were immunized IM at days 0, 14 and 28 with 3 μg of the ToxA-ToxB fusion proteins formulated in Adjuvant B or 10 μg of a non-adjuvanted mix of ToxA (6 μg)+ToxB (4 μg). In addition to F2, the four other fusion protein constructs are F54 Gly (SEQ ID NO:21), F54 New (SEQ ID NO:23), F5 ToxB (SEQ ID NO:25) and F52 New (SEQ ID NO:27)

Figure 13:
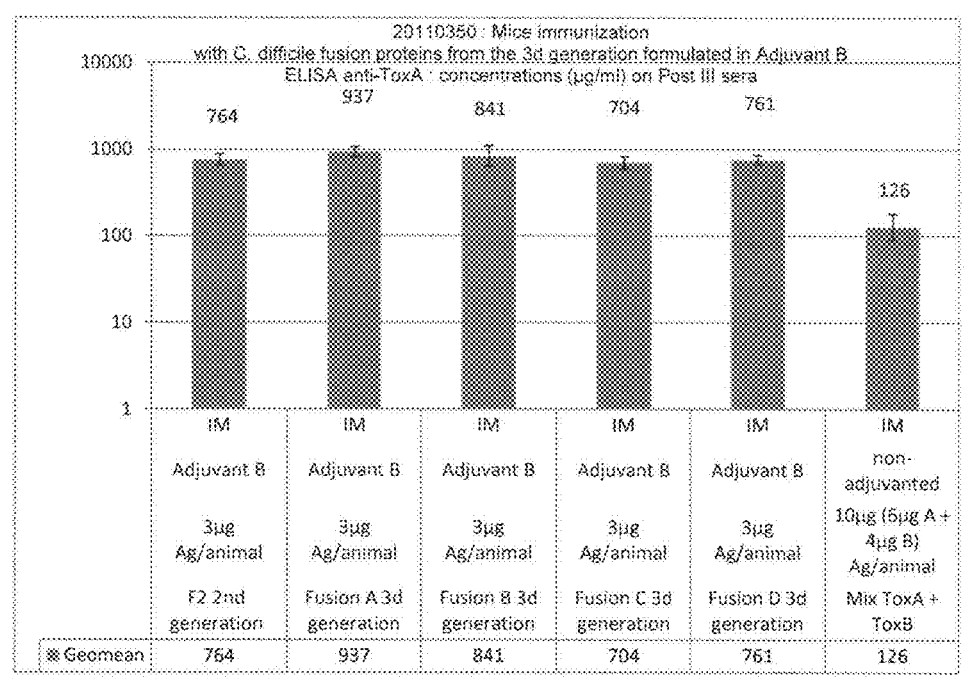
FIG. 13—Graph showing anti-ToxA ELISA results for mice immunised with the F2, F52New, F54Gly, G54New or F5 ToxB fusions formulated in Adjuvant B.
Figure 14:
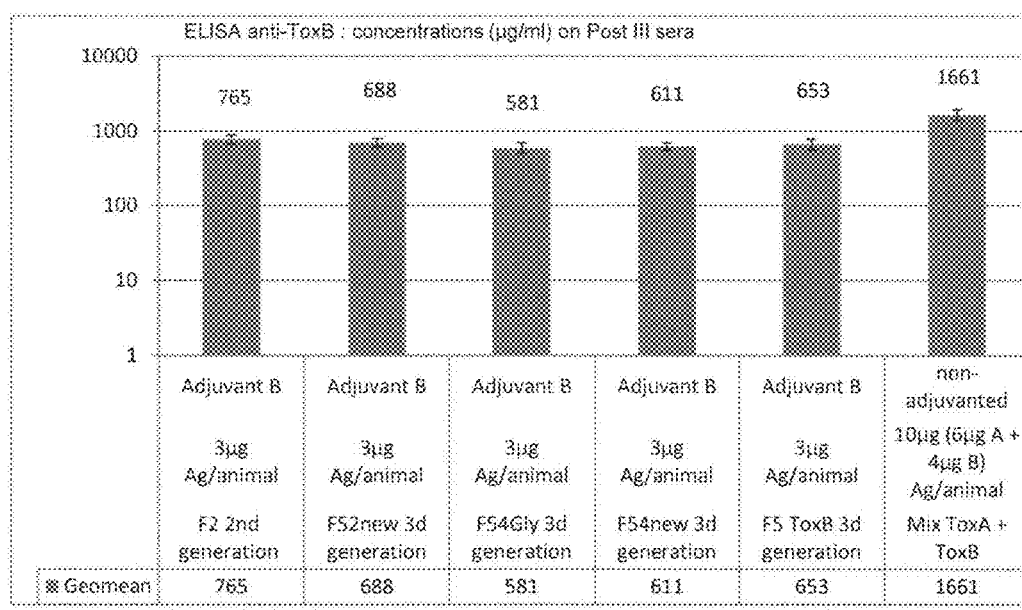
FIG. 14—Graph showing anti-ToxB ELISA results for mice immunised with the F2, F52New, F54Gly, F54New or F5ToxB fusions formulated in Adjuvant B.

Anti-ToxA and anti-ToxB ELISA titers were determined in individual sera collected at day 42 (Post III 14). FIGS. 13 and 14

TABLE 15

20110350: Mice immunization with *C. difficile* fusion proteins formulatd in Adjuvant B ELISA a-ToxA: concentrations (μg/ml) on Post III sera

| Groups | 1 | 2 | 3 | 4 | 5 | 6 |
|---|---|---|---|---|---|---|
| | F2 | Fusion A (F52new) | Fusion B (F54Gly) | Fusion C (F54new) | Fusion D (F5 ToxB) | Mix ToxA + ToxB |
| | 3 μg Ag/animal | 3 μg Ag/animal | 3 μg Ag/animal | 3 μg Ag/animal | 3 μg Ag/animal | 10 μg (6 μg A + 4 μg B) Ag/animal |
| | ADJUVANT B IM | ADJUVANT B IM | ADJUVANT B IM | ADJUVANT B IM | ADJUVANT B IM | non-adjuvanted IM |
| 1 | 518 | 681 | 735 | 436 | 586 | 328 |
| 2 | 761 | 1058 | 975 | 455 | 1252 | 22 |
| 3 | 557 | 718 | 977 | 684 | 1108 | 327 |
| 4 | 1415 | 992 | 862 | 577 | 555 | 152 |
| 5 | 782 | 457 | 1202 | 861 | 622 | 135 |
| 6 | 563 | 724 | 611 | 575 | 569 | 54 |
| 7 | 615 | 585 | 1330 | 824 | 807 | 147 |
| 8 | 994 | 878 | 611 | 576 | 1108 | 169 |
| 9 | 412 | 623 | Dead | 389 | 887 | 124 |
| 10 | 495 | 993 | Dead | 809 | 1146 | 219 |
| 11 | 366 | 1039 | 923 | 872 | 965 | 12 |
| 12 | 1075 | 1089 | 1454 | 748 | 950 | 122 |
| 13 | 882 | 754 | 1176 | 809 | 725 | 196 |
| 14 | 1028 | 1550 | 1164 | 1578 | 696 | 312 |

TABLE 15-continued

20110350: Mice immunization with *C. difficile* fusion proteins formulatd in Adjuvant B ELISA a-ToxA: concentrations (µg/ml) on Post III sera

| Groups | 1 | 2 | 3 | 4 | 5 | 6 |
|---|---|---|---|---|---|---|
| 15 | 738 | 1268 | 1170 | 1352 | 678 | 188 |
| 16 | 519 | 721 | 1028 | 781 | 930 | 224 |
| 17 | 927 | 890 | 805 | 346 | 791 | 209 |
| 18 | 946 | 992 | 647 | 1255 | 410 | 32 |
| 19 | 715 | 1346 | 1142 | 670 | 634 | 92 |
| 20 | 546 | Dead | 1061 | Dead | Dead | 166 |
| 21 | 1107 | 1604 | 826 | 1038 | 791 | 112 |
| 22 | 1351 | 1289 | 1223 | 708 | 778 | 66 |
| 23 | 889 | 1319 | 61 | 567 | 759 | 102 |
| 24 | 976 | 824 | 597 | 414 | 456 | 281 |
| 25 | 1153 | 1212 | 995 | 868 | 758 | 242 |
| Geomean | 764 | 937 | 841 | 704 | 761 | 126 |
| CI− | 656 | 818 | 641 | 597 | 674 | 89 |
| CI+ | 889 | 1074 | 1103 | 830 | 858 | 179 |

TABLE 16

20110350: Mice immunization with *C. difficile* fusion proteins formulatd in Adjuvant B ELISA a-ToxB: concentrations (µg/ml) on Post III sera

| Groups | 1 | 2 | 3 | 4 | 5 | 6 |
|---|---|---|---|---|---|---|
|  | F2 | Fusion A (F52new) | Fusion B (F54Gly) | Fusion C (F54new) | Fusion D (F5 ToxB) | Mix ToxA + ToxB |
|  | 3 µg Ag/animal | 3 µg Ag/animal | 3 µg Ag/animal | 3 µg Ag/animal | 3 µg Ag/animal | 10 µg (6 µg A + 4 µg B) Ag/animal |
|  | ADJUVANT B | ADJUVANT B | ADJUVANT B | ADJUVANT B | ADJUVANT B | ADJUVANT B |
| 1 | 916 | 749 | 736 | 454 | 581 | 1823 |
| 2 | 1090 | 551 | 491 | 517 | 872 | 575 |
| 3 | 687 | 1178 | 574 | 549 | 529 | 1386 |
| 4 | 940 | 868 | 501 | 536 | 828 | 854 |
| 5 | 837 | 522 | 653 | 420 | 866 | 1170 |
| 6 | 836 | 609 | 397 | 757 | 690 | 2132 |
| 7 | 309 | 702 | 405 | 792 | 732 | 1466 |
| 8 | 569 | 381 | 598 | 737 | 856 | 1539 |
| 9 | 382 | 450 | Dead | 914 | 632 | 1461 |
| 10 | 552 | 693 | Dead | 465 | 639 | 2267 |
| 11 | 679 | 832 | 1273 | 520 | 505 | 1037 |
| 12 | 1123 | 575 | 809 | 551 | 431 | 2273 |
| 13 | 764 | 659 | 532 | 1077 | 930 | 1405 |
| 14 | 944 | 970 | 909 | 1065 | 870 | 1978 |
| 15 | 812 | 628 | 222 | 727 | 1052 | 1414 |
| 16 | 502 | 552 | 736 | 560 | 1001 | 1269 |
| 17 | 983 | 639 | 551 | 431 | 728 | 1732 |
| 18 | 1133 | 628 | 604 | 561 | 1085 | 1211 |
| 19 | 938 | 1058 | 805 | 470 | 435 | 2017 |
| 20 | 519 | Dead | 857 | Dead | Dead | 2140 |
| 21 | 887 | 1025 | 319 | 670 | 310 | 2342 |
| 22 | 861 | 769 | 596 | 555 | 1025 | 2897 |
| 23 | 903 | 1161 | 552 | 694 | 260 | 2343 |
| 24 | 1327 | 536 | 431 | 737 | 313 | 3074 |
| 25 | 674 | 518 | 680 | 472 | 663 | 2697 |
| Geomean | 765 | 688 | 581 | 611 | 653 | 1661 |
| CI− | 663 | 607 | 495 | 545 | 550 | 1411 |
| CI+ | 884 | 781 | 682 | 686 | 776 | 1957 |

Figure 16:
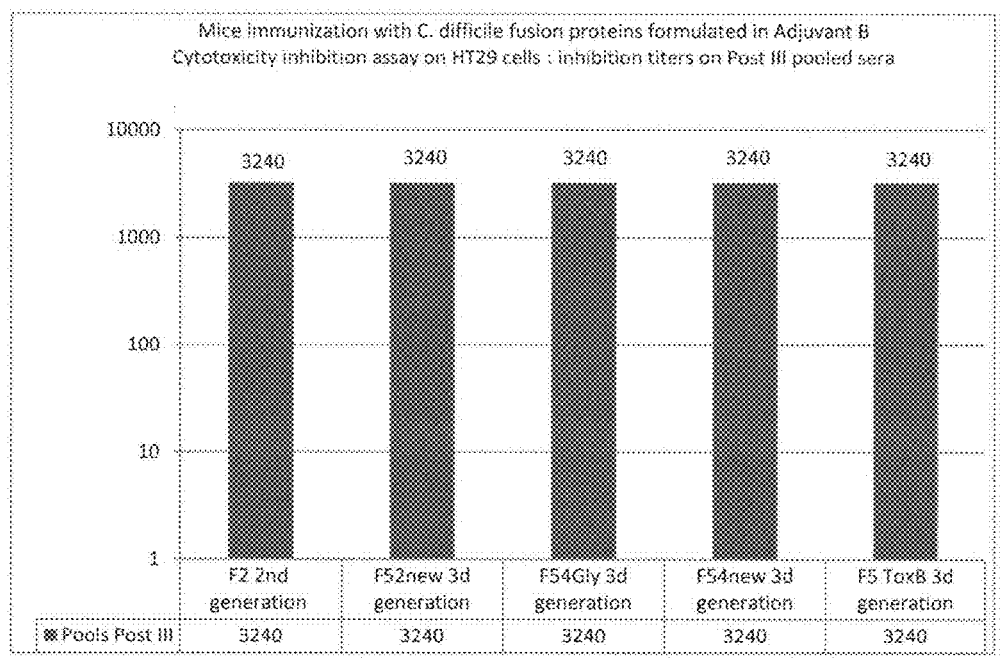
FIG. 16—Graph showing cytotoxicity titres in HT29 cells from mice immunised with the F2, F52New, F54Gly, F54New or F5ToxB fusions formulated in Adjuvant B.
Figure 17:
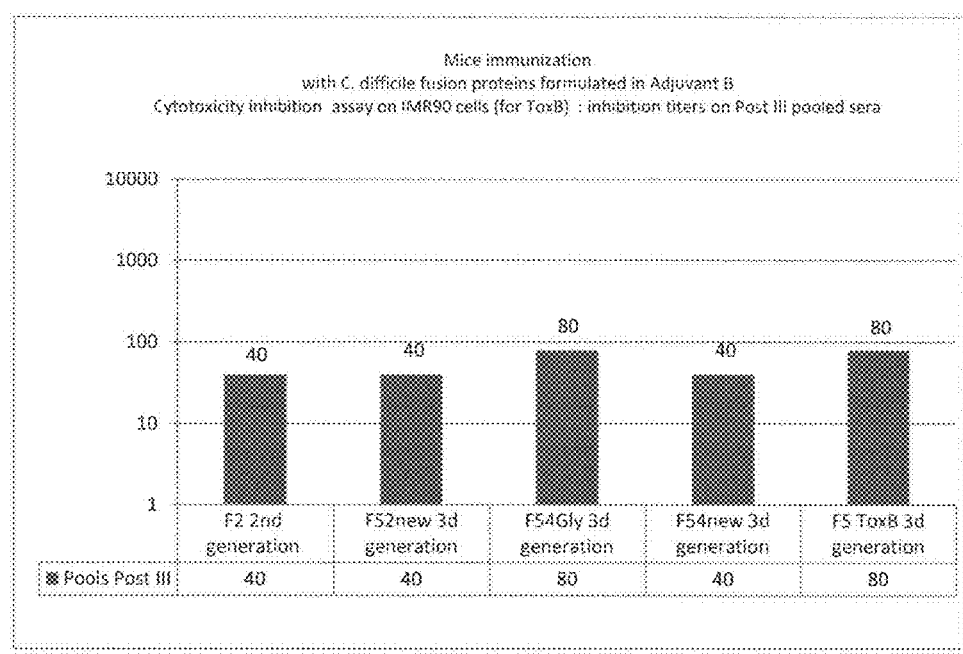
FIG. 17—Graph showing cytotoxicity titres in IMR90 cells from mice immunised with the F2, F52New, F54Gly, F54New or F5ToxB fusions formulated in Adjuvant B.

FIGS. 15 to 17

A hemagglutination inhibition assay was performed as described in example 5.

A toxB cytotoxicity assay was performed as described in example 5. A further toxA cytotoxicity assay was performed as described below.

ToxA Cytotoxicity Assay

HT29 cells were cultured at 37° C. with 5% $CO_2$ in DMEM+10% fetal bovine serum+1% glutamine+1% antibiotics (penicillin-streptomycin-amphotericin) and were seeded in 96-well tissue culture plates at a density of $5 \cdot 10^4$ cells/well. After 24 h, the cell media was removed from the wells. Serial twofold dilutions of mice pooled antisera (50 µl) were performed in cell media.

50 µl of native Toxin A (0.15 ng/ml) is then added and the plates incubated at 37° C. with 5% $CO_2$ for 48 hours. Cells were observed after 48 hours and the proportion of rounded cells were determined. The results of the anti-ToxA ELISA, anti-ToxB Elisa, Haemagglutination inhibition and cytotoxicity assays are described in the aforementioned FIGS. 13 to 17.

Example 7

Figure 18:
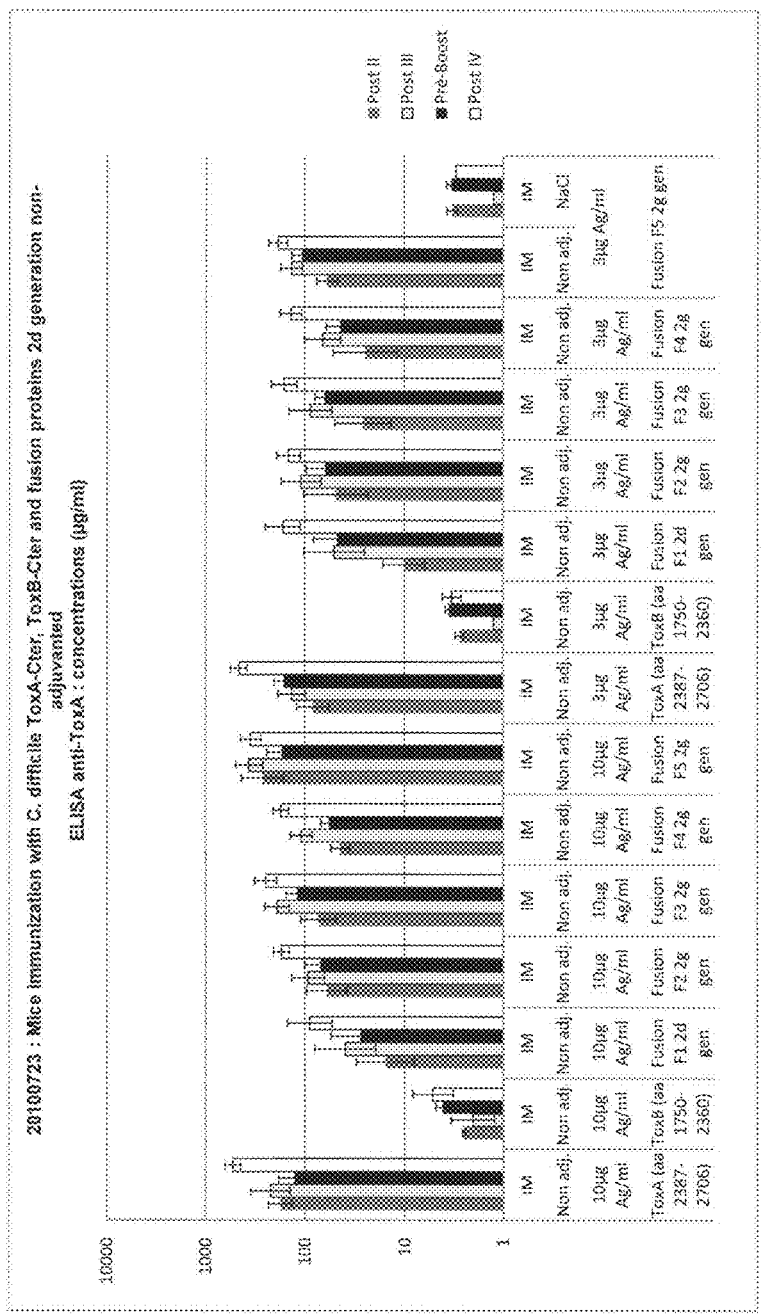
FIG. 18—Graph showing anti-ToxA ELISA results for mice immunised with *C. difficile* ToxA-Cter (aa 2387-2706), ToxB-Cter (aa 1750-2360) and fusion proteins (non-adjuvanted).
Figure 19:
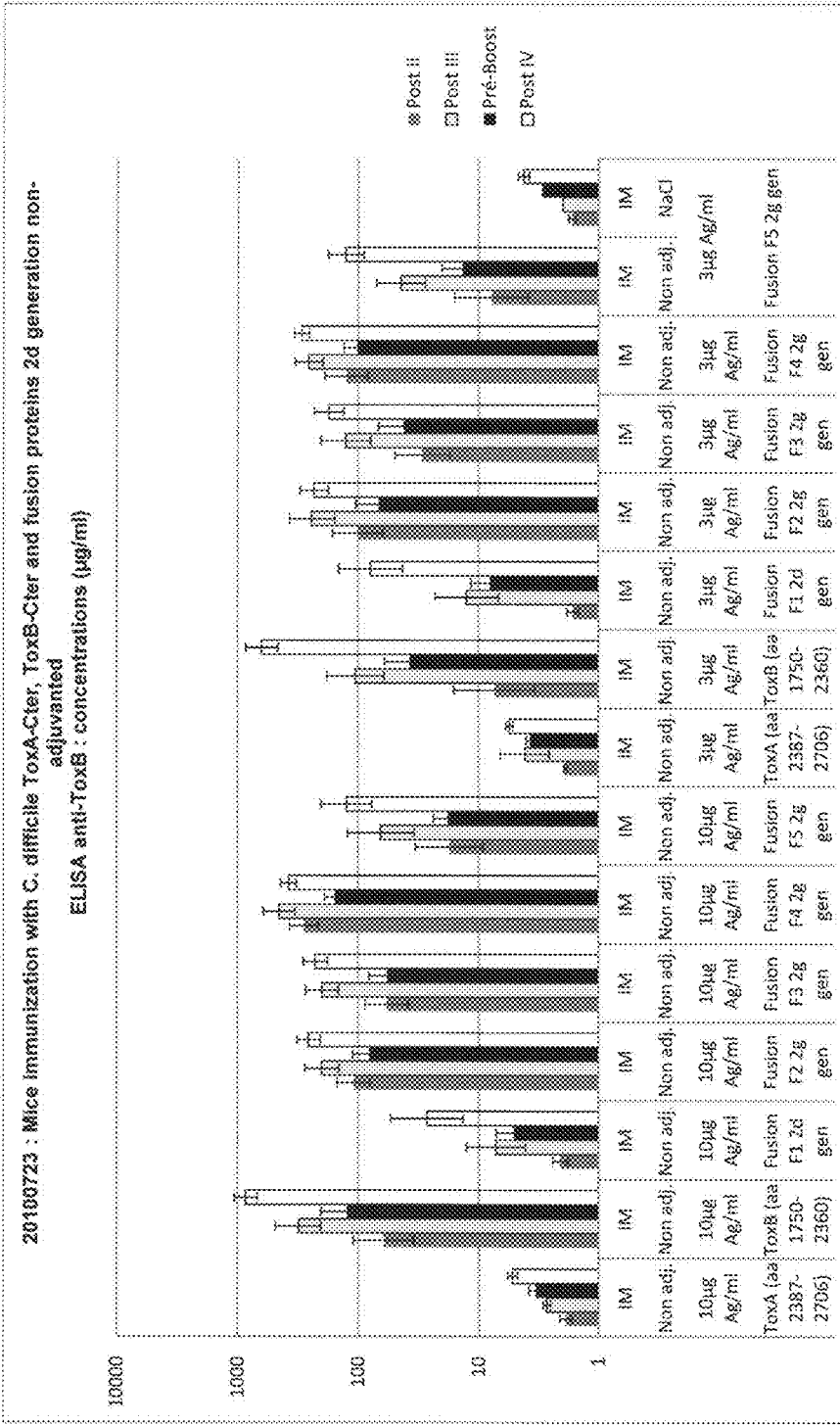
FIG. 19—Graph showing anti-ToxB ELISA results for mice immunised with *C. difficile* ToxA-Cter (aa 2387-2706), ToxB-Cter (aa 1750-2360) and fusion proteins (non-adjuvanted)

Immunisation of Mice with *C. difficile* ToxA-Cter, ToxB-Cter or Fusion Proteins in a Non-Adjuvanted Formulation Groups of 15 female mice were immunized IM at days 0, 14 28 and 120 with 1 or 3 μg of ToxA C-ter, ToxB C-ter or ToxA-ToxB fusion proteins. All these antigens were injected in a non-adjuvanted formulation. A control group (10 mice) was injected with the NaCl alone. Anti-ToxA and anti-ToxB ELISA titers were measured from individual sera collected at day 28 (Post II), day 42 (Post III 14), day 120 (Pre-Boost 87) and day 134 (Post IV 14). FIGS. 18 and 19.

TABLE 17

20100723: Mice immunization with *C. difficile* ToxA-Cter, ToxB-Cter and fusion proteins non-adjuvanted

| | ELISA a-ToxA: GMT concentrations (μg/ml) | | | | | | | |
|---|---|---|---|---|---|---|---|---|
| Bleeding | 1 | 2 | 3 | 4 | 5 | 6 | 7 | 8 |
| | ToxA (aa 2387-2706) | ToxB (aa 1750-2360) | Fusion F1 | Fusion F2 | Fusion F3 | Fusion F4 | Fusion F5 | ToxA (aa 2387-2706) |
| Ag/ml | 10 μg | 10 μg | 10 μg | 10 μg | 10 μg | 10 μg | 10 μg | 3 μg |
| Adjuvant | Non adj. IM | Non adj. IM | Non adj. IM | Non adj. IM | Non adj. IM | Non adj. IM | Non adj. IM | Non adj. IM |
| Post II | 178 | 3 | 16 | 60 | 74 | 44 | 269 | 84 |
| Post III | 222 | 2 | 40 | 94 | 192 | 109 | 366 | 137 |
| Pre-Boost | 128 | 4 | 28 | 70 | 120 | 58 | 172 | 165 |
| Post IV | 539 | 5 | 90 | 174 | 249 | 177 | 353 | 466 |

| | ELISA a-ToxA: GMT concentrations (μg/ml) | | | | | | |
|---|---|---|---|---|---|---|---|
| Bleeding | 9 | 10 | 11 | 12 | 13 | 14 | 15 |
| | ToxB (aa 1750-2360) | Fusion F1 | Fusion F2 | Fusion F3 | Fusion F4 | Fusion F5 | |
| Ag/ml | 3 μg | 3 μg | 3 μg | 3 μg | 3 μg | 3 μg Ag/ml | |
| Adjuvant | Non adj. IM | Non adj. IM | Non adj. IM | Non adj. IM | Non adj. IM | Non adj. IM | NaCl IM |
| Post II | 3 | 10 | 49 | 26 | 25 | 60 | 3 |
| Post III | 1.25 | 51 | 110 | 88 | 67 | 137 | 1.25 |
| Pre-Boost | 4 | 48 | 62 | 63 | 44 | 107 | 3 |
| Post IV | 3 | 168 | 147 | 163 | 139 | 188 | 3 |

TABLE 18

20100723: Mice immunization with *C. difficile* ToxA-Cter, ToxB-Cter and fusion proteins non-adjuvanted

| | ELISA a-ToxB: GMT concentrations (μg/ml) | | | | | | | |
|---|---|---|---|---|---|---|---|---|
| Bleeding | 1 | 2 | 3 | 4 | 5 | 6 | 7 | 8 |
| | ToxA (aa 2387-2706) | ToxB (aa 1750-2360) | Fusion F1 | Fusion F2 | Fusion F3 | Fusion F4 | Fusion F5 | ToxA (aa 2387-2706) |
| Ag/ml | 10 μg | 10 μg | 10 μg | 10 μg | 10 μg | 10 μg | 10 μg | 3 μg |
| Adjuvant | Non adj. IM | Non adj. IM | Non adj. IM | Non adj. IM | Non adj. IM | Non adj. IM | Non adj. IM | Non adj. IM |
| Post II | 2 | 62 | 2 | 110 | 58 | 283 | 18 | 2 |
| Post III | 3 | 316 | 7 | 200 | 199 | 455 | 65 | 4 |
| Pre-Boost | 3 | 125 | 5 | 81 | 58 | 157 | 18 | 4 |
| Post IV | 5 | 856 | 27 | 258 | 227 | 380 | 125 | 6 |

| | ELISA a-ToxB: GMT concentrations (μg/ml) | | | | | | |
|---|---|---|---|---|---|---|---|
| Bleeding | 9 | 10 | 11 | 12 | 13 | 14 | 15 |
| | ToxB (aa 1750-2360) | Fusion F1 | Fusion F2 | Fusion F3 | Fusion F4 | Fusion F5 | |
| Ag/ml | 3 μg | 3 μg | 3 μg | 3 μg | 3 μg | 3 μg Ag/ml | |
| Adjuvant | Non adj. IM | Non adj. IM | Non adj. IM | Non adj. IM | Non adj. IM | Non adj. IM | NaCl IM |
| Post II | 7 | 2 | 101 | 29 | 125 | 8 | 2 |

TABLE 18-continued

20100723: Mice immunization with *C. difficile* ToxA-Cter, ToxB-Cter and fusion proteins non-adjuvanted

| | | | | | | | |
|---|---|---|---|---|---|---|---|
| Post III | 105 | 13 | 242 | 126 | 257 | 44 | 2 |
| Pre-Boost | 38 | 8 | 68 | 42 | 101 | 14 | 3 |
| Post IV | 632 | 79 | 232 | 175 | 293 | 126 | 4 |

Example 8

Immunisation of Mice with *C. difficile* ToxA-Cter, ToxB-Cter or Fusion Proteins Formulated in Adjuvant B.

Figure 20:
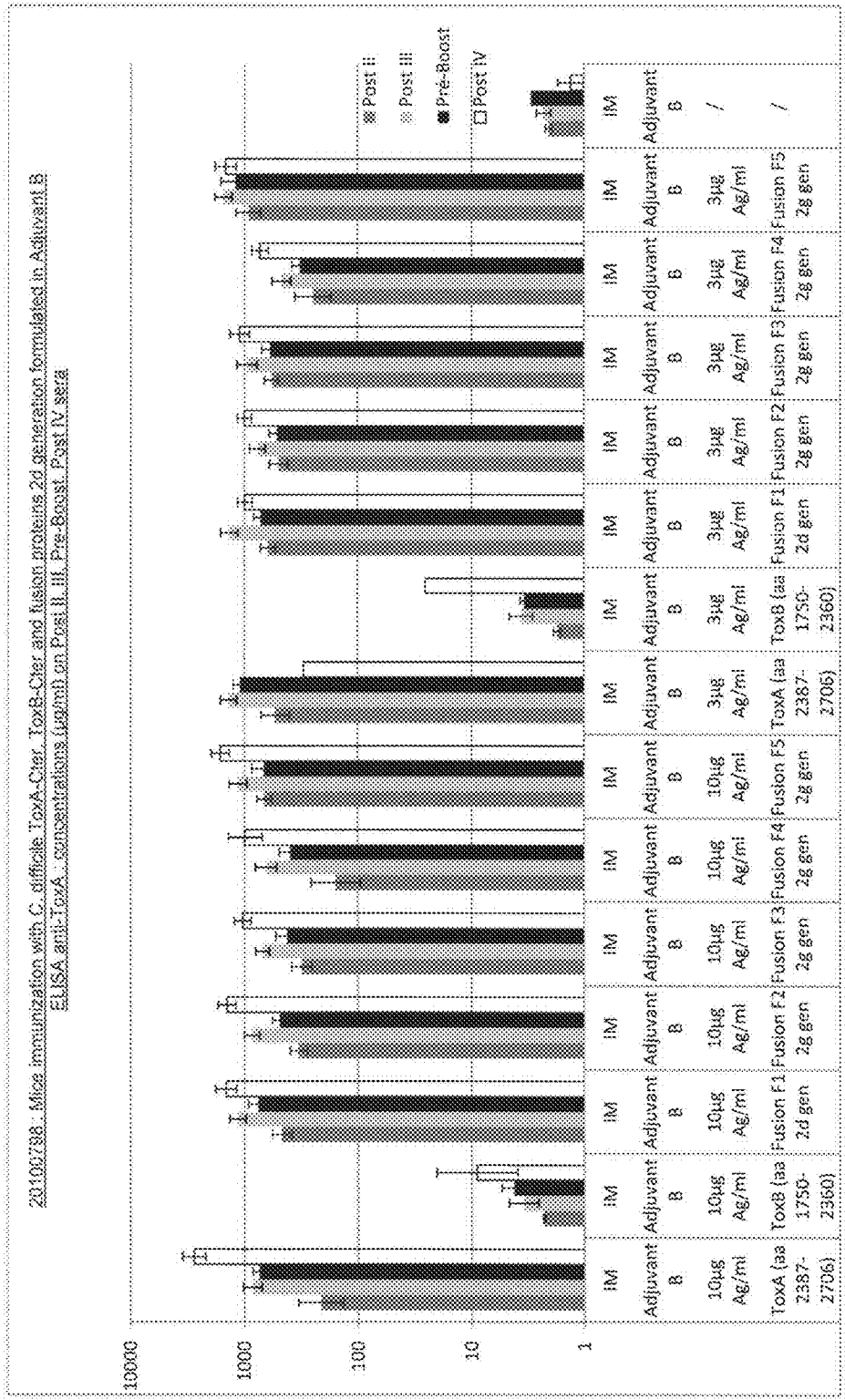
FIG. 20—Graph showing anti-ToxA ELISA results for mice immunised with *C. difficile* ToxA-Cter (aa 2387-2706), ToxB-Cter (aa 1750-2360) and fusion proteins formulated in Adjuvant B: Post II, III, Pre-Boost, Post IV sera.
Figure 21:
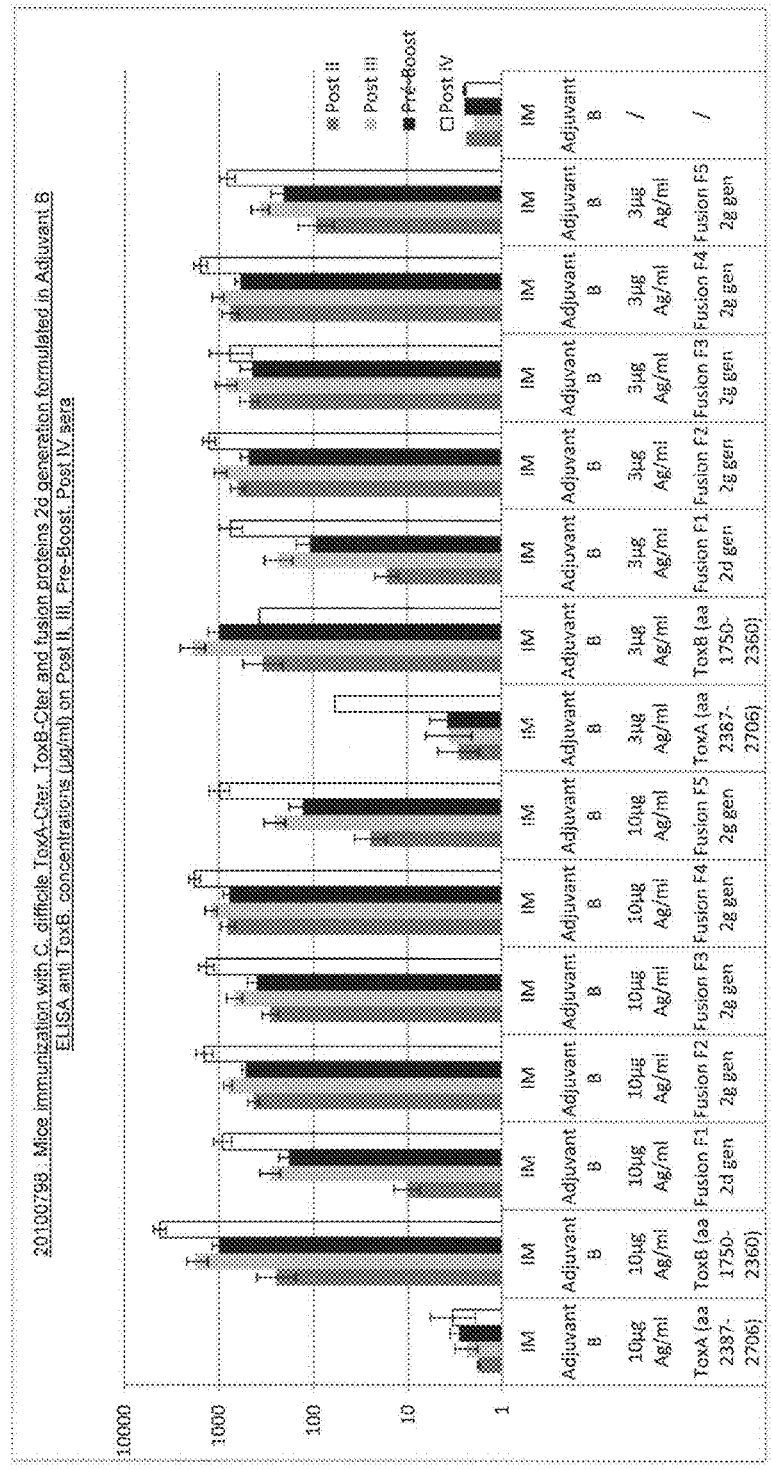
FIG. 21—Graph showing anti-ToxB ELISA results for mice immunised with *C. difficile* ToxA-Cter (aa 2387-2706), ToxB-Cter (aa 1750-2360) and fusion proteins formulated in Adjuvant B: Post II, III, Pre-Boost, Post IV sera.

FIGS. 20 and 21

Groups of 15 female mice were immunized IM at days 0, 14 and 28 with 1 or 3 µg of ToxA C-term (amino acids 2387-2706) and ToxB C-term (amino acids 1750-2360) or ToxA-ToxB fusion proteins. These proteins were injected in an Adjuvant B formulation.

A control group (10 mice) was injected with the Adjuvant B alone.

Anti-ToxA and anti-ToxB ELISA titers were determined in individual sera collected at day 28 (Post II), day 42 (Post III 14), day 120 (Pre Boost III 87) and day 134 (Post IV 14).

TABLE 19

Mice immunization with *C. difficile* ToxA-Cter, ToxB-Cter and fusion proteins formulated in Adjuvant B ELISA a-ToxA: concentrations (µg/ml) on Post II, III, Pre-Boost, Post IV sera

| Bleeding | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | ToxA (aa 2387-2706) | ToxB (aa 1750-2360) | F1 | F2 | F3 | F4 | F5 | ToxA (aa 2387-2706) | ToxB (aa 1750-2360) | F1 | F2 | F3 | F4 | F5 | n / |
| Ag/ml | 10 µg | 10 µg | 10 µg | 10 µg | 10 µg | 10 µg | 10 µg | 3 µg | 3 µg | 3 µg | 3 µg | 3 µg | 3 µg | 3 µg | / |
| ADJUVANT | B | B | B | B | B | B | B | B | B | B | B | B | B | B | B |
| | IM | IM | IM | IM | IM | IM | IM | IM | IM | IM | IM | IM | IM | IM | IM |
| Post II | 213 | 2.3 | 465 | 332 | 312 | 158 | 672 | 534 | 1.7 | 620 | 498 | 578 | 248 | 925 | 2.1 |
| Post III | 852 | 3 | 1144 | 859 | 695 | 644 | 1137 | 1376 | 4 | 1356 | 768 | 950 | 470 | 1537 | 2 |
| Pre-Boost | 738 | 4 | 762 | 484 | 417 | 394 | 674 | 1091 | 3 | 725 | 513 | 598 | 324 | 1197 | 3 |
| Post IV | 2764 | 9 | 1450 | 1423 | 1036 | 986 | 1626 | 301 | 26 | 990 | 1000 | 1099 | 732 | 1465 | 1 |

TABLE 20

20100798: Mice immunization with *C. difficile* ToxA-Cter, ToxB-Cter and fusion proteins formulated in Adjuvant B ELISA a-ToxB: concentrations (µg/ml) on Post II, III, Pre-Boost, Post IV sera

| Bleeding | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | ToxA (aa 2387-2706) | ToxB (aa 1750-2360) | F1 | F2 | F3 | F4 | F5 | ToxA (aa 2387-2706) | ToxB (aa 1750-2360) | F1 | F2 | F3 | F4 | F5 | / |
| Ag/ml | 10 µg | 10 µg | 10 µg | 10 µg | 10 µg | 10 µg | 10 µg | 3 µg | 3 µg | 3 µg | 3 µg | 3 µg | 3 µg | 3 µg | / |
| ADJUVANT | B | B | B | B | B | B | B | B | B | B | B | B | B | B | B |
| | IM | IM | IM | IM | IM | IM | IM | IM | IM | IM | IM | IM | IM | IM | IM |
| Post II | 2 | 246 | 10 | 424 | 284 | 794 | 25 | 3 | 338 | 17 | 619 | 471 | 753 | 93 | 2 |
| Post III | 2 | 1762 | 285 | 793 | 671 | 1204 | 253 | 4 | 1888 | 232 | 951 | 834 | 1026 | 365 | 2 |
| Pre-Boost | 3 | 989 | 180 | 512 | 396 | 761 | 129 | 4 | 984 | 108 | 479 | 441 | 581 | 205 | 3 |
| Post IV | 3 | 4212 | 911 | 1422 | 1353 | 1799 | 1046 | 78 | 657 | 738 | 1272 | 747 | 1572 | 812 | 2 |

Example 9

Cloning Expression and Purification of the Fusion Proteins
Expression Plasmid and Recombinant Strain Genes encoding the fusion proteins of partial C-terminal domains of ToxA and ToxB (SEQ ID NO:3, 4, 5, 6 and 7) and a His tag were cloned into the pET24b(+) expression vector (Novagen) using the NdeI/XhoI restriction sites using standard procedures. The final construct was generated by the transformation of *E. coli* strain BLR (DE3) with the recombinant expression vector according to standard method with CaCl2-treated cells (Hanahan D.<<Plasmid transformation by Simanis.>> In Glover, D. M. (Ed), DNA cloning. IRL Press London. (1985): p. 109-135.).

Host Strain:

BLR(DE3). BLR is a recA derivative of BL21. Strains having the designation (DE3) are lysogenic for a A prophage that contains an IPTG inducible T7 RNA polymerase. A DE3 lysogens are designed for protein expression from pET vectors This strain is also deficient in the Ion and ompT proteases.

Genotype: *E. coli* BLR::DE3 strain, $F^-$ ompT $hsdS_B(r_B^- m_B^-)$ gal dcm (DE3) Δ(srl-recA)306::Tn10 ($Tet^R$)

Expression of the Recombinant Proteins:

An *E. coli* transformant was stripped from agar plate and used to inoculate 200 ml of LBT broth±1% (w/v) glucose+kanamycin (50 μg/ml) to obtain O.D.600 nm between 0.1-0.2. Cultures were incubated overnight at 37° C., 250 RPM.

This overnight culture was diluted to 1:20 in 500 ml of LBT medium containing kanamycin (50 μg/ml) and grown at 37° C. at a stirring speed of 250 rpm until O.D.620 reached 0.5/0.6.

At O.D.600 nm around 0.6, the culture was cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After overnight induction (around 16 hours), $O.D._{600nm}$ was evaluated after induction and culture was centrifuged at 14 000 RPM for 15 minutes and pellets were frozen at −20° C. separately.

Purification:

The bacterial pellet was resuspended in 20 mM bicine buffer (pH 8.0) containing 500 mM NaCl and a mixture of protease inhibitor (Complete, Roche). Bacteria were lysed using a French Press system 20 000 PSI. Soluble (supernatant) and insoluble (pellet) components were separated by centrifugation for example at 20 000 g for 30 min at 4° C.

The 6-His tagged-protein was purified under native conditions on IMAC. The soluble components were loaded on a GE column (15 ml for example) (Ni loaded) preequilibrated with the same buffer used to bacterial resuspension. After loading on the column, the column was washed with the same buffer. Elution was performed using a 20 mM bicine buffer (pH 8.0) containing 500 mM NaCl and different concentrations of imidazole (5-600 mM). After gel analysis, more pure fractions were selected, concentrated and loaded on SEC chromatography for further purification step.

Fractions containing the fusion proteins were selected on the basis of purity by SDS-PAGE and dialyzed against bicine buffer (20 mM Bicine, 150 mM NaCl, with or without 5 mM EDTA pH8.0), Protein concentration was determined using DC Protein Assay of BioRad. Proteins were thus pooled, sterile-filtered on 0.22 μm, stored at −80° C.

Alternatively, IMAC purification was preceded by a DEAE purification step using 2 mM bicine buffer (pH 8.0) for loading and washing, and eluted using a gradient with the same buffer but with 1M NaCl added.

Example 10

Cloning Expression and Purification of the Separate *C. difficile* Tox A and Tox B Fragments Expression Plasmid and Recombinant Strain.

Genes encoding the protein fragments of ToxA and ToxB (SEQ ID NO:8 and SEQ ID NO:9) and a His tag were cloned into the pET24b(+) expression vector (Novagen) using the NdeI/XhoI restriction sites using standard procedures. The final construct was generated by the transformation of *E. coli* strain BLR (DE3) with the recombinant expression vector according to standard method with CaCl2-treated cells (Hanahan D.<<Plasmid transformation by Simanis.>> In Glover, D. M. (Ed), DNA cloning. IRL Press London. (1985): p. 109-135.).

Host Strain:

BLR(DE3). BLR is a recA derivative of BL21. Strains having the designation (DE3) are lysogenic for a λ prophage that contains an IPTG inducible T7 RNA polymerase. λ DE3 lysogens are designed for protein expression from pET vectors This strain is also deficient in the Ion and ompT proteases.

Genotype: *E. coli* BLR::DE3 strain, $F^-$ ompT $hsdS_B(r_B^- m_B^-)$ gal dcm (DE3) Δ(srl-recA)306::Tn10 ($Tet^R$)

Expression of the Recombinant Proteins:

A *E. coli* transformant was stripped from agar plate and used to inoculate 200 ml of LBT broth±1% (w/v) glucose+kanamycin (50 μg/ml) to obtain $O.D._{600nm}$ between 0.1-0.2. Cultures were incubated overnight at 37° C., 250 RPM.

This overnight culture was diluted to 1:20 in 500 ml of LBT medium containing kanamycin (50 μg/ml) and grown at 37° C. at a stirring speed of 250 rpm until $O.D._{620}$ reached 0.5/0.6.

At an O.D. at 600 nm of around 0.6, the culture was cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After the overnight induction (around 16 hours), O.D. at 600 nm was evaluated after induction and culture was centrifuged at 14 000 RPM for 15 minutes and pellets were frozen at −20° C. separately.

Purification:

The bacterial pellet was resuspended in 20 mM bicine buffer (pH 8.0) containing 500 mM NaCl supplemented by a mixture of protease inhibitor (Complete without EDTA, Roche cat 11873580001) and benzonase. (Roche cat 1.01695.0001). Bacteria were lysed using a French Press system 2×20 000 PSI. Soluble (supernatant) and insoluble (pellet) components were separated by centrifugation at 34 000 g or 48 000 g for 25-30 min at 4° C. Supernatant was harvested and filtrated on 0.22 μm filter.

The 6-His tagged-protein was purified under native conditions on IMAC. The soluble components were loaded on a GE column (for example 15 ml) (Ni loaded) pre-equilibrated with the same buffer used to bacterial resuspension. After loading, the column was washed with the same buffer.

For ToxA:

Elution was performed using a 20 mM bicine buffer (pH 8.0) containing 500 mM NaCl and different concentrations of imidazole (5-100 mM). After gel analysis, more pure fractions were selected, concentrated and loaded on SEC chromatography (SUPERDEX™ 75) for further purification step in the same buffer without imidazole.

For ToxB:

A second wash was performed with 20 mM bicine buffer (pH 8.0) containing 500 mM NaCl and 0.5% deoxycholate or same buffer with 150 mM NaCl. Elution was performed using a 20 mM bicine buffer (pH 8.0) containing 500 mM NaCl and different concentrations of imidazole (10-500 mM). After gel analysis, more pure fractions were selected, supplemented with 5 mM EDTA and loaded on SEC chromatography (SUPERDEX™ 200) for further purification step in same buffer with 5 mM EDTA.

Fractions containing ToxA or ToxB fragments were selected on the basis of purity by SDS-PAGE and dialyzed against bicine buffer (20 mM Bicine, 150 mM NaCl, pH8.0), protein concentration was determined using RCDC Protein Assay of BioRad. Proteins were thus pooled, sterile-filtered on 0.22 μm, stored at −80° C.

Example 11

Molecular Weight Evaluation of the Five *C. difficile* ToxA-ToxB Fusions

Analytical ultracentrifugation is used to determine the homogeneity and size distribution in solution of the different species within a protein sample by measuring the rate at which molecules move in response to a centrifugal force. This is based on the calculation of the coefficients of sedimentation of the different species that are obtained by sedimentation velocity experiment, which depend on their molecular shape and mass.

1. Protein samples are spun in a Beckman-Coulter PROTEOMELAB™ XL-1 analytical ultracentrifuge at 42 000 RPM after the AN-60Ti rotor had been equilibrated to 15° C.
   a. F1 fusion protein, 500 μg/ml, 20 mM Bicine, 150 mM NaCl, pH8.0
   b. F2 fusion protein, 500 μg/ml, 20 mM Bicine, 150 mM NaCl, pH8.0
   c. F3 fusion protein, 500 μg/ml, 20 mM Bicine, 150 mM NaCl, pH8.0
   d. F4 fusion protein, 500 μg/ml, 20 mM Bicine, 150 mM NaCl, pH8.0
   e. F5 fusion protein, 500 μg/ml, 20 mM Bicine, 150 mM NaCl, pH8.0
2. For data collection, 160 scans were recorded at 280 nm every 5 minutes.
3. Data analysis was performed using the program SEDFIT for determination of the C(S) distribution. Determination of the partial specific volume of the proteins was performed with the SEDNTERP software from their amino acid sequence. SEDNTERP was also used to determine the viscosity and the density of the buffer.
4. The molecular weight of the different species was determined from the C(S) distribution plot (concentration vs sedimentation coefficient), considering that it's a better representation of the raw data than the C(M) distribution (concentration vs molecular weight) to characterize the size distribution of a mixture. The molecular weight of the major species detected from the C(S) distribution of all five ToxA-ToxB fusion proteins corresponds to their monomeric form. The best fit frictional ratios determined for the five fusions are all between 2 and 2.2. This may indicate that the proteins are present in solution as an elongated form, which would be consistent with the protein structure.

Example 12

Evaluation of Secondary and Tertiary Structures of *C. difficile* ToxA-ToxB Fusions by Circular Dichroism and Fluorescence Spectroscopy Circular dichroism is used to determine the secondary structure composition of a protein by measuring the difference in the absorption of left-handed polarized light versus right-handed polarized light which is due to structural asymmetry. The shape and the magnitude of the CD spectra in the far-UV region (190-250 nm) are different whether a protein exhibits a beta-sheet, alpha-helix or random coil structure. The relative abundance of each secondary structure type in a given protein sample can be calculated by comparison to reference spectra.

The tertiary structure of a protein sample can be assessed by the evaluation of the immobilisation of the aromatic amino acids. The observation of a CD signal in the near-UV region (250-50 nm) may be attributable to the polarization of phenylalanine, tyrosine and tryptophane residues and is a good indication that the protein is folded into a well defined structure.

The following protocol was used:

1. Far UV spectra are measured using an optical path of 0.01 cm from 178 to 250 nm, with a 1 nm resolution and bandwidth on a Jasco J-720 spectropolarimeter. Temperature of the cell is maintained at 23° C. by a Peltier thermostated RTE-111 cell block. A nitrogen flow of 10 L/min is maintained during the measurements.
2. Near-UV spectra are measured using an optical path of 0.01 cm from 250 to 300 nm, with a 1 nm resolution and bandwidth on a Jasco J-720 spectropolarimeter. Temperature of the cell is maintained at 23° C. by a Peltier thermostated RTE-111 cell block. A nitrogen flow of 6 L/min is maintained during the measurements.

Figure 22:
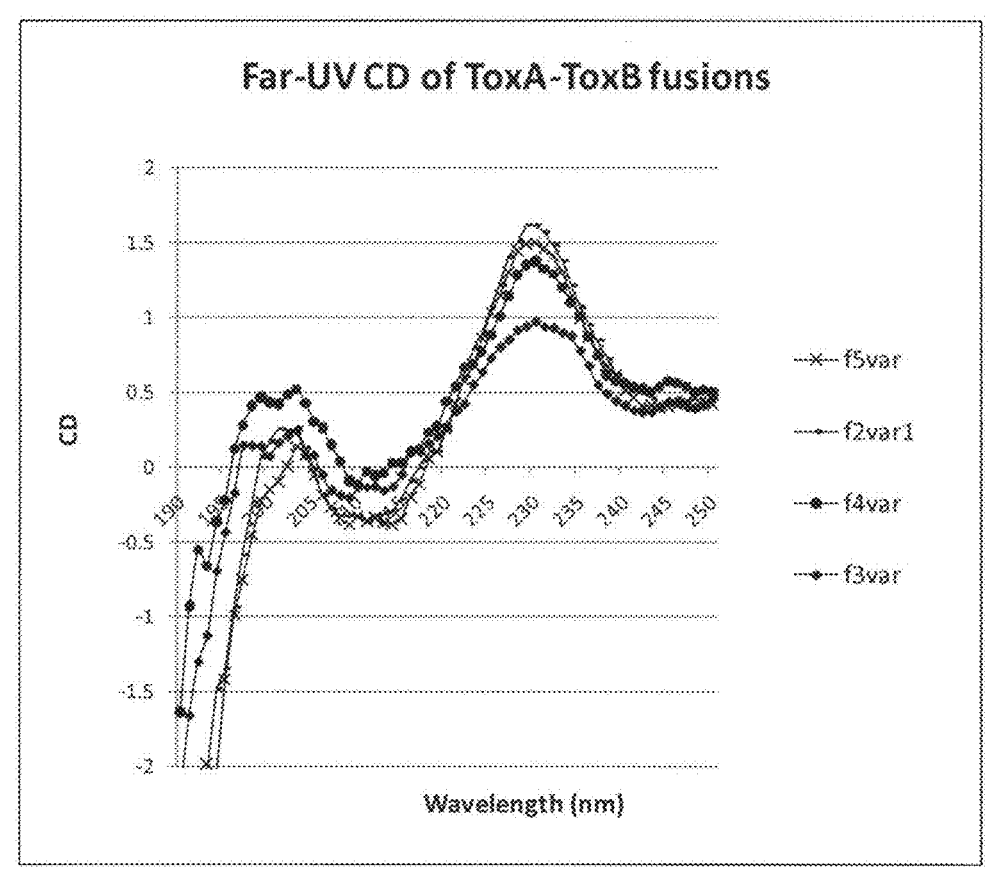

The observation of the far-UV spectra (FIG. 22) for all five ToxA-ToxB fusion proteins suggests a weak content of alpha helix structures and a high content of beta sheet structures. Also, all proteins exhibited a maximum at 230 nm, which is unusual for soluble globular proteins. This particularity has been well characterized in the literature and is associated with a small group of proteins known for their absence of alpha helix and their high content in beta sheet and aromatic amino acids (Zsila, Analytical Biochemistry, 391 (2009) 154-156). Those particularities are coherent with the structure that is expected for the ToxA-ToxB fusion proteins. Crystal structures of 13 proteins exhibiting the characteristic CD spectra with a positive signal at 230 nm were compared (Protein Data Bank). The average secondary structure content of those proteins is 42% beta sheet±9% and 7% alpha helix±6%. This strongly indicates that the spectral signature of the ToxA-ToxB fusion proteins is diagnostic of a high beta sheet and low alpha helix containing protein.

Figure 23:
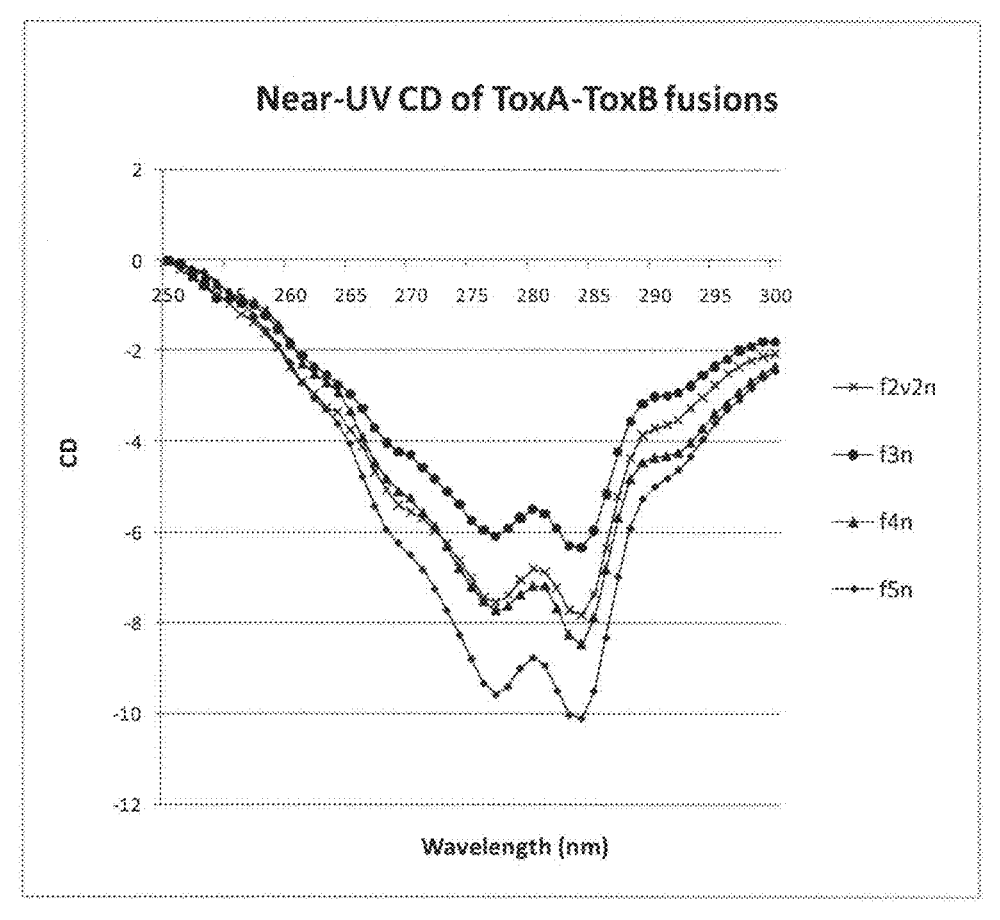

The observation of the shape of the near-UV spectra (FIG. 23) for all five fusion proteins indicates that at least some of the aromatic amino acids are immobilised, which is a strong indication of a compact and specific tertiary structure. Moreover, the treatment of the protein with a denaturing concentration of urea caused the disappearance of the near-UV signal, which is an additional indication that this characteristic spectra was due to protein folding.

Example 13

Design, Cloning, Expression and Purification of 4 Further Fusion Proteins

Four further fusion proteins were designed using the design principles described in example 1, these were named F54 Gly (SEQ ID NO:11), F54 New (SEQ ID NO:13), F5 ToxB (SEQ ID NO:15) and F52 New (SEQ ID NO:17).

Example 14

Molecular weight evaluation of the *C. difficile* ToxA-ToxB fusions described in SEQ ID NO:11, SEQ ID NO:13, SEQ ID NO:15, and SEQ ID NO:17

The molecular weight of the fusions described in SEQ ID NO:11, SEQ ID NO:13, SEQ ID NO:15, and SEQ ID NO:17 were determined as described in example 11.

The molecular weight of the main species determined from the C(S) distribution of all four protein fusions described in SEQ ID NO:11, SEQ ID NO:13, SEQ ID NO:15, and SEQ ID NO:17 corresponds to their monomeric form and all proteins exhibit sedimentation properties similar to F1 to F5 fusions.

These fusion proteins were expressed according to the procedure described in example 9.

Example 15

Evaluation of Secondary and Tertiary Structures of *C. difficile* ToxA-ToxB Fusions Described in SEQ ID NO:11, SEQ ID NO:13, SEQ ID NO:15, and SEQ ID NO:17

Figure 24:
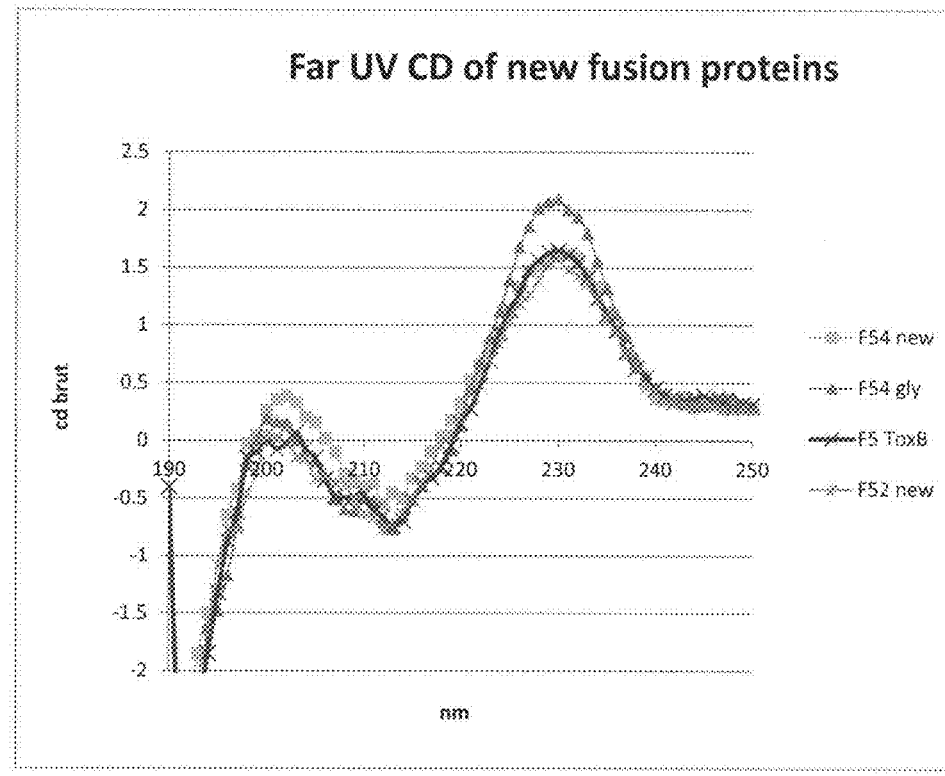
FIG. 24—Graph describing the Far-UV spectrum of fusions F52New, F54Gly, F54New and F5ToxB measured using circular dichroism. The spectrum for F52New is represented by a line with the points depicted as double crosses, the spectrum for F54Gly is represented by a line with the points depicted as triangles, F54New is represented by a line with the points depicted as squares, and F5ToxB is represented by a line with the points depicted as cross shapes.
Figure 25:
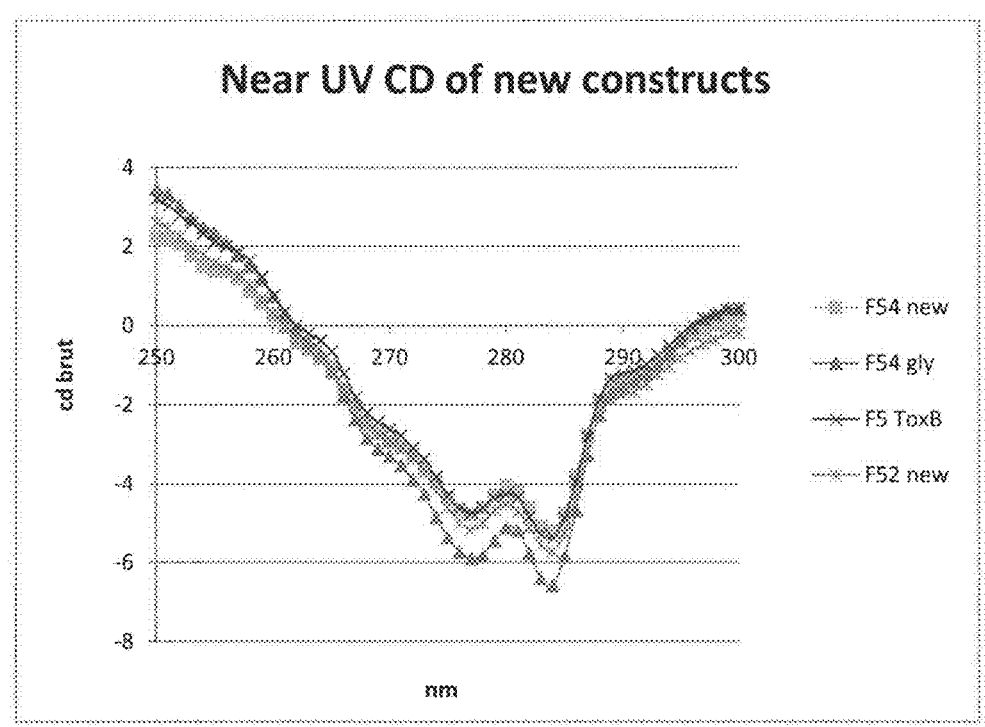
FIG. 25—Graph describing the Near-UV spectrum of fusions F52New, F54Gly, F54New and F5ToxB measured using circular dichroism. The spectrum for F52New is represented by a line with the points depicted as double crosses, the spectrum for F54Gly is represented by a line with the points depicted as triangles, F54New is represented by a line with the points depicted as squares, and F5ToxB is represented by a line with the points depicted as cross shapes.

The secondary and tertiary structures of the fusions described in SEQ ID NO:11, SEQ ID NO:13, SEQ ID NO:15, and SEQ ID NO:17 were assessed according to the method described in example 5. The far UV CD for these fusion proteins can be found in FIG. 24, and the near UV spectra for these fusions can be found in FIG. 25.

Analysis of the near and far UV CD spectra of the proteins described in SEQ ID NO:11, SEQ ID NO:13, SEQ ID NO:15, and SEQ ID NO:17 shows that all four have the same high beta sheet structure than F1 to F5 fusions. In addition, observation of the near UV spectra show no significant difference in the position of the aromatic amino acids in the tertiary structure compared to F1 to F5 fusions.

SEQUENCES

```
sequence of toxin A
                                                             SEQ ID NO: 1
MSLISKEELIKLAYSIRPRENEYKTILTNLDEYNKLTTNNNENKYLQLKKLNESIDVFMN

KYKTSSRNRALSNLKKDILKEVILIKNSNTSPVEKNLHFVWIGGEVSDIALEYIKQWADI

NAEYNIKLWYDSEAFLVNTLKKAIVESSTTEALQLLEEEIQNPQEDNMKEYKKRMEFIYD

RQKRFINYYKSQINKPTVPTIDDIIKSHLVSEYNRDETVLESYRTNSLRKINSNHGIDIR

ANSLFTEQELLNIYSQELLNRGNLAAASDIVRLLALKNFGGVYLDVDMLPGIHSDLFKTI

SRPSSIGLDRWEMIKLEAIMKYKKYINNYTSENFDKLDQQLKDNFKLIIESKSEKSEIFS

KLENLNVSDLEIKIAFALGSVINQALISKQGSYLTNLVIEQVKNRYQFLNQHLNPAIESD

NNFTDTTKIFHDSLENSATAENSMELTKIAPYLQVGEMPEARSTISLSGPGAYASAYYDF

INLQENTIEKTLKASDLIEFKFPENNLSQLTEQEINSLWSFDQASAKYQFEKYVRDYTGG

SLSEDNGVDENKNTALDKNYLLNNKIPSNNVEEAGSKNYVHYIIQLQGDDISYEATCNLF

SKNPKNSIIIQRNMNESAKSYFLSDDGESILELNKYRIPERLKNKEKVKVTFIGHGKDEF

NTSEFARLSVDSLSNEISSELDTIKLDISPKNVEVNLLGCNMESYDENVEETYPGKLLLS

IMDKITSTLPDVNKNSITIGANQYEVRINSEGRKELLAHSGKWINKEEAIMSDLSSKEYI

FFDSIDNKLKAKSKNIPGLASISEDIKTLLLLDASVSPDTKFILNNLKLNIESSIGDYIYY

EKLEPVKNIIHNSIDDLIDEFNLLENVSDELYELKKLNNLDEKYLISFEDISKNNSTYSV

RFINKSNGESVYVETEKEIFSKYSEHITKEISTIKNSIITDVNGNLLDNIQLDHTSQVNT

LNAAFFIQSLIDYSSNKDVLNDLSTSVKVQLYAQLFSTGLNTIYDSIQLVNLISNAVNDT

INVLPTITEGIPIVSTILDGINLGAAIKELLDEHDPLLKKELEAKVGVLAINMSLSIAAT

VASIVGIGAEVTIFLLPIAGISAGIPSLVNNELILHDKATSVVNYFNHLSESKKYGPLKT

EDDKILVPIDDLVISEIDFNNNSIKLGTCNILAMEGGSGHTVTGNIDHFFSSPSISSHIP

SLSIYSAIGIETENLDFSKKIMMLPNAPSRVFWWETGAVPGLRSLENDGTRLLDSIRDLY

PGKEYWREYAFFDYAITTLKPVYEDTNIKIKLDKDTRNFIMPTITTNEIRNKLSYSFDGA

GGTYSLLLSSYPISTNINLSKDDLWIFNIDNEVREISIENGTIKKGKLIKDVLSKIDINK

NKLIIGNQTIDFSGDIDNKDRYIFLTCELDDKISLIIEINLVAKSYSLLLSGDKNYLISN

LSNTIEKINTLGLDSKNIAYNYTDESNNKYFGAISKTSQKSIIHYKKDSKNILEFYNDST

LEFNSKDFIAEDINVFMKDDINTITGKYYVDNNTDKSIDESISLVSKNQVKVNGLYLNES

VYSSYLDFVKNSDGHHNTSNFMNLFLDNISFWKLFGFENINEVIDKYFTLVGKTNLGYVE

FICDNNKNIDIYFGEWKTSSSKSTIFSGNGRNVVVEPIYNPDTGEDISTSLDFSYEPLYG
```

-continued

IDRYINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNEKSF
NSENELDRDHLGFKIIDNKTYYYDEDSKLVKGLININNSLFYFDPIEFNLVTGWQTINGK
KYYFDINTGAALTSYKIINGKHEYFNNDGVMQLGVFKGPDGFEYFAPANTQNNNIEGQAI
VYQSKFLTLNGKKYYFDNNSKAVTGWRIINNEKYYFNPNNAIAAVGLQVIDNNKYYFNPD
TAIISKGWQTVNGSRYYFDTDTAIAFNGYKTIDGKHFYFDSDCVVKIGVESTSNGFEYFA
PANTYNNNIEGQAIVYQSKFLTLNGKKYYFDNNSKAVTGLQTIDSKKYYFNTNTAEAATG
WQTIDGKKYYFNTNTAEAATGWQTIDGKKYYFNTNTAIASTGYTIINGKHEYENTDGIMQ
IGVFKGPNGFEYFAPANTDANNIEGQAILYQNEFLTLNGKKYYFGSDSKAVTGWRIINNK
KYYFNPNNAIAAIHLCTINNDKYYFSYDGILQNGYITIERNNEYFDANNESKMVTGVFKG
PNGFEYFAPANTHNNNIEGQAIVYQNKFLTLNGKKYYFDNDSKAVTGWQTIDGKKYYFNL
NTAEAATGWQTIDGKKYYFNLNTAEAATGWQTIDGKKYYTNTNTFIASTGYTSINGKHEY
FNTDGIMQIGVFKGPNGFEYFAPANTDANNIEGQAILYQNKFLTLNGKKYYFGSDSKAVT
GLRTIDGKKYYFNTNTAVAVTGWQTINGKKYYFNTNTSIASTGYTIISGKHEYENTDGIM
QIGVFKGPDGFEYFAPANTDANNIEGQAIRYQNRFLYLHDNIYYFGNNSKAATGWVTIDG
NRYYFEPNTAMGANGYKTIDNKNFYFRNGLPQIGVFKGSNGFEYFAPANTDANNIEGQAI
RYQNRFLHLLGKIYYFGNNSKAVTGWQTINGKVYYFMPDTAMAAAGGLFEIDGVIYFFGV
DGVKAPGIYG sequence of toxin B                                              SEQ ID NO: 2

MSLVNRKQLEKMANVRFRTQEDEYVAILDALEEYHNMSENTVVEKYLKLKDINSLTDIYI
DTYKKSGRNKALKKEKEYLVTEVLELKNNNLTPVEKNLHFVWIGGQINDTAINYINQWKD
VNSDYNVNVEYDSNAFLINTLKKTVVESAINDTLESFRENLNDPREDYNKFFRKRMEIIY
DKQKNFINYYKAQREENPELIIDDIVKTYLSNEYSKEIDELNTYIEESLNKITQNSGNDV
RNFEEFKNGESFNLYEQELVERWNLAAASDILRISALKEIGGMYLDVDMLPGIQPDLFES
IEKPSSVTVDFWEMTKLEAIMKYKEYIPEYTSEHFDMLDEEVQSSFESVLASKSDKSEIF
SSLGDMEASPLEVKIAFNSKGIINQGLISVKDSYCSNLIVKQIENRYKILNNSLNPAISE
DNDENTTTNTFIDSIMAEANADNGREMMELGKYLRVGFFPDVKTTINLSGPEAYAAAYQD
LLMFKEGSMNIHLIEADLRNFEISKTNISQSTEQEMASLWSFDDARAKAQFEEYKRNYFE
GSLGEDDNLDFSQNIVVDKEYLLEKISSLARSSERGYIHYIVQLQGDKISYEAACNLFAK
TPYDSVLFQKNIEDSEIAYYYNPGDGEIQEIDKYKIPSIISDRPKIKLTFIGHGKDEFNT
DIFAGFDVDSLSTEIEAAIDLAKEDISPKSIEINLLGCNMESYSINVEETYPGKLLLKVK
DKISELMPSISQDSIIVSANQYEVRINSEGRRELLDHSGEWINKEESIIKDISSKEYISF
NPKENKITVKSKNLPELSTLLQEIRNNSNSSDIELEEKVMLTECEINVISNIDTQIVEER
IEEAKNLTSDSINYIKDEFKLIESISDALCDLKQQNELEDSHEISFEDISETDEGFSIRF
INKETGESIFVETEKTIFSEYANHITEEISKIKGTIFDTVNGKLVKKVNLDTTHEVNTLN
AAFFIQSLIEYNSSKESLSNLSVAMKVQVYAQLFSTGLNTITDAAKVVELVSTALDETID
LLPTLSEGLPIIATIIDGVSLGAAIKELSETSDPLLRQEIEAKIGIMAVNLTTATTAIIT
SSLGIASGFSILLVPLAGISAGIPSLVNNELVLRDKATKVVDYFKHVSLVETEGVFTLLD
DKIMMPQDDLVISEIDFNNNSIVLGKCEIWRMEGGSGHTVTDDIDHFFSAPSITYREPHL
SIYDVLEVQKEELDLSKDLMVLPNAPNRVFAWETGWTPGLRSLENDGTKLLDRIRDNYEG

-continued

EFYWRYFAFIADALITTLKPRYEDTNIRINLDSNTRSFIVPIITTEYIREKLSYSFYGSG
GTYALSLSQYNMGINIELSESDVWIIDVDNVVRDVTIESDKIKKGDLIEGILSTLSIEEN
KIILNSHEINFSGEVNGSNGFVSLTFSILEGINAIIEVDLLSKSYKLLISGELKILMLNS
NHIQQKIDYIGFNSELQKNIPYSFVDSEGKENGFINGSTKEGLFVSELPDVVLISKVYMD
DSKPSFGYYSNNLKDVKVITKDNVNILTGYYLKDDIKISLSLTLQDEKTIKLNSVHLDES
GVAEILKFMNRKGNTNTSDSLMSFLESMNIKSIFVNFLQSNIKFILDANFIISGTTSIGQ
FEFICDENDNIQPYFIKFNTLETNYTLYVGNRQNMIVEPNYDLDDSGDISSTVINFSQKY
LYGIDSCVNKVVISPNIYTDEINITPVYETNNTYPEVIVLDANYINEKINVNINDLSIRY
VWSNDGNDFILMSTSEENKVSQVKIRFVNVFKDKTLANKLSFNFSDKQDVPVSEIILSFT
PSYYEDGLIGYDLGLVSLYNEKFYINNFGMMVSGLIYINDSLYYFKPPVNNLITGFVTVG
DDKYYFNPINGGAASIGETIIDDKNYYFNQSGVLQTGVFSTEDGFKYFAPANTLDENLEG
EAIDFTGKLIIDENIYYFDDNYRGAVEWKELDGEMHYFSPETGKAFKGLNQIGDYKYYFN
SDGVMQKGFVSINDNKHYFDDSGVMKVGYTEIDGKHFYFAENGEMQIGVFNTEDGFKYFA

HHNEDLGNEEGEEISYSGILNFNNKIYYFDDSFTAVVGWKDLEDGSKYYFDEDTAEAYIG

LSLINDGQYYFNDDGIMQVGFVTINDKVFYFSDSGIIESGVQNIDDNYFYIDDNGIVQIG

VFDTSDGYKYFAPANTVNDNIYGQAVEYSGLVRVGEDVYYFGETYTIETGWIYDMENESD

KYYFNPETKKACKGINLIDDIKYYFDEKGIMRTGLISFENNNYYFNENGEMQFGYINIED

KMFYFGEDGVMQIGVFNTPDGFKYFAHQNTLDENFEGESINYTGWLDLDEKRYYFTDEYI

AATGSVIIDGEEYYFDPDTAQLVISE sequence of Fusion 1

SEQ ID NO: 3

MGWQTIDGKKYYFNTNTAIASTGYTIINGKHFYFNTDGIMQIGVFKGPNGFEYFAPANTDANNIEGQAILYQ

NEFLTLNGKKYYFGSDSKAVTGWRIINNKKYYFNPNNAIAAIHLCTINNDKYYFSYDGILQNGYITIERNNF

YFDANNESKMVTGVFKGPNGFEYFAPANTHNNNIEGQAIVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTLNGKKYYFGSDSKAVTGLRTIDGKKYYFNTNTAVA

VTGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGFE

YFAPANTDANNIEGQAIRYQNRFLHLLGKIYYFGNNSKAVTGWQTINGKVYYFMPDTAMAAAGGLFEIDGVI

YFFGVDGVKAPGFVSINDNKHYFDDSGVMKVGYTEIDGKHFYFAENGEMQIGVFNTEDGFKYFAHHNEDLGN

EEGEEISYSGILNFNNKIYYFDDSFTAVVGWKDLEDGSKYYFDEDTAEAYIGLSLINDGQYYFNDDGIMQVG

FVTINDKVFYFSDSGIIESGVQNIDDNYFYIDDNGIVQIGVFDTSDGYKYFAPANTVNDNIYGQAVEYSGLV

RVGEDVYYFGETYTIETGWIYDMENESDKYYFNPETKKACKGINLIDDIKYYFDEKGIMRTGLISFENNNYY

FNENGEMQFGYINIEDKMFYFGEDGVMQIGVFNTPDGFKYFAHQNTLDENFEGESINYTGWLDLDEKRYYFT

DEYIAATGSVIIDGEEYYFDPDTAQLVISE sequence of Fusion 2

SEQ ID NO: 4

MGWQTIDGKKYYFNTNTAIASTGYTIINGKHFYFNTDGIMQIGVFKGPNGFEYFAPANTDANNIEGQAILYQ

NEFLTLNGKKYYFGSDSKAVTGWRIINNKKYYFNPNNAIAAIHLCTINNDKYYFSYDGILQNGYITIERNNF

YFDANNESKMVTGVFKGPNGFEYFAPANTHNNNIEGQAIVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTLNGKKYYFGSDSKAVTGLRTIDGKKYYFNTNTAVA

VTGWQTINGKKYYFNTNTSIASTGYTIISGKHFYFNTDGIMQIGVFKGPDGFEYFAPANTDANNIEGQAIRY

-continued

QNRFLYLHDNIYYFGNNSKAATGWVTIDGNRYYFEPNTAMGANGYKTIDNKNFYFRNGLPQIGVFKGSNGFE
YFAPANTDANNIEGQAIRYQNRFLHLLGKIYYFGNNSKAVTGWQTINGKVYYFMPDTAMAAAGGLNQIGDYK
YYFNSDGVMQKGFVSINDNKHYFDDSGVMKVGYTEIDGKHFYFAENGEMQIGVFNTEDGFKYFAHHNEDLGN
EEGEEISYSGILNFNNKIYYFDDSFTAVVGWKDLEDGSKYYFDEDTAEAYIGLSLINDGQYYFNDDGIMQVG
FVTINDKVFYFSDSGIIESGVQNIDDNYFYIDDNGIVQIGVFDTSDGYKYFAPANTVNDNIYGQAVEYSGLV
RVGEDVYYFGETYTIETGWIYDMENESDKYYFNPETKKACKGINLIDDIKYYFDEKGIMRTGLISFENNNYY
FNENGEMQFGYINIEDKMFYFGEDGVMQIGVFNTPDGFKYFAHQNTLDENFEGESINYTGWLDLDEKRYYFT
DEYIAATGSVIIDGEEYYFDPDTAQLVISE sequence of Fusion 3 SEQ ID NO: 5

MGWQTIDGKKYYFNTNTAIASTGYTIINGKHFYFNTDGIMQIGVFKGPNGFEYFAPANTDANNIEGQAILYQ
NEFLTLNGKKYYFGSDSKAVTGWRIINNKKYYFNPNNAIAAIHLCTINNDKYYFSYDGILQNGYITIERNNF
YFDANNESKMVTGVFKGPNGFEYFAPANTHNNNIEGQAIVYQNKFLTLNGKKYYFDNDSKAVTGWQTIDGKK
YYFNLNTAEAATGWQTIDGKKYYFNLNTAEAATGWQTIDGKKYYFNTNTFIASTGYTSINGKHFYFNTDGIM
QIGVFKGPNGFEYFAPANTDANNIEGQAILYQNKFLTLNGKKYYFGSDSKAVTGLRTIDGKKYYFNTNTAVA
VTGWQTINGKKYYFNTNTSIASTGYTIISGKHFYFNTDGIMQIGVFKGPDGFEYFAPANTDANNIEGQAIRY
QNRFLYLHDNIYYFGNNSKAATGWVTIDGNRYYFEPNTAMGANGYKTIDNKNFYFRNGLPQIGVFKGSNGFE
YFAHHNEDLGNEEGEEISYSGILNENNKIYYFDDSFTAVVGWKDLEDGSKYYFDEDTAEAYIGLSLINDGQY
YFNDDGIMQVGFVTINDKVFYFSDSGIIESGVQNIDDNYFYIDDNGIVQIGVFDTSDGYKYFAPANTVNDNI
YGQAVEYSGLVRVGEDVYYFGETYTIETGWIYDMENESDKYYFNPETKKACKGINLIDDIKYYFDEKGIMRT
GLISFENNNYYFNENGEMQFGYINIEDKMFYFGEDGVMQIGVFNTPDGFKYFAHQNTLDENFEGESINYTGW
LDLDEKRYYFTDEYIAATGSVIIDGEEYYFDPDTAQLVISE sequence of Fusion 4 SEQ ID NO: 6

MGWQTIDGKKYYFNTNTAIASTGYTIINGKHFYFNTDGIMQIGVFKGPNGFEYFAPANTDANNIEGQAILYQ
NEFLTLNGKKYYFGSDSKAVTGWRIINNKKYYFNPNNAIAAIHLCTINNDKYYFSYDGILQNGYITIERNNF
YFDANNESKMVTGVFKGPNGFEYFAPANTHNNNIEGQAIVYQNKFLTLNGKKYYFDNDSKAVTGWQTIDGKK
YYFNLNTAEAATGWQTIDGKKYYFNLNTAEAATGWQTIDGKKYYFNTNTFIASTGYTSINGKHFYFNTDGIM
QIGVFKGPNGFEYFAPANTDANNIEGQAILYQNKFLTLNGKKYYFGSDSKAVTGLRTIDGKKYYFNTNTAVA
VTGWQTINGKKYITNTNTSIASTGYTIISGKHFYFNTDGIMQIGVFKGPDGFEYFAPANTDANNIEGQAIRY
QNRFLYLHDNIYYFGNNSKAATGWVTIDGNRYYFEPNTAMGANGYKTIDNKNFYFRNGLPQIGVFKGSNGFE
YFAPANTDANNIEGQAIRYQNRFLHLLGKIYYFGNNSKAVTGWQTINGKVYYFMPDTAMAAAGGETIIDDKN
YYFNQSGVLQTGVFSTEDGFKYFAPANTLDENLEGEAIDFTGKLIIDENIYYFDDNYRGAVEWKELDGEMHY
FSPETGKAFKGLNQIGDYKYYFNSDGVMQKGFVSINDNKHYFDDSGVMKVGYTEIDGKHFYFAENGEMQIGV
FNTEDGFKYFAHHNEDLGNEEGEEISYSGILNFNNKIYYFDDSFTAVVGWKDLEDGSKYYFDEDTAEAYIGL
SLINDGQYYFNDDGIMQVGFVTINDKVFYFSDSGIIESGVQNIDDNYFYIDDNGIVQIGVFDTSDGYKYFAP
ANTVNDNIYGQAVEYSGLVRVGEDVYYFGETYTIETGWIYDMENESDKYYFNPETKKACKGINLIDDIKYYF
DEKGIMRTGLISFENNNYYFNENGEMQFGYINIEDKMFYFGEDGVMQIGVFNTPDGFKYFAHQNTLDENFEG
ESINYTGWLDLDEKRYYFTDEYIAATGSVIIDGEEYYFDPDTAQLVISE sequence of Fusion 5 SEQ ID NO: 7

MGWQTIDGKKYYFNTNTAIASTGYTIINGKHFYFNTDGIMQIGVFKGPNGFEYFAPANTDANNIEGQAILYQ
NEFLTLNGKKYYFGSDSKAVTGWRIINNKKYYFNPNNAIAAIHLCTINNDKYYFSYDGILQNGYITIERNNF

```
YFDANNESKMVTGVFKGPNGFEYFAPANTHNNNIEGQAIVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTLNGKKYYFGSDSKAVTGLRTIDGKKYYFNTNTAVA

VTGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGFE

YFAPANTDANNIEGQAIRYQNRFLHLLGKIYYFGNNSKAVTGWQTINGKVYYFMPDTAMAAAGGLFEIDGVI

YFFGVDGVKAPGIYGGGFVSINDNKHYFDDSGVMKVGYTEIDGKHFYFAENGEMQIGVFNTEDGFKYFAHHN

EDLGNEEGEEISYSGILNFNNKIYYFDDSFTAVVGWKDLEDGSKYYFDEDTAEAYIGLSLINDGQYYFNDDG

IMQVGFVTINDKVFYFSDSGIIESGVQNIDDNYFYIDDNGIVQIGVFDTSDGYKYFAPANTVNDNIYGQAVE

YSGLVRVGEDVYYFGETYTIETGWIYDMENESDKYYFNPETKKACKGINLIDDIKYYFDEKGIMRTGLISFE

NNNYYFNENGEMQFGYINIEDKMFYFGEDGVMQIGVFNTPDGFKYFAHQNTLDENFEGESINYTGWLDLDEK

RYYFTDEYIAATGSVIIDGEEYYFDPDTAQLVISE
``` sequence of individual toxin A fragment      SEQ ID NO: 8

```
MASTGYTSINGKHFYFNTDGIMQIGVFKGPNGFEYFAPANTDANNIEGQAILYQNKFLTLNGKKYYFGSDSK

AVTGLRTIDGKKYYFNTNTAVAVTGWQTINGKKYYFNTNTSIASTGYTIISGKHFYFNTDGIMQIGVFKGPD

GFEYFAPANTDANNIEGQAIRYQNRFLYLHDNIYYFGNNSKAATGWVTIDGNRYYFEPNTAMGANGYKTIDN

KNFYFRNGLPQIGVFKGSNGFEYFAPANTDANNIEGQAIRYQNRFLHLLGKIYYFGNNSKAVTGWQTINGKV

YYFMPDTAMAAAGGLFEIDGVIYFFGVDGVKAP
``` sequence of individual toxin B fragment      SEQ ID NO: 9

```
MILMSTSEENKVSQVKIRFVNVFKDKTLANKLSFNFSDKQDVPVSEIILSFTPSYYEDGLIGYDLGLVSLYN

EKFYINNFGMMVSGLIYINDSLYYFKPPVNNLITGFVTVGDDKYYFNPINGGAASIGETIIDDKNYYFNQSG

VLQTGVFSTEDGFKYFAPANTLDENLEGEAIDFTGKLIIDENIYYFDDNYRGAVEWKELDGEMHYFSPETGK

AFKGLNQIGDYKYYFNSDGVMQKGFVSINDNKHYFDDSGVMKVGYTEIDGKHFYFAENGEMQIGVFNTEDGF

KYFAHHNEDLGNEEGEEISYSGILNFNNKIYYFDDSFTAVVGWKDLEDGSKYYFDEDTAEAYIGLSLINDGQ

YYFNDDGIMQVGFVTINDKVFYFSDSGIIESGVQNIDDNYFYIDDNGIVQIGVFDTSDGYKYFAPANTVNDN

IYGQAVEYSGLVRVGEDVYYFGETYTIETGWIYDMENESDKYYFNPETKKACKGINLIDDIKYYFDEKGIMR

TGLISFENNNYYFNENGEMQFGYINIEDKMFYFGEDGVMQIGVFNTPDGFKYFAHQNTLDENFEGESINYTG

WLDLDEKRYYFTDEYIAATGSVIIDGEEYYFDPDTA
``` sequence of toxin A fragment from fusion 1      SEQ ID NO: 10

```
MGWQTIDGKKYYFNTNTAIASTGYTIINGKHFYFNTDGIMQIGVFKGPNGFEYFAPANTDANNIEGQAILYQ

NEFLTLNGKKYYFGSDSKAVTGWRIINNKKYYFNPNNALAATHLCTINNDKYYFSYDGILQNGYITIERNNF

YFDANNESKMVTGVFKGPNGFEYFAPANTHNNNIEGQAIVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTLNGKKYYFGSDSKAVTGLRTIDGKKYYFNTNTAVA

VTGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGFE

YFAPANTDANNIEGQAIRYQNRFLHLLGKIYYFGNNSKAVTGWQTINGKVYYFMPDTAMAAAGGLFEIDGVI

YFFGVDGVKAP
``` sequence of toxin A fragment from fusion 2      SEQ ID NO: 11

```
MGWQTIDGKKYYFNTNTAIASTGYTIINGKHFYFNTDGIMQIGVFKGPNGFEYFAPANTDANNIEGQAILYQ

NEFLTLNGKKYYFGSDSKAVTGWRIINNKKYYFNPNNAIAAIHLCTINNDKYYFSYDGILQNGYITIERNNF
```

-continued

YFDANNESKMVTGVFKGPNGFEYFAPANTHNNNIEGQAIVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTLNGKKYYFGSDSKAVTGLRTIDGKKYYFNTNTAVA

VTGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGFE

YFAPANTDANNIEGQAIRYQNRFLHLLGKIYYFGNNSKAVTGWQTINGKVYYFMPDTAMAAAG sequence of toxin A fragment from fusion 3    SEQ ID NO: 12

MGWQTIDGKKYYFNTNTAIASTGYTIIINGKHFYFNTDGIMQIGVFKGPNGFEYFAPANTDANNIEGQAILYQ

NEFLTLNGKKYYFGSDSKAVTGWRIINNKKYYFNPNNAIAAIHLCTINNDKYYFSYDGILQNGYITIERNNF

YFDANNESKMVTGVFKGPNGFEYFAPANTHNNNIEGQAIVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTLNGKKYYFGSDSKAVTGLRTIDGKKYYFNTNTAVA

VTGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGFE

Y sequence of toxin A fragment from fusion 4    SEQ ID NO: 13

MGWQTIDGKKYYFNTNTAIASTGYTIINGKHFYFNTDGIMQIGVFKGPNGFEYFAPANTDANNIEGQAILYQ

NEFLTLNGKKYYFGSDSKAVTGWRIINNKKYYFNPNNAIAAIHLCTINNDKYYFSYDGILQNGYITIERNNF

YFDANNESKMVTGVFKGPNGFEYFAPANTHNNNIEGQATVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTLNGKKYYFGSDSKAVTGLRTIDGKKYYFNTNTAVA

VTGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGFE

YFAPANTDANNIEGQAIRYQNRFLHLLGKIYYFGNNSKAVTGWQTINGKVYYFMPDTAMAAAG sequence of toxin A fragment from fusion 5    SEQ ID NO: 14

MGWQTIDGKKYYFNTNTAIASTGYTIINGKHFYFNTDGIMQIGVFKGPNGFEYFAPANTDANNIEGQAILYQ

NEFLTLNGKKYYFGSDSKAVTGWRIINNKKYYFNPNNAIAAIHLCTINNDKYYFSYDGILQNGYITIERNNF

YFDANNESKMVTGVFKGPNGFEYFAPANTHNNNIEGQAIVYQNKFLTLNGKKYYFDNDSKAVTGWQTIDGKK

YYFNLNTAEAATGWQTIDGKKYYFNLNTAEAATGWQTIDGKKYYFNTNTFIASTGYTSINGKHFYFNTDGIM

QIGVFKGPNGFEYFAPANTDANNIEGQAILYQNKFLTENGKKYYFGSDSKAVTGERTIDGKKYYFNTNTAVA

VTGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGFE

YFAPANTDANNIEGQAIRYQNRFLHLLGKIYYFGNNSKAVTGWQTINGKVYYFMPDTAMAAAGGLFEIDGVI

YFFGVDGVKAPGIYG sequence of toxin B fragment from fusion 1    SEQ ID NO: 15

GFVSINDNKHYFDDSGVMKVGYTEIDGKHFYFAENGEMQIGVFNTEDGFKYFAHHNEDLGNEEGEEISYSGI

LNFNNKIYYFDDSFTAVVGWKDLEDGSKYYFDEDTAEAYIGLSLINDGQYYFNDDGIMQVGFVTINDKVFYF

SDSGIIESGVQNIDDNYFYIDDNGIVQIGVFDTSDGYKYFAPANTVNDNIYGQAVEYSGLVRVGEDVYYFGE

TYTIETGWIYDMENESDKYYFNPETKKACKGINLIDDIKYYFDEKGIMRTGLISFENNNYYFNENGEMQFGY
INIEDKMFYFGEDGVMQIGVFNTPDGFKYFAHQNTLDENFEGESINYTGWLDLDEKRYYFTDEYIAATGSVI
IDGEEYYFDPDTAQLVISE sequence of toxin B fragment from fusion 2                                    SEQ ID NO: 16

GLNQIGDYKYYFNSDGVMQKGFVSINDNKHYFDDSGVMKVGYTEIDGKHFYFAENGEMQIGVFNTEDGFKYF
AHHNEDLGNEEGEEISYSGILNFNNKIYYFDDSFTAVVGWKDLEDGSKYYFDEDTAEAYIGLSLINDGQYYF
NDDGIMQVGFVTINDKVFYFSDSGIIESGVQNIDDNYFYIDDNGIVQIGVFDTSDGYKYFAPANTVNDNIYG
QAVEYSGLVRVGEDVYYFGETYTIETGWIYDMENESDKYYFNPETKKACKGINLIDDIKYYFDEKGIMRTGL
ISFENNNYYFNENGEMQFGYINIEDKMFYFGEDGVMQIGVFNTPDGFKYFAHQNTLDENFEGESINYTGWLD
LDEKRYYFTDEYIAATGSVIIDGEEYYFDPDTAQLVISE sequence of toxin B fragment from fusion 3                                    SEQ ID NO: 17

FAHHNEDLGNEEGEEISYSGILNFNNKIYYFDDSFTAVVGWKDLEDGSKYYFDEDTAEAYIGLSLINDGQYY
FNDDGIMQVGFVTINDKVFYFSDSGIIESGVQNIDDNYFYIDDNGIVQIGVFDTSDGYKYFAPANTVNDNIY
GQAVEYSGLVRVGEDVYYFGETYTIETGWIYDMENESDKYYFNPETKKACKGINLIDDIKYYFDEKGIMRTG
LISFENNNYYFNENGEMQFGYINIEDKMFYFGEDGVMQIGVFNTPDGFKYFAHQNTLDENFEGESINYTGWL
DLDEKRYYFTDEYIAATGSVIIDGEEYYFDPDTAQLVISE sequence of toxin B fragment from fusion 4                                    SEQ ID NO: 18

GETIIDDKNYYFNQSGVLQTGVFSTEDGFKYFAPANTLDENLEGEAIDFTGKLIIDENIYYFDDNYRGAVEW
KELDGEMHYFSPETGKAFKGLNQIGDYKYYFNSDGVMQKGFVSINDNKHYFDDSGVMKVGYTEIDGKHFYFA
ENGEMQIGVFNTEDGFKYFAHHNEDLGNEEGEEISYSGILNFNNKIYYFDDSFTAVVGWKDLEDGSKYYFDE
DTAEAYIGLSLINDGQYYFNDDGIMQVGFVTINDKVEYESDSGIIESGVQNIDDNYFYIDDNGIVQIGVFDT
SDGYKYFAPANTVNDNIYGQAVEYSGLVRVGEDVYYFGETYTIETGWIYDMENESDKYYFNPETKKACKGIN
LIDDIKYYFDEKGIMRTGLISFENNNYYFNENGEMQFGYINIEDKMFYFGEDGVMQIGVENTPDGEKYFAHQ
NTLDENFEGESINYTGWLDLDEKRYYFTDEYIAATGSVIIDGEEYYFDPDTAQLVISE sequence of toxin B fragment from fusion 5                                    SEQ ID NO: 19

GFVSINDNKHYFDDSGVMKVGYTEIDGKHFYFAENGEMQIGVENTEDGEKYFAHHNEDLGNEEGEEISYSGI
LNENNKIYYFDDSFTAVVGWKDLEDGSKYYFDEDTAEAYIGLSLINDGQYYFNDDGIMQVGFVTINDKVFYF
SDSGIIESGVQNIDDNYFYIDDNGIVQIGVFDTSDGYKYFAPANTVNDNIYGQAVEYSGLVRVGEDVYYFGE
TYTIETGWIYDMENESDKYYFNPETKKACKGINLIDDIKYYFDEKGIMRTGLISFENNNYYFNENGEMQFGY
INIEDKMFYFGEDGVMQIGVENTPDGEKYFAHQNTLDENFEGESINYTGWLDLDEKRYYFTDEYIAATGSVI
IDGEEYYFDPDTAQLVISE nucleotide sequence of F54 Gly fusion protein                                 SEQ ID NO: 20

ATGGCAACCGGTTGGCAGACCATCGATGGCAAAAAATATTATTTTAATACCAACACCGCAATTGCAAGCACCGGCTATACCATTATCAAC
GGCAAACACTTTTATTTTAACACCGACGGCATTATGCAGATTGGTGTGTTTAAAGGTCCGAACGGCTTTGAATACTTTGCACCGGCAAAT
ACCGATGCCAATAATATTGAAGGCCAGGCCATTCTGTATCAGAATGAATTTCTGACCCTGAACGGCAAAAAATACTACTTTGGCAGCGAT
AGCAAAGCAGTTACCGGTTGGCGCATCATCAACAATAAGAAATATTACTTCAACCCGAATAATGCAATTGCAGCAATTCATCTGTGCACC
ATTAACAACGACAAATATTATTTCAGCTATGACGGTATTCTGCAGAATGGCTACATTACCATCGAACGCAACAACTTTTATTTCGATGCC
AACAACGAAAGCAAAATGGTGACCGGTGTTTTCAAAGGCCCTAATGGTTTTGAGTATTTCGCTCCGGCAAACACCCATAATAACAACATT
GAAGGTCAGGCGATCGTTTATCAGAACAAATTCCTGACGCTGAATGGTAAGAAATACTATTTCGATAATGACAGCAAAGCCGTGACCGGC
TGGCAGACAATTGACGGGAAGAAATATTACTTTAATCTGAATACCGCAGAAGCAGCAACCGGTTGGCAAACGATCGACGGTAAAAAGTAC
TACTTCAACCTGAACACAGCCGAAGCAGCCACAGGATGGCAGACTATTGATGGAAAAAAATACTATTTCAACACCAACACCTTTATTGCA

-continued

```
TCTACCGGTTATACCAGCATTAACGGTAAACATTTCTACTTCAACACCGATGGTATCATGCAGATCGGCGTTTTCAAAGGTCCAAATGGT
TTCGAATACTTTGCCCCTGCCAATACAGATGCAAATAACATCGAGGGTCAGGCAATCCTGTACCAAAACAAATTTCTGACCCTGAATGGG
AAAAAATATTACTTTGGTAGCGATTCTAAAGCCGTTACCGGTCTGCGTACCATTGATGGTAAAAAATACTACTTTAATACGAATACAGCC
GTTGCGGTTACAGGCTGGCAGACCATTAACGGGAAAAAATACTATTTTAACACAAATACCAGCATTGCCTCAACGGGTTATACCATTATT
TCGGGTAAACACTTCTACTTTAATACCGATGGTATTATGCAAATCGGAGTCTTTAAAGGACCTGATGGGTTCGAATATTTTGCGCCTGCG
AACACTGATGCAACAATATCGAAGGACAGGCAATCCGCTATCAGAATCGCTTTCTGTATCTGCACGACAACATCTATTATTTTGGCAAC
AATTCAAAAGCAGCCACCGGCTGGGTTACAATTGATGGCAACCGCTACTATTTCGAACCGAATACCGCAATGGGTGCAAATGGCTACAAA
ACCATCGATAATAAAAATTTCTATTTTCGCAACGGTCTGCCGCAGATCGGGGTATTTAAAGGTAGCAACGGCTTCGAATACTTCGCTCCA
GCGAATACGGACGCGAACAATATTGAGGGTCAAGCGATTCGTTATCAAAACCGTTTTCTGCATCTGCTGGGCAAAATCTACTACTTTGGC
AATAACAGTAAAGCAGTTACTGGATGGCAGACAATCAATGGTAAAGTGTACTATTTTATGCCGGATACCGCCATGGCAGCAGCCGGTGGT
CTGTTTGAAATTGATGGCGTGATCTATTTTTTTGGTGTGGATGGTGTTAAAGCACCGGGAATATACGGTGGTACCGGCTTTGTGACCGTG
GGTGATGATAAATACTATTTCAATCCGATTAACGGTGGTGCAGCGAGCATTGGCGAAACCATCATCGATGACAAAAACTATTATTTCAAC
CAGAGCGGTGTGCTGCAGACCGGTGTGTTTAGCACCGAAGATGGCTTTAAATATTTTGCGCCAGCGAACACCCTGGATGAAAACCTGGAA
GGCGAAGCGATTGATTTTACCGGCAAACTGATCATCGATGAAAACATCTATTACTTCGATGATAACTATCGTGGTGCGGTGGAATGGAAA
GAACTGGATGGCGAAATGCATTATTTTTCTCCGGAAACCGGTAAAGCGTTTAAAGGCCTGAACCAGATCGGCGATTACAAATACTACTTC
AACAGCGATGGCGTGATGCAGAAAGGCTTTGTGAGCATCAACGATAACAAACACTATTTCGATGATAGCGGTGTGATGAAAGTGGGCTAT
ACCGAAATTGATGGCAAACATTTCTACTTCGCGGAAAACGGCGAAATGCAGATTGGCGTGTTCAATACCGAAGATGGTTTCAAATACTTC
GCGCACCATAACGAAGATCTGGGTAACGAAGAAGGCGAAGAAATTAGCTATAGCGGCATCCTGAACTTCAACAACAAAATCTACTACTTT
GATGATAGCTTTACCGCGGTGGTGGGCTGGAAAGATCTGGAAGATGGCAGCAAATATTATTTCGATGAAGATACCGCGGAAGCGTATATT
GGCCTGAGCCTGATTAACGATGGCCAGTACTATTTTAACGATGATGGCATTATGCAGGTGGGTTTCGTGACCATTAATGATAAAGTGTTC
TATTTCAGCGATAGCGGCATTATTGAAAGCGGCGTGCAGAACATTGATGATAACTACTTCTACATCGATGATAACGGCATTGTGCAGATC
GGCGTTTTTGATACCAGCGATGGCTACAAATATTTCGCACCGGCCAATACCGTGAACGATAAACATTTATGGCCAGGCGGTGGAATATAGC
GGTCTGGTGCGTGTGGGCGAAGATGTGTATTATTTCGGCGAAACCTATACCATCGAAACCGGCTGGATTTATGATATGGAAAACGAAAGC
GATAAATATTACTTTAATCCGGAAACGAAAAAAGCGTGCAAAGGCATTAACCTGATCGATGATATCAAATACTATTTTGATGAAAAAGGC
ATTATGCGTACCGGTCTGATTAGCTTCGAAAACAACAACTATTACTTCAACGAAAACGGTGAAATGCAGTTCGGCTACATCAACATCGAA
GATAAAATGTTCTACTTCGGCGAAGATGGTGTTATGCAGATTGGTGTTTTTAACACCCCGGATGGCTTCAAATACTTTGCCCATCAGAAT
ACCCTGGATGAAAATTTCGAAGGTGAAAGCATTAACTATACCGGCTGGCTGGATCTGGATGAAAAACGCTACTACTTCACCGATGAATAC
ATTGCGGCGACCGGCAGCGTGATTATTGATGGCGAAGAATACTACTTCGATCCGGATACCGCGCAGCTGGTGATTAGCGAACATCATCAT
CATCACCAT
``` amino acid of F54Gly fusion protein

SEQ ID NO: 21

MATGWQTIDGKKYYFNTNTAIASTGYTIINGKHFYFNTDGIMQIGVFKGPNGFEYFAPANTDANNIEGQAILYQNEFLTLN
GKKYYFGSDSKAVTGWRIINNKKYYFNPNNAIAAIHLCTINNDKYYFSYDGILQNGYITIERNNFYFDANNESKMVTGVF
KGPNGFEYFAPANTHNNNIEGQAIVYQNKFLTLNGKKYYFDNDSKAVTGWQTIDGKKYYFNLNTAEAATGWQTIDGKKYY
FNLNTAEAATGWQTIDGKKYYFNTNTFIASTGYTSINGKHFYFNTDGIMQIGVFKGPNGFEYFAPANTDANNIEGQAILY
QNKFLTLNGKKYYFGSDSKAVTGLRTIDGKKYYFNTNTAVAVTGWQTINGKKYYFNTNTSIASTGYTIISGKHFYFNTDG
IMQIGVFKGPDGFEYFAPANTDANNIEGQAIRYQNRFLYLHDNIYYFGNNSKAATGWVTIDGNRYYFEPNTAMGANGYKT
IDNKNFYFRNGLPQIGVFKGSNGFEYFAPANTDANNIEGQAIRYQNRFLHLLGKIYYFGNNSKAVTGWQTINGKVYYFMP
DTAMAAAGGLFEIDGVIYFFGVDGVKAPGIYGGTGFVTVGDDKYYFNPINGGAASIGETIIDDKNYYFNQSGVLQTGVFS
TEDGFKYFAPANTLDENLEGEAIDFTGKLIIDENIYYFDDNYRGAVEWKELDGEMHYFSPETGKAFKGLNQIGDYKYYFN
SDGVMQKGFVSINDNKHYFDDSGVMKVGYTEIDGKHFYFAENGEMQIGVFNTEDGFKYFAHHNEDLGNEEGEEISYSGIL

NFNNKIYYFDDSFTAVVGWKDLEDGSKYYFDEDTAEAYIGLSLINDGQYYFNDDGIMQVGFVTINDKVFYFSDSGIIESG
VQNIDDNYFYIDDNGIVQIGVFDTSDGYKYFAPANTVNDNIYGQAVEYSGLVRVGEDVYYFGETYTIETGWIYDMENESD
KYYFNPETKKACKGINLIDDIKYYFDEKGIMRTGLISFENNNYYFNENGEMQFGYINIEDKMTYFGEDGVMQIGVFNTPD
GFKYFAHQNTLDENFEGESINYTGWLDLDEKRYYFTDEYIAATGSVIIDGEEYYFDPDTAQLVISEHHHHHH nucleotide sequence of F54 New fusion protein

SEQ ID NO: 22

ATGGCAACCGGTTGGCAGACCATCGATGGCAAAAAATATTATTTTAATACCAACACCGCAATTGCAAGCACCGGCTATACCATTATCAAC

GGCAAACACTTTTATTTTAACACCGACGGCATTATGCAGATTGGTGTGTTTAAAGGTCCGAACGGCTTTGAATACTTTGCACCGGCAAAT

ACCGATGCCAATAATATTGAAGGCCAGGCCATTCTGTATCAGAATGAATTTCTGACCCTGAACGGCAAAAAATACTACTTTGGCAGCGAT

AGCAAAGCAGTTACCGGTTGGCGCATCATCAACAATAAGAAATATTACTTCAACCCGAATAATGCAATTGCAGCAATTCATCTGTGCACC

ATTAACAACGACAAATATTATTTCAGCTATGACGGTATTCTGCAGAATGGCTACATTACCATCGAACGCAACAACTTTTATTTCGATGCC

AACAACGAAAGCAAAATGGTGACCGGTGTTTTCAAAGGCCCTAATGGTTTTGAGTATTTCGCTCCGGCAAACACCCATAATAACAACATT

GAAGGTCAGGCGATCGTTTATCAGAACAAATTCCTGACGCTGAATGGTAAGAAATACTATTTCGATAATGACAGCAAAGCCGTGACCGGC

TGGCAGACAATTGACGGGAAGAAATATTACTTTAATCTGAATACCGCAGAAGCAGCAACCGGTTGGCAAACGATCGACGGTAAAAAGTAC

TACTTCAACCTGAACACAGCCGAAGCAGCCACAGGATGGCAGACTATTGATGGAAAAAAATACTATTTCAACACCAACACCTTTATTGCA

TCTACCGGTTATACCAGCATTAACGGTAAACATTTCTACTTCAACACCGATGGTATCATGCAGATCGGCGTTTTCAAAGGTCCAAATGGT

TTCGAATACTTTGCCCCTGCCAATACAGATGCAAATAACATCGAGGGTCAGGCAATCCTGTACCAAAACAAATTTCTGACCCTGAATGGG

AAAAAATATTACTTTGGTAGCGATTCTAAAGCCGTTACCGGTCTGCGCTACCATTGATGGTAAAAAATACTACTTTAATACGAATACAGCC

GTTGCGGTTACAGGCTGGCAGACCATTAACGGGAAAAAATACTATTTTAACACAAATACCAGCATTGCCTCAACGGGTTATACCATTATT

TCGGGTAAACACTTCTACTTTAATACCGATGGTATTATGCAAATCGGAGTCTTTAAAGGACCTGATGGGTTCGAATATTTTGCGCCTGCG

AACACTGATGCGAACAATATCGAAGGACAGGCAATCCGCTATCAGAATCGCTTTCTGTATCTGCACGACAACATCTATTATTTTGGCAAC

AATTCAAAAGCAGCCACCGGCTGGGTTACAATTGATGGCAACCGCTACTATTTCGAACCGAATACCGCAATGGGTGCAAATGGCTACAAA

ACCATCGATAATAAAAATTTCTATTTTCGCAACGGTCTGCCGCAGATCGGGGTATTTAAAGGTAGCAACGGCTTCGAATACTTCGCTCCA

GCGAATACGGACGCGAACAATATTGAGGGTCAAGCGATTCGTTATCAAAACCGTTTTCTGCATCTGCTGGGCAAAATCTACTACTTTGGC

AATAACAGTAAAGCAGTTACTGGATGGCAGACAATCAATGGTAAAGTGTACTATTTTATGCCGGATACCGCCATGGCAGCAGCCGGTGGT

CTGTTTGAAATTGATGGCGTGATCTATTTTTTGGTGTGGATGGTGTTAAAGCAGTTACCGGCTTTGTGACCGTGGGTGATGATAAATAC

TATTTCAATCCGATTAACGGTGGTGCAGCGAGCATTGGCGAAACCATCATCGATGACAAAAACTATTATTTCAACCAGAGCGGTGTGCTG

CAGACCGGTGTGTTTAGCACCGAAGATGGCTTTAAATATTTTGCGCCAGCGAACACCCTGGATGAAAACCTGGAAGGCGAAGCGATTGAT

TTTACCGGCAAACTGATCATCGATGAAAACATCTATTACTTCGATGATAACTATCGTGGTGCGGTGGAATGGAAAGAACTGGATGGCGAA

ATGCATTATTTTCTCCGGAAACCGGTAAAGCGTTTAAAGGCCTGAACCAGATCGGCGATTACAAATACTACTTCAACAGCGATGGCGTG

ATGCAGAAAGGCTTTGTGAGCATCAACGATAACAAACACTATTTCGATGATAGCGGTGTGATGAAAGTGGGCTATACCGAAATTGATGGC

AAACATTTCTACTTCGCGGAAAACGGCGAAATGCAGATTGGCGTGTTCAATACCGAAGATGGTTTCAAATACTTCGCGCACCATAACGAA

GATCTGGGTAACGAAGAAGGCGAAGAAATTAGCTATAGCGGCATCCTGAACTTCAACAACAAAATCTACTACTTTGATGATAGCTTTACC

GCGGTGGTGGGCTGGAAAGATCTGGAAGATGGCAGCAAATATTTTTCGATGAAGATACCGCGGAAGCGTATATTGGCCTGAGCCTGATT

AACGATGGCCAGTACTATTTTAACGATGATGGCATTATGCAGGTGGGTTTCGTGACCATTAATGATAAAGTGTTCTATTTCAGCGATAGC

GGCATTATTGAAAGCGGCGTGCAGAACATTGATGATAACTACTTCTACATCGATGATAACGGCATTGTGCAGATCGGCGTTTTTGATACC

AGCGATGGCTACAAATATTTCGCACCGGCCAATACCGTGAACGATAACATTTATGGCCAGGCGGTGGAATATAGCGGTCTGGTGCGTGTG

GGCGAAGATGTGTATTATTTCGGCGAAACCTATACCATCGAAACCGGCTGGATTTATGATATGGAAAACGAAAGCGATAAATATTACTTT

AATCCGGAAACGAAAAAAGCGTGCAAAGGCATTAACCTGATCGATGATATCAAATACTATTTTGATGAAAAAGGCATTATGCGTACCGGT

CTGATTAGCTTCGAAAACAACAACTATTACTTCAACGAAAACGGTGAAATGCAGTTCGGCTACATCAACATCGAAGATAAAATGTTCTAC

TTCGGCGAAGATGGTGTTATGCAGATTGGTGTTTTTAACACCCCGGATGGCTTCAAATACTTTGCCCATCAGAATACCCTGGATGAAAAT

TTCGAAGGTGAAAGCATTAACTATACCGGCTGGCTGGATCTGGATGAAAAACGCTACTACTTCACCGATGAATACATTGCGGCGACCGGC
AGCGTGATTATTGATGGCGAAGAATACTACTTCGATCCGGATACCGCGCAGCTGGTGATTAGCGAACATCATCATCATCACCAT amino acid sequence of F54 New fusion protein

SEQ ID NO: 23

MATGWQTIDGKKYYFNTNTAIASTGYTIINGKHFYFNTDGIMQIGVFKGPNGFEYFAPANTDANNIEGQAILYQN
EFLTLNGKKYYFGSDSKAVTGWRIINNKKYYFNPNNAIAAIHLCTINNDKYYFSYDGILQNGYITIERNNFYFDANNESK
MVTGVFKGPNGFEYFAPANTHNNNIEGQAIVYQNKFLTLNGKKYYFDNDSKAVTGWQTIDGKKYYFNLNTAEAATGWQTI
DGKKYYFNLNTAEAATGWQTIDGKKYYFNTNTFIASTGYTSINGKHFYFNTDGIMQIGVFKGPNGFEYFAPANTDANNIE
GQAILYQNKFLTLNGEXTYFGSDSKAVTGLRTIDGKKYYFNTNTAVAVTGWQTINGKKYYFNTNTSIASTGYTIISGKHF
YFNTDGIMQIGVFKGPDGFEYFAPANTDANNIEGQAIRYQNRFLYLHDNIYYFGNNSKAATGWVTIDGNRYYFEPNTAMG
ANGYKTIDNKNFYFRNGLPQIGVFKGSNGFEYFAPANTDANNIEGQAIRYQNRFLHLLGKITTFGNNSKAVTGWQTINGK
VYYFMPDTAMAAAGGLFEIDGVIYFFGVDGVKAVTGFVTVGDDKYYFNPINGGAASIGETIIDDKNYYFNQSGVLQTGVF
STEDGFKYFAPANTLDENLEGEAIDFTGKLIIDENIYYFDDNYRGAVEWKELDGEMHYFSPETGKAFKGLNQIGDYKYYF
NSDGVMQKGFVSINDNKHYFDDSGVMKVGYTEIDGKHFYFAENGEMQIGVFNTEDGFKYFAHHNEDLGNEEGEEISYSGI
LNFNNKIYYFDDSFTAVVGWKDLEDGSKYYFDEDTAEAYIGLSLINDGQYYFNDDGIMQVGFVTINDKVFYFSDSGIIES
GVQNIDDNYFYIDDNGIVQIGVFDTSDGYKYFAPANTVNDNIYGQAVEYSGLVRVGEDVYYFGETYTIETGWIYDMENES
DKYYFNPETKKACKGINLIDDIKYYFDEKGIMRTGLISFENNNYYFNENGEMQFGYINIEDKMFYFGEDGVMQIGVFNTP
DGFKYFAHQNTLDENFEGESINYTGWLDLDEKRYYFTDEYIAATGSVIIDGEEYYFDPDTAQLVISEHHHHHH nucleotide sequence of F5 ToxB fusion protein

SEQ ID NO: 24

ATGGCAACCGGTTGGCAGACCATCGATGGCAAAAAATATTATTTTAATACCAACACCGCAATTGCAAGCACCGGCTATACCATTATCAAC
GGCAAACACTTTTATTTTAACACCGACGGCATTATGCAGATTGGTGTGTTTAAAGGTCCGAACGGCTTTGAATACTTTGCACCGGCAAAT
ACCGATGCCAATAATATTGAAGGCCAGGCCATTCTGTATCAGAATGAATTTCTGACCCTGAACGGCAAAAAATACTACTTTGGCAGCGAT
AGCAAAGCAGTTACCGGTTGGCGCATCATCAACAATAAGAAATATTACTTCAACCCGAATAATGCAATTGCAGCAATTCATCTGTGCACC
ATTAACAACGACAAATATTATTTCAGCTATGACGGTATTCTGCAGAATGGCTACATTACCATCGAACGCAACAACTTTTATTTCGATGCC
AACAACGAAAGCAAAATGGTGACCGGTGTTTTCAAAGGCCCTAATGGTTTTGAGTATTTCGCTCCGGCAAACACCCATAATAACAACATT
GAAGGTCAGGCGATCGTTTATCAGAACAAATTCCTGACGCTGAATGGTAAGAAATACTATTTCGATAATGACAGCAAAGCCGTGACCGGC
TGGCAGACAATTGACGGGAAGAAATATTACTTTAATCTGAATACCGCAGAAGCAGCAACCGGTTGGCAAACGATCGACGGTAAAAAGTAC
TACTTCAACCTGAACACAGCCGAAGCAGCCACAGGATGGCAGACTATTGATGGAAAAAAATACTATTTCAACACCAACACCTTTATTGCA
TCTACCGGTTATACCAGCATTAACGGTAAACATTTCTACTTCAACACCGATGGTATCATGCAGATCGGCGTTTTCAAAGGTCCAAATGGT
TTCGAATACTTTGCCCCTGCCAATACAGATGCAAATAACATCGAGGGTCAGGCAATCCTGTACCAAAACAAATTTCTGACCCTGAATGGG
AAAAAATATTACTTTGGTAGCGATTCTAAAGCCGTTACCGGTCTGCGTACCATTGATGGTAAAAAATACTACTTTAATACGAATACAGCC
GTTGCGGTTACAGGCTGGCAGACCATTAACGGGAAAAAATACTATTTTAACACAAATACCAGCATTGCCTCAACGGGTTATACCATTATT
TCGGGTAAACACTTCTACTTTAATACCGATGGTATTATGCAAATCGGAGTCTTTAAAGGACCTGATGGGTTCGAATATTTTGCGCCTGCG
AACACTGATGCGAACAATATCGAAGGACAGGCAATCCGCTATCAGAATCGCTTTCTGTATCTGCACGACAACATCTATTATTTTGGCAAC
AATTCAAAAGCAGCCACCGGCTGGGTTACAATTGATGGCAACCGCTACTATTTCGAACCGAATACCGCAATGGGTGCAAATGGCTACAAA
ACCATCGATAATAAAAATTTCTATTTTCGCAACGGTCTGCCGCAGATCGGGGTATTTAAAGGTAGCAACGGCTTCGAATACTTCGCTCCA
GCGAATACGGACGCGAACAATATTGAGGGTCAAGCGATTCGTTATCAAAACCGTTTTCTGCATCTGCTGGGCAAAATCTACTACTTTGGC
AATAACAGTAAAGCAGTTACTGGATGGCAGACAATCAATGGTAAAGTGTACTATTTTATGCCGGATACCGCCATGGCAGCAGCCGGTGGT
CTGTTTGAAATTGATGGCGTGATCTATTTTTTTGGTGTGGATGGTGTTAAAGCAGTGAGCGGTCTGATTTATATTAACGATAGCCTGTAT
TAGTTTAAACCACCGGTGAATAACCTGATTACCGGCTTTGTGACCGTGGGTGATGATAAATACTATTTCAATCCGATTAACGGTGGTGCA
GCGAGCATTGGCGAAACCATCATCGATGACAAAAACTATTATTTCAACCAGAGCGGTGTGCTGCAGACCGGTGTGTTTAGCACCGAAGAT

-continued

GGCTTTAAATATTTTGCGCCAGCGAACACCCTGGATGAAAACCTGGAAGGCGAAGCGATTGATTTTACCGGCAAACTGATCATCGATGAA

AACATCTATTACTTCGATGATAACTATCGTGGTGCGGTGGAATGGAAAGAACTGGATGGCGAAATGCATTATTTTTCTCCGGAAACCGGT

AAAGCGTTTAAAGGCCTGAACCAGATCGGCGATTACAAATACTACTTCAACAGCGATGGCGTGATGCAGAAAGGCTTTGTGAGCATCAAC

GATAACAAACACTATTTCGATGATAGCGGTGTGATGAAAGTGGGCTATACCGAAATTGATGGCAAACATTTCTAGTTCGCGGAAAACGGC

GAAATGCAGATTGGCGTGTTCAATACCGAAGATGGTTTCAAATACTTCGCGCACCATAACGAAGATCTGGGTAACGAAGAAGGCGAAGAA

ATTAGCTATAGCGGCATCCTGAACTTCAACAACAAAATCTACTACTTTGATGATAGCTTTACCGCGGTGGTGGGCTGGAAAGATCTGGAA

GATGGCAGCAAATATTATTTCGATGAAGATACCGCGGAAGCGTATATTGGCCTGAGCCTGATTAACGATGGCCAGTACTATTTTAACGAT

GATGGCATTATGCAGGTGGGTTTCGTGACCATTAATGATAAAGTGTTCTATTTCAGCGATAGCGGCATTATTGAAAGCGGCGTGCAGAAC

ATTGATGATAACTACTTCTACATCGATGATAACGGCATTGTGCAGATCGGCGTTTTTGATACCAGCGATGGCTACAAATATTTCGCACCG

GCCAATACCGTGAACGATAACATTTATGCCAGGCGGTGGAATATAGCGGTCTGGTGCGTGTGGGCGAAGATGTGTATTATTTCGGCGAA

ACCTATACCATCGAAACCGGCTGGATTTATGATATGGAAAACGAAAGCGATAAATATTACTTTAATCCGGAAACGAAAAAAGCGTGCAAA

GGCATTAACCTGATCGATGATATCAAATACTATTTTGATGAAAAAGGCATTATGCGTACCGGTCTGATTAGCTTCGAAAACAACAACTAT

TAGTTCAACGAAAACGGTGAAATGCAGTTCGGCTACATCAACATCGAAGATAAAATGTTCTACTTCGGCGAAGATGGTGTTATGCAGATT

GGTGTTTTTAACACCCCGGATGGCTTCAAATACTTTGCCCATCAGAATACCCTGGATGAAAATTTCGAAGGTGAAAGCATTAACTATACC

GGCTGGCTGGATCTGGATGAAAAACGCTACTACTTCACCGATGAATACATTGCGGCGACCGGCAGCGTGATTATTGATGGCGAAGAATAC

TACTTCGATCCGGATACCGCGCAGCTGGTGATTAGCGAACATCATCATCATCACCAT amino acid sequence of F5 ToxB fusion protein

SEQ ID NO: 25

MATGWQTIDGKKYYFNTNTAIASTGYTIINGKHFYFNTDGIMQIGVFKGPNGFEYFAPANTDANNIEGQAILYQN

EFLTLNGKKYYFGSDSKAVTGWRIINNKKYYFNPNNAIAAIHLCTINNDKYYFSYDGILQNGYITIERNNFYFDANNESK

MVTGVFKGPNGFEYFAPANTHNNNIEGQAIVYQNKFLTLNGKKYYFDNDSKAVTGWQTIDGKKYYFNLNTAEAATGWQTI

DGKKYYFNLNTAEAATGWQTIDGKKYYFNTNTFIASTGYTSINGKHFYFNTDGIMQIGVFKGPNGFEYFAPANTDANNIE

GQAILYQNKFLTLNGKKYYFGSDSKAVTGIRTIDGKKYYFNTNTAVAVTGWQTINGKKYYFNTNTSIASTGYTIISGKHF

YFNTDGIMQIGVFKGPDGFEYFAPANTDANNIEGQAIRYQNRFLYLHDNIYYFGNNSKAATGWVTIDGNRYYFEPNTAMG

ANGYKTIDNKNFYFRNGLPQIGVFKGSNGFEYFAPANTDANNIEGQAIRYQNRFLHLLGKIYYFGNNSKAVTGWQTINGK

VYYFMPDTAMAAAGGLFEIDGVIYFFGVDGVKAVSGLIYINDSLYYFKPPVNNLITGFVTVGDDKYYFNPINGGAAS1GE

TIIDDKNYYFNQSGVLQTGVFSTEDGFKYFAPANTLDENLEGEAIDFTGKLIIDENIYYFDDNYRGAVEWKELDGEMHYF

SPETGKAFKGLNQIGDYKYYFNSDGVMQKGFVSINDNKHYFDDSGVMKVGYTEIDGKHFYFAENGEMQIGVFNTEDGFKY

FAHHNEDLGNEEGEEISYSGILNFNNKIYYFDDSFTAVVGWKDLEDGSKYYFDEDTAEAYIGLSLINDGQYYFNDDGIMQ

VGFVTINDKVFYFSDSGIIESGVQNIDDNYFYIDDNGIVQIGVFDTSDGYKYFAPANTVNDNIYGQAVEYSGLVRVGEDV

YYFGETYTIETGWIYDMENESDKYYFNPETKKACKGINLIDDIKYYFDEKGIMRTGLISFENNNYYFNENGEMQFGYINI

EDKMFYFGEDGVMQIGVFNTPDGFKYFAHQNTLDENFEGESINYTGWLDLDEKRYYFTDEYIAATGSVIIDGEEYYFDPD

TAQLVISEHHHHHH nucleotide sequence of F52 new fusion protein

SEQ ID NO: 26

ATGGCAACCGGTTGGCAGACCATCGATGGCAAAAAATATTATTTTAATACCAACACCGCAATTGCAAGCACCGGCTATACCATTATCAAC

GGCAAACACTTTTATTTTAACACCGACGGCATTATGCAGATTGGTGTGTTTAAAGGTCCGAACGGCTTTGAATACTTTGCACCGGCAAAT

ACCGATGCCAATAATATTGAAGGCCAGGCCATTCTGTATCAGAATGAATTTCTGACCCTGAACGGCAAAAAATACTACTTTGGCAGCGAT

AGCAAAGCAGTTACCGGTTGGCGCATCATCAACAATAAGAAATATTACTTCAACCCGAATAATGCAATTGCAGCAATTCATCTGTGCACC

ATTAACAACGACAAATATTATTTCAGCTATGACGGTATTCTGCAGAATGGCTACATTACCATCGAACGCAACAACTTTTATTTCGATGCC

AACAACGAAAGCAAAATGGTGACCGGTGTATTTCAAAGGCCCTAATGGTTTTGAGTATTTCGCTCCGGCAAACACCCATAATAACAACATT

GAAGGTCAGGCGATCGTTTATCAGAACAAATTCCTGACGCTGAATGGTAAGAAATACTATTTCGATAATGACAGCAAAGCCGTGACCGGC

TGGCAGACAATTGACGGGAAGAAATATTACTTTAATCTGAATACCGCAGAAGCAGCAACCGGTTGGCAAACGATCGACGGTAAAAAGTAC

```
TACTTCAACCTGAACACAGCCGAAGCAGCCACAGGATGGCAGACTATTGATGGAAAAAAATACTATTTCAACACCAACACCTTTATTGCA
TCTACCGGTTATACCAGCATTAACGGTAAACATTTCTACTTCAACACCGATGGTATCATGCAGATCGGCGTTTTCAAAGGTCCAAATGGT
TTCGAATACTTTGCCCCTGCCAATACAGATGCAAATAACATCGAGGGTCAGGCAATCCTGTACCAAAACAAATTTCTGACCCTGAATGGG
AAAAAATATTACTTTGGTAGCGATTCTAAAGCCGTTACCGGTCTGCGTACCATTGATGGTAAAAAATACTACTTTAATACGAATACAGCC
GTTGCGGTTACAGGCTGGCAGACCATTAACGGGAAAAAATACTATTTTAACACAAATACCAGCATTGCCTCAACGGGTTATACCATTATT
TCGGGTAAACACTTCTACTTTAATACCGATGGTATTATGCAAATCGGAGTCTTTAAAGGACCTGATGGGTTCGAATATTTTGCGCCTGCG
AACACTGATGCGAACAATATCGAAGGACAGGCAATCCGCTATCAGAATCGCTTTCTGTATCTGCACGACAACATCTATTATTTTGGCAAC
AATTCAAAAGCAGCCACCGGCTGGGTTACAATTGATGGCAACCGCTACTATTTCGAACCGAATACCGCAATGGGTGCAAATGGCTACAAA
ACCATCGATAATAAAAATTTCTATTTTCGCAACGGTCTGCCGCAGATCGGGGTATTTAAAGGTAGCAACGGCTTCGAATACTTCGCTCCA
GCGAATACGGACGCGAACAATATTGAGGGTCAAGCGATTCGTTATCAAAACCGTTTTCTGCATCTGCTGGGCAAAATCTACTACTTTGGC
AATAACAGTAAAGCAGTTACTGGATGGCAGACAATCAATGGTAAAGTGTACTATTTTATGCCGGATACCGCCATGGCAGCAGCCGGTGGT
CTGTTTGAAATTGATGGCGTGATCTATTTTTTTGGTGTGGATGGTGTTAAAGCAGTGAAAGGCCTGAACCAGATCGGCGATTACAAATAC
TACTTCAACAGCGATGGCGTGATGCAGAAAGGCTTTGTGAGCATCAACGATAACAAACACTATTTCGATGATAGCGGTGTGATGAAAGTG
GGCTATACCGAAATTGATGGCAAACATTTCTACTTCGCGAAAACGGCGAAATGCAGATTGGCGTGTTCAATACCGAAGATGGTTTCAAA
TACTTCGCGCACCATAACGAAGATCTGGGTAACGAAGAAGGCGAAGAAATTAGCTATAGCGGCATCCTGAACTTCAACAACAAATCTAC
TACTTTGATGATAGCTTTACCGCGGTGGTGGGCTGGAAAGATCTGGAAGATGGCAGCAAATATTATTTCGATGAAGATACCGCGGAAGCG
TATATTGGCCTGAGCCTGATTAACGATGGCCAGTACTATTTTAACGATGATGGCATTATGCAGGTGGGTTTCGTGACCATTAATGATAAA
GTGTTCTATTTCAGCGATAGCGGCATTATTGAAAGCGGCGTGCAGAACATTGATGATAACTACTTCTACATCGATGATAACGGCATTGTG
CAGATCGGCGTTTTTGATACCAGCGATGGCTACAAATATTTCGCACCGGCCAATACCGTGAACGATAACATTTATGGCCAGGCGGTGGAA
TATAGCGGTCTGGTGCGTGTGGGCGAAGATGTGTATTATTTCGGCGAAACCTATACCATCGAAACCGGCTGGATTTATGATATGGAAAAC
GAAAGCGATAAATATTACTTTAATCCGGAAACGAAAAAAGCGTGCAAAGGCATTAACCTGATCGATGATATCAAATACTATTTTGATGAA
AAAGGCATTATGCGTACCGGTCTGATTAGCTTCGAAAACAACAACTATTACTTCAACGAAAACGGTGAAATGCAGTTCGGCTACATCAAC
ATCGAAGATAAAATGTTCTACTTCGGCGAAGATGGTGTTATGCAGATTGGTGTTTTTAACACCCCGGATGGCTTCAAATACTTTGCCCAT
CAGAATACCCTGGATGAAAATTTCGAAGGTGAAAGCATTAACTATACCGGCTGGCTGGATCTGGATGAAAAACGCTACTACTTCACCGAT
GAATACATTGCGGCGACCGGCAGCGTGATTATTGATGGCGAAGAATACTACTTCGATCCGGATACCGCGCAGCTGGTGATTAGCGAACAT
CATCATCATCACCAT
``` amino acid sequence of F52 New fusion protein

SEQ ID NO: 27

```
MATGWQTIDGKKYYFNTNTAIASTGYTIINGKHFYFNTDGIMQIGVFKGPNGFEYFAPANTDANNIEGQAILYQNEFLTLN
GKKYYFGSDSKAVTGWRIINNKKYYFNPNNAIAAIHLCTINNDKYYFSYDGILQNGYITIERNNFYFDANNESEMVTGVF
KGPNGFEYFAPANTHNNNIEGQAIVYQNKFLTLNGKKYYFDNDSKAVTGWQTIDGKKYYFNLNTAEAATGWQTIDGKKYY
FNLNTAEAATGWQTIDGKKYYFNTNTFIASTGYTSINGKHFYFNTDGIMQIGVFKGPNGFEYFAPANTDANNIEGQAILY
QNKFLTLNGKKYYFGSDSKAVTGLRTIDGKKYYFNTNTAVAVTGWQTINGKKYYFNTNTSIASTGYTIISGKHFYFNTDG
IMQIGVFKGPDGFEYFAPANTDANNIEGQAIRYQNRFLYLHDNIYYFGNNSKAATGWVTIDGNRYYFEPNTAMGANGYKT
IDNKNFYFRNGLPQIGVFKGSNGFEYFAPANTDANNIEGQAIRYQNRFLHLLGKIYYFGNNSKAVTGWQTINGKVYYFMP
DTAMAAAGGLFEIDGVIYFFGVDGVKAVKGLNQIGDYKYYFNSDGVMQKGFVSINDNKHYEDDSGVMKVGYTEIDGKHFY
FAENGEMQIGVFNTEDGFKYFAHHNEDLGNEEGEEISYSGILNFNNKIYYFDDSFTAVVGWKDLEDGSKYYFDEDTAEAY
IGLSLINDGQYYFNDDGIMQVGFVTINDKVFYFSDSGIIESGVQNIDDNYFYIDDNGIVQIGVFDTSDGYKYFAPANTVN
DNIYGQAVEYSGLVRVGEDVYYFGETYTIETGWIYDMENESDKYYFNPETKKACKGINLIDDIKYYFDEKGIMRTGLISF
ENNNYYFNENGEMQFGYINIEDKMFYFGEDGVMQIGVFNTPDGFKYFAHQNTLDENFEGESINYTGWLDLDEKRYYFTDE
YIAATGSVIIDGEEYYFDPDTAQLVISEHHHHHH
``` sequence of toxin A fragment of F54 Gly

SEQ ID NO: 28

MATGWQTIDGKKYYFNTNTAIASTGYTIINGKHFYFNTDGIMQIGVFKGPNGFEYFAPANTDANNIEGQAIL
YQNEFLTLNGKKYYFGSDSKAVTGWRIINNKKYYFNPNNAIAAIHLCTINNDKYYFSYDGILQNGYITTERN
NFYFDANNESKMVTGVFKGPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFIASTGYTSINGKHFYFNTDG
IMQIGVFKGPNGFEYFAPANTDANNIEGQAILYQNKFLTLNGKKYYFGSDSKAVTGLRTIDGKKYYFNTNTA
VAVTGWQTINGKKYYFNTNTSIASTGYTIISGKHFYFNTDGIMQIGVFKGPDGFEYFAPANTDANNIEGQAI
RYQNRFLYLHDNIYYFGNNSKAATGWVTIDGNRYYFEPNTAMGANGYKTIDNKNFYFRNGLPQIGVFKGSNG
FEYFAPANTDANNIEGQATRYQNRELHLLGKIYYFGNNSKAVTGWQTINGKVYYFMPDTAMAAAGGLFEIDG
VIYFFGVDGVKAPGIYG sequence of toxin A fragment of F54 New

SEQ ID NO: 29

MATGWQTIDGKKYYFNTNTAIASTGYTIINGKHFYFNTDGIMQIGVFKGPNGFEYFAPANTDANNIEGQATL
YQNEFLTLNGKKYYFGSDSKAVTGWRIINNKKYYFNPNNAIAAIHLCTINNDKYYFSYDGILQNGYITIERN
NFYFDANNESKMVTGVFKGPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFIASTGYTSINGKHFYFNTDG
IMQIGVFKGPNGFEYFAPANTDANNIEGQAILYQNKFLTLNGKKYYFGSDSKAVTGLRTIDGKKYYFNTNTA
VAVTGWQTINGKKYYFNTNTSIASTGYTIISGKHFYFNTDGIMQIGVFKGPDGFEYFAPANTDANNIEGQAT
RYQNRFLYLHDNIYYFGNNSKAATGWVTIDGNRYYFEPNTAMGANGYKTIDNKNFYFRNGLPQIGVFKGSNG
FEYFAPANTDANNIEGQAIRYQNRFLHLLGKIYYFGNNSKAVTGWQTINGKVYYFMPDTAMAAAGGLFEIDG
VIYFFGVDGVKAV sequence of toxin A fragment of F5 ToxB

SEQ ID NO: 30

MATGWQTIDGKKYYFNTNTAIASTGYTIINGKHFYENTDGIMQIGVFKGPNGFEYFAPANTDANNIEGQAIL
YQNEFLTLNGKKYYFGSDSKAVTGWRIINNKKYYFNPNNAIAAIHLCTINNDKYYFSYDGILQNGYITIERN
NFYFDANNESKMVTGVFKGPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFIASTGYTSINGKHFYFNTDG
IMQIGVFKGPNGFEYFAPANTDANNIEGQAILYQNKFLTLNGKKYYFGSDSKAVTGLRTIDGKKYYFNTNTA
VAVTGWQTINGKKYYFNTNTSIASTGYTIISGKHFYFNTDGIMQIGVFKGPDGFEYFAPANTDANNIEGQAT
RYQNRFLYLHDNIYYFGNNSKAATGWVTIDGNRYYFEPNTAMGANGYKTIDNKNFYFRNGLPQIGVFKGSNG
FEYFAPANTDANNIEGQAIRYQNRFLHLLGKIYYFGNNSKAVTGWQTINGKVYYFMPDTAMAAAGGLFEIDG
VIYFFGVDGVKAV sequence of toxin A fragment of F52 New

SEQ ID NO: 31

MATGWQTIDGKKYYFNTNTAIASTGYTIINGKHFYFNTDGIMQIGVFKGPNGFEYFAPANTDANNIEGQAIL
YQNEFLTLNGKKYYFGSDSKAVTGWRIINNKKYYFNPNNAIAAIHLCTINNDKYYFSYDGILQNGYITIERN
NFYFDANNESKMVTGVFKGPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFIASTGYTSINGKHFYFNTDG
IMQIGVFKGPNGFEYFAPANTDANNIEGQAILYQNKFLTLNGKKYYFGSDSKAVTGLRTIDGKKYYFNTNTA
VAVTGWQTINGKKYYFNTNTSIASTGYTIISGKHFYFNTDGIMQIGVFKGPDGFEYFAPANTDANNIEGQAI
RYQNRFLYLHDNIYYFGNNSKAATGWVTIDGNRYYFEPNTAMGANGYKTIDNKNFYFRNGLPQIGVFKGSNG
FEYFAPANTDANNIEGQAIRYQNRFLHLLGKIYYFGNNSKAVTGWQTINGKVYYFMPDTAMAAAGGLFEIDG
VIYFFGVDGVKAV

| | |
|---|---|
| sequence of toxin B fragment of F54Gly | SEQ ID NO: 32 |

TGFVTVGDDKYYFNPINGGAASIGETIIDDKNYYFNQSGVLQTGVESTEDGEKYFAPANTLDENLEGEAIDF
TGKLIIDENIYYFDDNYRGAVEWKELDGEMHYFSPETGKAFKGLNQIGDYKYYFNSDGVMQKGFVSINDNKH
YFDDSGVMKVGYTEIDGKHEYFAENGEMQIGVENTEDGEKYFAHHNEDLGNEEGEEISYSGILNFNNKIYYF
DDSFTAVVGWKDLEDGSKYYFDEDTAEAYIGLSLINDGQYYFNDDGIMQVGFVTINDKVEYESDSGIIESGV
QNIDDNYFYIDDNGIVQIGVFDTSDGYKYFAPANTVNDNIYGQAVEYSGLVRVGEDVYYFGETYTIETGWIY
DMENESDKYYFNPETKKACKGINLIDDIKYYFDEKGIMRTGLISFENNNYYFNENGEMQFGYINIEDKMFYF
GEDGVMQIGVENTPDGEKYFAHQNTLDENFEGESINYTGWLDLDEKRYYFTDEYIAATGSVIIDGEEYYFDP
DTAQLVISE

| | |
|---|---|
| sequence of toxin B fragment of F54 New | SEQ ID NO: 33 |

TGFVTVGDDKYYFNPINGGAASIGETIIDDKNYYFNQSGVLQTGVESTEDGEKYFAPANTLDENLEGEAIDF
TGKLIIDENIYYFDDNYRGAVEWKELDGEMHYFSPETGKAFKGLNQIGDYKYYFNSDGVMQKGFVSINDNKH
YFDDSGVMKVGYTEIDGKHFYFAENGEMQIGVENTEDGFKYFAHHNEDLGNEEGEEISYSGILNENNKIYYF
DDSFTAVVGWKDLEDGSKYYFDEDTAEAYIGLSLINDGQYYFNDDGIMQVGFVTINDKVEYESDSGIIESGV
QNIDDNYFYIDDNGIVQIGVFDTSDGYKYFAPANTVNDNIYGQAVEYSGLVRVGEDVYYFGETYTIETGWIY
DMENESDKYYFNPETKKACKGINLIDDIKYYFDEKGIMRTGLISFENNNYYFNENGEMQFGYINIEDKMFYF
GEDGVMQIGVENTPDGEKYFAHQNTLDENFEGESINYTGWLDLDEKRYYFTDEYIAATGSVIIDGEEYYFDP
DTAQLVISE

| | |
|---|---|
| sequence of toxin B fragment of F5 ToxB | SEQ ID NO: 34 |

SGLIYINDSLYYFKPPVNNLITGFVTVGDDKYYFNPINGGAASIGETIIDDKNYYFNQSGVLQTGVESTEDG
FKYFAPANTLDENLEGEAIDFTGKLIIDENIYYFDDNYRGAVEWKELDGEMHYFSPETGKAFKGLNQIGDYK
YYFNSDGVMQKGFVSINDNKHYFDDSGVMKVGYTEIDGKHFYFAENGEMQIGVENTEDGEKYFAHHNEDLGN
EEGEEISYSGILNENNKIYYFDDSFTAVVGWKDLEDGSKYYFDEDTAEAYIGLSLINDGQYYENDDGIMQVG
FVTINDKVEYESDSGIIESGVQNIDDNYFYIDDNGIVQIGVFDTSDGYKYFAPANTVNDNIYGQAVEYSGLV
RVGEDVYYFGETYTIETGWIYDMENESDKYYFNPETKKACKGINLIDDIKYYFDEKGIMRTGLISFENNNYY
FNENGEMQFGYINIEDKMFYFGEDGVMQIGVENTPDGEKYFAHQNTLDENFEGESINYTGWLDLDEKRYYFT
DEYIAATGSVIIDGEEYYFDPDTAQLVISE

| | |
|---|---|
| sequence of toxin B fragment of F52 New | SEQ ID NO: 35 |

KGLNQIGDYKYYFNSDGVMQKGFVSINDNKHYFDDSGVMKVGYTEIDGKHFYFAENGEMQIGVFNTEDGFKY
FAHHNEDLGNEEGEEISYSGILNENNKIYYFDDSFTAVVGWKDLEDGSKYYFDEDTAEAYIGLSLINDGQYY
FNDDGIMQVGFVTINDKVEYESDSGIIESGVQNIDDNYFYIDDNGIVQIGVFDTSDGYKYFAPANTVNDNIY
GQAVEYSGLVRVGEDVYYFGETYTIETGWIYDMENESDKYYFNPETKKACKGINLIDDIKYYFDEKGIMRTG
LISFENNNYYFNENGEMQFGYINIEDKMFYFGEDGVMQIGVFNTPDGFKYFAHQNTLDENFEGESINYTGWL
DLDEKRYYFTDEYIAATGSVIIDGEEYYFDPDTAQLVISE

| | |
|---|---|
| C-TAB.G5 fusion protein | SEQ ID NO: 36 |

MVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPN
GFEYFAPANTHNNNIEGQAILYQNKFLTLNGKKYYFGSDSKAVTGLRTIDGKKYYFNTNTAVAVTGWQTING
KKYYFNTNTSIASTGYTIISGKHFYFNTDGIMQIGVFKGPDGFEYFAPANTDANNIEGQAIRYQNRFLYHD
NIYYFGNNSKAATGWVTIDGNRYYFEPNTAMGANGYKTIDNKNFYFRNGLPQIGVFKGSNGFEYFAPANTDA

-continued

NNIEGQAIRYQNRFLHLLGKIYYFGNNSKAVTGWQTINGKVYYFMPDTAMAAAGGLFEIDGVIYFFGVDGVK

APGIYGRSMHNLITGFVTVGDDKYYFNPINGGAASIGETIIDDKNYYFNQSGVLQTGVFSTEDGFKYFAPAN

TLDENLEGEAIDFTGKLIIDENIYYFDDNYRGAVEWKELDGEMHYFSPETGKAFKGLNQIGDYKYYFNSDGV

MQKGFVSINDNKHYFDDSGVMKVGYTEIDGKHFYFAENGEMQIGVFNTEDGFKYFAHHNEDLGNEEGEEISY

SGILNFNNKIYYFDDSFTAVVGWKDLEDGSKYYFDEDTAEAYIGLSLINDGQYYFNDDGIMQVGFVTINDKV

FYFSDSGIIESGVQNIDDNYFIDDNGIVQIGVFDTSDGYKYFAPANTVNDNIYGQAVEYSGLVRVGEDVYY

FGETYTIETGWIYDMENESDKYYFNPETKKACKGINLIDDIKYYFDEKGIMRTGLISFENNNYYFNENGEMQ

FGYINIEDKMFYFGEDGVMQIGVFNTPDGFKYFAHQNTLDENFEGESINYTGWLDLDEKRYYFTDEYIAATG

SVIIDGEEYYFDPDTAQLVISE

C-TAB.G5.1 fusion protein

VTGVFKGPNGFEYFAPANTHNNNIEGQAIVYQNKFLTLNGKKYYFDNDSKAVTGWQTIDGKKYYFNLNTAEA    SEQ ID NO: 37

ATGWQTIDGKKYYFNLNTAEAATGWQTIDGKKYYFNTNTFIASTGYTSINGKHFYFNTDGIMQIGVFKGPNG

FEYFAPANTDANNIEGQAILYQNKFLTLNGKKYYFGSDSKAVTGLRTIDGKKYYFNTNTAVAVTGWQTINGK

KYYFNTNTSIASTGYTIISGKHFYFNIDGIMQIGVFKGPDGFEYFAPANTDANNIEGQAIRYQNRFLYLHDN

IYYFGNNSKAATGWVTIDGNRYYFEPNTAMGANGYKTIDNKNFYFRNGLPQIGVFKGSNGFEYFAPANTDAN

NIEGQAIRYQNRFLHLLGKIYYFGNNSKAVTGWQTINGKVYYEMPDTAMAAAGGLFEIDGVIYFFGVDGVKA

PGIYGRSMHNLITGFVTVGDDKYYFNPINGGAASIGETIIDDKNYYFNQSGVLQTGVFSTEDGFKYFAPANT

LDENLEGEAIDFTGKLIIDENIYYFDDNYRGAVEWKELDGEMHYFSPETGKAFKGLNQIGDYKYYFNSDGVM

QKGFVSINDNKHYFDDSGVMKVGYTEIDGKHFYFAENGEMQIGVENTEDGFKYFAHHNEDLGNEEGEEISYS

GILNFNNKIYYFDDSFTAVVGWKDLEDGSKYYFDEDTAEAYIGLSLINDGQYYFNDDGIMQVGFVTINDKVF

YFSDSGIIESGVQNIDDNYFIDDNGIVQIGVFDTSDGYKYFAPANTVNDNIYGQAVEYSGLVRVGEDVYYF

GETYTIETGWIYDMENESDKYYFNPETKKACKGINLIDDIKYYFDEKGIMRTGLISFENNNYYFNENGEMQF

GYINIEDKMFYFGEDGVMQIGVFNTPDGFKYFAHQNTLDENFEGESINYTGWLDLDEKRYYFTDEYIAATGS

VIIDGEEYYFDPDTAQLVISE

---

The invention claimed is:
1. An immunogenic composition comprising:
a) a fusion polypeptide comprising a *Clostridium difficile* toxin A fragment and *C. difficile* toxin B fragment; and
b) an adjuvant comprising an oil in water emulsion, wherein said oil in water emulsion comprises a metabolisable oil, a tocol and an emulsifier.

2. An immunogenic composition according to claim 1, wherein the oil in water emulsion comprises 1-10, 2-10, 3-9, 4-8, 5-7, or 5-6 mg metabolisable oil, per dose.

3. An immunogenic composition according to claim 1, wherein the oil in water emulsion comprises 0.5-11, 1-11, 2-10, 3-9, 4-8, 5-7, 5-6 mg tocol, per dose.

4. An immunogenic composition according to claim 1, wherein the oil in water emulsion comprises 0.1-5, 0.2-5, 0.3-4, 0.4-3 or 2-3 mg emulsifying agent, per dose.

5. An immunogenic composition according to claim 1, wherein the metabolisable oil is squalene.

6. An immunogenic composition according to claim 1, wherein the tocol is alpha-tocopherol.

7. An immunogenic composition according to claim 1, wherein the emulsifying agent is polyoxyethylene sorbitan monooleate.

8. An immunogenic composition according to claim 7, wherein the polyoxyethylene sorbitan monooleate is polysorbate 80.

9. An immunogenic composition according claim 1, wherein the immunogenic composition has a volume of 0.5 to 1.5 ml.

10. An immunogenic composition according to claim 1, wherein the polypeptide is a fusion polypeptide comprising a first fragment and a second fragment, wherein (i) the first fragment is a toxin A repeating domain fragment;
(ii) the second fragment is a toxin B repeating domain fragment;
(iii) the first fragment has a first proximal end;
(iv) the second fragment has a second proximal end; and
wherein the first fragment and the second fragment are adjacent to one another.

11. An immunogenic composition according to claim 10, wherein the first proximal end is within a short repeat and/or the second proximal end is within a short repeat.

12. An immunogenic composition according to claim 10, wherein the first proximal end and the second proximal end do not disrupt short repeat-long repeat-short repeat (SR-LR-SR) portions.

13. An immunogenic composition according to claim 10, wherein the polypeptide comprises an immunogenic fragment of SEQ ID NO: 4.

14. An immunogenic composition according to claim 10, wherein the polypeptide is a polypeptide comprising a first fragment and a second fragment, wherein (i) the first fragment is a toxin A repeating domain fragment;
(ii) the second fragment is a toxin B repeating domain fragment;
(iii) the first fragment comprises a first proximal end within a first repeat portion;
(iv) the second fragment comprises a second proximal end within a second repeat portion; and
wherein the first fragment and the second fragment are adjacent to one another and wherein the first repeat portion and the second repeat portion have high structural similarity at least 60% sequence identity to one another.

15. An immunogenic composition according to claim 14, wherein the first proximal end is within repeat portion VII of toxin A and the second proximal end is within repeat portion II of toxin B.

16. An immunogenic composition according to claim 15, wherein the first proximal end is within a long repeat and/or the second proximal end is within a long repeat.

17. A vaccine comprising the immunogenic composition of claim 1, and a pharmaceutically acceptable excipient.

18. A method of preventing or treating *C. difficile* disease comprising administering the immunogenic composition of claim 1 to a patient.

19. An immunogenic composition according to claim 1, wherein the polypeptide is a polypeptide comprising a first fragment and a second fragment, wherein
- (i) the first fragment is a toxin A repeating domain fragment as set forth in SEQ ID NO:11;
- (ii) the second fragment is a toxin B repeating domain fragment as set forth in SEQ ID NO:16;
- (iii) the first fragment has a first proximal end; and
- (iv) the second fragment has a second proximal end; and wherein the first fragment and the second fragment are adjacent to one another.

* * * * *

SEQUENCE LISTING

<160> NUMBER OF SEQ ID NOS: 37

<210> SEQ ID NO 1
<211> LENGTH: 2710
<212> TYPE: PRT
<213> ORGANISM: clostridium difficile

<400> SEQUENCE: 1

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
            130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Ser Arg Pro Ser
290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
            355                 360                 365

Asp Leu Glu Ile Lys Ile Ala Phe Ala Leu Gly Ser Val Ile Asn Gln
370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445

Ile Ala Pro Tyr Leu Gln Val Gly Phe Met Pro Glu Ala Arg Ser Thr
450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr

```
              515                 520                 525
Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
                595                 600                 605

Ile Ile Gln Arg Asn Met Asn Glu Ser Ala Lys Ser Tyr Phe Leu Ser
        610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
930                 935                 940
```

```
Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
        995                 1000                1005

Leu Val Asn Leu Ile Ser Asn Ala Val Asn Asp Thr Ile Asn Val Leu
    1010                1015                1020

Pro Thr Ile Thr Glu Gly Ile Pro Ile Val Ser Thr Ile Leu Asp Gly
1025                1030                1035                1040

Ile Asn Leu Gly Ala Ala Ile Lys Glu Leu Leu Asp Glu His Asp Pro
                1045                1050                1055

Leu Leu Lys Lys Glu Leu Glu Ala Lys Val Gly Val Leu Ala Ile Asn
            1060                1065                1070

Met Ser Leu Ser Ile Ala Ala Thr Val Ala Ser Ile Val Gly Ile Gly
        1075                1080                1085

Ala Glu Val Thr Ile Phe Leu Leu Pro Ile Ala Gly Ile Ser Ala Gly
    1090                1095                1100

Ile Pro Ser Leu Val Asn Asn Glu Leu Ile Leu His Asp Lys Ala Thr
1105                1110                1115                1120

Ser Val Val Asn Tyr Phe Asn His Leu Ser Glu Ser Lys Lys Tyr Gly
                1125                1130                1135

Pro Leu Lys Thr Glu Asp Asp Lys Ile Leu Val Pro Ile Asp Asp Leu
            1140                1145                1150

Val Ile Ser Glu Ile Asp Phe Asn Asn Asn Ser Ile Lys Leu Gly Thr
        1155                1160                1165

Cys Asn Ile Leu Ala Met Glu Gly Gly Ser Gly His Thr Val Thr Gly
    1170                1175                1180

Asn Ile Asp His Phe Phe Ser Ser Pro Ser Ile Ser Ser His Ile Pro
1185                1190                1195                1200

Ser Leu Ser Ile Tyr Ser Ala Ile Gly Ile Glu Thr Glu Asn Leu Asp
                1205                1210                1215

Phe Ser Lys Lys Ile Met Met Leu Pro Asn Ala Pro Ser Arg Val Phe
            1220                1225                1230

Trp Trp Glu Thr Gly Ala Val Pro Gly Leu Arg Ser Leu Glu Asn Asp
        1235                1240                1245

Gly Thr Arg Leu Leu Asp Ser Ile Arg Asp Leu Tyr Pro Gly Lys Phe
    1250                1255                1260

Tyr Trp Arg Phe Tyr Ala Phe Phe Asp Tyr Ala Ile Thr Thr Leu Lys
1265                1270                1275                1280

Pro Val Tyr Glu Asp Thr Asn Ile Lys Ile Lys Leu Asp Lys Asp Thr
                1285                1290                1295

Arg Asn Phe Ile Met Pro Thr Ile Thr Thr Asn Glu Ile Arg Asn Lys
            1300                1305                1310

Leu Ser Tyr Ser Phe Asp Gly Ala Gly Gly Thr Tyr Ser Leu Leu Leu
        1315                1320                1325

Ser Ser Tyr Pro Ile Ser Thr Asn Ile Asn Leu Ser Lys Asp Asp Leu
    1330                1335                1340

Trp Ile Phe Asn Ile Asp Asn Glu Val Arg Glu Ile Ser Ile Glu Asn
1345                1350                1355                1360
```

-continued

Gly Thr Ile Lys Lys Gly Lys Leu Ile Lys Asp Val Leu Ser Lys Ile
          1365                1370                1375

Asp Ile Asn Lys Asn Lys Leu Ile Ile Gly Asn Gln Thr Ile Asp Phe
          1380                1385                1390

Ser Gly Asp Ile Asp Asn Lys Asp Arg Tyr Ile Phe Leu Thr Cys Glu
          1395                1400                1405

Leu Asp Asp Lys Ile Ser Leu Ile Ile Glu Ile Asn Leu Val Ala Lys
          1410                1415                1420

Ser Tyr Ser Leu Leu Leu Ser Gly Asp Lys Asn Tyr Leu Ile Ser Asn
1425                1430                1435                1440

Leu Ser Asn Thr Ile Glu Lys Ile Asn Thr Leu Gly Leu Asp Ser Lys
          1445                1450                1455

Asn Ile Ala Tyr Asn Tyr Thr Asp Glu Ser Asn Asn Lys Tyr Phe Gly
          1460                1465                1470

Ala Ile Ser Lys Thr Ser Gln Lys Ser Ile Ile His Tyr Lys Lys Asp
          1475                1480                1485

Ser Lys Asn Ile Leu Glu Phe Tyr Asn Asp Ser Thr Leu Glu Phe Asn
          1490                1495                1500

Ser Lys Asp Phe Ile Ala Glu Asp Ile Asn Val Phe Met Lys Asp Asp
1505                1510                1515                1520

Ile Asn Thr Ile Thr Gly Lys Tyr Tyr Val Asp Asn Asn Thr Asp Lys
          1525                1530                1535

Ser Ile Asp Phe Ser Ile Ser Leu Val Ser Lys Asn Gln Val Lys Val
          1540                1545                1550

Asn Gly Leu Tyr Leu Asn Glu Ser Val Tyr Ser Ser Tyr Leu Asp Phe
          1555                1560                1565

Val Lys Asn Ser Asp Gly His His Asn Thr Ser Asn Phe Met Asn Leu
          1570                1575                1580

Phe Leu Asp Asn Ile Ser Phe Trp Lys Leu Phe Gly Phe Glu Asn Ile
1585                1590                1595                1600

Asn Phe Val Ile Asp Lys Tyr Phe Thr Leu Val Gly Lys Thr Asn Leu
          1605                1610                1615

Gly Tyr Val Glu Phe Ile Cys Asp Asn Asn Lys Asn Ile Asp Ile Tyr
          1620                1625                1630

Phe Gly Glu Trp Lys Thr Ser Ser Ser Lys Ser Thr Ile Phe Ser Gly
          1635                1640                1645

Asn Gly Arg Asn Val Val Val Glu Pro Ile Tyr Asn Pro Asp Thr Gly
          1650                1655                1660

Glu Asp Ile Ser Thr Ser Leu Asp Phe Ser Tyr Glu Pro Leu Tyr Gly
1665                1670                1675                1680

Ile Asp Arg Tyr Ile Asn Lys Val Leu Ile Ala Pro Asp Leu Tyr Thr
          1685                1690                1695

Ser Leu Ile Asn Ile Asn Thr Asn Tyr Tyr Ser Asn Glu Tyr Tyr Pro
          1700                1705                1710

Glu Ile Ile Val Leu Asn Pro Asn Thr Phe His Lys Lys Val Asn Ile
          1715                1720                1725

Asn Leu Asp Ser Ser Ser Phe Glu Tyr Lys Trp Ser Thr Glu Gly Ser
          1730                1735                1740

Asp Phe Ile Leu Val Arg Tyr Leu Glu Glu Ser Asn Lys Lys Ile Leu
1745                1750                1755                1760

Gln Lys Ile Arg Ile Lys Gly Ile Leu Ser Asn Thr Gln Ser Phe Asn
          1765                1770                1775

Lys Met Ser Ile Asp Phe Lys Asp Ile Lys Lys Leu Ser Leu Gly Tyr

-continued

```
            1780              1785              1790
Ile Met Ser Asn Phe Lys Ser Phe Asn Ser Glu Asn Glu Leu Asp Arg
        1795              1800              1805

Asp His Leu Gly Phe Lys Ile Ile Asp Asn Lys Thr Tyr Tyr Tyr Asp
    1810              1815              1820

Glu Asp Ser Lys Leu Val Lys Gly Leu Ile Asn Ile Asn Asn Ser Leu
1825              1830              1835              1840

Phe Tyr Phe Asp Pro Ile Glu Phe Asn Leu Val Thr Gly Trp Gln Thr
                1845              1850              1855

Ile Asn Gly Lys Lys Tyr Tyr Phe Asp Ile Asn Thr Gly Ala Ala Leu
        1860              1865              1870

Thr Ser Tyr Lys Ile Ile Asn Gly Lys His Phe Tyr Phe Asn Asn Asp
        1875              1880              1885

Gly Val Met Gln Leu Gly Val Phe Lys Gly Pro Asp Gly Phe Glu Tyr
        1890              1895              1900

Phe Ala Pro Ala Asn Thr Gln Asn Asn Asn Ile Glu Gly Gln Ala Ile
1905              1910              1915              1920

Val Tyr Gln Ser Lys Phe Leu Thr Leu Asn Gly Lys Lys Tyr Tyr Phe
                1925              1930              1935

Asp Asn Asn Ser Lys Ala Val Thr Gly Trp Arg Ile Ile Asn Asn Glu
        1940              1945              1950

Lys Tyr Tyr Phe Asn Pro Asn Asn Ala Ile Ala Ala Val Gly Leu Gln
        1955              1960              1965

Val Ile Asp Asn Asn Lys Tyr Tyr Phe Asn Pro Asp Thr Ala Ile Ile
        1970              1975              1980

Ser Lys Gly Trp Gln Thr Val Asn Gly Ser Arg Tyr Tyr Phe Asp Thr
1985              1990              1995              2000

Asp Thr Ala Ile Ala Phe Asn Gly Tyr Lys Thr Ile Asp Gly Lys His
                2005              2010              2015

Phe Tyr Phe Asp Ser Asp Cys Val Val Lys Ile Gly Val Phe Ser Thr
        2020              2025              2030

Ser Asn Gly Phe Glu Tyr Phe Ala Pro Ala Asn Thr Tyr Asn Asn Asn
        2035              2040              2045

Ile Glu Gly Gln Ala Ile Val Tyr Gln Ser Lys Phe Leu Thr Leu Asn
2050              2055              2060

Gly Lys Lys Tyr Tyr Phe Asp Asn Asn Ser Lys Ala Val Thr Gly Leu
2065              2070              2075              2080

Gln Thr Ile Asp Ser Lys Lys Tyr Tyr Phe Asn Thr Asn Thr Ala Glu
        2085              2090              2095

Ala Ala Thr Gly Trp Gln Thr Ile Asp Gly Lys Lys Tyr Tyr Phe Asn
        2100              2105              2110

Thr Asn Thr Ala Glu Ala Ala Thr Gly Trp Gln Thr Ile Asp Gly Lys
        2115              2120              2125

Lys Tyr Tyr Phe Asn Thr Asn Thr Ala Ile Ala Ser Thr Gly Tyr Thr
        2130              2135              2140

Ile Ile Asn Gly Lys His Phe Tyr Phe Asn Thr Asp Gly Ile Met Gln
2145              2150              2155              2160

Ile Gly Val Phe Lys Gly Pro Asn Gly Phe Glu Tyr Phe Ala Pro Ala
                2165              2170              2175

Asn Thr Asp Ala Asn Asn Ile Glu Gly Gln Ala Ile Leu Tyr Gln Asn
        2180              2185              2190

Glu Phe Leu Thr Leu Asn Gly Lys Lys Tyr Tyr Phe Gly Ser Asp Ser
        2195              2200              2205
```

```
Lys Ala Val Thr Gly Trp Arg Ile Ile Asn Asn Lys Lys Tyr Tyr Phe
    2210            2215                2220

Asn Pro Asn Asn Ala Ile Ala Ala Ile His Leu Cys Thr Ile Asn Asn
2225            2230                2235                2240

Asp Lys Tyr Tyr Phe Ser Tyr Asp Gly Ile Leu Gln Asn Gly Tyr Ile
            2245                2250                2255

Thr Ile Glu Arg Asn Asn Phe Tyr Phe Asp Ala Asn Asn Glu Ser Lys
        2260                2265                2270

Met Val Thr Gly Val Phe Lys Gly Pro Asn Gly Phe Glu Tyr Phe Ala
        2275                2280                2285

Pro Ala Asn Thr His Asn Asn Asn Ile Glu Gly Gln Ala Ile Val Tyr
        2290                2295                2300

Gln Asn Lys Phe Leu Thr Leu Asn Gly Lys Lys Tyr Tyr Phe Asp Asn
2305            2310                2315                2320

Asp Ser Lys Ala Val Thr Gly Trp Gln Thr Ile Asp Gly Lys Lys Tyr
            2325                2330                2335

Tyr Phe Asn Leu Asn Thr Ala Glu Ala Ala Thr Gly Trp Gln Thr Ile
            2340                2345                2350

Asp Gly Lys Lys Tyr Tyr Phe Asn Leu Asn Thr Ala Glu Ala Ala Thr
            2355                2360                2365

Gly Trp Gln Thr Ile Asp Gly Lys Lys Tyr Tyr Phe Asn Thr Asn Thr
        2370                2375                2380

Phe Ile Ala Ser Thr Gly Tyr Thr Ser Ile Asn Gly Lys His Phe Tyr
2385            2390                2395                2400

Phe Asn Thr Asp Gly Ile Met Gln Ile Gly Val Phe Lys Gly Pro Asn
            2405                2410                2415

Gly Phe Glu Tyr Phe Ala Pro Ala Asn Thr Asp Ala Asn Asn Ile Glu
            2420                2425                2430

Gly Gln Ala Ile Leu Tyr Gln Asn Lys Phe Leu Thr Leu Asn Gly Lys
            2435                2440                2445

Lys Tyr Tyr Phe Gly Ser Asp Ser Lys Ala Val Thr Gly Leu Arg Thr
        2450                2455                2460

Ile Asp Gly Lys Lys Tyr Tyr Phe Asn Thr Asn Thr Ala Val Ala Val
2465            2470                2475                2480

Thr Gly Trp Gln Thr Ile Asn Gly Lys Lys Tyr Tyr Phe Asn Thr Asn
            2485                2490                2495

Thr Ser Ile Ala Ser Thr Gly Tyr Thr Ile Ile Ser Gly Lys His Phe
            2500                2505                2510

Tyr Phe Asn Thr Asp Gly Ile Met Gln Ile Gly Val Phe Lys Gly Pro
        2515                2520                2525

Asp Gly Phe Glu Tyr Phe Ala Pro Ala Asn Thr Asp Ala Asn Asn Ile
        2530                2535                2540

Glu Gly Gln Ala Ile Arg Tyr Gln Asn Arg Phe Leu Tyr Leu His Asp
2545            2550                2555                2560

Asn Ile Tyr Tyr Phe Gly Asn Asn Ser Lys Ala Ala Thr Gly Trp Val
            2565                2570                2575

Thr Ile Asp Gly Asn Arg Tyr Tyr Phe Glu Pro Asn Thr Ala Met Gly
            2580                2585                2590

Ala Asn Gly Tyr Lys Thr Ile Asp Asn Lys Asn Phe Tyr Phe Arg Asn
            2595                2600                2605

Gly Leu Pro Gln Ile Gly Val Phe Lys Gly Ser Asn Gly Phe Glu Tyr
            2610                2615                2620
```

```
Phe Ala Pro Ala Asn Thr Asp Ala Asn Asn Ile Glu Gly Gln Ala Ile
2625                2630                2635                2640

Arg Tyr Gln Asn Arg Phe Leu His Leu Leu Gly Lys Ile Tyr Tyr Phe
                2645                2650                2655

Gly Asn Asn Ser Lys Ala Val Thr Gly Trp Gln Thr Ile Asn Gly Lys
            2660                2665                2670

Val Tyr Tyr Phe Met Pro Asp Thr Ala Met Ala Ala Ala Gly Gly Leu
        2675                2680                2685

Phe Glu Ile Asp Gly Val Ile Tyr Phe Phe Gly Val Asp Gly Val Lys
    2690                2695                2700

Ala Pro Gly Ile Tyr Gly
2705                2710

<210> SEQ ID NO 2
<211> LENGTH: 2366
<212> TYPE: PRT
<213> ORGANISM: Clostridium difficile

<400> SEQUENCE: 2

Met Ser Leu Val Asn Arg Lys Gln Leu Glu Lys Met Ala Asn Val Arg
 1               5                  10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285
```

```
Met Leu Pro Gly Ile Gln Pro Asp Leu Phe Glu Ser Ile Glu Lys Pro
    290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
                340                 345                 350
Lys Ser Asp Lys Ser Glu Ile Phe Ser Ser Leu Gly Asp Met Glu Ala
            355                 360                 365
Ser Pro Leu Glu Val Lys Ile Ala Phe Asn Ser Lys Gly Ile Ile Asn
370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
                420                 425                 430
Asp Ser Ile Met Ala Glu Ala Asn Ala Asp Asn Gly Arg Phe Met Met
            435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
                500                 505                 510
Glu Gln Glu Met Ala Ser Leu Trp Ser Phe Asp Asp Ala Arg Ala Lys
            515                 520                 525
Ala Gln Phe Glu Glu Tyr Lys Arg Asn Tyr Phe Glu Gly Ser Leu Gly
    530                 535                 540
Glu Asp Asp Asn Leu Asp Phe Ser Gln Asn Ile Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
                580                 585                 590
Ala Ala Cys Asn Leu Phe Ala Lys Thr Pro Tyr Asp Ser Val Leu Phe
            595                 600                 605
Gln Lys Asn Ile Glu Asp Ser Glu Ile Ala Tyr Tyr Asn Pro Gly
    610                 615                 620
Asp Gly Glu Ile Gln Glu Ile Asp Lys Tyr Lys Ile Pro Ser Ile Ile
625                 630                 635                 640
Ser Asp Arg Pro Lys Ile Lys Leu Thr Phe Ile Gly His Gly Lys Asp
                645                 650                 655
Glu Phe Asn Thr Asp Ile Phe Ala Gly Phe Asp Val Asp Ser Leu Ser
                660                 665                 670
Thr Glu Ile Glu Ala Ala Ile Asp Leu Ala Lys Glu Asp Ile Ser Pro
            675                 680                 685
Lys Ser Ile Glu Ile Asn Leu Leu Gly Cys Asn Met Phe Ser Tyr Ser
    690                 695                 700
```

-continued

```
Ile Asn Val Glu Glu Thr Tyr Pro Gly Lys Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Ile
                755                 760                 765

Ile Lys Asp Ile Ser Ser Lys Glu Tyr Ile Ser Phe Asn Pro Lys Glu
            770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
                915                 920                 925

Ile Ser Lys Ile Lys Gly Thr Ile Phe Asp Thr Val Asn Gly Lys Leu
            930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
                995                1000                1005

Glu Leu Val Ser Thr Ala Leu Asp Glu Thr Ile Asp Leu Leu Pro Thr
        1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Ser Asp Pro Leu Leu
                1045                1050                1055

Arg Gln Glu Ile Glu Ala Lys Ile Gly Ile Met Ala Val Asn Leu Thr
                1060                1065                1070

Thr Ala Thr Thr Ala Ile Ile Thr Ser Ser Leu Gly Ile Ala Ser Gly
            1075                1080                1085

Phe Ser Ile Leu Leu Val Pro Leu Ala Gly Ile Ser Ala Gly Ile Pro
                1090                1095                1100

Ser Leu Val Asn Asn Glu Leu Val Leu Arg Asp Lys Ala Thr Lys Val
1105                1110                1115                1120

Val Asp Tyr Phe Lys His Val Ser Leu Val Glu Thr Glu Gly Val Phe
```

```
                1125                1130                1135
Thr Leu Leu Asp Asp Lys Ile Met Met Pro Gln Asp Leu Val Ile
            1140                1145                1150

Ser Glu Ile Asp Phe Asn Asn Asn Ser Ile Val Leu Gly Lys Cys Glu
        1155                1160                1165

Ile Trp Arg Met Glu Gly Gly Ser Gly His Thr Val Thr Asp Asp Ile
    1170                1175                1180

Asp His Phe Phe Ser Ala Pro Ser Ile Thr Tyr Arg Glu Pro His Leu
1185                1190                1195                1200

Ser Ile Tyr Asp Val Leu Glu Val Gln Lys Glu Glu Leu Asp Leu Ser
            1205                1210                1215

Lys Asp Leu Met Val Leu Pro Asn Ala Pro Asn Arg Val Phe Ala Trp
        1220                1225                1230

Glu Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr Trp
1250                1255                1260

Arg Tyr Phe Ala Phe Ile Ala Asp Ala Leu Ile Thr Thr Leu Lys Pro
1265                1270                1275                1280

Arg Tyr Glu Asp Thr Asn Ile Arg Ile Asn Leu Asp Ser Asn Thr Arg
            1285                1290                1295

Ser Phe Ile Val Pro Ile Ile Thr Thr Glu Tyr Ile Arg Glu Lys Leu
        1300                1305                1310

Ser Tyr Ser Phe Tyr Gly Ser Gly Thr Tyr Ala Leu Ser Leu Ser
    1315                1320                1325

Gln Tyr Asn Met Gly Ile Asn Ile Glu Leu Ser Glu Ser Asp Val Trp
1330                1335                1340

Ile Ile Asp Val Asp Asn Val Val Arg Asp Val Thr Ile Glu Ser Asp
1345                1350                1355                1360

Lys Ile Lys Lys Gly Asp Leu Ile Glu Gly Ile Leu Ser Thr Leu Ser
            1365                1370                1375

Ile Glu Glu Asn Lys Ile Ile Leu Asn Ser His Glu Ile Asn Phe Ser
        1380                1385                1390

Gly Glu Val Asn Gly Ser Asn Gly Phe Val Ser Leu Thr Phe Ser Ile
    1395                1400                1405

Leu Glu Gly Ile Asn Ala Ile Ile Glu Val Asp Leu Leu Ser Lys Ser
1410                1415                1420

Tyr Lys Leu Leu Ile Ser Gly Glu Leu Lys Ile Leu Met Leu Asn Ser
1425                1430                1435                1440

Asn His Ile Gln Gln Lys Ile Asp Tyr Ile Gly Phe Asn Ser Glu Leu
            1445                1450                1455

Gln Lys Asn Ile Pro Tyr Ser Phe Val Asp Ser Glu Gly Lys Glu Asn
        1460                1465                1470

Gly Phe Ile Asn Gly Ser Thr Lys Glu Gly Leu Phe Val Ser Glu Leu
    1475                1480                1485

Pro Asp Val Val Leu Ile Ser Lys Val Tyr Met Asp Asp Ser Lys Pro
1490                1495                1500

Ser Phe Gly Tyr Tyr Ser Asn Asn Leu Lys Asp Val Lys Val Ile Thr
1505                1510                1515                1520

Lys Asp Asn Val Asn Ile Leu Thr Gly Tyr Tyr Leu Lys Asp Asp Ile
            1525                1530                1535

Lys Ile Ser Leu Ser Leu Thr Leu Gln Asp Glu Lys Thr Ile Lys Leu
        1540                1545                1550
```

```
Asn Ser Val His Leu Asp Glu Ser Gly Val Ala Glu Ile Leu Lys Phe
        1555                1560                1565

Met Asn Arg Lys Gly Asn Thr Asn Thr Ser Asp Ser Leu Met Ser Phe
        1570                1575                1580

Leu Glu Ser Met Asn Ile Lys Ser Ile Phe Val Asn Phe Leu Gln Ser
1585                1590                1595                1600

Asn Ile Lys Phe Ile Leu Asp Ala Asn Phe Ile Ile Ser Gly Thr Thr
        1605                1610                1615

Ser Ile Gly Gln Phe Glu Phe Ile Cys Asp Glu Asn Asp Asn Ile Gln
        1620                1625                1630

Pro Tyr Phe Ile Lys Phe Asn Thr Leu Glu Thr Asn Tyr Thr Leu Tyr
        1635                1640                1645

Val Gly Asn Arg Gln Asn Met Ile Val Glu Pro Asn Tyr Asp Leu Asp
        1650                1655                1660

Asp Ser Gly Asp Ile Ser Ser Thr Val Ile Asn Phe Ser Gln Lys Tyr
1665                1670                1675                1680

Leu Tyr Gly Ile Asp Ser Cys Val Asn Lys Val Ile Ser Pro Asn
        1685                1690                1695

Ile Tyr Thr Asp Glu Ile Asn Ile Thr Pro Val Tyr Gly Thr Asn Asn
        1700                1705                1710

Thr Tyr Pro Glu Val Ile Val Leu Asp Ala Asn Tyr Ile Asn Glu Lys
        1715                1720                1725

Ile Asn Val Asn Ile Asn Asp Leu Ser Ile Arg Tyr Val Trp Ser Asn
        1730                1735                1740

Asp Gly Asn Asp Phe Ile Leu Met Ser Thr Ser Glu Asn Lys Val
1745                1750                1755                1760

Ser Gln Val Lys Ile Arg Phe Val Asn Val Phe Lys Asp Lys Thr Leu
        1765                1770                1775

Ala Asn Lys Leu Ser Phe Asn Phe Ser Asp Lys Gln Asp Val Pro Val
        1780                1785                1790

Ser Glu Ile Ile Leu Ser Phe Thr Pro Ser Tyr Tyr Glu Asp Gly Leu
        1795                1800                1805

Ile Gly Tyr Asp Leu Gly Leu Val Ser Leu Tyr Asn Gly Lys Phe Tyr
        1810                1815                1820

Ile Asn Asn Phe Gly Met Met Val Ser Gly Leu Ile Tyr Ile Asn Asp
1825                1830                1835                1840

Ser Leu Tyr Tyr Phe Lys Pro Pro Val Asn Asn Leu Ile Thr Gly Phe
        1845                1850                1855

Val Thr Val Gly Asp Asp Lys Tyr Tyr Phe Asn Pro Ile Asn Gly Gly
        1860                1865                1870

Ala Ala Ser Ile Gly Glu Thr Ile Ile Asp Asp Lys Asn Tyr Tyr Phe
        1875                1880                1885

Asn Gln Ser Gly Val Leu Gln Thr Gly Val Phe Ser Thr Glu Asp Gly
        1890                1895                1900

Phe Lys Tyr Phe Ala Pro Ala Asn Thr Leu Asp Glu Asn Leu Glu Gly
1905                1910                1915                1920

Glu Ala Ile Asp Phe Thr Gly Lys Leu Ile Ile Asp Glu Asn Ile Tyr
        1925                1930                1935

Tyr Phe Asp Asp Asn Tyr Arg Gly Ala Val Glu Trp Lys Glu Leu Asp
        1940                1945                1950

Gly Glu Met His Tyr Phe Ser Pro Glu Thr Gly Lys Ala Phe Lys Gly
        1955                1960                1965
```

Leu Asn Gln Ile Gly Asp Tyr Lys Tyr Tyr Phe Asn Ser Asp Gly Val
    1970                1975                1980

Met Gln Lys Gly Phe Val Ser Ile Asn Asp Asn Lys His Tyr Phe Asp
1985                1990                1995                2000

Asp Ser Gly Val Met Lys Val Gly Tyr Thr Glu Ile Asp Gly Lys His
            2005                2010                2015

Phe Tyr Phe Ala Glu Asn Gly Glu Met Gln Ile Gly Val Phe Asn Thr
            2020                2025                2030

Glu Asp Gly Phe Lys Tyr Phe Ala His His Asn Glu Asp Leu Gly Asn
        2035                2040                2045

Glu Glu Gly Glu Glu Ile Ser Tyr Ser Gly Ile Leu Asn Phe Asn Asn
2050                2055                2060

Lys Ile Tyr Tyr Phe Asp Asp Ser Phe Thr Ala Val Val Gly Trp Lys
2065                2070                2075                2080

Asp Leu Glu Asp Gly Ser Lys Tyr Tyr Phe Asp Asp Thr Ala Glu
            2085                2090                2095

Ala Tyr Ile Gly Leu Ser Leu Ile Asn Asp Gly Gln Tyr Tyr Phe Asn
            2100                2105                2110

Asp Asp Gly Ile Met Gln Val Gly Phe Val Thr Ile Asn Asp Lys Val
        2115                2120                2125

Phe Tyr Phe Ser Asp Ser Gly Ile Ile Glu Ser Gly Val Gln Asn Ile
        2130                2135                2140

Asp Asp Asn Tyr Phe Tyr Ile Asp Asp Asn Gly Ile Val Gln Ile Gly
2145                2150                2155                2160

Val Phe Asp Thr Ser Asp Gly Tyr Lys Tyr Phe Ala Pro Ala Asn Thr
            2165                2170                2175

Val Asn Asp Asn Ile Tyr Gly Gln Ala Val Glu Tyr Ser Gly Leu Val
            2180                2185                2190

Arg Val Gly Glu Asp Val Tyr Tyr Phe Gly Glu Thr Tyr Thr Ile Glu
        2195                2200                2205

Thr Gly Trp Ile Tyr Asp Met Glu Asn Glu Ser Asp Lys Tyr Tyr Phe
        2210                2215                2220

Asn Pro Glu Thr Lys Lys Ala Cys Lys Gly Ile Asn Leu Ile Asp Asp
2225                2230                2235                2240

Ile Lys Tyr Tyr Phe Asp Glu Lys Gly Ile Met Arg Thr Gly Leu Ile
            2245                2250                2255

Ser Phe Glu Asn Asn Asn Tyr Tyr Phe Asn Glu Asn Gly Glu Met Gln
            2260                2265                2270

Phe Gly Tyr Ile Asn Ile Glu Asp Lys Met Phe Tyr Phe Gly Glu Asp
        2275                2280                2285

Gly Val Met Gln Ile Gly Val Phe Asn Thr Pro Asp Gly Phe Lys Tyr
        2290                2295                2300

Phe Ala His Gln Asn Thr Leu Asp Glu Asn Phe Glu Gly Glu Ser Ile
2305                2310                2315                2320

Asn Tyr Thr Gly Trp Leu Asp Leu Asp Glu Lys Arg Tyr Tyr Phe Thr
            2325                2330                2335

Asp Glu Tyr Ile Ala Ala Thr Gly Ser Val Ile Ile Asp Gly Glu Glu
            2340                2345                2350

Tyr Tyr Phe Asp Pro Asp Thr Ala Gln Leu Val Ile Ser Glu
        2355                2360                2365

<210> SEQ ID NO 3
<211> LENGTH: 966
<212> TYPE: PRT

<213> ORGANISM: Artificial Sequence
<220> FEATURE:
<223> OTHER INFORMATION: Fusion 1

<400> SEQUENCE: 3

```
Met Gly Trp Gln Thr Ile Asp Gly Lys Lys Tyr Tyr Phe Asn Thr Asn
 1               5                  10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
```

-continued

```
              385                 390                 395                 400
Met Gln Ile Gly Val Phe Lys Gly Pro Asp Gly Phe Glu Tyr Phe Ala
                    405                 410                 415

Pro Ala Asn Thr Asp Ala Asn Ile Glu Gly Gln Ala Ile Arg Tyr
                420                 425                 430

Gln Asn Arg Phe Leu Tyr Leu His Asp Asn Ile Tyr Tyr Phe Gly Asn
                435                 440                 445

Asn Ser Lys Ala Ala Thr Gly Trp Val Thr Ile Asp Gly Asn Arg Tyr
450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                    485                 490                 495

Phe Lys Gly Ser Asn Gly Phe Glu Tyr Phe Ala Pro Ala Asn Thr Asp
                500                 505                 510

Ala Asn Asn Ile Glu Gly Gln Ala Ile Arg Tyr Gln Asn Arg Phe Leu
                515                 520                 525

His Leu Leu Gly Lys Ile Tyr Tyr Phe Gly Asn Asn Ser Lys Ala Val
                530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Phe Glu Ile Asp Gly Val Ile
                    565                 570                 575

Tyr Phe Phe Gly Val Asp Gly Val Lys Ala Pro Gly Phe Val Ser Ile
                580                 585                 590

Asn Asp Asn Lys His Tyr Phe Asp Asp Ser Gly Val Met Lys Val Gly
                595                 600                 605

Tyr Thr Glu Ile Asp Gly Lys His Phe Tyr Phe Ala Glu Asn Gly Glu
            610                 615                 620

Met Gln Ile Gly Val Phe Asn Thr Glu Asp Gly Phe Lys Tyr Phe Ala
625                 630                 635                 640

His His Asn Glu Asp Leu Gly Asn Glu Glu Gly Glu Glu Ile Ser Tyr
                    645                 650                 655

Ser Gly Ile Leu Asn Phe Asn Asn Lys Ile Tyr Tyr Phe Asp Asp Ser
                660                 665                 670

Phe Thr Ala Val Val Gly Trp Lys Asp Leu Glu Asp Gly Ser Lys Tyr
                675                 680                 685

Tyr Phe Asp Glu Asp Thr Ala Glu Ala Tyr Ile Gly Leu Ser Leu Ile
                690                 695                 700

Asn Asp Gly Gln Tyr Tyr Phe Asn Asp Asp Gly Ile Met Gln Val Gly
705                 710                 715                 720

Phe Val Thr Ile Asn Asp Lys Val Phe Tyr Phe Ser Asp Ser Gly Ile
                    725                 730                 735

Ile Glu Ser Gly Val Gln Asn Ile Asp Asp Asn Tyr Phe Tyr Ile Asp
                740                 745                 750

Asp Asn Gly Ile Val Gln Ile Gly Val Phe Asp Thr Ser Asp Gly Tyr
                755                 760                 765

Lys Tyr Phe Ala Pro Ala Asn Thr Val Asn Asp Asn Ile Tyr Gly Gln
                770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
                    805                 810                 815
```

```
Asn Glu Ser Asp Lys Tyr Tyr Phe Asn Pro Glu Thr Lys Lys Ala Cys
            820                 825                 830

Lys Gly Ile Asn Leu Ile Asp Ile Lys Tyr Tyr Phe Asp Glu Lys
        835                 840                 845

Gly Ile Met Arg Thr Gly Leu Ile Ser Phe Glu Asn Asn Tyr Tyr
    850                 855                 860

Phe Asn Glu Asn Gly Glu Met Gln Phe Gly Tyr Ile Asn Ile Glu Asp
865                 870                 875                 880

Lys Met Phe Tyr Phe Gly Glu Asp Gly Val Met Gln Ile Gly Val Phe
                885                 890                 895

Asn Thr Pro Asp Gly Phe Lys Tyr Phe Ala His Gln Asn Thr Leu Asp
                900                 905                 910

Glu Asn Phe Glu Gly Glu Ser Ile Asn Tyr Thr Gly Trp Leu Asp Leu
            915                 920                 925

Asp Glu Lys Arg Tyr Tyr Phe Thr Asp Glu Tyr Ile Ala Ala Thr Gly
        930                 935                 940

Ser Val Ile Ile Asp Gly Glu Glu Tyr Tyr Phe Asp Pro Asp Thr Ala
945                 950                 955                 960

Gln Leu Val Ile Ser Glu
                965

<210> SEQ ID NO 4
<211> LENGTH: 966
<212> TYPE: PRT
<213> ORGANISM: Artificial Sequence
<220> FEATURE:
<223> OTHER INFORMATION: Fusion 2

<400> SEQUENCE: 4

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
                100                 105                 110

Ala Ile His Leu Cys Thr Ile Asn Asn Asp Lys Tyr Tyr Phe Ser Tyr
            115                 120                 125

Asp Gly Ile Leu Gln Asn Gly Tyr Ile Thr Ile Glu Arg Asn Asn Phe
        130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
                180                 185                 190

Asn Gly Lys Lys Tyr Tyr Phe Asp Asn Asp Ser Lys Ala Val Thr Gly
            195                 200                 205
```

```
Trp Gln Thr Ile Asp Gly Lys Lys Tyr Tyr Phe Asn Leu Asn Thr Ala
            210                 215                 220
Glu Ala Ala Thr Gly Trp Gln Thr Ile Asp Gly Lys Lys Tyr Tyr Phe
225                 230                 235                 240
Asn Leu Asn Thr Ala Glu Ala Ala Thr Gly Trp Gln Thr Ile Asp Gly
                245                 250                 255
Lys Lys Tyr Tyr Phe Asn Thr Asn Thr Phe Ile Ala Ser Thr Gly Tyr
                260                 265                 270
Thr Ser Ile Asn Gly Lys His Phe Tyr Phe Asn Thr Asp Gly Ile Met
            275                 280                 285
Gln Ile Gly Val Phe Lys Gly Pro Asn Gly Phe Glu Tyr Phe Ala Pro
            290                 295                 300
Ala Asn Thr Asp Ala Asn Asn Ile Glu Gly Gln Ala Ile Leu Tyr Gln
305                 310                 315                 320
Asn Lys Phe Leu Thr Leu Asn Gly Lys Lys Tyr Tyr Phe Gly Ser Asp
                325                 330                 335
Ser Lys Ala Val Thr Gly Leu Arg Thr Ile Asp Gly Lys Lys Tyr Tyr
                340                 345                 350
Phe Asn Thr Asn Thr Ala Val Ala Val Thr Gly Trp Gln Thr Ile Asn
            355                 360                 365
Gly Lys Lys Tyr Tyr Phe Asn Thr Asn Thr Ser Ile Ala Ser Thr Gly
            370                 375                 380
Tyr Thr Ile Ile Ser Gly Lys His Phe Tyr Phe Asn Thr Asp Gly Ile
385                 390                 395                 400
Met Gln Ile Gly Val Phe Lys Gly Pro Asp Gly Phe Glu Tyr Phe Ala
                405                 410                 415
Pro Ala Asn Thr Asp Ala Asn Asn Ile Glu Gly Gln Ala Ile Arg Tyr
                420                 425                 430
Gln Asn Arg Phe Leu Tyr Leu His Asp Asn Ile Tyr Tyr Phe Gly Asn
            435                 440                 445
Asn Ser Lys Ala Ala Thr Gly Trp Val Thr Ile Asp Gly Asn Arg Tyr
            450                 455                 460
Tyr Phe Glu Pro Asn Thr Ala Met Gly Ala Asn Gly Tyr Lys Thr Ile
465                 470                 475                 480
Asp Asn Lys Asn Phe Tyr Phe Arg Asn Gly Leu Pro Gln Ile Gly Val
                485                 490                 495
Phe Lys Gly Ser Asn Gly Phe Glu Tyr Phe Ala Pro Ala Asn Thr Asp
                500                 505                 510
Ala Asn Asn Ile Glu Gly Gln Ala Ile Arg Tyr Gln Asn Arg Phe Leu
            515                 520                 525
His Leu Leu Gly Lys Ile Tyr Tyr Phe Gly Asn Asn Ser Lys Ala Val
            530                 535                 540
Thr Gly Trp Gln Thr Ile Asn Gly Lys Val Tyr Tyr Phe Met Pro Asp
545                 550                 555                 560
Thr Ala Met Ala Ala Ala Gly Gly Leu Asn Gln Ile Gly Asp Tyr Lys
                565                 570                 575
Tyr Tyr Phe Asn Ser Asp Gly Val Met Gln Lys Gly Phe Val Ser Ile
                580                 585                 590
Asn Asp Asn Lys His Tyr Phe Asp Asp Ser Gly Val Met Lys Val Gly
            595                 600                 605
Tyr Thr Glu Ile Asp Gly Lys His Phe Tyr Phe Ala Glu Asn Gly Glu
610                 615                 620
```

Met Gln Ile Gly Val Phe Asn Thr Glu Asp Gly Lys Tyr Phe Ala
625                 630                 635                 640

His His Asn Glu Asp Leu Gly Asn Glu Gly Glu Glu Ile Ser Tyr
            645                 650                 655

Ser Gly Ile Leu Asn Phe Asn Asn Lys Ile Tyr Tyr Phe Asp Asp Ser
            660                 665                 670

Phe Thr Ala Val Val Gly Trp Lys Asp Leu Glu Asp Gly Ser Lys Tyr
        675                 680                 685

Tyr Phe Asp Glu Asp Thr Ala Glu Ala Tyr Ile Gly Leu Ser Leu Ile
        690                 695                 700

Asn Asp Gly Gln Tyr Tyr Phe Asn Asp Asp Gly Ile Met Gln Val Gly
705                 710                 715                 720

Phe Val Thr Ile Asn Asp Lys Val Phe Tyr Phe Ser Asp Ser Gly Ile
            725                 730                 735

Ile Glu Ser Gly Val Gln Asn Ile Asp Asp Asn Tyr Phe Tyr Ile Asp
            740                 745                 750

Asp Asn Gly Ile Val Gln Ile Gly Val Phe Asp Thr Ser Asp Gly Tyr
        755                 760                 765

Lys Tyr Phe Ala Pro Ala Asn Thr Val Asn Asp Asn Ile Tyr Gly Gln
770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
            805                 810                 815

Asn Glu Ser Asp Lys Tyr Tyr Phe Asn Pro Glu Thr Lys Lys Ala Cys
        820                 825                 830

Lys Gly Ile Asn Leu Ile Asp Asp Ile Lys Tyr Tyr Phe Asp Glu Lys
        835                 840                 845

Gly Ile Met Arg Thr Gly Leu Ile Ser Phe Glu Asn Asn Tyr Tyr
        850                 855                 860

Phe Asn Glu Asn Gly Glu Met Gln Phe Gly Tyr Ile Asn Ile Glu Asp
865                 870                 875                 880

Lys Met Phe Tyr Phe Gly Glu Asp Gly Val Met Gln Ile Gly Val Phe
            885                 890                 895

Asn Thr Pro Asp Gly Phe Lys Tyr Phe Ala His Gln Asn Thr Leu Asp
            900                 905                 910

Glu Asn Phe Glu Gly Glu Ser Ile Asn Tyr Thr Gly Trp Leu Asp Leu
        915                 920                 925

Asp Glu Lys Arg Tyr Tyr Phe Thr Asp Glu Tyr Ile Ala Ala Thr Gly
        930                 935                 940

Ser Val Ile Ile Asp Gly Glu Glu Tyr Tyr Phe Asp Pro Asp Thr Ala
945                 950                 955                 960

Gln Leu Val Ile Ser Glu
                965

<210> SEQ ID NO 5
<211> LENGTH: 833
<212> TYPE: PRT
<213> ORGANISM: Artificial Sequence
<220> FEATURE:
<223> OTHER INFORMATION: Fusion 3

<400> SEQUENCE: 5

Met Gly Trp Gln Thr Ile Asp Gly Lys Lys Tyr Tyr Phe Asn Thr Asn
1               5                   10                  15

-continued

```
Thr Ala Ile Ala Ser Thr Gly Tyr Thr Ile Ile Asn Gly Lys His Phe
                20                  25                  30

Tyr Phe Asn Thr Asp Gly Ile Met Gln Ile Gly Val Phe Lys Gly Pro
            35                  40                  45

Asn Gly Phe Glu Tyr Phe Ala Pro Ala Asn Thr Asp Ala Asn Asn Ile
        50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
```

```
                435                 440                 445
Asn Ser Lys Ala Ala Thr Gly Trp Val Thr Ile Asp Gly Asn Arg Tyr
450                 455                 460

Tyr Phe Glu Pro Asn Thr Ala Met Gly Ala Asn Gly Tyr Lys Thr Ile
465                 470                 475                 480

Asp Asn Lys Asn Phe Tyr Arg Asn Gly Leu Pro Gln Ile Gly Val
                485                 490                 495

Phe Lys Gly Ser Asn Gly Phe Glu Tyr Phe Ala His His Asn Glu Asp
                500                 505                 510

Leu Gly Asn Glu Glu Gly Glu Ile Ser Tyr Ser Gly Ile Leu Asn
                515                 520                 525

Phe Asn Asn Lys Ile Tyr Tyr Phe Asp Asp Ser Phe Thr Ala Val Val
530                 535                 540

Gly Trp Lys Asp Leu Glu Asp Gly Ser Lys Tyr Tyr Phe Asp Glu Asp
545                 550                 555                 560

Thr Ala Glu Ala Tyr Ile Gly Leu Ser Leu Ile Asn Asp Gly Gln Tyr
                565                 570                 575

Tyr Phe Asn Asp Asp Gly Ile Met Gln Val Gly Phe Val Thr Ile Asn
                580                 585                 590

Asp Lys Val Phe Tyr Phe Ser Asp Ser Gly Ile Ile Glu Ser Gly Val
                595                 600                 605

Gln Asn Ile Asp Asp Asn Tyr Phe Tyr Ile Asp Asp Asn Gly Ile Val
610                 615                 620

Gln Ile Gly Val Phe Asp Thr Ser Asp Gly Tyr Lys Tyr Phe Ala Pro
625                 630                 635                 640

Ala Asn Thr Val Asn Asp Asn Ile Tyr Gly Gln Ala Val Glu Tyr Ser
                645                 650                 655

Gly Leu Val Arg Val Gly Glu Asp Val Tyr Tyr Phe Gly Glu Thr Tyr
                660                 665                 670

Thr Ile Glu Thr Gly Trp Ile Tyr Asp Met Glu Asn Glu Ser Asp Lys
                675                 680                 685

Tyr Tyr Phe Asn Pro Glu Thr Lys Lys Ala Cys Lys Gly Ile Asn Leu
690                 695                 700

Ile Asp Asp Ile Lys Tyr Tyr Phe Asp Glu Lys Gly Ile Met Arg Thr
705                 710                 715                 720

Gly Leu Ile Ser Phe Glu Asn Asn Asn Tyr Tyr Phe Asn Glu Asn Gly
                725                 730                 735

Glu Met Gln Phe Gly Tyr Ile Asn Ile Glu Asp Lys Met Phe Tyr Phe
                740                 745                 750

Gly Glu Asp Gly Val Met Gln Ile Gly Val Phe Asn Thr Pro Asp Gly
                755                 760                 765

Phe Lys Tyr Phe Ala His Gln Asn Thr Leu Asp Glu Asn Phe Glu Gly
                770                 775                 780

Glu Ser Ile Asn Tyr Thr Gly Trp Leu Asp Leu Asp Glu Lys Arg Tyr
785                 790                 795                 800

Tyr Phe Thr Asp Glu Tyr Ile Ala Ala Thr Gly Ser Val Ile Ile Asp
                805                 810                 815

Gly Glu Glu Tyr Tyr Phe Asp Pro Asp Thr Ala Gln Leu Val Ile Ser
                820                 825                 830

Glu

<210> SEQ ID NO 6
<211> LENGTH: 1057
```

```
<212> TYPE: PRT
<213> ORGANISM: Artificial Sequence
<220> FEATURE:
<223> OTHER INFORMATION: Fusion 4

<400> SEQUENCE: 6

Met Gly Trp Gln Thr Ile Asp Gly Lys Lys Tyr Tyr Phe Asn Thr Asn
 1               5                  10                  15

Thr Ala Ile Ala Ser Thr Gly Tyr Thr Ile Ile Asn Gly Lys His Phe
             20                  25                  30

Tyr Phe Asn Thr Asp Gly Ile Met Gln Ile Gly Val Phe Lys Gly Pro
         35                  40                  45

Asn Gly Phe Glu Tyr Phe Ala Pro Ala Asn Thr Asp Ala Asn Asn Ile
 50                  55                  60

Glu Gly Gln Ala Ile Leu Tyr Gln Asn Glu Phe Leu Thr Leu Asn Gly
 65                  70                  75                  80

Lys Lys Tyr Tyr Phe Gly Ser Asp Ser Lys Ala Val Thr Gly Trp Arg
                 85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
            115                 120                 125

Asp Gly Ile Leu Gln Asn Gly Tyr Ile Thr Ile Glu Arg Asn Asn Phe
130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
            195                 200                 205

Trp Gln Thr Ile Asp Gly Lys Lys Tyr Tyr Phe Asn Leu Asn Thr Ala
210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
            275                 280                 285

Gln Ile Gly Val Phe Lys Gly Pro Asn Gly Phe Glu Tyr Phe Ala Pro
290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
            355                 360                 365

Gly Lys Lys Tyr Tyr Phe Asn Thr Asn Thr Ser Ile Ala Ser Thr Gly
370                 375                 380
```

```
Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
            405                 410                 415

Pro Ala Asn Thr Asp Ala Asn Asn Ile Glu Gly Gln Ala Ile Arg Tyr
                420                 425                 430

Gln Asn Arg Phe Leu Tyr Leu His Asp Asn Ile Tyr Tyr Phe Gly Asn
            435                 440                 445

Asn Ser Lys Ala Ala Thr Gly Trp Val Thr Ile Asp Gly Asn Arg Tyr
        450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
        515                 520                 525

His Leu Leu Gly Lys Ile Tyr Tyr Phe Gly Asn Asn Ser Lys Ala Val
        530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Glu Thr Ile Ile Asp Asp Lys Asn
                565                 570                 575

Tyr Tyr Phe Asn Gln Ser Gly Val Leu Gln Thr Gly Val Phe Ser Thr
            580                 585                 590

Glu Asp Gly Phe Lys Tyr Phe Ala Pro Ala Asn Thr Leu Asp Glu Asn
        595                 600                 605

Leu Glu Gly Glu Ala Ile Asp Phe Thr Gly Lys Leu Ile Ile Asp Glu
610                 615                 620

Asn Ile Tyr Tyr Phe Asp Asp Asn Tyr Arg Gly Ala Val Glu Trp Lys
625                 630                 635                 640

Glu Leu Asp Gly Glu Met His Tyr Phe Ser Pro Glu Thr Gly Lys Ala
                645                 650                 655

Phe Lys Gly Leu Asn Gln Ile Gly Asp Tyr Lys Tyr Tyr Phe Asn Ser
            660                 665                 670

Asp Gly Val Met Gln Lys Gly Phe Val Ser Ile Asn Asp Asn Lys His
        675                 680                 685

Tyr Phe Asp Asp Ser Gly Val Met Lys Val Gly Tyr Thr Glu Ile Asp
690                 695                 700

Gly Lys His Phe Tyr Phe Ala Glu Asn Gly Glu Met Gln Ile Gly Val
705                 710                 715                 720

Phe Asn Thr Glu Asp Gly Phe Lys Tyr Phe Ala His His Asn Glu Asp
                725                 730                 735

Leu Gly Asn Glu Glu Gly Glu Glu Ile Ser Tyr Ser Gly Ile Leu Asn
            740                 745                 750

Phe Asn Asn Lys Ile Tyr Tyr Phe Asp Asp Ser Phe Thr Ala Val Val
        755                 760                 765

Gly Trp Lys Asp Leu Glu Asp Gly Ser Lys Tyr Tyr Phe Asp Glu Asp
        770                 775                 780

Thr Ala Glu Ala Tyr Ile Gly Leu Ser Leu Ile Asn Asp Gly Gln Tyr
785                 790                 795                 800

Tyr Phe Asn Asp Asp Gly Ile Met Gln Val Gly Phe Val Thr Ile Asn
```

```
                    805                 810                 815
Asp Lys Val Phe Tyr Phe Ser Asp Ser Gly Ile Ile Glu Ser Gly Val
                820                 825                 830

Gln Asn Ile Asp Asp Asn Tyr Phe Tyr Ile Asp Asp Asn Gly Ile Val
            835                 840                 845

Gln Ile Gly Val Phe Asp Thr Ser Asp Gly Tyr Lys Tyr Phe Ala Pro
        850                 855                 860

Ala Asn Thr Val Asn Asp Asn Ile Tyr Gly Gln Ala Val Glu Tyr Ser
865                 870                 875                 880

Gly Leu Val Arg Val Gly Glu Asp Val Tyr Tyr Phe Gly Glu Thr Tyr
                885                 890                 895

Thr Ile Glu Thr Gly Trp Ile Tyr Asp Met Glu Asn Glu Ser Asp Lys
            900                 905                 910

Tyr Tyr Phe Asn Pro Glu Thr Lys Lys Ala Cys Lys Gly Ile Asn Leu
        915                 920                 925

Ile Asp Asp Ile Lys Tyr Tyr Phe Asp Glu Lys Gly Ile Met Arg Thr
930                 935                 940

Gly Leu Ile Ser Phe Glu Asn Asn Asn Tyr Tyr Phe Asn Glu Asn Gly
945                 950                 955                 960

Glu Met Gln Phe Gly Tyr Ile Asn Ile Glu Asp Lys Met Phe Tyr Phe
                965                 970                 975

Gly Glu Asp Gly Val Met Gln Ile Gly Val Phe Asn Thr Pro Asp Gly
            980                 985                 990

Phe Lys Tyr Phe Ala His Gln Asn Thr Leu Asp Glu Asn Phe Glu Gly
        995                 1000                1005

Glu Ser Ile Asn Tyr Thr Gly Trp Leu Asp Leu Asp Glu Lys Arg Tyr
    1010                1015                1020

Tyr Phe Thr Asp Glu Tyr Ile Ala Ala Thr Gly Ser Val Ile Ile Asp
1025                1030                1035                1040

Gly Glu Glu Tyr Tyr Phe Asp Pro Asp Thr Ala Gln Leu Val Ile Ser
                1045                1050                1055

Glu

<210> SEQ ID NO 7
<211> LENGTH: 971
<212> TYPE: PRT
<213> ORGANISM: Artificial Sequence
<220> FEATURE:
<223> OTHER INFORMATION: Fusion 5

<400> SEQUENCE: 7

Met Gly Trp Gln Thr Ile Asp Gly Lys Lys Tyr Tyr Phe Asn Thr Asn
  1               5                  10                  15

Thr Ala Ile Ala Ser Thr Gly Tyr Thr Ile Ile Asn Gly Lys His Phe
                20                  25                  30

Tyr Phe Asn Thr Asp Gly Ile Met Gln Ile Gly Val Phe Lys Gly Pro
            35                  40                  45

Asn Gly Phe Glu Tyr Phe Ala Pro Ala Asn Thr Asp Ala Asn Asn Ile
        50                  55                  60

Glu Gly Gln Ala Ile Leu Tyr Gln Asn Glu Phe Leu Thr Leu Asn Gly
 65                 70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110
```

```
Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
        130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
                180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
        210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
        260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
        290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
                340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
        370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
                420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
        450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
                500                 505                 510

Ala Asn Asn Ile Glu Gly Gln Ala Ile Arg Tyr Gln Asn Arg Phe Leu
                515                 520                 525
```

```
His Leu Leu Gly Lys Ile Tyr Tyr Phe Gly Asn Asn Ser Lys Ala Val
            530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Phe Glu Ile Asp Gly Val Ile
                565                 570                 575

Tyr Phe Phe Gly Val Asp Gly Val Lys Ala Pro Gly Ile Tyr Gly Gly
            580                 585                 590

Gly Phe Val Ser Ile Asn Asp Asn Lys His Tyr Phe Asp Asp Ser Gly
            595                 600                 605

Val Met Lys Val Gly Tyr Thr Glu Ile Asp Gly Lys His Phe Tyr Phe
610                 615                 620

Ala Glu Asn Gly Glu Met Gln Ile Gly Val Phe Asn Thr Glu Asp Gly
625                 630                 635                 640

Phe Lys Tyr Phe Ala His His Asn Glu Asp Leu Gly Asn Glu Glu Gly
                645                 650                 655

Glu Glu Ile Ser Tyr Ser Gly Ile Leu Asn Phe Asn Asn Lys Ile Tyr
            660                 665                 670

Tyr Phe Asp Asp Ser Phe Thr Ala Val Val Gly Trp Lys Asp Leu Glu
            675                 680                 685

Asp Gly Ser Lys Tyr Tyr Phe Asp Glu Asp Thr Ala Glu Ala Tyr Ile
690                 695                 700

Gly Leu Ser Leu Ile Asn Asp Gly Gln Tyr Tyr Phe Asn Asp Asp Gly
705                 710                 715                 720

Ile Met Gln Val Gly Phe Val Thr Ile Asn Asp Lys Val Phe Tyr Phe
                725                 730                 735

Ser Asp Ser Gly Ile Ile Glu Ser Gly Val Gln Asn Ile Asp Asp Asn
            740                 745                 750

Tyr Phe Tyr Ile Asp Asp Asn Gly Ile Val Gln Ile Gly Val Phe Asp
            755                 760                 765

Thr Ser Asp Gly Tyr Lys Tyr Phe Ala Pro Ala Asn Thr Val Asn Asp
770                 775                 780

Asn Ile Tyr Gly Gln Ala Val Glu Tyr Ser Gly Leu Val Arg Val Gly
785                 790                 795                 800

Glu Asp Val Tyr Tyr Phe Gly Glu Thr Tyr Thr Ile Glu Thr Gly Trp
                805                 810                 815

Ile Tyr Asp Met Glu Asn Glu Ser Asp Lys Tyr Tyr Phe Asn Pro Glu
            820                 825                 830

Thr Lys Lys Ala Cys Lys Gly Ile Asn Leu Ile Asp Asp Ile Lys Tyr
            835                 840                 845

Tyr Phe Asp Glu Lys Gly Ile Met Arg Thr Gly Leu Ile Ser Phe Glu
850                 855                 860

Asn Asn Asn Tyr Tyr Phe Asn Glu Asn Gly Glu Met Gln Phe Gly Tyr
865                 870                 875                 880

Ile Asn Ile Glu Asp Lys Met Phe Tyr Phe Gly Glu Asp Gly Val Met
                885                 890                 895

Gln Ile Gly Val Phe Asn Thr Pro Asp Gly Phe Lys Tyr Phe Ala His
            900                 905                 910

Gln Asn Thr Leu Asp Glu Asn Phe Glu Gly Glu Ser Ile Asn Tyr Thr
            915                 920                 925

Gly Trp Leu Asp Leu Asp Glu Lys Arg Tyr Tyr Phe Thr Asp Glu Tyr
930                 935                 940

Ile Ala Ala Thr Gly Ser Val Ile Ile Asp Gly Glu Glu Tyr Tyr Phe
```

Asp Pro Asp Thr Ala Gln Leu Val Ile Ser Glu
            945                 950                 955                 960
                965                 970

<210> SEQ ID NO 8
<211> LENGTH: 321
<212> TYPE: PRT
<213> ORGANISM: Artificial Sequence
<220> FEATURE:
<223> OTHER INFORMATION: individual toxin A fragment

<400> SEQUENCE: 8

Met Ala Ser Thr Gly Tyr Thr Ser Ile Asn Gly Lys His Phe Tyr Phe
 1               5                  10                  15

Asn Thr Asp Gly Ile Met Gln Ile Gly Val Phe Lys Gly Pro Asn Gly
            20                  25                  30

Phe Glu Tyr Phe Ala Pro Ala Asn Thr Asp Ala Asn Asn Ile Gl

```
<211> LENGTH: 612
<212> TYPE: PRT
<213> ORGANISM: Artificial Sequence
<220> FEATURE:
<223> OTHER INFORMATION: individual toxin B fragment

<400> SEQUENCE: 9
```

| | | | | | | | | | | | | | | | |
|---|---|---|---|---|---|---|---|---|---|---|---|---|---|---|---|
| Met | Ile | Leu | Met | Ser | Thr | Ser | Glu | Glu | Asn | Lys | Val | Ser | Gln | Val | Lys |
| 1 | | | | 5 | | | | | 10 | | | | | 15 | |
| Ile | Arg | Phe | Val | Asn | Val | Phe | Lys | Asp | Lys | Thr | Leu | Ala | Asn | Lys | Leu |
| | | | 20 | | | | | 25 | | | | | 30 | | |
| Ser | Phe | Asn | Phe | Ser | Asp | Lys | Gln | Asp | Val | Pro | Val | Ser | Glu | Ile | Ile |
| | | | | 35 | | | | | 40 | | | | | 45 | |
| Leu | Ser | Phe | Thr | Pro | Ser | Tyr | Tyr | Glu | Asp | Gly | Leu | Ile | Gly | Tyr | Asp |
| | 50 | | | | | 55 | | | | | 60 | | | | |
| Leu | Gly | Leu | Val | Ser | Leu | Tyr | Asn | Glu | Lys | Phe | Tyr | Ile | Asn | Asn | Phe |
| 65 | | | | | 70 | | | | | 75 | | | | | 80 |
| Gly | Met | Met | Val | Ser | Gly | Leu | Ile | Tyr | Ile | Asn | Asp | Ser | Leu | Tyr | Tyr |
| | | | | 85 | | | | | 90 | | | | | 95 | |
| Phe | Lys | Pro | Pro | Val | Asn | Asn | Leu | Ile | Thr | Gly | Phe | Val | Thr | Val | Gly |
| | | | 100 | | | | | 105 | | | | | 110 | | |
| Asp | Asp | Lys | Tyr | Tyr | Phe | Asn | Pro | Ile | Asn | Gly | Gly | Ala | Ala | Ser | Ile |
| | | | 115 | | | | | 120 | | | | | 125 | | |
| Gly | Glu | Thr | Ile | Ile | Asp | Asp | Lys | Asn | Tyr | Tyr | Phe | Asn | Gln | Ser | Gly |
| | | | 130 | | | | | 135 | | | | | 140 | | |
| Val | Leu | Gln | Thr | Gly | Val | Phe | Ser | Thr | Glu | Asp | Gly | Phe | Lys | Tyr | Phe |
| 145 | | | | | 150 | | | | | 155 | | | | | 160 |
| Ala | Pro | Ala | Asn | Thr | Leu | Asp | Glu | Asn | Leu | Glu | Gly | Glu | Ala | Ile | Asp |
| | | | | 165 | | | | | 170 | | | | | 175 | |
| Phe | Thr | Gly | Lys | Leu | Ile | Ile | Asp | Glu | Asn | Ile | Tyr | Tyr | Phe | Asp | Asp |
| | | | 180 | | | | | 185 | | | | | 190 | | |
| Asn | Tyr | Arg | Gly | Ala | Val | Glu | Trp | Lys | Glu | Leu | Asp | Gly | Glu | Met | His |
| | | 195 | | | | | 200 | | | | | 205 | | | |
| Tyr | Phe | Ser | Pro | Glu | Thr | Gly | Lys | Ala | Phe | Lys | Gly | Leu | Asn | Gln | Ile |
| | 210 | | | | | 215 | | | | | 220 | | | | |
| Gly | Asp | Tyr | Lys | Tyr | Tyr | Phe | Asn | Ser | Asp | Gly | Val | Met | Gln | Lys | Gly |
| 225 | | | | | 230 | | | | | 235 | | | | | 240 |
| Phe | Val | Ser | Ile | Asn | Asp | Asn | Lys | His | Tyr | Phe | Asp | Asp | Ser | Gly | Val |
| | | | | 245 | | | | | 250 | | | | | 255 | |
| Met | Lys | Val | Gly | Tyr | Thr | Glu | Ile | Asp | Gly | Lys | His | Phe | Tyr | Phe | Ala |
| | | | 260 | | | | | 265 | | | | | 270 | | |
| Glu | Asn | Gly | Glu | Met | Gln | Ile | Gly | Val | Phe | Asn | Thr | Glu | Asp | Gly | Phe |
| | | | 275 | | | | | 280 | | | | | 285 | | |
| Lys | Tyr | Phe | Ala | His | His | Asn | Glu | Asp | Leu | Gly | Asn | Glu | Glu | Gly | Glu |
| | | 290 | | | | | 295 | | | | | 300 | | | |
| Glu | Ile | Ser | Tyr | Ser | Gly | Ile | Leu | Asn | Phe | Asn | Asn | Lys | Ile | Tyr | Tyr |
| 305 | | | | | 310 | | | | | 315 | | | | | 320 |
| Phe | Asp | Asp | Ser | Phe | Thr | Ala | Val | Val | Gly | Trp | Lys | Asp | Leu | Glu | Asp |
| | | | | 325 | | | | | 330 | | | | | 335 | |
| Gly | Ser | Lys | Tyr | Tyr | Phe | Asp | Glu | Asp | Thr | Ala | Glu | Ala | Tyr | Ile | Gly |
| | | | 340 | | | | | 345 | | | | | 350 | | |
| Leu | Ser | Leu | Ile | Asn | Asp | Gly | Gln | Tyr | Tyr | Phe | Asn | Asp | Asp | Gly | Ile |
| | | | | 355 | | | | | 360 | | | | | 365 | |
| Met | Gln | Val | Gly | Phe | Val | Thr | Ile | Asn | Asp | Lys | Val | Phe | Tyr | Phe | Ser |
| | | | 370 | | | | | 375 | | | | | 380 | | |

```
Asp Ser Gly Ile Ile Glu Ser Gly Val Gln Asn Ile Asp Asp Asn Tyr
385                 390                 395                 400

Phe Tyr Ile Asp Asp Asn Gly Ile Val Gln Ile Gly Val Phe Asp Thr
                405                 410                 415

Ser Asp Gly Tyr Lys Tyr Phe Ala Pro Ala Asn Thr Val Asn Asp Asn
            420                 425                 430

Ile Tyr Gly Gln Ala Val Glu Tyr Ser Gly Leu Val Arg Val Gly Glu
            435                 440                 445

Asp Val Tyr Tyr Phe Gly Glu Thr Tyr Thr Ile Glu Thr Gly Trp Ile
        450                 455                 460

Tyr Asp Met Glu Asn Glu Ser Asp Lys Tyr Tyr Phe Asn Pro Glu Thr
465                 470                 475                 480

Lys Lys Ala Cys Lys Gly Ile Asn Leu Ile Asp Asp Ile Lys Tyr Tyr
                485                 490                 495

Phe Asp Glu Lys Gly Ile Met Arg Thr Gly Leu Ile Ser Phe Glu Asn
            500                 505                 510

Asn Asn Tyr Tyr Phe Asn Glu Asn Gly Glu Met Gln Phe Gly Tyr Ile
            515                 520                 525

Asn Ile Glu Asp Lys Met Phe Tyr Phe Gly Glu Asp Gly Val Met Gln
530                 535                 540

Ile Gly Val Phe Asn Thr Pro Asp Gly Phe Lys Tyr Phe Ala His Gln
545                 550                 555                 560

Asn Thr Leu Asp Glu Asn Phe Glu Gly Glu Ser Ile Asn Tyr Thr Gly
                565                 570                 575

Trp Leu Asp Leu Asp Glu Lys Arg Tyr Tyr Phe Thr Asp Glu Tyr Ile
                580                 585                 590

Ala Ala Thr Gly Ser Val Ile Ile Asp Gly Glu Glu Tyr Tyr Phe Asp
            595                 600                 605

Pro Asp Thr Ala
    610

<210> SEQ ID NO 10
<211> LENGTH: 587
<212> TYPE: PRT
<213> ORGANISM: Artificial Sequence
<220> FEATURE:
<223> OTHER INFORMATION: toxin A fragment from fusion 1

<400> SEQUENCE: 10

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
                20                  25                  30

Tyr Phe Asn Thr Asp Gly Ile Met Gln Ile Gly Val Phe Lys Gly Pro

```
Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
                180                 185                 190

Asn Gly Lys Lys Tyr Tyr Phe Asp Asn Asp Ser Lys Ala Val Thr Gly
            195                 200                 205

Trp Gln Thr Ile Asp Gly Lys Lys Tyr Phe Asn Leu Asn Thr Ala
    210                 215                 220

Glu Ala Ala Thr Gly Trp Gln Thr Ile Asp Gly Lys Lys Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
        370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
                420                 425                 430

Gln Asn Arg Phe Leu Tyr Leu His Asp Asn Ile Tyr Tyr Phe Gly Asn
            435                 440                 445

Asn Ser Lys Ala Ala Thr Gly Trp Val Thr Ile Asp Gly Asn Arg Tyr
        450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
            515                 520                 525

His Leu Leu Gly Lys Ile Tyr Tyr Phe Gly Asn Asn Ser Lys Ala Val
    530                 535                 540
```

```
Thr Gly Trp Gln Thr Ile Asn Gly Lys Val Tyr Tyr Phe Met Pro Asp
545                 550                 555                 560

Thr Ala Met Ala Ala Gly Gly Leu Phe Glu Ile Asp Gly Val Ile
                565                 570                 575

Tyr Phe Phe Gly Val Asp Gly Val Lys Ala Pro
                580                 585

<210> SEQ ID NO 11
<211> LENGTH: 567
<212> TYPE: PRT
<213> ORGANISM: Artificial Sequence
<220> FEATURE:
<223> OTHER INFORMATION: toxin A fragment from fusion 2

<400> SEQUENCE: 11

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
                20                  25                  30

Tyr Phe Asn Thr Asp Gly Ile Met Gln Ile Gly Val Phe L

Asn Lys Phe Leu Thr Leu Asn Gly Lys Lys Tyr Tyr Phe Gly Ser Asp
            325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
            355                 360                 365

Gly Lys Lys Tyr Tyr Phe Asn Thr Asn Thr Ser Ile Ala Ser Thr Gly
            370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
                420                 425                 430

Gln Asn Arg Phe Leu Tyr Leu His Asp Asn Ile Tyr Tyr Phe Gly Asn
            435                 440                 445

Asn Ser Lys Ala Ala Thr Gly Trp Val Thr Ile Asp Gly Asn Arg Tyr
            450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
            515                 520                 525

His Leu Leu Gly Lys Ile Tyr Tyr Phe Gly Asn Asn Ser Lys Ala Val
            530                 535                 540

Thr Gly Trp Gln Thr Ile Asn Gly Lys Val Tyr Tyr Phe Met Pro Asp
545                 550                 555                 560

Thr Ala Met Ala Ala Ala Gly
            565

<210> SEQ ID NO 12
<211> LENGTH: 505
<212> TYPE: PRT
<213> ORGANISM: Artificial Sequence
<220> FEATURE:
<223> OTHER INFORMATION: toxin A fragment from fusion 3

<400> SEQUENCE: 12

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
            35                  40                  45

Asn Gly Phe Glu Tyr Phe Ala Pro Ala Asn Thr Asp Ala Asn Asn Ile
        50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
            130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
    275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr
            500                 505

<210> SEQ ID NO 13
<211> LENGTH: 567
<212> TYPE: PRT

<213> ORGANISM: Artificial Sequence
<220> FEATURE:
<223> OTHER INFORMATION: toxin A fragment from fusion 4

<400> SEQUENCE: 13

```

```
                385                 390                 395                 400
Met Gln Ile Gly Val Phe Lys Gly Pro Asp Gly Phe Glu Tyr Phe Ala
                    405                 410                 415

Pro Ala Asn Thr Asp Ala Asn Asn Ile Glu Gly Gln Ala Ile Arg Tyr
                420                 425                 430

Gln Asn Arg Phe Leu Tyr Leu His Asp Asn Ile Tyr Tyr Phe Gly Asn
            435                 440                 445

Asn Ser Lys Ala Ala Thr Gly Trp Val Thr Ile Asp Gly Asn Arg Tyr
        450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                    485                 490                 495

Phe Lys Gly Ser Asn Gly Phe Glu Tyr Phe Ala Pro Ala Asn Thr Asp
                500                 505                 510

Ala Asn Asn Ile Glu Gly Gln Ala Ile Arg Tyr Gln Asn Arg Phe Leu
            515                 520                 525

His Leu Leu Gly Lys Ile Tyr Tyr Phe Gly Asn Asn Ser Lys Ala Val
        530                 535                 540

Thr Gly Trp Gln Thr Ile Asn Gly Lys Val Tyr Tyr Phe Met Pro Asp
545                 550                 555                 560

Thr Ala Met Ala Ala Ala Gly
                    565

<210> SEQ ID NO 14
<211> LENGTH: 591
<212> TYPE: PRT
<213> ORGANISM: Artificial Sequence
<220> FEATURE:
<223> OTHER INFORMATION: toxin A fragment from fusion 5

<400>

```
            180                 185                 190
Asn Gly Lys Lys Tyr Tyr Phe Asp Asn Asp Ser Lys Ala Val Thr Gly
            195                 200                 205

Trp Gln Thr Ile Asp Gly Lys Lys Tyr Tyr Phe Asn Leu Asn Thr Ala
            210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
            275                 280                 285

Gln Ile Gly Val Phe Lys Gly Pro Asn Gly Phe Glu Tyr Phe Ala Pro
            290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
                340                 345                 350

Phe Asn Thr Asn Thr Ala Val Ala Val Thr Gly Trp Gln Thr Ile Asn
            355                 360                 365

Gly Lys Lys Tyr Tyr Phe Asn Thr Asn Thr Ser Ile Ala Ser Thr Gly
            370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
                420                 425                 430

Gln Asn Arg Phe Leu Tyr Leu His Asp Asn Ile Tyr Tyr Phe Gly Asn
            435                 440                 445

Asn Ser Lys Ala Ala Thr Gly Trp Val Thr Ile Asp Gly Asn Arg Tyr
            450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
            515                 520                 525

His Leu Leu Gly Lys Ile Tyr Tyr Phe Gly Asn Asn Ser Lys Ala Val
            530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Phe Glu Ile Asp Gly Val Ile
                565                 570                 575

Tyr Phe Phe Gly Val Asp Gly Val Lys Ala Pro Gly Ile Tyr Gly
            580                 585                 590

<210> SEQ ID NO 15
```

<211> LENGTH: 379
<212> TYPE: PRT
<213> ORGANISM: Artificial Sequence
<220> FEATURE:
<223> OTHER INFORMATION: toxin B fragment from fusion 1

<400> SEQUENCE: 15

```
Gly Phe Val Ser Ile Asn Asp Asn Lys His Tyr Phe Asp Asp Ser Gly
  1               5                  10                  15
Val Met Lys Val Gly Tyr Thr Glu Ile Asp Gly Lys His Phe Tyr Phe
                 20                  25                  30
Ala Glu Asn Gly Glu Met Gln Ile Gly Val Phe Asn Thr Glu Asp Gly
             35                  40                  45
Phe Lys Tyr Phe Ala His His Asn Glu Asp Leu Gly Asn Glu Glu Gly
 50                  55                  60
Glu Glu Ile Ser Tyr Ser Gly Ile Leu Asn Phe Asn Asn Lys Ile Tyr
 65                  70                  75                  80
Tyr Phe Asp Asp Ser Phe Thr Ala Val Val Gly Trp Lys Asp Leu Glu
                 85                  90                  95
Asp Gly Ser Lys Tyr Tyr Phe Asp Glu Asp Thr Ala Glu Ala Tyr Ile
                100                 105                 110
Gly Leu Ser Leu Ile Asn Asp Gly Gln Tyr Tyr Phe Asn Asp Asp Gly
             115                 120                 125
Ile Met Gln Val Gly Phe Val Thr Ile Asn Asp Lys Val Phe Tyr Phe
130                 135                 140
Ser Asp Ser Gly Ile Ile Glu Ser Gly Val Gln Asn Ile Asp Asp Asn
145                 150                 155                 160
Tyr Phe Tyr Ile Asp Asp Asn Gly Ile Val Gln Ile Gly Val Phe Asp
                165                 170                 175
Thr Ser Asp Gly Tyr Lys Tyr Phe Ala Pro Ala Asn Thr Val Asn Asp
                180                 185                 190
Asn Ile Tyr Gly Gln Ala Val Glu Tyr Ser Gly Leu Val Arg Val Gly
            195                 200                 205
Glu Asp Val Tyr Tyr Phe Gly Glu Thr Tyr Thr Ile Glu Thr Gly Trp
210                 215                 220
Ile Tyr Asp Met Glu Asn Glu Ser Asp Lys Tyr Tyr Phe Asn Pro Glu
225                 230                 235                 240
Thr Lys Lys Ala Cys Lys Gly Ile Asn Leu Ile Asp Asp Ile Lys Tyr
                245                 250                 255
Tyr Phe Asp Glu Lys Gly Ile Met Arg Thr Gly Leu Ile Ser Phe Glu
                260                 265                 270
Asn Asn Asn Tyr Tyr Phe Asn Glu Asn Gly Glu Met Gln Phe Gly Tyr
            275                 280                 285
Ile Asn Ile Glu Asp Lys Met Phe Tyr Phe Gly Glu Asp Gly Val Met
290                 295                 300
Gln Ile Gly Val Phe Asn Thr Pro Asp Gly Phe Lys Tyr Phe Ala His
305                 310                 315                 320
Gln Asn Thr Leu Asp Glu Asn Phe Glu Gly Glu Ser Ile Asn Tyr Thr
                325                 330                 335
Gly Trp Leu Asp Leu Asp Glu Lys Arg Tyr Tyr Phe Thr Asp Glu Tyr
                340                 345                 350
Ile Ala Ala Thr Gly Ser Val Ile Ile Asp Gly Glu Glu Tyr Tyr Phe
            355                 360                 365
Asp Pro Asp Thr Ala Gln Leu Val Ile Ser Glu
370                 375
```

<210> SEQ ID NO 16
<211> LENGTH: 399
<212> TYPE: PRT
<213> ORGANISM: Artificial Sequence
<220> FEATURE:
<223> OTHER INFORMATION: toxin B fragment from fusion 2

<400> SEQUENCE: 16

```
Gly Leu Asn Gln Ile Gly Asp Tyr Lys Tyr Tyr Phe Asn Ser Asp Gly
1               5                   10                  15

Val Met Gln Lys Gly Phe Val Ser Ile Asn Asp Asn Lys His Tyr Phe
            20                  25                  30

Asp Asp Ser Gly Val Met Lys Val Gly Tyr Thr Glu Ile Asp Gly Lys
        35                  40                  45

His Phe Tyr Phe Ala Glu Asn Gly Glu Met Gln Ile Gly Val Phe Asn
    50                  55                  60

Thr Glu Asp Gly Phe Lys Tyr Phe Ala His His Asn Glu Asp Leu Gly
65                  70                  75                  80

Asn Glu Glu Gly Glu Glu Ile Ser Tyr Ser Gly Ile Leu Asn Phe Asn
                85                  90                  95

Asn Lys Ile Tyr Tyr Phe Asp Asp Ser Phe Thr Ala Val Val Gly Trp
            100                 105                 110

Lys Asp Leu Glu Asp Gly Ser Lys Tyr Tyr Phe Asp Glu Asp Thr Ala
        115                 120                 125

Glu Ala Tyr Ile Gly Leu Ser Leu Ile Asn Asp Gly Gln Tyr Tyr Phe
    130                 135                 140

Asn Asp Asp Gly Ile Met Gln Val Gly Phe Val Thr Ile Asn Asp Lys
145                 150                 155                 160

Val Phe Tyr Phe Ser Asp Ser Gly Ile Ile Glu Ser Gly Val Gln Asn
                165                 170                 175

Ile Asp Asp Asn Tyr Phe Tyr Ile Asp Asp Asn Gly Ile Val Gln Ile
            180                 185                 190

Gly Val Phe Asp Thr Ser Asp Gly Tyr Lys Tyr Phe Ala Pro Ala Asn
        195                 200                 205

Thr Val Asn Asp Asn Ile Tyr Gly Gln Ala Val Glu Tyr Ser Gly Leu
    210                 215                 220

Val Arg Val Gly Glu Asp Val Tyr Tyr Phe Gly Glu Thr Tyr Thr Ile
225                 230                 235                 240

Glu Thr Gly Trp Ile Tyr Asp Met Glu Asn Glu Ser Asp Lys Tyr Tyr
                245                 250                 255

Phe Asn Pro Glu Thr Lys Lys Ala Cys Lys Gly Ile Asn Leu Ile Asp
            260                 265                 270

Asp Ile Lys Tyr Tyr Phe Asp Glu Lys Gly Ile Met Arg Thr Gly Leu
        275                 280                 285

Ile Ser Phe Glu Asn Asn Asn Tyr Tyr Phe Asn Glu Asn Gly Glu Met
    290                 295                 300

Gln Phe Gly Tyr Ile Asn Ile Glu Asp Lys Met Phe Tyr Phe Gly Glu
305                 310                 315                 320

Asp Gly Val Met Gln Ile Gly Val Phe Asn Thr Pro Asp Gly Phe Lys
                325                 330                 335

Tyr Phe Ala His Gln Asn Thr Leu Asp Glu Asn Phe Glu Gly Glu Ser
            340                 345                 350

Ile Asn Tyr Thr Gly Trp Leu Asp Leu Asp Glu Lys Arg Tyr Tyr Phe
        355                 360                 365
```

```
Thr Asp Glu Tyr Ile Ala Ala Thr Gly Ser Val Ile Ile Asp Gly Glu
    370                 375                 380

Glu Tyr Tyr Phe Asp Pro Asp Thr Ala Gln Leu Val Ile Ser Glu
385                 390                 395
```

<210> SEQ ID NO 17
<211> LENGTH: 328
<212> TYPE: PRT
<213> ORGANISM: Artificial Sequence
<220> FEATURE:
<223> OTHER INFORMATION: toxin B fragment from fusion 3

<400> SEQUENCE: 17

```
Phe Ala His His Asn Glu Asp Leu Gly Asn Glu Gly Glu Glu Ile
 1               5                  10                  15

Ser Tyr Ser Gly Ile Leu Asn Phe Asn Asn Lys Ile Tyr Tyr Phe Asp
                20                  25                  30

Asp Ser Phe Thr Ala Val Val Gly Trp Lys Asp Leu Glu Asp Gly Ser
            35                  40                  45

Lys Tyr Tyr Phe Asp Glu Asp Thr Ala Glu Ala Tyr Ile Gly Leu Ser
        50                  55                  60

Leu Ile Asn Asp Gly Gln Tyr Tyr Phe Asn Asp Asp Gly Ile Met Gln
65                  70                  75                  80

Val Gly Phe Val Thr Ile Asn Asp Lys Val Phe Tyr Phe Ser Asp Ser
                85                  90                  95

Gly Ile Ile Glu Ser Gly Val Gln Asn Ile Asp Asp Asn Tyr Phe Tyr
                100                 105                 110

Ile Asp Asp Asn Gly Ile Val Gln Ile Gly Val Phe Asp Thr Ser Asp
                115                 120                 125

Gly Tyr Lys Tyr Phe Ala Pro Ala Asn Thr Val Asn Asp Asn Ile Tyr
        130                 135                 140

Gly Gln Ala Val Glu Tyr Ser Gly Leu Val Arg Val Gly Glu Asp Val
145                 150                 155                 160

Tyr Tyr Phe Gly Glu Thr Tyr Thr Ile Glu Thr Gly Trp Ile Tyr Asp
                165                 170                 175

Met Glu Asn Glu Ser Asp Lys Tyr Tyr Phe Asn Pro Glu Thr Lys Lys
                180                 185                 190

Ala Cys Lys Gly Ile Asn Leu Ile Asp Asp Ile Lys Tyr Tyr Phe Asp
            195                 200                 205

Glu Lys Gly Ile Met Arg Thr Gly Leu Ile Ser Phe Glu Asn Asn Asn
        210                 215                 220

Tyr Tyr Phe Asn Glu Asn Gly Glu Met Gln Phe Gly Tyr Ile Asn Ile
225                 230                 235                 240

Glu Asp Lys Met Phe Tyr Phe Gly Glu Asp Gly Val Met Gln Ile Gly
                245                 250                 255

Val Phe Asn Thr Pro Asp Gly Phe Lys Tyr Phe Ala His Gln Asn Thr
                260                 265                 270

Leu Asp Glu Asn Phe Glu Gly Glu Ser Ile Asn Tyr Thr Gly Trp Leu
            275                 280                 285

Asp Leu Asp Glu Lys Arg Tyr Tyr Phe Thr Asp Glu Tyr Ile Ala Ala
        290                 295                 300

Thr Gly Ser Val Ile Ile Asp Gly Glu Glu Tyr Tyr Phe Asp Pro Asp
305                 310                 315                 320

Thr Ala Gln Leu Val Ile Ser Glu
                325
```

<210> SEQ ID NO 18
<211> LENGTH: 490
<212> TYPE: PRT
<213> ORGANISM: Artificial Sequence
<220> FEATURE:
<223> OTHER INFORMATION: toxin B fragment from fusion 4

<400> SEQUENCE: 18

```
Gly Glu Thr Ile Ile Asp Asp Lys Asn Tyr Tyr Phe Asn Gln Ser Gly
  1               5                  10                  15

Val Leu Gln Thr Gly Val Phe Ser Thr Glu Asp Gly Phe Lys Tyr Phe
                 20                  25                  30

Ala Pro Ala Asn Thr Leu Asp Glu Asn Leu Glu Gly Glu Ala Ile Asp
             35                  40                  45

Phe Thr Gly Lys Leu Ile Ile Asp Glu Asn Ile Tyr Tyr Phe Asp Asp
 50                  55                  60

Asn Tyr Arg Gly Ala Val Glu Trp Lys Glu Leu Asp Gly Glu Met His
 65                  70                  75                  80

Tyr Phe Ser Pro Glu Thr Gly Lys Ala Phe Lys Gly Leu Asn Gln Ile
                 85                  90                  95

Gly Asp Tyr Lys Tyr Tyr Phe Asn Ser Asp Gly Val Met Gln Lys Gly
            100                 105                 110

Phe Val Ser Ile Asn Asp Asn Lys His Tyr Phe Asp Asp Ser Gly Val
            115                 120                 125

Met Lys Val Gly Tyr Thr Glu Ile Asp Gly Lys His Phe Tyr Phe Ala
130                 135                 140

Glu Asn Gly Glu Met Gln Ile Gly Val Phe Asn Thr Glu Asp Gly Phe
145                 150                 155                 160

Lys Tyr Phe Ala His His Asn Glu Asp Leu Gly Asn Glu Glu Gly Glu
                165                 170                 175

Glu Ile Ser Tyr Ser Gly Ile Leu Asn Phe Asn Asn Lys Ile Tyr Tyr
            180                 185                 190

Phe Asp Asp Ser Phe Thr Ala Val Val Gly Trp Lys Asp Leu Glu Asp
            195                 200                 205

Gly Ser Lys Tyr Tyr Phe Asp Glu Asp Thr Ala Glu Ala Tyr Ile Gly
    210                 215                 220

Leu Ser Leu Ile Asn Asp Gly Gln Tyr Tyr Phe Asn Asp Asp Gly Ile
225                 230                 235                 240

Met Gln Val Gly Phe Val Thr Ile Asn Asp Lys Val Phe Tyr Phe Ser
                245                 250                 255

Asp Ser Gly Ile Ile Glu Ser Gly Val Gln Asn Ile Asp Asp Asn Tyr
            260                 265                 270

Phe Tyr Ile Asp Asp Asn Gly Ile Val Gln Ile Gly Val Phe Asp Thr
            275                 280                 285

Ser Asp Gly Tyr Lys Tyr Phe Ala Pro Ala Asn Thr Val Asn Asp Asn
    290                 295                 300

Ile Tyr Gly Gln Ala Val Glu Tyr Ser Gly Leu Val Arg Val Gly Glu
305                 310                 315                 320

Asp Val Tyr Tyr Phe Gly Glu Thr Tyr Thr Ile Glu Thr Gly Trp Ile
                325                 330                 335

Tyr Asp Met Glu Asn Glu Ser Asp Lys Tyr Tyr Phe Asn Pro Glu Thr
            340                 345                 350

Lys Lys Ala Cys Lys Gly Ile Asn Leu Ile Asp Asp Ile Lys Tyr Tyr
    355                 360                 365
```

```
Phe Asp Glu Lys Gly Ile Met Arg Thr Gly Leu Ile Ser Phe Glu Asn
        370                 375                 380

Asn Asn Tyr Tyr Phe Asn Glu Asn Gly Glu Met Gln Phe Gly Tyr Ile
385                 390                 395                 400

Asn Ile Glu Asp Lys Met Phe Tyr Phe Gly Glu Asp Gly Val Met Gln
                405                 410                 415

Ile Gly Val Phe Asn Thr Pro Asp Gly Phe Lys Tyr Phe Ala His Gln
            420                 425                 430

Asn Thr Leu Asp Glu Asn Phe Glu Gly Glu Ser Ile Asn Tyr Thr Gly
        435                 440                 445

Trp Leu Asp Leu Asp Glu Lys Arg Tyr Tyr Phe Thr Asp Glu Tyr Ile
    450                 455                 460

Ala Ala Thr Gly Ser Val Ile Ile Asp Gly Glu Glu Tyr Tyr Phe Asp
465                 470                 475                 480

Pro Asp Thr Ala Gln Leu Val Ile Ser Glu
                485                 490

<210> SEQ ID NO 19
<211> LENGTH: 379
<212> TYPE: PRT
<213> ORGANISM: Artificial Sequence
<220> FEATURE:
<223> OTHER INFORMATION: toxin B fragment from fusion 5

<400> SEQUENCE: 19

Gly Phe Val Ser Ile Asn Asp Asn Lys His Tyr Phe Asp Asp Ser Gly
1               5                   10                  15

Val Met Lys Val Gly Tyr Thr Glu Ile Asp Gly Lys His Phe Tyr Phe
                20                  25                  30

Ala Glu Asn Gly Glu Met Gln Ile Gly Val Phe Asn Thr Glu Asp Gly
            35                  40                  45

Phe Lys Tyr Phe Ala His His Asn Glu Asp Leu Gly Asn Glu Glu Gly
        50                  55                  60

Glu Glu Ile Ser Tyr Ser Gly Ile Leu Asn Phe Asn Asn Lys Ile Tyr
65                  70                  75                  80

Tyr Phe Asp Asp Ser Phe Thr Ala Val Val Gly Trp Lys Asp Leu Glu
                85                  90                  95

Asp Gly Ser Lys Tyr Tyr Phe Asp Glu Asp Thr Ala Glu Ala Tyr Ile
                100                 105                 110

Gly Leu Ser Leu Ile Asn Asp Gly Gln Tyr Tyr Phe Asn Asp Asp Gly
            115                 120                 125

Ile Met Gln Val Gly Phe Val Thr Ile Asn Asp Lys Val Phe Tyr Phe
130                 135                 140

Ser Asp Ser Gly Ile Ile Glu Ser Gly Val Gln Asn Ile Asp Asp Asn
145                 150                 155                 160

Tyr Phe Tyr Ile Asp Asp Asn Gly Ile Val Gln Ile Gly Val Phe Asp
                165                 170                 175

Thr Ser Asp Gly Tyr Lys Tyr Phe Ala Pro Ala Asn Thr Val Asn Asp
            180                 185                 190

Asn Ile Tyr Gly Gln Ala Val Glu Tyr Ser Gly Leu Val Arg Val Gly
        195                 200                 205

Glu Asp Val Tyr Tyr Phe Gly Glu Thr Tyr Thr Ile Glu Thr Gly Trp
    210                 215                 220

Ile Tyr Asp Met Glu Asn Glu Ser Asp Lys Tyr Tyr Phe Asn Pro Glu
225                 230                 235                 240
```

```
Thr Lys Lys Ala Cys Lys Gly Ile Asn Leu Ile Asp Asp Ile Lys Tyr
                245                 250                 255

Tyr Phe Asp Glu Lys Gly Ile Met Arg Thr Gly Leu Ile Ser Phe Glu
            260                 265                 270

Asn Asn Asn Tyr Tyr Phe Asn Glu Asn Gly Glu Met Gln Phe Gly Tyr
                275                 280                 285

Ile Asn Ile Glu Asp Lys Met Phe Tyr Phe Gly Glu Asp Gly Val Met
            290                 295                 300

Gln Ile Gly Val Phe Asn Thr Pro Asp Gly Phe Lys Tyr Phe Ala His
305                 310                 315                 320

Gln Asn Thr Leu Asp Glu Asn Phe Glu Gly Ser Ile Asn Tyr Thr
                325                 330                 335

Gly Trp Leu Asp Leu Asp Glu Lys Arg Tyr Tyr Phe Thr Asp Glu Tyr
            340                 345                 350

Ile Ala Ala Thr Gly Ser Val Ile Ile Asp Gly Glu Glu Tyr Tyr Phe
                355                 360                 365

Asp Pro Asp Thr Ala Gln Leu Val Ile Ser Glu
        370                 375
```

```
<210> SEQ ID NO 20
<211> LENGTH: 3339
<212> TYPE: DNA
<213> ORGANISM: Artificial Sequence
<220> FEATURE:
<223> OTHER INFORMATION: nucleotide sequence of F54 Gly fusion protein

<400> SEQUENCE: 20
atggcaaccg ttggcagac catcgatggc aaaaaatatt attttaatac caacaccgca      60
attgcaagca ccggctatac cattatcaac ggcaaacact tttattttaa caccgacggc     120
attatgcaga ttggtgtgtt taaaggtccg aacggctttg atactttgc accggcaaat      180 accgatgcca taatattga aggccaggcc attctgtatc agaatgaatt tctgaccctg      240
aacggcaaaa aatactactt tggcagcgat agcaaagcag ttaccggttg cgcatcatc      300 aacaataaga aatattactt caacccgaat aatgcaattg cagcaattca tctgtgcacc     360
attaacaacg acaaatatta tttcagctat gacggtattc tgcagaatgg ctacattacc     420
atcgaacgca caaactttta tttcgatgcc aacaacgaaa gcaaaatggt gaccggtgtt     480
ttcaaaggcc ctaatggttt tgagtatttc gctccggcaa cacccataa taacaacatt     540 gaaggtcagg cgatcgttta tcagaacaaa ttcctgacgc tgaatggtaa gaaatactat     600
ttcgataatg acagcaaagc cgtgaccggc tggcagacaa ttgacgggaa gaaatattac     660
tttaatctga ataccgcaga agcagcaacc ggttggcaaa cgatcgacgg taaaaagtac     720
tacttcaacc tgaacacagc cgaagcagcc acaggatggc agactattga tggaaaaaaa     780
tactatttca caccaacac ctttattgca tctaccggtt ataccagcat taacggtaaa     840
catttctact caacaccga tggtatcatg cagatcggcg ttttcaaagg tccaaatggt     900
ttcgaatact ttgcccctgc aatacagat gcaaataaca tcgagggtca ggcaatcctg     960
taccaaaaca aatttctgac cctgaatggg aaaaaatatt actttggtag cgattctaaa    1020
gccgttaccg gtctgcgtac cattgatggt aaaaaatact actttaatac gaatacagcc    1080
gttgcggtta caggctggca gaccattaac gggaaaaaat actatttaa cacaaatacc    1140 agcattgcct caacgggtta taccattatt tcgggtaaac acttctactt taataccgat    1200
ggtattatgc aaatcggagt ctttaaagga cctgatgggt tcgaatattt tgcgcctgcg    1260
```

```
aacactgatg cgaacaatat cgaaggacag gcaatccgct atcagaatcg ctttctgtat    1320
ctgcacgaca acatctatta ttttggcaac aattcaaaag cagccaccgg ctgggttaca    1380
attgatggca accgctacta tttcgaaccg aataccgcaa tgggtgcaaa tggctacaaa    1440
accatcgata taaaaatttt ctattttcgc aacggtctgc cgcagatcgg ggtatttaaa    1500
ggtagcaacg gcttcgaata cttcgctcca gcgaatacgg acgcgaacaa tattgagggt    1560
caagcgattc gttatcaaaa ccgttttctg catctgctgg gcaaaatcta ctactttggc    1620
aataacagta aagcagttac tggatggcag acaatcaatg gtaaagtgta ctattttatg    1680
ccggataccg ccatggcagc agccggtggt ctgtttgaaa ttgatggcgt gatctatttt    1740
tttggtgtgg atggtgttaa agcaccggga atatacggtg gtaccggctt tgtgaccgtg    1800
ggtgatgata aatactattt caatccgatt aacggtggtg cagcgagcat ggcgaaacc    1860
atcatcgatg acaaaaacta ttatttcaac cagagcggtg tgctgcagac cggtgtgttt    1920
agcaccgaag atggctttaa atattttgcg ccagcgaaca ccctggatga aacctggaa    1980
ggcgaagcga ttgattttac cggcaaactg atcatcgatg aaaacatcta ttacttcgat    2040
gataactatc gtggtgcggt ggaatggaaa gaactggatg gcgaaatgca ttattttct    2100
ccggaaaccg gtaaagcgtt taaaggcctg aaccagatcg gcgattacaa atactacttc    2160
aacagcgatg gcgtgatgca gaaaggcttt gtgagcatca acgataacaa acactatttc    2220
gatgatagcg gtgtgatgaa agtgggctat accgaaattg atggcaaaca tttctacttc    2280
gcggaaaacg gcgaaatgca gattggcgtg ttcaataccg aagatggttt caaatacttc    2340
gcgcaccata acgaagatct gggtaacgaa gaaggcgaag aaattagcta tagcggcatc    2400
ctgaacttca caacaaaat ctactacttt gatgatagct ttaccgcggt ggtgggctgg    2460
aaagatctgg aagatggcag caaatattat ttcgatgaag ataccgcgga agcgtatatt    2520
ggcctgagcc tgattaacga tggccagtac tattttaacg atgatggcat tatgcaggtg    2580
ggtttcgtga ccattaatga taaagtgttc tatttcagcg atagcggcat tattgaaagc    2640
ggcgtgcaga acattgatga taactacttc tacatcgatg ataacggcat tgtgcagatc    2700
ggcgttttg ataccagcga tggctacaaa tatttcgcac cggccaatac cgtgaacgat    2760
aacatttatg ccaggcggt ggaatatagc ggtctggtgc gtgtgggcga agatgtgtat    2820
tatttcggcg aaacctatac catcgaaacc ggctggattt atgatatgga aaacgaaagc    2880
gataaatatt actttaatcc ggaaacgaaa aaagcgtgca aaggcattaa cctgatcgat    2940
gatatcaaat actattttga tgaaaaaggc attatgcgta ccggtctgat tagcttcgaa    3000
aacaacaact attacttcaa cgaaaacggt gaaatgcagt tcggctacat caacatcgaa    3060
gataaaatgt tctacttcgg cgaagatggt gttatgcaga ttggtgtttt taacaccccg    3120
gatggcttca atactttgc ccatcagaat accctggatg aaaatttcga aggtgaaagc    3180
attaactata ccggctggct ggatctggat gaaaaacgct actacttcac cgatgaatac    3240
attgcggcga ccggcagcgt gattattgat ggcgaagaat actacttcga tccggatacc    3300
gcgcagctgg tgattagcga acatcatcat catcaccat                          3339
```

<210> SEQ ID NO 21  
<211> LENGTH: 1113  
<212> TYPE: PRT  
<213> ORGANISM: Artificial Sequence  
<220> FEATURE:  
<223> OTHER INFORMATION: amino acid of F54Gly fusion protein

<400> SEQUENCE: 21

```
Met Ala Thr Gly Trp Gln Thr Ile Asp Gly Lys Lys Tyr Tyr Phe Asn
  1               5                  10                  15

Thr Asn Thr Ala Ile Ala Ser Thr Gly Tyr Thr Ile Ile Asn Gly Lys
             20                  25                  30

His Phe Tyr Phe Asn Thr Asp Gly Ile Met Gln Ile Gly Val Phe Lys
             35                  40                  45

Gly Pro Asn Gly Phe Glu Tyr Phe Ala Pro Ala Asn Thr Asp Ala Asn
         50                  55                  60

Asn Ile Glu Gly Gln Ala Ile Leu Tyr Gln Asn Glu Phe Leu Thr Leu
 65                  70                  75                  80

Asn Gly Lys Lys Tyr Tyr Phe Gly Ser Asp Ser Lys Ala Val Thr Gly
                 85                  90                  95

Trp Arg Ile Ile Asn Asn Lys Lys Tyr Tyr Phe Asn Pro Asn Asn Ala
             100                 105                 110

Ile Ala Ala Ile His Leu Cys Thr Ile Asn Asn Asp Lys Tyr Tyr Phe
             115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415
```

```
Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
            435                 440                 445

Gly Asn Asn Ser Lys Ala Ala Thr Gly Trp Val Thr Ile Asp Gly Asn
450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
            485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
            515                 520                 525

Phe Leu His Leu Leu Gly Lys Ile Tyr Tyr Phe Gly Asn Asn Ser Lys
            530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
            565                 570                 575

Val Ile Tyr Phe Phe Gly Val Asp Gly Val Lys Ala Pro Gly Ile Tyr
            580                 585                 590

Gly Gly Thr Gly Phe Val Thr Val Gly Asp Asp Lys Tyr Tyr Phe Asn
            595                 600                 605

Pro Ile Asn Gly Gly Ala Ala Ser Ile Gly Glu Thr Ile Ile Asp Asp
            610                 615                 620

Lys Asn Tyr Tyr Phe Asn Gln Ser Gly Val Leu Gln Thr Gly Val Phe
625                 630                 635                 640

Ser Thr Glu Asp Gly Phe Lys Tyr Phe Ala Pro Ala Asn Thr Leu Asp
                645                 650                 655

Glu Asn Leu Glu Gly Glu Ala Ile Asp Phe Thr Gly Lys Leu Ile Ile
            660                 665                 670

Asp Glu Asn Ile Tyr Tyr Phe Asp Asp Asn Tyr Arg Gly Ala Val Glu
            675                 680                 685

Trp Lys Glu Leu Asp Gly Glu Met His Tyr Phe Ser Pro Glu Thr Gly
            690                 695                 700

Lys Ala Phe Lys Gly Leu Asn Gln Ile Gly Asp Tyr Lys Tyr Tyr Phe
705                 710                 715                 720

Asn Ser Asp Gly Val Met Gln Lys Gly Phe Val Ser Ile Asn Asp Asn
                725                 730                 735

Lys His Tyr Phe Asp Asp Ser Gly Val Met Lys Val Gly Tyr Thr Glu
            740                 745                 750

Ile Asp Gly Lys His Phe Tyr Phe Ala Glu Asn Gly Glu Met Gln Ile
            755                 760                 765

Gly Val Phe Asn Thr Glu Asp Gly Phe Lys Tyr Phe Ala His His Asn
            770                 775                 780

Glu Asp Leu Gly Asn Glu Glu Gly Glu Glu Ile Ser Tyr Ser Gly Ile
785                 790                 795                 800

Leu Asn Phe Asn Asn Lys Ile Tyr Tyr Phe Asp Asp Ser Phe Thr Ala
            805                 810                 815

Val Val Gly Trp Lys Asp Leu Glu Asp Gly Ser Lys Tyr Tyr Phe Asp
            820                 825                 830
```

```
Glu Asp Thr Ala Glu Ala Tyr Ile Gly Leu Ser Leu Ile Asn Asp Gly
            835                 840                 845
Gln Tyr Tyr Phe Asn Asp Gly Ile Met Gln Val Gly Phe Val Thr
850                 855                 860
Ile Asn Asp Lys Val Phe Tyr Phe Ser Asp Ser Gly Ile Ile Glu Ser
865                 870                 875                 880
Gly Val Gln Asn Ile Asp Asp Asn Tyr Phe Tyr Ile Asp Asp Asn Gly
                885                 890                 895
Ile Val Gln Ile Gly Val Phe Asp Thr Ser Asp Gly Tyr Lys Tyr Phe
                900                 905                 910
Ala Pro Ala Asn Thr Val Asn Asp Asn Ile Tyr Gly Gln Ala Val Glu
                915                 920                 925
Tyr Ser Gly Leu Val Arg Val Gly Glu Asp Val Tyr Tyr Phe Gly Glu
            930                 935                 940
Thr Tyr Thr Ile Glu Thr Gly Trp Ile Tyr Asp Met Glu Asn Glu Ser
945                 950                 955                 960
Asp Lys Tyr Tyr Phe Asn Pro Glu Thr Lys Lys Ala Cys Lys Gly Ile
                965                 970                 975
Asn Leu Ile Asp Asp Ile Lys Tyr Tyr Phe Asp Glu Lys Gly Ile Met
                980                 985                 990
Arg Thr Gly Leu Ile Ser Phe Glu Asn Asn Asn Tyr Tyr Phe Asn Glu
            995                 1000                1005
Asn Gly Glu Met Gln Phe Gly Tyr Ile Asn Ile Glu Asp Lys Met Phe
            1010                1015                1020
Tyr Phe Gly Glu Asp Gly Val Met Gln Ile Gly Val Phe Asn Thr Pro
1025                1030                1035                1040
Asp Gly Phe Lys Tyr Phe Ala His Gln Asn Thr Leu Asp Glu Asn Phe
                1045                1050                1055
Glu Gly Glu Ser Ile Asn Tyr Thr Gly Trp Leu Asp Leu Asp Glu Lys
                1060                1065                1070
Arg Tyr Tyr Phe Thr Asp Glu Tyr Ile Ala Ala Thr Gly Ser Val Ile
            1075                1080                1085
Ile Asp Gly Glu Glu Tyr Tyr Phe Asp Pro Asp Thr Ala Gln Leu Val
1090                1095                1100
Ile Ser Glu His His His His His His
1105                1110

<210> SEQ ID NO 22
<211> LENGTH: 3324
<212> TYPE: DNA
<213> ORGANISM: Artificial Sequence
<220> FEATURE:
<223> OTHER INFORMATION: nucleotide sequence of F54 New fusion protein

<400> SEQUENCE: 22
atggcaaccg gttggcagac catcgatggc aaaaaatatt attttaatac caacaccgca      60
attgcaagca ccggctatac cattatcaac ggcaaacact ttatttttaa caccgacggc     120
attatgcaga ttggtgtgtt taaaggtccg aacggctttg aatactttgc accggcaaat     180
accgatgcca ataatattga aggccaggcc attctgtatc agaatgaatt tctgaccctg     240
aacggcaaaa atactactt tggcagcgat agcaaagcag ttaccggttg cgcatcatc     300 aacaataaga atattactt caaccccgaat aatgcaattg cagcaattca tctgtgcacc     360
attaacaacg acaatatta tttcagctat gacggtattc tgcagaatgg ctacattacc     420
atcgaacgca acaactttta tttcgatgcc aacaacgaaa gcaaaatggt gaccggtgtt     480
```

```
ttcaaaggcc ctaatggttt tgagtatttc gctccggcaa acacccataa taacaacatt    540
gaaggtcagg cgatcgttta tcagaacaaa ttcctgacgc tgaatggtaa gaaatactat    600
ttcgataatg acagcaaagc cgtgaccggc tggcagacaa ttgacgggaa gaaatattac    660
tttaatctga ataccgcaga agcagcaacc ggttggcaaa cgatcgacgg taaaaagtac    720
tacttcaacc tgaacacagc cgaagcagcc acaggatggc agactattga tggaaaaaaa    780
tactatttca acaccaacac ctttattgca tctaccggtt ataccagcat aacggtaaa     840 catttctact tcaacaccga tggtatcatg cagatcggcg ttttcaaagg tccaaatggt    900
ttcgaatact ttgcccctgc caatacagat gcaaataaca tcgagggtca ggcaatcctg    960
taccaaaaca aatttctgac cctgaatggg aaaaaatatt actttggtag cgattctaaa   1020
gccgttaccg tctgcgtac cattgatggt aaaaaatact actttaatac gaatacagcc    1080
gttgcggtta caggctggca gaccattaac gggaaaaaat actatttaa cacaaatacc    1140 agcattgcct caacgggtta taccattatt tcgggtaaac acttctactt taataccgat   1200
ggtattatgc aaatcggagt cttaaagga cctgatgggt tcgaatattt tgcgcctgcg    1260
aacactgatg cgaacaatat cgaaggacag gcaatccgct atcagaatcg ctttctgtat   1320
ctgcacgaca acatctatta ttttggcaac aattcaaaag cagccaccgg ctgggttaca   1380
attgatggca accgctacta tttcgaaccg aataccgcaa tgggtgcaaa tggctacaaa   1440
accatcgata taaaaatttt ctatttcgc aacggtctgc cgcagatcgg ggtatttaaa    1500
ggtagcaacg gcttcgaata cttcgctcca gcgaatacgg acgcgaacaa tattgagggt   1560
caagcgattc gttatcaaaa ccgttttctg catctgctgg gcaaaatcta ctactttggc   1620
aataacagta aagcagttac tggatggcag acaatcaatg gtaaagtgta ctattttatg   1680
ccggataccg ccatggcagc agccggtggt ctgtttgaaa ttgatggcgt gatctatttt   1740
tttggtgtgg atggtgttaa agcagttacc ggctttgtga ccgtgggtga tgataaatac   1800
tatttcaatc cgattaacgg tggtgcagcg agcattggcg aaaccatcat cgatgacaaa   1860
aactattatt tcaaccagag cggtgtgctg cagaccggtg tgtttagcac cgaagatggc   1920
tttaaatatt ttgcgccagc gaacaccctg gatgaaaacc tggaaggcga agcgattgat   1980
tttaccggca aactgatcat cgatgaaaac atctattact tcgatgataa ctatcgtggt   2040
gcggtggaat ggaaagaact ggatggcgaa atgcattatt tttctccgga accggtaaa    2100 gcgtttaaag gcctgaacca gatcggcgat tacaaatact acttcaacag cgatggcgtg   2160
atgcagaaag gctttgtgag catcaacgat aacaaacact atttcgatga tagcggtgtg   2220
atgaaagtgg gctataccga aattgatggc aaacatttct acttcgcgga aaacggcgaa   2280
atgcagattg gcgtgttcaa taccgaagat ggtttcaaat acttcgcgca ccataacgaa   2340
gatctgggta cgaagaagg cgaagaaatt agctatagcg gcatcctgaa cttcaacaac    2400
aaaatctact actttgatga tagctttacc gcggtggtgg gctggaaaga tctggaagat   2460
ggcagcaaat attatttcga tgaagatacc gcggaagcgt atattggcct gagcctgatt   2520
aacgatggcc agtactattt taacgatgat ggcattatgc aggtgggttt cgtgaccatt   2580
aatgataaag tgttctattt cagcgatagc ggcattattg aaagcggcgt gcagaacatt   2640
gatgataact acttctacat cgatgataac ggcattgtgc agatcggcgt ttttgatacc   2700 agcgatggc acaaatattt cgcaccggcc aataccgtga cgataacat ttatggccag     2760 gcggtggaat atagcggtct ggtgcgtgtg ggcgaagatg tgtattattt cggcgaaacc   2820
```

```
tataccatcg aaaccggctg gatttatgat atggaaaacg aaagcgataa atattacttt    2880
aatccggaaa cgaaaaaagc gtgcaaaggc attaacctga tcgatgatat caaatactat    2940
tttgatgaaa aaggcattat gcgtaccggt ctgattagct cgaaaacaa caactattac     3000 ttcaacgaaa acggtgaaat gcagttcggc tacatcaaca tcgaagataa aatgttctac    3060
ttcggcgaag atggtgttat gcagattggt gtttttaaca ccccggatgg cttcaaatac    3120
tttgcccatc agaatacccct ggatgaaaat ttcgaaggtg aaagcattaa ctataccggc   3180
tggctggatc tggatgaaaa acgctactac ttcaccgatg aatacattgc ggcgaccggc    3240
agcgtgatta ttgatggcga agaatactac ttcgatccgg ataccgcgca gctggtgatt    3300
agcgaacatc atcatcatca ccat                                           3324
```

<210> SEQ ID NO 23
<211> LENGTH: 1108
<212> TYPE: PRT
<213> ORGANISM: Artificial Sequence
<220> FEATURE:
<223> OTHER INFORMATION: amino acid sequence of F54 New fusion protein

<400> SEQUENCE: 23

```
Met Ala Thr Gly Trp Gln Thr Ile Asp Gly Lys Lys Tyr Tyr Phe Asn
1               5                   10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45

Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270
```

-continued

```
Gly Tyr Thr Ser Ile Asn Gly Lys His Phe Tyr Phe Asn Thr Asp Gly
            275                 280                 285
Ile Met Gln Ile Gly Val Phe Lys Gly Pro Asn Gly Phe Glu Tyr Phe
290                 295                 300
Ala Pro Ala Asn Thr Asp Ala Asn Asn Ile Glu Gly Gln Ala Ile Leu
305                 310                 315                 320
Tyr Gln Asn Lys Phe Leu Thr Leu Asn Gly Lys Lys Tyr Tyr Phe Gly
                325                 330                 335
Ser Asp Ser Lys Ala Val Thr Gly Leu Arg Thr Ile Asp Gly Lys Lys
            340                 345                 350
Tyr Tyr Phe Asn Thr Asn Thr Ala Val Ala Val Thr Gly Trp Gln Thr
        355                 360                 365
Ile Asn Gly Lys Lys Tyr Tyr Phe Asn Thr Asn Thr Ser Ile Ala Ser
370                 375                 380
Thr Gly Tyr Thr Ile Ile Ser Gly Lys His Phe Tyr Phe Asn Thr Asp
385                 390                 395                 400
Gly Ile Met Gln Ile Gly Val Phe Lys Gly Pro Asp Gly Phe Glu Tyr
                405                 410                 415
Phe Ala Pro Ala Asn Thr Asp Ala Asn Asn Ile Glu Gly Gln Ala Ile
            420                 425                 430
Arg Tyr Gln Asn Arg Phe Leu Tyr Leu His Asp Asn Ile Tyr Tyr Phe
        435                 440                 445
Gly Asn Asn Ser Lys Ala Ala Thr Gly Trp Val Thr Ile Asp Gly Asn
450                 455                 460
Arg Tyr Tyr Phe Glu Pro Asn Thr Ala Met Gly Ala Asn Gly Tyr Lys
465                 470                 475                 480
Thr Ile Asp Asn Lys Asn Phe Tyr Phe Arg Asn Gly Leu Pro Gln Ile
                485                 490                 495
Gly Val Phe Lys Gly Ser Asn Gly Phe Glu Tyr Phe Ala Pro Ala Asn
            500                 505                 510
Thr Asp Ala Asn Asn Ile Glu Gly Gln Ala Ile Arg Tyr Gln Asn Arg
        515                 520                 525
Phe Leu His Leu Leu Gly Lys Ile Tyr Tyr Phe Gly Asn Asn Ser Lys
530                 535                 540
Ala Val Thr Gly Trp Gln Thr Ile Asn Gly Lys Val Tyr Tyr Phe Met
545                 550                 555                 560
Pro Asp Thr Ala Met Ala Ala Ala Gly Gly Leu Phe Glu Ile Asp Gly
                565                 570                 575
Val Ile Tyr Phe Phe Gly Val Asp Gly Val Lys Ala Val Thr Gly Phe
            580                 585                 590
Val Thr Val Gly Asp Asp Lys Tyr Tyr Phe Asn Pro Ile Asn Gly Gly
        595                 600                 605
Ala Ala Ser Ile Gly Glu Thr Ile Ile Asp Asp Lys Asn Tyr Tyr Phe
610                 615                 620
Asn Gln Ser Gly Val Leu Gln Thr Gly Val Phe Ser Thr Glu Asp Gly
625                 630                 635                 640
Phe Lys Tyr Phe Ala Pro Ala Asn Thr Leu Asp Glu Asn Leu Glu Gly
                645                 650                 655
Glu Ala Ile Asp Phe Thr Gly Lys Leu Ile Ile Asp Glu Asn Ile Tyr
            660                 665                 670
Tyr Phe Asp Asp Asn Tyr Arg Gly Ala Val Glu Trp Lys Glu Leu Asp
        675                 680                 685
Gly Glu Met His Tyr Phe Ser Pro Glu Thr Gly Lys Ala Phe Lys Gly
```

```
                690                 695                 700
Leu Asn Gln Ile Gly Asp Tyr Lys Tyr Tyr Phe Asn Ser Asp Gly Val
705                 710                 715                 720

Met Gln Lys Gly Phe Val Ser Ile Asn Asp Asn Lys His Tyr Phe Asp
                725                 730                 735

Asp Ser Gly Val Met Lys Val Gly Tyr Thr Glu Ile Asp Gly Lys His
                740                 745                 750

Phe Tyr Phe Ala Glu Asn Gly Glu Met Gln Ile Gly Val Phe Asn Thr
                755                 760                 765

Glu Asp Gly Phe Lys Tyr Phe Ala His His Asn Glu Asp Leu Gly Asn
                770                 775                 780

Glu Glu Gly Glu Glu Ile Ser Tyr Ser Gly Ile Leu Asn Phe Asn Asn
785                 790                 795                 800

Lys Ile Tyr Tyr Phe Asp Asp Ser Phe Thr Ala Val Val Gly Trp Lys
                805                 810                 815

Asp Leu Glu Asp Gly Ser Lys Tyr Tyr Phe Asp Glu Asp Thr Ala Glu
                820                 825                 830

Ala Tyr Ile Gly Leu Ser Leu Ile Asn Asp Gly Gln Tyr Tyr Phe Asn
                835                 840                 845

Asp Asp Gly Ile Met Gln Val Gly Phe Val Thr Ile Asn Asp Lys Val
                850                 855                 860

Phe Tyr Phe Ser Asp Ser Gly Ile Ile Glu Ser Gly Val Gln Asn Ile
865                 870                 875                 880

Asp Asp Asn Tyr Phe Tyr Ile Asp Asp Asn Gly Ile Val Gln Ile Gly
                885                 890                 895

Val Phe Asp Thr Ser Asp Gly Tyr Lys Tyr Phe Ala Pro Ala Asn Thr
                900                 905                 910

Val Asn Asp Asn Ile Tyr Gly Gln Ala Val Glu Tyr Ser Gly Leu Val
                915                 920                 925

Arg Val Gly Glu Asp Val Tyr Tyr Phe Gly Glu Thr Tyr Thr Ile Glu
930                 935                 940

Thr Gly Trp Ile Tyr Asp Met Glu Asn Glu Ser Asp Lys Tyr Tyr Phe
945                 950                 955                 960

Asn Pro Glu Thr Lys Lys Ala Cys Lys Gly Ile Asn Leu Ile Asp Asp
                965                 970                 975

Ile Lys Tyr Tyr Phe Asp Glu Lys Gly Ile Met Arg Thr Gly Leu Ile
                980                 985                 990

Ser Phe Glu Asn Asn Asn Tyr Tyr Phe Asn Glu Asn Gly Glu Met Gln
                995                 1000                1005

Phe Gly Tyr Ile Asn Ile Glu Asp Lys Met Phe Tyr Phe Gly Glu Asp
                1010                1015                1020

Gly Val Met Gln Ile Gly Val Phe Asn Thr Pro Asp Gly Phe Lys Tyr
1025                1030                1035                1040

Phe Ala His Gln Asn Thr Leu Asp Glu Asn Phe Glu Gly Glu Ser Ile
                1045                1050                1055

Asn Tyr Thr Gly Trp Leu Asp Leu Asp Glu Lys Arg Tyr Tyr Phe Thr
                1060                1065                1070

Asp Glu Tyr Ile Ala Ala Thr Gly Ser Val Ile Ile Asp Gly Glu Glu
                1075                1080                1085

Tyr Tyr Phe Asp Pro Asp Thr Ala Gln Leu Val Ile Ser Glu His His
                1090                1095                1100

His His His His
1105
```

<210> SEQ ID NO 24
<211> LENGTH: 3387
<212> TYPE: DNA
<213> ORGANISM: Artificial Sequence
<220> FEATURE:
<223> OTHER INFORMATION: nucleotide sequence of F5 ToxB fusion protein

<400> SEQUENCE: 24

| | | | | | | |
|---|---|---|---|---|---|---|
| atggcaaccg | gttggcagac | catcgatggc | aaaaaatatt | attttaatac | caacaccgca | 60 |
| attgcaagca | ccggctatac | cattatcaac | ggcaaacact | tttattttaa | caccgacggc | 120 |
| attatgcaga | ttggtgtgtt | taaaggtccg | aacggctttg | aatactttgc | accggcaaat | 180 |
| accgatgcca | taatattga | aggccaggcc | attctgtatc | agaatgaatt | tctgaccctg | 240 |
| aacggcaaaa | aatactactt | tggcagcgat | agcaaagcag | ttaccggttg | gcgcatcatc | 300 |
| aacaataaga | aatattactt | caacccgaat | aatgcaattg | cagcaattca | tctgtgcacc | 360 |
| attaacaacg | acaaatatta | tttcagctat | gacggtattc | tgcagaatgg | ctacattacc | 420 |
| atcgaacgca | caacttttta | tttcgatgcc | aacaacgaaa | gcaaaatggt | gaccggtgtt | 480 |
| ttcaaaggcc | ctaatggttt | tgagtatttc | gctccggcaa | acacccataa | taacaacatt | 540 |
| gaaggtcagg | cgatcgttta | tcagaacaaa | ttcctgacgc | tgaatggtaa | gaaatactat | 600 |
| ttcgataatg | acagcaaagc | cgtgaccggc | tggcagacaa | ttgacgggaa | gaaatattac | 660 |
| tttaatctga | ataccgcaga | agcagcaacc | ggttggcaaa | cgatcgacgg | taaaaagtac | 720 |
| tacttcaacc | tgaacacagc | cgaagcagcc | acaggatggc | agactattga | tggaaaaaaa | 780 |
| tactatttca | acaccaacac | ctttattgca | tctaccggtt | ataccagcat | taacggtaaa | 840 |
| catttctact | tcaacaccga | tggtatcatg | cagatcggcg | ttttcaaagg | tccaaatggt | 900 |
| ttcgaatact | tgccccctgc | caatacagat | gcaaataaca | tcgagggtca | ggcaatcctg | 960 |
| taccaaaaca | aatttctgac | cctgaatggg | aaaaaatatt | actttggtag | cgattctaaa | 1020 |
| gccgttaccg | gtctgcgtac | cattgatggt | aaaaaatact | actttaatac | gaatacagcc | 1080 |
| gttgcggtta | caggctggca | gaccattaac | gggaaaaaat | actatttaa | cacaaatacc | 1140 |
| agcattgcct | caacgggtta | taccattatt | tcgggtaaac | acttctactt | taataccgat | 1200 |
| ggtattatgc | aaatcggagt | ctttaaagga | cctgatgggt | tcgaatattt | tgcgcctgcg | 1260 |
| aacactgatg | cgaacaatat | cgaaggacag | gcaatccgct | atcagaatcg | ctttctgtat | 1320 |
| ctgcacgaca | catctatta | ttttggcaac | aattcaaaag | cagccaccgg | ctgggttaca | 1380 |
| attgatggca | accgctacta | tttcgaaccg | aataccgcaa | tgggtgcaaa | tggctacaaa | 1440 |
| accatcgata | taaaaattt | ctattttcgc | aacggtctgc | cgcagatcgg | ggtatttaaa | 1500 |
| ggtagcaacg | gcttcgaata | cttcgctcca | gcgaatacgg | acgcgaacaa | tattgagggt | 1560 |
| caagcgattc | gttatcaaaa | ccgttttctg | catctgctgg | gcaaaatcta | ctactttggc | 1620 |
| aataacagta | aagcagttac | tggatggcag | acaatcaatg | gtaaagtgta | ctattttatg | 1680 |
| ccggataccg | ccatggcagc | agccggtggt | ctgtttgaaa | ttgatggcgt | gatctatttt | 1740 |
| tttggtgtgg | atggtgttaa | agcagtgagc | ggtctgattt | atattaacga | tagcctgtat | 1800 |
| tactttaaac | caccggtgaa | taacctgatt | accggctttg | tgaccgtggg | tgatgataaa | 1860 |
| tactatttca | atccgattaa | cggtggtgca | gcgagcattg | gcgaaaccat | catcgatgac | 1920 |
| aaaaactatt | atttcaacca | gagcggtgtg | ctgcagaccg | tgtgtttag | caccgaagat | 1980 |
| ggctttaaat | attttgcgcc | agcgaacacc | ctggatgaaa | acctggaagg | cgaagcgatt | 2040 |

| | | |
|---|---|---|
| gattttaccg gcaaactgat catcgatgaa aacatctatt acttcgatga taactatcgt | | 2100 |
| ggtgcggtgg aatggaaaga actgatggc gaaatgcatt attttctcc ggaaaccggt | | 2160 |
| aaagcgttta aaggcctgaa ccagatcggc gattacaaat actacttcaa cagcgatggc | | 2220 |
| gtgatgcaga aaggctttgt gagcatcaac gataacaaac actatttcga tgatagcggt | | 2280 |
| gtgatgaaag tgggctatac cgaaattgat ggcaaacatt tctacttcgc ggaaaacggc | | 2340 |
| gaaatgcaga ttggcgtgtt caataccgaa gatggtttca atacttcgc gcaccataac | | 2400 |
| gaagatctgg gtaacgaaga aggcgaagaa attagctata gcggcatcct gaacttcaac | | 2460 |
| aacaaaatct actactttga tgatagcttt accgcggtgg tgggctggaa agatctggaa | | 2520 |
| gatggcagca atattatttt cgatgaagat accgcggaag cgtatattgg cctgagcctg | | 2580 |
| attaacgatg ccagtactta ttttaacgat gatggcatta tgcaggtggg tttcgtgacc | | 2640 |
| attaatgata aagtgttcta tttcagcgat agcggcatta ttgaaagcgg cgtgcagaac | | 2700 |
| attgatgata actacttcta catcgatgat aacggcattg tgcagatcgg cgttttttgat | | 2760 |
| accagcgatg gctacaaata tttcgcaccg gccaataccg tgaacgataa catttatggc | | 2820 |
| caggcggtgg aatatagcgg tctggtgcgt gtgggcgaag atgtgtatta tttcggcgaa | | 2880 |
| acctatacca tcgaaaccgg ctggatttat gatatgaaaa cgaaagcga taaatattac | | 2940 |
| tttaatccgg aaacgaaaaa agcgtgcaaa ggcattaacc tgatcgatga tatcaaatac | | 3000 |
| tattttgatg aaaaaggcat tatgcgtacc ggtctgatta gcttcgaaaa caacaactat | | 3060 |
| tacttcaacg aaaacggtga atgcagttc ggctacatca acatcgaaga taaaatgttc | | 3120 |
| tacttcggcg aagatggtgt tatgcagatt ggtgttttta cacccccgga tggcttcaaa | | 3180 |
| tactttgccc atcagaatac cctggatgaa aatttcgaag gtgaaagcat taactatacc | | 3240 |
| ggctggctgg atctggatga aaaacgctac tacttcaccg atgaatacat tgcggcgacc | | 3300 |
| ggcagcgtga ttattgatgg cgaagaatac tacttcgatc cggataccgc gcagctggtg | | 3360 |
| attagcgaac atcatcatca tcaccat | | 3387 |

<210> SEQ ID NO 25
<211> LENGTH: 1129
<212> TYPE: PRT
<213> ORGANISM: Artificial Sequence
<220> FEATURE:
<223> OTHER INFORMATION: amino acid sequence of F5 ToxB fusion protein

<400> SEQUENCE: 25

Met Ala Thr Gly Trp Gln Thr Ile Asp Gly Lys Lys Tyr Tyr Phe Asn
1               5                   10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45

Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

```
Ser Tyr Asp Gly Ile Leu Gln Asn Gly Tyr Ile Thr Ile Glu Arg Asn
        130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
        210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
        290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
        370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn
450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
        515                 520                 525

Phe Leu His Leu Leu Gly Lys Ile Tyr Tyr Phe Gly Asn Asn Ser Lys
530                 535                 540
```

-continued

```
Ala Val Thr Gly Trp Gln Thr Ile Asn Gly Lys Val Tyr Tyr Phe Met
545                 550                 555                 560

Pro Asp Thr Ala Met Ala Ala Gly Gly Leu Phe Glu Ile Asp Gly
            565                 570                 575

Val Ile Tyr Phe Phe Gly Val Asp Gly Val Lys Ala Val Ser Gly Leu
                580                 585                 590

Ile Tyr Ile Asn Asp Ser Leu Tyr Tyr Phe Lys Pro Pro Val Asn Asn
            595                 600                 605

Leu Ile Thr Gly Phe Val Thr Val Gly Asp Asp Lys Tyr Tyr Phe Asn
            610                 615                 620

Pro Ile Asn Gly Gly Ala Ala Ser Ile Gly Glu Thr Ile Ile Asp Asp
625                 630                 635                 640

Lys Asn Tyr Tyr Phe Asn Gln Ser Gly Val Leu Gln Thr Gly Val Phe
                645                 650                 655

Ser Thr Glu Asp Gly Phe Lys Tyr Phe Ala Pro Ala Asn Thr Leu Asp
            660                 665                 670

Glu Asn Leu Glu Gly Glu Ala Ile Asp Phe Thr Gly Lys Leu Ile Ile
            675                 680                 685

Asp Glu Asn Ile Tyr Tyr Phe Asp Asp Asn Tyr Arg Gly Ala Val Glu
690                 695                 700

Trp Lys Glu Leu Asp Gly Glu Met His Tyr Phe Ser Pro Glu Thr Gly
705                 710                 715                 720

Lys Ala Phe Lys Gly Leu Asn Gln Ile Gly Asp Tyr Lys Tyr Tyr Phe
                725                 730                 735

Asn Ser Asp Gly Val Met Gln Lys Gly Phe Val Ser Ile Asn Asp Asn
            740                 745                 750

Lys His Tyr Phe Asp Asp Ser Gly Val Met Lys Val Gly Tyr Thr Glu
            755                 760                 765

Ile Asp Gly Lys His Phe Tyr Phe Ala Glu Asn Gly Glu Met Gln Ile
            770                 775                 780

Gly Val Phe Asn Thr Glu Asp Gly Phe Lys Tyr Phe Ala His His Asn
785                 790                 795                 800

Glu Asp Leu Gly Asn Glu Glu Gly Glu Glu Ile Ser Tyr Ser Gly Ile
            805                 810                 815

Leu Asn Phe Asn Asn Lys Ile Tyr Tyr Phe Asp Asp Ser Phe Thr Ala
            820                 825                 830

Val Val Gly Trp Lys Asp Leu Glu Asp Gly Ser Lys Tyr Tyr Phe Asp
            835                 840                 845

Glu Asp Thr Ala Glu Ala Tyr Ile Gly Leu Ser Leu Ile Asn Asp Gly
850                 855                 860

Gln Tyr Tyr Phe Asn Asp Asp Gly Ile Met Gln Val Gly Phe Val Thr
865                 870                 875                 880

Ile Asn Asp Lys Val Phe Tyr Phe Ser Asp Ser Gly Ile Ile Glu Ser
            885                 890                 895

Gly Val Gln Asn Ile Asp Asp Asn Tyr Phe Tyr Ile Asp Asp Asn Gly
            900                 905                 910

Ile Val Gln Ile Gly Val Phe Asp Thr Ser Asp Gly Tyr Lys Tyr Phe
            915                 920                 925

Ala Pro Ala Asn Thr Val Asn Asp Asn Ile Tyr Gly Gln Ala Val Glu
            930                 935                 940

Tyr Ser Gly Leu Val Arg Val Gly Glu Asp Val Tyr Tyr Phe Gly Glu
945                 950                 955                 960

Thr Tyr Thr Ile Glu Thr Gly Trp Ile Tyr Asp Met Glu Asn Glu Ser
```

```
                965                 970                 975
Asp Lys Tyr Tyr Phe Asn Pro Glu Thr Lys Lys Ala Cys Lys Gly Ile
                980                 985                 990

Asn Leu Ile Asp Asp Ile Lys Tyr Tyr Phe Asp Glu Lys Gly Ile Met
            995                 1000                1005

Arg Thr Gly Leu Ile Ser Phe Glu Asn Asn Asn Tyr Tyr Phe Asn Glu
        1010                1015                1020

Asn Gly Glu Met Gln Phe Gly Tyr Ile Asn Ile Glu Asp Lys Met Phe
1025                1030                1035                1040

Tyr Phe Gly Glu Asp Gly Val Met Gln Ile Gly Val Phe Asn Thr Pro
                1045                1050                1055

Asp Gly Phe Lys Tyr Phe Ala His Gln Asn Thr Leu Asp Glu Asn Phe
            1060                1065                1070

Glu Gly Glu Ser Ile Asn Tyr Thr Gly Trp Leu Asp Leu Asp Glu Lys
        1075                1080                1085

Arg Tyr Tyr Phe Thr Asp Glu Tyr Ile Ala Ala Thr Gly Ser Val Ile
    1090                1095                1100

Ile Asp Gly Glu Glu Tyr Tyr Phe Asp Pro Asp Thr Ala Gln Leu Val
1105                1110                1115                1120

Ile Ser Glu His His His His His His
            1125
```

<210> SEQ ID NO 26
<211> LENGTH: 2985
<212> TYPE: DNA
<213> ORGANISM: Artificial Sequence
<220> FEATURE:
<223> OTHER INFORMATION: nucleotide sequence of F52 new fusion protein

<400> SEQUENCE: 26

```
atggcaaccg gttggcagac catcgatggc aaaaaatatt attttaatac caacaccgca      60
attgcaagca ccggctatac cattatcaac ggcaaacact tttatttaa  caccgacggc     120
attatgcaga ttggtgtgtt taaaggtccg aacggctttg aatactttgc accggcaaat     180
accgatgcca ataatattga aggccaggcc attctgtatc agaatgaatt ctctgaccctg    240
aacggcaaaa atactactt  tggcagcgat agcaaagcag ttaccggttg cgcatcatc      300
aacaataaga atattactt  caacccgaat aatgcaattg cagcaattca tctgtgcacc     360
attaacaacg acaaatatta tttcagctat gacggtattc tgcagaatgg ctacattacc     420
atcgaacgca caactttta  tttcgatgcc aacaacgaaa gcaaaatggt gaccggtgtt     480
ttcaaaggcc ctaatggttt tgagtatttc gctccggcaa cacccataa  taacaacatt     540
gaaggtcagg cgatcgttta tcagaacaaa ttcctgacgc tgaatggtaa gaaatactat     600
ttcgataatg acagcaaagc cgtgaccggc tggcagacaa ttgacgggaa gaaatattac     660
tttaatctga ataccgcaga agcagcaacc ggttggcaaa cgatcgacgg taaaaagtac     720
tacttcaacc tgaacacagc cgaagcagcc acaggatggc agactattga tggaaaaaaa     780
tactatttca caccaacac  ctttattgca tctaccggtt ataccagcat taacggtaaa     840
catttctact caacaccga  tggtatcatg cagatcggcg ttttcaaagg tccaaatggt     900
ttcgaatact tgcccctgc  aatacagat  gcaaataaca tcgagggtca ggcaatcctg     960
taccaaaaca aatttctgac cctgaatggg aaaaaatatt actttggtag cgattctaaa    1020
gccgttaccg gtctgcgtac cattgatggt aaaaaatact actttaatac gaatacagcc    1080
gttgcggtta caggctggca gaccattaac gggaaaaaat actatttaa  cacaaatacc    1140
```

```
agcattgcct caacgggtta taccattatt tcgggtaaac acttctactt taataccgat    1200
ggtattatgc aaatcggagt cttttaaagga cctgatgggt tcgaatattt tgcgcctgcg    1260
aacactgatg cgaacaatat cgaaggacag gcaatccgct atcagaatcg ctttctgtat    1320
ctgcacgaca acatctatta ttttggcaac aattcaaaag cagccaccgg ctgggttaca    1380
attgatggca accgctacta tttcgaaccg aataccgcaa tgggtgcaaa tggctacaaa    1440
accatcgata taaaaattt ctattttcgc aacggtctgc cgcagatcgg ggtatttaaa    1500
ggtagcaacg gcttcgaata cttcgctcca gcgaatacgg acgcgaacaa tattgagggt    1560
caagcgattc gttatcaaaa ccgttttctg catctgctgg gcaaaatcta ctactttggc    1620
aataacagta aagcagttac tggatggcag acaatcaatg gtaaagtgta ctattttatg    1680
ccggataccg ccatggcagc agccggtggt ctgtttgaaa ttgatggcgt gatctatttt    1740
tttggtgtgg atggtgttaa agcagtgaaa ggcctgaacc agatcggcga ttacaaatac    1800
tacttcaaca gcgatggcgt gatgcagaaa ggctttgtga gcatcaacga taacaaacac    1860
tatttcgatg atagcggtgt gatgaaagtg ggctataccg aaattgatgg caaacatttc    1920
tacttcgcgg aaaacggcga aatgcagatt ggcgtgttca ataccgaaga tggtttcaaa    1980
tacttcgcgc accataacga agatctgggt aacgaagaag cgaagaaat tagctatagc    2040 ggcatcctga acttcaacaa caaaatctac tactttgatg atagctttac cgcggtggtg    2100
ggctggaaag atctggaaga tggcagcaaa tattatttcg atgaagatac cgcggaagcg    2160
tatattggcc tgagcctgat taacgatggc cagtactatt ttaacgatga tggcattatg    2220
caggtgggtt tcgtgaccat taatgataaa gtgttctatt tcagcgatag cggcattatt    2280
gaaagcggcg tgcagaacat tgatgataac tacttctaca tcgatgataa cggcattgtg    2340
cagatcggcg ttttgatac cagcgatggc tacaaatatt tcgcaccggc caataccgtg    2400
aacgataaca tttatggcca ggcggtggaa tatagcggtc tggtgcgtgt gggcgaagat    2460
gtgtattatt tcggcgaaac ctataccatc gaaaccggct ggatttatga tatggaaaac    2520
gaaagcgata aatattactt taatccggaa acgaaaaaag cgtgcaaagg cattaacctg    2580
atcgatgata tcaaatacta ttttgatgaa aaaggcatta tgcgtaccgg tctgattagc    2640
ttcgaaaaca caactatta cttcaacgaa acggtgaaa tgcagttcgg ctacatcaac    2700
atcgaagata aatgttcta cttcggcgaa gatggtgtta tgcagattgg tgtttttaac    2760
accccggatg gcttcaaata ctttgcccat cagaataccc tggatgaaaa tttcgaaggt    2820
gaaagcatta actataccgg ctggctggat ctggatgaaa aacgctacta cttcaccgat    2880
gaatacattg cggcgaccgg cagcgtgatt attgatggcg aagaatacta cttcgatccg    2940
gataccgcgc agctggtgat tagcgaacat catcatcatc accat    2985
```

<210> SEQ ID NO 27
<211> LENGTH: 995
<212> TYPE: PRT
<213> ORGANISM: Artificial Sequence
<220> FEATURE:
<223> OTHER INFORMATION: amino acid sequence of F52 New fusion protein

<400> SEQUENCE: 27

Met Ala Thr Gly Trp Gln Thr Ile Asp Gly Lys Lys Tyr Tyr Phe Asn
1               5                   10                  15

Thr Asn Thr Ala Ile Ala Ser Thr Gly Tyr Thr Ile Ile Asn Gly Lys
            20                  25                  30

-continued

His Phe Tyr Phe Asn Thr Asp Gly Ile Met Gln Ile Gly Val Phe Lys
                35                  40                  45

Gly Pro Asn Gly Phe Glu Tyr Phe Ala Pro Ala Asn Thr Asp Ala Asn
 50                  55                  60

Asn Ile Glu Gly Gln Ala Ile Leu Tyr Gln Asn Glu Phe Leu Thr Leu
 65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
                100                 105                 110

Ile Ala Ala Ile His Leu Cys Thr Ile Asn Asn Asp Lys Tyr Tyr Phe
                115                 120                 125

Ser Tyr Asp Gly Ile Leu Gln Asn Gly Tyr Ile Thr Ile Glu Arg Asn
        130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
                180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
        210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
                260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
        290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
                340                 345                 350

Tyr Tyr Phe Asn Thr Asn Thr Ala Val Ala Val Thr Gly Trp Gln Thr
                355                 360                 365

Ile Asn Gly Lys Lys Tyr Tyr Phe Asn Thr Asn Thr Ser Ile Ala Ser
        370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
                420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn

```
               450                 455                 460
Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
                500                 505                 510

Thr Asp Ala Asn Asn Ile Glu Gly Gln Ala Ile Arg Tyr Gln Asn Arg
                515                 520                 525

Phe Leu His Leu Leu Gly Lys Ile Tyr Tyr Phe Gly Asn Asn Ser Lys
                530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
                565                 570                 575

Val Ile Tyr Phe Phe Gly Val Asp Gly Val Lys Ala Val Lys Gly Leu
                580                 585                 590

Asn Gln Ile Gly Asp Tyr Lys Tyr Tyr Phe Asn Ser Asp Gly Val Met
                595                 600                 605

Gln Lys Gly Phe Val Ser Ile Asn Asp Asn Lys His Tyr Phe Asp Asp
                610                 615                 620

Ser Gly Val Met Lys Val Gly Tyr Thr Glu Ile Asp Gly Lys His Phe
625                 630                 635                 640

Tyr Phe Ala Glu Asn Gly Glu Met Gln Ile Gly Val Phe Asn Thr Glu
                645                 650                 655

Asp Gly Phe Lys Tyr Phe Ala His His Asn Glu Asp Leu Gly Asn Glu
                660                 665                 670

Glu Gly Glu Glu Ile Ser Tyr Ser Gly Ile Leu Asn Phe Asn Asn Lys
                675                 680                 685

Ile Tyr Tyr Phe Asp Asp Ser Phe Thr Ala Val Val Gly Trp Lys Asp
                690                 695                 700

Leu Glu Asp Gly Ser Lys Tyr Tyr Phe Asp Glu Asp Thr Ala Glu Ala
705                 710                 715                 720

Tyr Ile Gly Leu Ser Leu Ile Asn Asp Gly Gln Tyr Tyr Phe Asn Asp
                725                 730                 735

Asp Gly Ile Met Gln Val Gly Phe Val Thr Ile Asn Asp Lys Val Phe
                740                 745                 750

Tyr Phe Ser Asp Ser Gly Ile Ile Glu Ser Gly Val Gln Asn Ile Asp
                755                 760                 765

Asp Asn Tyr Phe Tyr Ile Asp Asp Asn Gly Ile Val Gln Ile Gly Val
                770                 775                 780

Phe Asp Thr Ser Asp Gly Tyr Lys Tyr Phe Ala Pro Ala Asn Thr Val
785                 790                 795                 800

Asn Asp Asn Ile Tyr Gly Gln Ala Val Glu Tyr Ser Gly Leu Val Arg
                805                 810                 815

Val Gly Glu Asp Val Tyr Tyr Phe Gly Glu Thr Tyr Thr Ile Glu Thr
                820                 825                 830

Gly Trp Ile Tyr Asp Met Glu Asn Glu Ser Asp Lys Tyr Tyr Phe Asn
                835                 840                 845

Pro Glu Thr Lys Lys Ala Cys Lys Gly Ile Asn Leu Ile Asp Asp Ile
                850                 855                 860

Lys Tyr Tyr Phe Asp Glu Lys Gly Ile Met Arg Thr Gly Leu Ile Ser
865                 870                 875                 880
```

```
Phe Glu Asn Asn Asn Tyr Tyr Phe Asn Glu Asn Gly Glu Met Gln Phe
                885                 890                 895

Gly Tyr Ile Asn Ile Glu Asp Lys Met Phe Tyr Phe Gly Glu Asp Gly
            900                 905                 910

Val Met Gln Ile Gly Val Phe Asn Thr Pro Asp Gly Phe Lys Tyr Phe
            915                 920                 925

Ala His Gln Asn Thr Leu Asp Glu Asn Phe Glu Gly Glu Ser Ile Asn
        930                 935                 940

Tyr Thr Gly Trp Leu Asp Leu Asp Glu Lys Arg Tyr Tyr Phe Thr Asp
945                 950                 955                 960

Glu Tyr Ile Ala Ala Thr Gly Ser Val Ile Ile Asp Gly Glu Glu Tyr
                965                 970                 975

Tyr Phe Asp Pro Asp Thr Ala Gln Leu Val Ile Ser Glu His His His
            980                 985                 990

His His His
        995

<210> SEQ ID NO 28
<211> LENGTH: 593
<212> TYPE: PRT
<213> ORGANISM: Artificial Sequence
<220> FEATURE:
<223> OTHER INFORMATION: toxin A fragment of F54 Gly

<400> SEQUENCE: 28

Met Ala Thr Gly Trp Gln Thr Ile Asp Gly Lys Lys Tyr Tyr Phe Asn
 1               5                  10                  15

Thr Asn Thr Ala Ile Ala Ser Thr Gly Tyr Thr Ile Ile Asn Gly Lys
                20                  25                  30

His Phe Tyr Phe Asn Thr Asp Gly Ile Met Gln Ile Gly Val Phe Lys
            35                  40                  45

Gly Pro Asn Gly Phe Glu Tyr Phe Ala Pro Ala Asn Thr Asp Ala Asn
        50                  55                  60

Asn Ile Glu Gly Gln Ala Ile Leu Tyr Gln Asn Gl

```
Tyr Phe Asn Leu Asn Thr Ala Glu Ala Ala Thr Gly Trp Gln Thr Ile
            245                 250                 255

Asp Gly Lys Lys Tyr Tyr Phe Asn Thr Asn Thr Phe Ile Ala Ser Thr
        260                 265                 270

Gly Tyr Thr Ser Ile Asn Gly Lys His Phe Tyr Phe Asn Thr Asp Gly
    275                 280                 285

Ile Met Gln Ile Gly Val Phe Lys Gly Pro Asn Gly Phe Glu Tyr Phe
290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn
    450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
        515                 520                 525

Phe Leu His Leu Leu Gly Lys Ile Tyr Tyr Phe Gly Asn Asn Ser Lys
    530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
                565                 570                 575

Val Ile Tyr Phe Phe Gly Val Asp Gly Val Lys Ala Pro Gly Ile Tyr
            580                 585                 590

Gly

<210> SEQ ID NO 29
<211> LENGTH: 589
<212> TYPE: PRT
<213> ORGANISM: Artificial Sequence
<220> FEATURE:
<223> OTHER INFORMATION: toxin A fragment of F54 New

<400> SEQUENCE: 29
```

```
Met Ala Thr Gly Trp Gln Thr Ile Asp Gly Lys Lys Tyr Tyr Phe Asn
  1               5                  10                  15
Thr Asn Thr Ala Ile Ala Ser Thr Gly Tyr Thr Ile Ile Asn Gly Lys
             20                  25                  30
His Phe Tyr Phe Asn Thr Asp Gly Ile Met Gln Ile Gly Val Phe Lys
             35                  40                  45
Gly Pro Asn Gly Phe Glu Tyr Phe Ala Pro Ala Asn Thr Asp Ala Asn
 50                  55                  60
Asn Ile Glu Gly Gln Ala Ile Leu Tyr Gln Asn Glu Phe Leu Thr Leu
 65                  70                  75                  80
Asn Gly Lys Lys Tyr Tyr Phe Gly Ser Asp Ser Lys Ala Val Thr Gly
                 85                  90                  95
Trp Arg Ile Ile Asn Asn Lys Lys Tyr Tyr Phe Asn Pro Asn Asn Ala
                100                 105                 110
Ile Ala Ala Ile His Leu Cys Thr Ile Asn Asn Asp Lys Tyr Tyr Phe
                115                 120                 125
Ser Tyr Asp Gly Ile Leu Gln Asn Gly Tyr Ile Thr Ile Glu Arg Asn
             130                 135                 140
Asn Phe Tyr Phe Asp Ala Asn Asn Glu Ser Lys Met Val Thr Gly Val
145                 150                 155                 160
Phe Lys Gly Pro Asn Gly Phe Glu Tyr Phe Ala Pro Ala Asn Thr His
                165                 170                 175
Asn Asn Asn Ile Glu Gly Gln Ala Ile Val Tyr Gln Asn Lys Phe Leu
                180                 185                 190
Thr Leu Asn Gly Lys Lys Tyr Tyr Phe Asp Asn Asp Ser Lys Ala Val
             195                 200                 205
Thr Gly Trp Gln Thr Ile Asp Gly Lys Lys Tyr Tyr Phe Asn Leu Asn
             210                 215                 220
Thr Ala Glu Ala Ala Thr Gly Trp Gln Thr Ile Asp Gly Lys Lys Tyr
225                 230                 235                 240
Tyr Phe Asn Leu Asn Thr Ala Glu Ala Ala Thr Gly Trp Gln Thr Ile
                245                 250                 255
Asp Gly Lys Lys Tyr Tyr Phe Asn Thr Asn Thr Phe Ile Ala Ser Thr
                260                 265                 270
Gly Tyr Thr Ser Ile Asn Gly Lys His Phe Tyr Phe Asn Thr Asp Gly
             275                 280                 285
Ile Met Gln Ile Gly Val Phe Lys Gly Pro Asn Gly Phe Glu Tyr Phe
             290                 295                 300
Ala Pro Ala Asn Thr Asp Ala Asn Asn Ile Glu Gly Gln Ala Ile Leu
305                 310                 315                 320
Tyr Gln Asn Lys Phe Leu Thr Leu Asn Gly Lys Lys Tyr Tyr Phe Gly
                325                 330                 335
Ser Asp Ser Lys Ala Val Thr Gly Leu Arg Thr Ile Asp Gly Lys Lys
             340                 345                 350
Tyr Tyr Phe Asn Thr Asn Thr Ala Val Ala Val Thr Gly Trp Gln Thr
             355                 360                 365
Ile Asn Gly Lys Lys Tyr Tyr Phe Asn Thr Asn Thr Ser Ile Ala Ser
             370                 375                 380
Thr Gly Tyr Thr Ile Ile Ser Gly Lys His Phe Tyr Phe Asn Thr Asp
385                 390                 395                 400
Gly Ile Met Gln Ile Gly Val Phe Lys Gly Pro Asp Gly Phe Glu Tyr
                405                 410                 415
Phe Ala Pro Ala Asn Thr Asp Ala Asn Asn Ile Glu Gly Gln Ala Ile
```

```
                420              425              430
Arg Tyr Gln Asn Arg Phe Leu Tyr Leu His Asp Asn Ile Tyr Tyr Phe
            435              440              445

Gly Asn Asn Ser Lys Ala Ala Thr Gly Trp Val Thr Ile Asp Gly Asn
    450              455              460

Arg Tyr Tyr Phe Glu Pro Asn Thr Ala Met Gly Ala Asn Gly Tyr Lys
465              470              475              480

Thr Ile Asp Asn Lys Asn Phe Tyr Phe Arg Asn Gly Leu Pro Gln Ile
            485              490              495

Gly Val Phe Lys Gly Ser Asn Gly Phe Glu Tyr Phe Ala Pro Ala Asn
                500              505              510

Thr Asp Ala Asn Asn Ile Glu Gly Gln Ala Ile Arg Tyr Gln Asn Arg
            515              520              525

Phe Leu His Leu Leu Gly Lys Ile Tyr Tyr Phe Gly Asn Asn Ser Lys
        530              535              540

Ala Val Thr Gly Trp Gln Thr Ile Asn Gly Lys Val Tyr Tyr Phe Met
545              550              555              560

Pro Asp Thr Ala Met Ala Ala Gly Gly Leu Phe Glu Ile Asp Gly
            565              570              575

Val Ile Tyr Phe Phe Gly Val Asp Gly Val Lys Ala Val
            580              585
```

<210> SEQ ID NO 30
<211> LENGTH: 589
<212> TYPE: PRT
<213> ORGANISM: Artificial Sequence
<220> FEATURE:
<223> OTHER INFORMATION: toxin A fragment of F5 ToxB

<400> SEQUENCE: 30

```
Met Ala Thr Gly Trp Gln Thr Ile Asp Gly Lys Lys Tyr Tyr Phe Asn
 1               5               10               15

Thr Asn Thr Ala Ile Ala Ser Thr Gly Tyr Thr Ile Ile Asn Gly Lys
            20               25               30

His Phe Tyr Phe Asn Thr Asp Gly Ile Met Gln Ile Gly Val Phe Lys
        35               40               45

Gly Pro Asn Gly Phe Glu Tyr Phe Ala Pro Ala Asn Thr Asp Ala Asn
    50               55               60

Asn Ile Glu Gly Gln Ala Ile Leu Tyr Gln Asn Glu Phe Leu Thr Leu
65               70               75               80

Asn Gly Lys Lys Tyr Tyr Phe Gly Ser Asp Ser Lys Ala Val Thr Gly
            85               90               95

Trp Arg Ile Ile Asn Asn Lys Lys Tyr Tyr Phe Asn Pro Asn Asn Ala
        100              105              110

Ile Ala Ala Ile His Leu Cys Thr Ile Asn Asn Asp Lys Tyr Tyr Phe
    115              120              125

Ser Tyr Asp Gly Ile Leu Gln Asn Gly Tyr Ile Thr Ile Glu Arg Asn
        130              135              140

Asn Phe Tyr Phe Asp Ala Asn Asn Glu Ser Lys Met Val Thr Gly Val
145              150              155              160

Phe Lys Gly Pro Asn Gly Phe Glu Tyr Phe Ala Pro Ala Asn Thr His
            165              170              175

Asn Asn Asn Ile Glu Gly Gln Ala Ile Val Tyr Gln Asn Lys Phe Leu
        180              185              190

Thr Leu Asn Gly Lys Lys Tyr Tyr Phe Asp Asn Asp Ser Lys Ala Val
```

```
            195             200             205
Thr Gly Trp Gln Thr Ile Asp Gly Lys Lys Tyr Tyr Phe Asn Leu Asn
210             215             220

Thr Ala Glu Ala Ala Thr Gly Trp Gln Thr Ile Asp Gly Lys Lys Tyr
225             230             235             240

Tyr Phe Asn Leu Asn Thr Ala Glu Ala Thr Gly Trp Gln Thr Ile
            245             250             255

Asp Gly Lys Lys Tyr Tyr Phe Asn Thr Asn Thr Phe Ile Ala Ser Thr
            260             265             270

Gly Tyr Thr Ser Ile Asn Gly Lys His Phe Tyr Phe Asn Thr Asp Gly
            275             280             285

Ile Met Gln Ile Gly Val Phe Lys Gly Pro Asn Gly Phe Glu Tyr Phe
290             295             300

Ala Pro Ala Asn Thr Asp Ala Asn Asn Ile Glu Gly Gln Ala Ile Leu
305             310             315             320

Tyr Gln Asn Lys Phe Leu Thr Leu Asn Gly Lys Lys Tyr Tyr Phe Gly
            325             330             335

Ser Asp Ser Lys Ala Val Thr Gly Leu Arg Thr Ile Asp Gly Lys Lys
            340             345             350

Tyr Tyr Phe Asn Thr Asn Thr Ala Val Ala Val Thr Gly Trp Gln Thr
            355             360             365

Ile Asn Gly Lys Lys Tyr Tyr Phe Asn Thr Asn Thr Ser Ile Ala Ser
370             375             380

Thr Gly Tyr Thr Ile Ile Ser Gly Lys His Phe Tyr Phe Asn Thr Asp
385             390             395             400

Gly Ile Met Gln Ile Gly Val Phe Lys Gly Pro Asp Gly Phe Glu Tyr
            405             410             415

Phe Ala Pro Ala Asn Thr Asp Ala Asn Asn Ile Glu Gly Gln Ala Ile
            420             425             430

Arg Tyr Gln Asn Arg Phe Leu Tyr Leu His Asp Asn Ile Tyr Tyr Phe
            435             440             445

Gly Asn Asn Ser Lys Ala Ala Thr Gly Trp Val Thr Ile Asp Gly Asn
450             455             460

Arg Tyr Tyr Phe Glu Pro Asn Thr Ala Met Gly Ala Asn Gly Tyr Lys
465             470             475             480

Thr Ile Asp Asn Lys Asn Phe Tyr Phe Arg Asn Gly Leu Pro Gln Ile
            485             490             495

Gly Val Phe Lys Gly Ser Asn Gly Phe Glu Tyr Phe Ala Pro Ala Asn
            500             505             510

Thr Asp Ala Asn Asn Ile Glu Gly Gln Ala Ile Arg Tyr Gln Asn Arg
            515             520             525

Phe Leu His Leu Leu Gly Lys Ile Tyr Tyr Phe Gly Asn Asn Ser Lys
530             535             540

Ala Val Thr Gly Trp Gln Thr Ile Asn Gly Lys Val Tyr Tyr Phe Met
545             550             555             560

Pro Asp Thr Ala Met Ala Ala Ala Gly Gly Leu Phe Glu Ile Asp Gly
            565             570             575

Val Ile Tyr Phe Phe Gly Val Asp Gly Val Lys Ala Val
            580             585

<210> SEQ ID NO 31
<211> LENGTH: 589
<212> TYPE: PRT
<213> ORGANISM: Artificial Sequence
```

```
<220> FEATURE:
<223> OTHER INFORMATION: toxin A fragment of F52 New

<400> SEQUENCE: 31
```

| | | | | | | | | | | | | | | |
|---|---|---|---|---|---|---|---|---|---|---|---|---|---|---|
| Met | Ala | Thr | Gly | Trp | Gln | Thr | Ile | Asp | Gly | Lys | Lys | Tyr | Tyr | Phe | Asn |
| 1 | | | | 5 | | | | | 10 | | | | | 15 | |

Thr Asn Thr Ala Ile Ala Ser Thr Gly Tyr Thr Ile Ile Asn Gly Lys
                20                  25                  30

His Phe Tyr Phe Asn Thr Asp Gly Ile Met Gln Ile Gly Val Phe Lys
            35                  40                  45

Gly Pro Asn Gly Phe Glu Tyr Phe Ala Pro Ala Asn Thr Asp Ala Asn
        50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val

-continued

```
Gly Ile Met Gln Ile Gly Val Phe Lys Gly Pro Asp Gly Phe Glu Tyr
                405                 410                 415
Phe Ala Pro Ala Asn Thr Asp Ala Asn Asn Ile Glu Gly Gln Ala Ile
            420                 425                 430
Arg Tyr Gln Asn Arg Phe Leu Tyr Leu His Asp Asn Ile Tyr Tyr Phe
        435                 440                 445
Gly Asn Asn Ser Lys Ala Ala Thr Gly Trp Val Thr Ile Asp Gly Asn
    450                 455                 460
Arg Tyr Tyr Phe Glu Pro Asn Thr Ala Met Gly Ala Asn Gly Tyr Lys
465                 470                 475                 480
Thr Ile Asp Asn Lys Asn Phe Tyr Phe Arg Asn Gly Leu Pro Gln Ile
                485                 490                 495
Gly Val Phe Lys Gly Ser Asn Gly Phe Glu Tyr Phe Ala Pro Ala Asn
            500                 505                 510
Thr Asp Ala Asn Asn Ile Glu Gly Gln Ala Ile Arg Tyr Gln Asn Arg
        515                 520                 525
Phe Leu His Leu Leu Gly Lys Ile Tyr Tyr Phe Gly Asn Asn Ser Lys
    530                 535                 540
Ala Val Thr Gly Trp Gln Thr Ile Asn Gly Lys Val Tyr Tyr Phe Met
545                 550                 555                 560
Pro Asp Thr Ala Met Ala Ala Ala Gly Gly Leu Phe Glu Ile Asp Gly
                565                 570                 575
Val Ile Tyr Phe Phe Gly Val Asp Gly Val Lys Ala Val
            580                 585
```

<210> SEQ ID NO 32
<211> LENGTH: 513
<212> TYPE: PRT
<213> ORGANISM: Artificial Sequence
<220> FEATURE:
<223> OTHER INFORMATION: toxin B fragment of F54Gly

<400> SEQUENCE: 32

```
Thr Gly Phe Val Thr Val Gly Asp Asp Lys Tyr Tyr Phe Asn Pro Ile
1               5                   10                  15
Asn Gly Gly Ala Ala Ser Ile Gly Glu Thr Ile Ile Asp Asp Lys Asn
                20                  25                  30
Tyr Tyr Phe Asn Gln Ser Gly Val Leu Gln Thr Gly Val Phe Ser Thr
            35                  40                  45
Glu Asp Gly Phe Lys Tyr Phe Ala Pro Ala Asn Thr Leu Asp Glu Asn
        50                  55                  60
Leu Glu Gly Glu Ala Ile Asp Phe Thr Gly Lys Leu Ile Ile Asp Glu
65                  70                  75                  80
Asn Ile Tyr Tyr Phe Asp Asp Asn Tyr Arg Gly Ala Val Glu Trp Lys
                85                  90                  95
Glu Leu Asp Gly Glu Met His Tyr Phe Ser Pro Glu Thr Gly Lys Ala
            100                 105                 110
Phe Lys Gly Leu Asn Gln Ile Gly Asp Tyr Lys Tyr Tyr Phe Asn Ser
        115                 120                 125
Asp Gly Val Met Gln Lys Gly Phe Val Ser Ile Asn Asp Asn Lys His
    130                 135                 140
Tyr Phe Asp Asp Ser Gly Val Met Lys Val Gly Tyr Thr Glu Ile Asp
145                 150                 155                 160
Gly Lys His Phe Tyr Phe Ala Glu Asn Gly Glu Met Gln Ile Gly Val
                165                 170                 175
```

Phe Asn Thr Glu Asp Gly Phe Lys Tyr Phe Ala His His Asn Glu Asp
                180                 185                 190

Leu Gly Asn Glu Gly Glu Ile Ser Tyr Ser Gly Ile Leu Asn
            195                 200                 205

Phe Asn Asn Lys Ile Tyr Tyr Phe Asp Ser Phe Thr Ala Val Val
210                 215                 220

Gly Trp Lys Asp Leu Glu Asp Gly Ser Lys Tyr Tyr Phe Asp Glu Asp
225                 230                 235                 240

Thr Ala Glu Ala Tyr Ile Gly Leu Ser Leu Ile Asn Asp Gly Gln Tyr
                245                 250                 255

Tyr Phe Asn Asp Asp Gly Ile Met Gln Val Gly Phe Val Thr Ile Asn
                260                 265                 270

Asp Lys Val Phe Tyr Phe Ser Asp Ser Gly Ile Glu Ser Gly Val
                275                 280                 285

Gln Asn Ile Asp Asp Asn Tyr Phe Tyr Ile Asp Asp Asn Gly Ile Val
290                 295                 300

Gln Ile Gly Val Phe Asp Thr Ser Asp Gly Tyr Lys Tyr Phe Ala Pro
305                 310                 315                 320

Ala Asn Thr Val Asn Asp Asn Ile Tyr Gly Gln Ala Val Glu Tyr Ser
                325                 330                 335

Gly Leu Val Arg Val Gly Glu Asp Val Tyr Tyr Phe Gly Thr Tyr
                340                 345                 350

Thr Ile Glu Thr Gly Trp Ile Tyr Asp Met Glu Asn Glu Ser Asp Lys
                355                 360                 365

Tyr Tyr Phe Asn Pro Glu Thr Lys Lys Ala Cys Lys Gly Ile Asn Leu
                370                 375                 380

Ile Asp Asp Ile Lys Tyr Tyr Phe Asp Glu Lys Gly Ile Met Arg Thr
385                 390                 395                 400

Gly Leu Ile Ser Phe Glu Asn Asn Asn Tyr Tyr Phe Asn Glu Asn Gly
                405                 410                 415

Glu Met Gln Phe Gly Tyr Ile Asn Ile Glu Asp Lys Met Phe Tyr Phe
                420                 425                 430

Gly Glu Asp Gly Val Met Gln Ile Gly Val Phe Asn Thr Pro Asp Gly
                435                 440                 445

Phe Lys Tyr Phe Ala His Gln Asn Thr Leu Asp Glu Asn Phe Glu Gly
                450                 455                 460

Glu Ser Ile Asn Tyr Thr Gly Trp Leu Asp Leu Asp Glu Lys Arg Tyr
465                 470                 475                 480

Tyr Phe Thr Asp Glu Tyr Ile Ala Ala Thr Gly Ser Val Ile Ile Asp
                485                 490                 495

Gly Glu Glu Tyr Tyr Phe Asp Pro Asp Thr Ala Gln Leu Val Ile Ser
                500                 505                 510

Glu

<210> SEQ ID NO 33
<211> LENGTH: 513
<212> TYPE: PRT
<213> ORGANISM: Artificial Sequence
<220> FEATURE:
<223> OTHER INFORMATION: toxin B fragment of F54 New

<400> SEQUENCE: 33

Thr Gly Phe Val Thr Val Gly Asp Asp Lys Tyr Tyr Phe Asn Pro Ile
1               5                   10                  15

-continued

```
Asn Gly Gly Ala Ala Ser Ile Gly Glu Thr Ile Ile Asp Asp Lys Asn
             20                  25                  30

Tyr Tyr Phe Asn Gln Ser Gly Val Leu Gln Thr Gly Val Phe Ser Thr
         35                  40                  45

Glu Asp Gly Phe Lys Tyr Phe Ala Pro Ala Asn Thr Leu Asp Glu Asn
     50                  55                  60

Leu Glu Gly Glu Ala Ile Asp Phe Thr Gly Lys Leu Ile Ile Asp Glu
 65                  70                  75                  80

Asn Ile Tyr Tyr Phe Asp Asp Asn Tyr Arg Gly Ala Val Glu Trp Lys
                 85                  90                  95

Glu Leu Asp Gly Glu Met His Tyr Phe Ser Pro Glu Thr Gly Lys Ala
             100                 105                 110

Phe Lys Gly Leu Asn Gln Ile Gly Asp Tyr Lys Tyr Tyr Phe Asn Ser
         115                 120                 125

Asp Gly Val Met Gln Lys Gly Phe Val Ser Ile Asn Asp Asn Lys His
     130                 135                 140

Tyr Phe Asp Asp Ser Gly Val Met Lys Val Gly Tyr Thr Glu Ile Asp
145                 150                 155                 160

Gly Lys His Phe Tyr Phe Ala Glu Asn Gly Glu Met Gln Ile Gly Val
                 165                 170                 175

Phe Asn Thr Glu Asp Gly Phe Lys Tyr Phe Ala His His Asn Glu Asp
             180                 185                 190

Leu Gly Asn Glu Glu Gly Glu Glu Ile Ser Tyr Ser Gly Ile Leu Asn
         195                 200                 205

Phe Asn Asn Lys Ile Tyr Tyr Phe Asp Asp Ser Phe Thr Ala Val Val
     210                 215                 220

Gly Trp Lys Asp Leu Glu Asp Gly Ser Lys Tyr Tyr Phe Asp Glu Asp
225                 230                 235                 240

Thr Ala Glu Ala Tyr Ile Gly Leu Ser Leu Ile Asn Asp Gly Gln Tyr
                 245                 250                 255

Tyr Phe Asn Asp Asp Gly Ile Met Gln Val Gly Phe Val Thr Ile Asn
             260                 265                 270

Asp Lys Val Phe Tyr Phe Ser Asp Ser Gly Ile Ile Glu Ser Gly Val
         275                 280                 285

Gln Asn Ile Asp Asp Asn Tyr Phe Tyr Ile Asp Asn Gly Ile Val
     290                 295                 300

Gln Ile Gly Val Phe Asp Thr Ser Asp Gly Tyr Lys Tyr Phe Ala Pro
305                 310                 315                 320

Ala Asn Thr Val Asn Asp Asn Ile Tyr Gly Gln Ala Val Glu Tyr Ser
                 325                 330                 335

Gly Leu Val Arg Val Gly Glu Asp Val Tyr Tyr Phe Gly Glu Thr Tyr
             340                 345                 350

Thr Ile Glu Thr Gly Trp Ile Tyr Asp Met Glu Asn Glu Ser Asp Lys
         355                 360                 365

Tyr Tyr Phe Asn Pro Glu Thr Lys Lys Ala Cys Lys Gly Ile Asn Leu
     370                 375                 380

Ile Asp Asp Ile Lys Tyr Tyr Phe Asp Glu Lys Gly Ile Met Arg Thr
385                 390                 395                 400

Gly Leu Ile Ser Phe Glu Asn Asn Asn Tyr Tyr Phe Asn Glu Asn Gly
                 405                 410                 415

Glu Met Gln Phe Gly Tyr Ile Asn Ile Glu Asp Lys Met Phe Tyr Phe
             420                 425                 430

Gly Glu Asp Gly Val Met Gln Ile Gly Val Phe Asn Thr Pro Asp Gly
```

```
                435                 440                 445
Phe Lys Tyr Phe Ala His Gln Asn Thr Leu Asp Glu Asn Phe Glu Gly
    450                 455                 460

Glu Ser Ile Asn Tyr Thr Gly Trp Leu Asp Leu Asp Glu Lys Arg Tyr
465                 470                 475                 480

Tyr Phe Thr Asp Glu Tyr Ile Ala Ala Thr Gly Ser Val Ile Ile Asp
                485                 490                 495

Gly Glu Glu Tyr Tyr Phe Asp Pro Asp Thr Ala Gln Leu Val Ile Ser
            500                 505                 510

Glu

<210> SEQ ID NO 34
<211> LENGTH: 534
<212> TYPE: PRT
<213> ORGANISM: Artificial Sequence
<220> FEATURE:
<223> OTHER INFORMATION: toxin B fragment of F5 ToxB

<400> SEQUENCE: 34

Ser Gly Leu Ile Tyr Ile Asn Asp Ser Leu Tyr Tyr Phe Lys Pro Pro
1               5                   10                  15

Val Asn Asn Leu Ile Thr Gly Phe Val Thr Val Gly Asp Asp Lys Tyr
            20                  25                  30

Tyr Phe Asn Pro Ile Asn Gly Gly Ala Ala Ser Ile Gly Glu Thr Ile
        35                  40                  45

Ile Asp Asp Lys Asn Tyr Tyr Phe Asn Gln Ser Gly Val Leu Gln Thr
    50                  55                  60

Gly Val Phe Ser Thr Glu Asp Gly Phe Lys Tyr Phe Ala Pro Ala Asn
65                  70                  75                  80

Thr Leu Asp Glu Asn Leu Glu Gly Glu Ala Ile Asp Phe Thr Gly Lys
                85                  90                  95

Leu Ile Ile Asp Glu Asn Ile Tyr Tyr Phe Asp Asp Asn Tyr Arg Gly
            100                 105                 110

Ala Val Glu Trp Lys Glu Leu Asp Gly Glu Met His Tyr Phe Ser Pro
        115                 120                 125

Glu Thr Gly Lys Ala Phe Lys Gly Leu Asn Gln Ile Gly Asp Tyr Lys
    130                 135                 140

Tyr Tyr Phe Asn Ser Asp Gly Val Met Gln Lys Gly Phe Val Ser Ile
145                 150                 155                 160

Asn Asp Asn Lys His Tyr Phe Asp Asp Ser Gly Val Met Lys Val Gly
                165                 170                 175

Tyr Thr Glu Ile Asp Gly Lys His Phe Tyr Phe Ala Glu Asn Gly Glu
            180                 185                 190

Met Gln Ile Gly Val Phe Asn Thr Glu Asp Gly Phe Lys Tyr Phe Ala
        195                 200                 205

His His Asn Glu Asp Leu Gly Asn Glu Glu Gly Glu Glu Ile Ser Tyr
    210                 215                 220

Ser Gly Ile Leu Asn Phe Asn Asn Lys Ile Tyr Tyr Phe Asp Asp Ser
225                 230                 235                 240

Phe Thr Ala Val Val Gly Trp Lys Asp Leu Glu Asp Gly Ser Lys Tyr
                245                 250                 255

Tyr Phe Asp Glu Asp Thr Ala Glu Ala Tyr Ile Gly Leu Ser Leu Ile
            260                 265                 270

Asn Asp Gly Gln Tyr Tyr Phe Asn Asp Asp Gly Ile Met Gln Val Gly
        275                 280                 285
```

-continued

Phe Val Thr Ile Asn Asp Lys Val Phe Tyr Phe Ser Asp Ser Gly Ile
        290                 295                 300

Ile Glu Ser Gly Val Gln Asn Ile Asp Asp Asn Tyr Phe Tyr Ile Asp
305                 310                 315                 320

Asp Asn Gly Ile Val Gln Ile Gly Val Phe Asp Thr Ser Asp Gly Tyr
                325                 330                 335

Lys Tyr Phe Ala Pro Ala Asn Thr Val Asn Asp Asn Ile Tyr Gly Gln
            340                 345                 350

Ala Val Glu Tyr Ser Gly Leu Val Arg Val Gly Glu Asp Val Tyr Tyr
        355                 360                 365

Phe Gly Glu Thr Tyr Thr Ile Glu Thr Gly Trp Ile Tyr Asp Met Glu
    370                 375                 380

Asn Glu Ser Asp Lys Tyr Tyr Phe Asn Pro Glu Thr Lys Lys Ala Cys
385                 390                 395                 400

Lys Gly Ile Asn Leu Ile Asp Asp Ile Lys Tyr Tyr Phe Asp Glu Lys
                405                 410                 415

Gly Ile Met Arg Thr Gly Leu Ile Ser Phe Glu Asn Asn Tyr Tyr
            420                 425                 430

Phe Asn Glu Asn Gly Glu Met Gln Phe Gly Tyr Ile Asn Ile Glu Asp
        435                 440                 445

Lys Met Phe Tyr Phe Gly Glu Asp Gly Val Met Gln Ile Gly Val Phe
    450                 455                 460

Asn Thr Pro Asp Gly Phe Lys Tyr Phe Ala His Gln Asn Thr Leu Asp
465                 470                 475                 480

Glu Asn Phe Glu Gly Glu Ser Ile Asn Tyr Thr Gly Trp Leu Asp Leu
                485                 490                 495

Asp Glu Lys Arg Tyr Tyr Phe Thr Asp Glu Tyr Ile Ala Ala Thr Gly
            500                 505                 510

Ser Val Ile Ile Asp Gly Glu Glu Tyr Tyr Phe Asp Pro Asp Thr Ala
        515                 520                 525

Gln Leu Val Ile Ser Glu
    530

<210> SEQ ID NO 35
<211> LENGTH: 400
<212> TYPE: PRT
<213> ORGANISM: Artificial Sequence
<220> FEATURE:
<223> OTHER INFORMATION: toxin B fragment of F52 New

<400> SEQUENCE: 35

Lys Gly Leu Asn Gln Ile Gly Asp Tyr Lys Tyr Tyr Phe Asn Ser Asp
1               5                   10                  15

Gly Val Met Gln Lys Gly Phe Val Ser Ile Asn Asp Asn Lys His Tyr
            20                  25                  30

Phe Asp Asp Ser Gly Val Met Lys Val Gly Tyr Thr Glu Ile Asp Gly
        35                  40                  45

Lys His Phe Tyr Phe Ala Glu Asn Gly Glu Met Gln Ile Gly Val Phe
    50                  55                  60

Asn Thr Glu Asp Gly Phe Lys Tyr Phe Ala His His Asn Glu Asp Leu
65                  70                  75                  80

Gly Asn Glu Glu Gly Glu Glu Ile Ser Tyr Ser Gly Ile Leu Asn Phe
                85                  90                  95

Asn Asn Lys Ile Tyr Tyr Phe Asp Asp Ser Phe Thr Ala Val Val Gly
            100                 105                 110

Trp Lys Asp Leu Glu Asp Gly Ser Lys Tyr Tyr Phe Asp Glu Asp Thr
            115                 120                 125

Ala Glu Ala Tyr Ile Gly Leu Ser Leu Ile Asn Asp Gly Gln Tyr Tyr
        130                 135                 140

Phe Asn Asp Asp Gly Ile Met Gln Val Gly Phe Val Thr Ile Asn Asp
145                 150                 155                 160

Lys Val Phe Tyr Phe Ser Asp Ser Gly Ile Ile Glu Ser Gly Val Gln
                165                 170                 175

Asn Ile Asp Asp Asn Tyr Phe Tyr Ile Asp Asp Asn Gly Ile Val Gln
            180                 185                 190

Ile Gly Val Phe Asp Thr Ser Asp Gly Tyr Lys Tyr Phe Ala Pro Ala
        195                 200                 205

Asn Thr Val Asn Asp Asn Ile Tyr Gly Gln Ala Val Glu Tyr Ser Gly
    210                 215                 220

Leu Val Arg Val Gly Glu Asp Val Tyr Tyr Phe Gly Glu Thr Tyr Thr
225                 230                 235                 240

Ile Glu Thr Gly Trp Ile Tyr Asp Met Glu Asn Glu Ser Asp Lys Tyr
                245                 250                 255

Tyr Phe Asn Pro Glu Thr Lys Lys Ala Cys Lys Gly Ile Asn Leu Ile
            260                 265                 270

Asp Asp Ile Lys Tyr Tyr Phe Asp Glu Lys Gly Ile Met Arg Thr Gly
        275                 280                 285

Leu Ile Ser Phe Glu Asn Asn Asn Tyr Tyr Phe Asn Glu Asn Gly Glu
    290                 295                 300

Met Gln Phe Gly Tyr Ile Asn Ile Glu Asp Lys Met Phe Tyr Phe Gly
305                 310                 315                 320

Glu Asp Gly Val Met Gln Ile Gly Val Phe Asn Thr Pro Asp Gly Phe
                325                 330                 335

Lys Tyr Phe Ala His Gln Asn Thr Leu Asp Glu Asn Phe Glu Gly Glu
            340                 345                 350

Ser Ile Asn Tyr Thr Gly Trp Leu Asp Leu Asp Glu Lys Arg Tyr Tyr
        355                 360                 365

Phe Thr Asp Glu Tyr Ile Ala Ala Thr Gly Ser Val Ile Ile Asp Gly
    370                 375                 380

Glu Glu Tyr Tyr Phe Asp Pro Asp Thr Ala Gln Leu Val Ile Ser Glu
385                 390                 395                 400

<210> SEQ ID NO 36
<211> LENGTH: 958
<212> TYPE: PRT
<213> ORGANISM: Artificial Sequence
<220> FEATURE:
<223> OTHER INFORMATION: C-TAB.G5 fusion

<400> SEQUENCE: 36

Met Val Thr Gly Val Phe Lys Gly Pro Asn Gly Phe Glu Tyr Phe Ala
1               5                   10                  15

Pro Ala Asn Thr His Asn Asn Asn Ile Glu Gly Gln Ala Ile Val Tyr
            20                  25                  30

Gln Asn Lys Phe Leu Thr Leu Asn Gly Lys Lys Tyr Tyr Phe Asp Asn
        35                  40                  45

Asp Ser Lys Ala Val Thr Gly Trp Gln Thr Ile Asp Gly Lys Lys Tyr
    50                  55                  60

Tyr Phe Asn Leu Asn Thr Ala Glu Ala Ala Thr Gly Trp Gln Thr Ile
65                  70                  75                  80

```
Asp Gly Lys Lys Tyr Tyr Phe Asn Leu Asn Thr Ala Glu Ala Ala Thr
                85                  90                  95
Gly Trp Gln Thr Ile Asp Gly Lys Lys Tyr Tyr Phe Asn Thr Asn Thr
                100                 105                 110
Phe Ile Ala Ser Thr Gly Tyr Thr Ser Ile Asn Gly Lys His Phe Tyr
                115                 120                 125
Phe Asn Thr Asp Gly Ile Met Gln Ile Gly Val Phe Lys Gly Pro Asn
        130                 135                 140
Gly Phe Glu Tyr Phe Ala Pro Ala Asn Thr His Asn Asn Asn Ile Glu
145                 150                 155                 160
Gly Gln Ala Ile Leu Tyr Gln Asn Lys Phe Leu Thr Leu Asn Gly Lys
                165                 170                 175
Lys Tyr Tyr Phe Gly Ser Asp Ser Lys Ala Val Thr Gly Leu Arg Thr
                180                 185                 190
Ile Asp Gly Lys Lys Tyr Tyr Phe Asn Thr Asn Thr Ala Val Ala Val
            195                 200                 205
Thr Gly Trp Gln Thr Ile Asn Gly Lys Lys Tyr Tyr Phe Asn Thr Asn
                210                 215                 220
Thr Ser Ile Ala Ser Thr Gly Tyr Thr Ile Ile Ser Gly Lys His Phe
225                 230                 235                 240
Tyr Phe Asn Thr Asp Gly Ile Met Gln Ile Gly Val Phe Lys Gly Pro
                245                 250                 255
Asp Gly Phe Glu Tyr Phe Ala Pro Ala Asn Thr Asp Ala Asn Asn Ile
                260                 265                 270
Glu Gly Gln Ala Ile Arg Tyr Gln Asn Arg Phe Leu Tyr Leu His Asp
                275                 280                 285
Asn Ile Tyr Tyr Phe Gly Asn Asn Ser Lys Ala Ala Thr Gly Trp Val
            290                 295                 300
Thr Ile Asp Gly Asn Arg Tyr Tyr Phe Glu Pro Asn Thr Ala Met Gly
305                 310                 315                 320
Ala Asn Gly Tyr Lys Thr Ile Asp Asn Lys Asn Phe Tyr Phe Arg Asn
                325                 330                 335
Gly Leu Pro Gln Ile Gly Val Phe Lys Gly Ser Asn Gly Phe Glu Tyr
                340                 345                 350
Phe Ala Pro Ala Asn Thr Asp Ala Asn Asn Ile Glu Gly Gln Ala Ile
            355                 360                 365
Arg Tyr Gln Asn Arg Phe Leu His Leu Leu Gly Lys Ile Tyr Tyr Phe
    370                 375                 380
Gly Asn Asn Ser Lys Ala Val Thr Gly Trp Gln Thr Ile Asn Gly Lys
385                 390                 395                 400
Val Tyr Tyr Phe Met Pro Asp Thr Ala Met Ala Ala Ala Gly Gly Leu
                405                 410                 415
Phe Glu Ile Asp Gly Val Ile Tyr Phe Phe Gly Val Asp Gly Val Lys
                420                 425                 430
Ala Pro Gly Ile Tyr Gly Arg Ser Met His Asn Leu Ile Thr Gly Phe
        435                 440                 445
Val Thr Val Gly Asp Asp Lys Tyr Tyr Phe Asn Pro Ile Asn Gly Gly
        450                 455                 460
Ala Ala Ser Ile Gly Glu Thr Ile Ile Asp Asp Lys Asn Tyr Tyr Phe
465                 470                 475                 480
Asn Gln Ser Gly Val Leu Gln Thr Gly Val Phe Ser Thr Glu Asp Gly
                485                 490                 495
```

```
Phe Lys Tyr Phe Ala Pro Ala Asn Thr Leu Asp Glu Asn Leu Glu Gly
            500                 505                 510

Glu Ala Ile Asp Phe Thr Gly Lys Leu Ile Ile Asp Glu Asn Ile Tyr
        515                 520                 525

Tyr Phe Asp Asp Asn Tyr Arg Gly Ala Val Glu Trp Lys Glu Leu Asp
        530                 535                 540

Gly Glu Met His Tyr Phe Ser Pro Glu Thr Gly Lys Ala Phe Lys Gly
545                 550                 555                 560

Leu Asn Gln Ile Gly Asp Tyr Lys Tyr Tyr Phe Asn Ser Asp Gly Val
                565                 570                 575

Met Gln Lys Gly Phe Val Ser Ile Asn Asp Asn Lys His Tyr Phe Asp
            580                 585                 590

Asp Ser Gly Val Met Lys Val Gly Tyr Thr Glu Ile Asp Gly Lys His
        595                 600                 605

Phe Tyr Phe Ala Glu Asn Gly Glu Met Gln Ile Gly Val Phe Asn Thr
        610                 615                 620

Glu Asp Gly Phe Lys Tyr Phe Ala His His Asn Glu Asp Leu Gly Asn
625                 630                 635                 640

Glu Glu Gly Glu Glu Ile Ser Tyr Ser Gly Ile Leu Asn Phe Asn Asn
                645                 650                 655

Lys Ile Tyr Tyr Phe Asp Asp Ser Phe Thr Ala Val Val Gly Trp Lys
            660                 665                 670

Asp Leu Glu Asp Gly Ser Lys Tyr Tyr Phe Asp Glu Asp Thr Ala Glu
        675                 680                 685

Ala Tyr Ile Gly Leu Ser Leu Ile Asn Asp Gly Gln Tyr Tyr Phe Asn
        690                 695                 700

Asp Asp Gly Ile Met Gln Val Gly Phe Val Thr Ile Asn Asp Lys Val
705                 710                 715                 720

Phe Tyr Phe Ser Asp Ser Gly Ile Ile Glu Ser Gly Val Gln Asn Ile
                725                 730                 735

Asp Asp Asn Tyr Phe Tyr Ile Asp Asp Asn Gly Ile Val Gln Ile Gly
            740                 745                 750

Val Phe Asp Thr Ser Asp Gly Tyr Lys Tyr Phe Ala Pro Ala Asn Thr
        755                 760                 765

Val Asn Asp Asn Ile Tyr Gly Gln Ala Val Glu Tyr Ser Gly Leu Val
        770                 775                 780

Arg Val Gly Glu Asp Val Tyr Tyr Phe Gly Glu Thr Tyr Thr Ile Glu
785                 790                 795                 800

Thr Gly Trp Ile Tyr Asp Met Glu Asn Glu Ser Asp Lys Tyr Tyr Phe
                805                 810                 815

Asn Pro Glu Thr Lys Lys Ala Cys Lys Gly Ile Asn Leu Ile Asp Asp
            820                 825                 830

Ile Lys Tyr Tyr Phe Asp Glu Lys Gly Ile Met Arg Thr Gly Leu Ile
        835                 840                 845

Ser Phe Glu Asn Asn Asn Tyr Tyr Phe Asn Glu Asn Gly Glu Met Gln
        850                 855                 860

Phe Gly Tyr Ile Asn Ile Glu Asp Lys Met Phe Tyr Phe Gly Glu Asp
865                 870                 875                 880

Gly Val Met Gln Ile Gly Val Phe Asn Thr Pro Asp Gly Phe Lys Tyr
                885                 890                 895

Phe Ala His Gln Asn Thr Leu Asp Glu Asn Phe Glu Gly Glu Ser Ile
            900                 905                 910

Asn Tyr Thr Gly Trp Leu Asp Leu Asp Glu Lys Arg Tyr Tyr Phe Thr
```

```
            915                 920                 925
Asp Glu Tyr Ile Ala Ala Thr Gly Ser Val Ile Ile Asp Gly Glu Glu
        930                 935                 940

Tyr Tyr Phe Asp Pro Asp Thr Ala Gln Leu Val Ile Ser Glu
945                 950                 955

<210> SEQ ID NO 37
<211> LENGTH: 957
<212> TYPE: PRT
<213> ORGANISM: Artificial Sequence
<220> FEATURE:
<223> OTHER INFORMATION: C-TAB.G5.1 fusion

<400> SEQUENCE: 37

Val Thr Gly Val Phe Lys Gly Pro Asn Gly Phe Glu Tyr Phe Ala Pro
1               5                   10                  15

Ala Asn Thr His Asn Asn Ile Glu Gly Gln Ala Ile Val Tyr Gln
            20                  25                  30

Asn Lys Phe Leu Thr Leu Asn Gly Lys Lys Tyr Tyr Phe Asp Asn Asp
            35                  40                  45

Ser Lys Ala Val Thr Gly Trp Gln Thr Ile Asp Gly Lys Lys Tyr Tyr
50                  55                  60

Phe Asn Leu Asn Thr Ala Glu Ala Ala Thr Gly Trp Gln Thr Ile Asp
65                  70                  75                  80

Gly Lys Lys Tyr Tyr Phe Asn Leu Asn Thr Ala Glu Ala Ala Thr Gly
                85                  90                  95

Trp Gln Thr Ile Asp Gly Lys Lys Tyr Tyr Phe Asn Thr Asn Thr Phe
            100                 105                 110

Ile Ala Ser Thr Gly Tyr Thr Ser Ile Asn Gly Lys His Phe Tyr Phe
            115                 120                 125

Asn Thr Asp Gly Ile Met Gln Ile Gly Val Phe Lys Gly Pro Asn Gly
        130                 135                 140

Phe Glu Tyr Phe Ala Pro Ala Asn Thr Asp Ala Asn Asn Ile Glu Gly
145                 150                 155                 160

Gln Ala Ile Leu Tyr Gln Asn Lys Phe Leu Thr Leu Asn Gly Lys Lys
                165                 170                 175

Tyr Tyr Phe Gly Ser Asp Ser Lys Ala Val Thr Gly Leu Arg Thr Ile
            180                 185                 190

Asp Gly Lys Lys Tyr Tyr Phe Asn Thr Asn Thr Ala Val Ala Val Thr
        195                 200                 205

Gly Trp Gln Thr Ile Asn Gly Lys Lys Tyr Tyr Phe Asn Thr Asn Thr
210                 215                 220

Ser Ile Ala Ser Thr Gly Tyr Thr Ile Ile Ser Gly Lys His Phe Tyr
225                 230                 235                 240

Phe Asn Thr Asp Gly Ile Met Gln Ile Gly Val Phe Lys Gly Pro Asp
                245                 250                 255

Gly Phe Glu Tyr Phe Ala Pro Ala Asn Thr Asp Ala Asn Asn Ile Glu
            260                 265                 270

Gly Gln Ala Ile Arg Tyr Gln Asn Arg Phe Leu Tyr Leu His Asp Asn
        275                 280                 285

Ile Tyr Tyr Phe Gly Asn Asn Ser Lys Ala Ala Thr Gly Trp Val Thr
290                 295                 300

Ile Asp Gly Asn Arg Tyr Tyr Phe Glu Pro Asn Thr Ala Met Gly Ala
305                 310                 315                 320

Asn Gly Tyr Lys Thr Ile Asp Asn Lys Asn Phe Tyr Phe Arg Asn Gly
```

```
                    325                 330                 335
Leu Pro Gln Ile Gly Val Phe Lys Gly Ser Asn Gly Phe Glu Tyr Phe
                340                 345                 350
Ala Pro Ala Asn Thr Asp Ala Asn Asn Ile Glu Gly Gln Ala Ile Arg
                355                 360                 365
Tyr Gln Asn Arg Phe Leu His Leu Leu Gly Lys Ile Tyr Tyr Phe Gly
            370                 375                 380
Asn Asn Ser Lys Ala Val Thr Gly Trp Gln Thr Ile Asn Gly Lys Val
385                 390                 395                 400
Tyr Tyr Phe Met Pro Asp Thr Ala Met Ala Ala Gly Gly Leu Phe
                405                 410                 415
Glu Ile Asp Gly Val Ile Tyr Phe Phe Gly Val Asp Gly Val Lys Ala
                420                 425                 430
Pro Gly Ile Tyr Gly Arg Ser Met His Asn Leu Ile Thr Gly Phe Val
                435                 440                 445
Thr Val Gly Asp Asp Lys Tyr Tyr Phe Asn Pro Ile Asn Gly Gly Ala
            450                 455                 460
Ala Ser Ile Gly Glu Thr Ile Ile Asp Asp Lys Asn Tyr Tyr Phe Asn
465                 470                 475                 480
Gln Ser Gly Val Leu Gln Thr Gly Val Phe Ser Thr Glu Asp Gly Phe
                485                 490                 495
Lys Tyr Phe Ala Pro Ala Asn Thr Leu Asp Glu Asn Leu Glu Gly Glu
                500                 505                 510
Ala Ile Asp Phe Thr Gly Lys Leu Ile Ile Asp Glu Asn Ile Tyr Tyr
                515                 520                 525
Phe Asp Asp Asn Tyr Arg Gly Ala Val Glu Trp Lys Glu Leu Asp Gly
            530                 535                 540
Glu Met His Tyr Phe Ser Pro Glu Thr Gly Lys Ala Phe Lys Gly Leu
545                 550                 555                 560
Asn Gln Ile Gly Asp Tyr Lys Tyr Tyr Phe Asn Ser Asp Gly Val Met
                565                 570                 575
Gln Lys Gly Phe Val Ser Ile Asn Asp Asn Lys His Tyr Phe Asp Asp
                580                 585                 590
Ser Gly Val Met Lys Val Gly Tyr Thr Glu Ile Asp Gly Lys His Phe
            595                 600                 605
Tyr Phe Ala Glu Asn Gly Glu Met Gln Ile Gly Val Phe Asn Thr Glu
            610                 615                 620
Asp Gly Phe Lys Tyr Phe Ala His His Asn Glu Asp Leu Gly Asn Glu
625                 630                 635                 640
Glu Gly Glu Glu Ile Ser Tyr Ser Gly Ile Leu Asn Phe Asn Asn Lys
                645                 650                 655
Ile Tyr Tyr Phe Asp Asp Ser Phe Thr Ala Val Val Gly Trp Lys Asp
                660                 665                 670
Leu Glu Asp Gly Ser Lys Tyr Tyr Phe Asp Glu Asp Thr Ala Glu Ala
                675                 680                 685
Tyr Ile Gly Leu Ser Leu Ile Asn Asp Gly Gln Tyr Tyr Phe Asn Asp
            690                 695                 700
Asp Gly Ile Met Gln Val Gly Phe Val Thr Ile Asn Asp Lys Val Phe
705                 710                 715                 720
Tyr Phe Ser Asp Ser Gly Ile Ile Glu Ser Gly Val Gln Asn Ile Asp
                725                 730                 735
Asp Asn Tyr Phe Tyr Ile Asp Asp Asn Gly Ile Val Gln Ile Gly Val
                740                 745                 750
```

-continued

```
Phe Asp Thr Ser Asp Gly Tyr Lys Tyr Phe Ala Pro Ala Asn Thr Val
        755                 760             765

Asn Asp Asn Ile Tyr Gly Gln Ala Val Glu Tyr Ser Gly Leu Val Arg
    770             775                 780

Val Gly Glu Asp Val Tyr Tyr Phe Gly Glu Thr Tyr Thr Ile Glu Thr
785             790                 795                     800

Gly Trp Ile Tyr Asp Met Glu Asn Glu Ser Asp Lys Tyr Tyr Phe Asn
                805                 810                 815

Pro Glu Thr Lys Lys Ala Cys Lys Gly Ile Asn Leu Ile Asp Asp Ile
            820                 825             830

Lys Tyr Tyr Phe Asp Glu Lys Gly Ile Met Arg Thr Gly Leu Ile Ser
        835                 840                 845

Phe Glu Asn Asn Asn Tyr Tyr Phe Asn Glu Asn Gly Glu Met Gln Phe
    850                 855                 860

Gly Tyr Ile Asn Ile Glu Asp Lys Met Phe Tyr Phe Gly Glu Asp Gly
865             870                 875                     880

Val Met Gln Ile Gly Val Phe Asn Thr Pro Asp Gly Phe Lys Tyr Phe
                885                 890                 895

Ala His Gln Asn Thr Leu Asp Glu Asn Phe Glu Gly Glu Ser Ile Asn
            900                 905                 910

Tyr Thr Gly Trp Leu Asp Leu Asp Glu Lys Arg Tyr Tyr Phe Thr Asp
        915                 920                 925

Glu Tyr Ile Ala Ala Thr Gly Ser Val Ile Ile Asp Gly Glu Glu Tyr
    930                 935                 940

Tyr Phe Asp Pro Asp Thr Ala Gln Leu Val Ile Ser Glu
945             950                 955
```